(12) United States Patent
Rao et al.

(10) Patent No.: US 9,163,078 B2
(45) Date of Patent: *Oct. 20, 2015

(54) REGULATORS OF NFAT

(75) Inventors: Anjana Rao, Cambridge, MA (US);
Stefan Feske, New York, NY (US);
Patrick Hogan, Cambridge, MA (US);
Yousang Gwack, Los Angeles, CA (US)

(73) Assignee: Children's Medical Center Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/161,307

(22) Filed: Jun. 15, 2011

(65) Prior Publication Data

US 2011/0269174 A1    Nov. 3, 2011

Related U.S. Application Data

(63) Continuation of application No. 12/160,030, filed as application No. PCT/US2007/000280 on Jan. 5, 2007.

(60) Provisional application No. 60/756,934, filed on Jan. 5, 2006.

(51) Int. Cl.
| | |
|---|---|
| *C12Q 1/00* | (2006.01) |
| *A61K 48/00* | (2006.01) |
| *C12N 15/63* | (2006.01) |
| *C07H 21/04* | (2006.01) |
| *C07K 16/18* | (2006.01) |
| *G01N 33/50* | (2006.01) |
| *C12N 5/16* | (2006.01) |
| *C12N 15/90* | (2006.01) |

(52) U.S. Cl.
CPC .............. *C07K 16/18* (2013.01); *G01N 33/5041* (2013.01); *C07H 21/04* (2013.01); *C12N 5/16* (2013.01); *C12N 15/63* (2013.01); *C12N 15/907* (2013.01); *C12Q 1/00* (2013.01)

(58) Field of Classification Search
CPC ........ C12N 5/16; C12N 15/63; C12N 15/907; C12Q 1/00; C07H 21/04
USPC .................... 435/4, 455; 424/93.21; 536/23.5
See application file for complete search history.

(56) References Cited

U.S. PATENT DOCUMENTS

| 6,875,581 | B1 | 4/2005 | Voelkel |
|---|---|---|---|
| 2001/0018196 | A1 | 8/2001 | Mendoza et al. |
| 2004/0219521 | A1 | 11/2004 | Tang et al. |
| 2005/0107588 | A1 | 5/2005 | Duggan et al. |
| 2005/0255487 | A1 | 11/2005 | Khvorova et al. |
| 2006/0286605 | A1 | 12/2006 | Liou et al. |
| 2007/0031814 | A1 | 2/2007 | Roos et al. |
| 2008/0039392 | A1 | 2/2008 | Cahalan |
| 2008/0096227 | A1 | 4/2008 | Penner |
| 2008/0293092 | A1 | 11/2008 | Stauderman et al. |
| 2009/0143308 | A1 | 6/2009 | Monk et al. |
| 2009/0186422 | A1 | 7/2009 | Hogan et al. |
| 2010/0081129 | A1 | 4/2010 | Belouchi et al. |

FOREIGN PATENT DOCUMENTS

| CN | 1329064 | | 1/2002 |
|---|---|---|---|
| EP | 0976823 | A | 2/2000 |
| EP | 1074617 | | 2/2001 |
| EP | 1293569 | | 3/2003 |
| WO | 02/30976 | A1 | 4/2002 |
| WO | 02/070539 | | 9/2002 |
| WO | 03/048305 | | 6/2003 |
| WO | 03/052049 | | 6/2003 |
| WO | WO2005/016962 | A2 * | 2/2005 |
| WO | 2005/019258 | | 3/2005 |
| WO | 2007/081804 | A2 | 7/2007 |

OTHER PUBLICATIONS

Skolnick et al., 2000, Trends in Biotech, vol. 18, p. 34-39.*
Tomasinsig et al., 2005, Current Protein and Peptide Science, vol. 6, p. 23-34.*
Smallwood et al., 2002, Virology, vol. 304, p. 135-145.*
Chattopadhyay et al., 2004. Virus Research, vol. 99, p. 139-145.*
Abbas et al., 2005, computer printout pp. 2-6.*
Strausberg et al., 2004, GenEmbl Accession No. BC069270, computer printout, pp. 13-17.*
Roos et al., 2007, US 20070031814 A1, effective filing date Mar. 4, 2003.*
Zhang et al., U.S. Appl. No. 11/582,861, US 20070099251, effective filing date Oct. 17, 2005, see computer printout, pp. 8-10.*
Harkin et al., U.S. Appl. No. 11/266,748, US 20060134663, effective filing date Jul. 18, 2005, computer printout, pp. 6-9.*

(Continued)

*Primary Examiner* — Shin Lin Chen
(74) *Attorney, Agent, or Firm* — Nixon Peabody LLP

(57) ABSTRACT

Disclosed are methods of identifying an agent that modulates an NFAT regulator protein. One such method comprises contacting at least one test agent with a recombinant cell comprising at least one NFAT regulator protein or fragment or derivative thereof, assessing the effect of the test agent on an activity, interaction, expression, or binding to the NFAT regulator protein or fragment or derivative thereof, and identifying the test agent that has an effect on an activity, interaction, expression, or binding to the NFAT regulator protein or fragment or derivative thereof, whereby the identified test agent is characterized as an agent that modulates an NFAT regulator protein. Methods of identifying an agent that modulates intracellular calcium, methods to screen for an agent that modulates NFAT regulator function, methods to diagnose unexplained immunodeficiency in a subject, and methods for identifying an agent for treating or preventing a disease or disorder associated with a NFAT regulator protein or calcium signaling are also disclosed.

27 Claims, 33 Drawing Sheets

(56) References Cited

OTHER PUBLICATIONS

Strausberg et al., 2004, GenEmbl Accession No. BC075831, direct submission on Jul. 6, 2004, ORAI1, Strauysberg1.*
Strausberg et al., 2004, GenEmbl Accession No. BC069270, direct submission on Apr. 26, 2004, ORAI2, Strausberg2.*
Strausberg et al., 2001, GenEmbl Accession No. BC015555, direct submission on Oct. 1, 2001, ORAI3, Strausberg3.*
Abecasis, G. R. et al., "Merlin-rapid analysis of dense genetic maps using sparse gene flow trees." Nature Genetics 30:97-101, 2002.
Altshuler, D. et al., "A haplotype map of the human genome." Nature 437(7063):1299-1320, 2005.
Aramburu, J. et al., "Affinity-Driven Peptide Selection of an NFAT Inhibitor More Selective Than Cyclosporin A." Science 285:2129-2133, 1999.
Badou, A. et al., "Requirement of Voltage-Gated Calcium Channel β4 Subunit for T Lymphocyte Functions." Science 307:117-121, 2005.
Beals, C. R. et al., "Nuclear Export of NF-ATc Enhanced by Glycogen Synthase Kinase-3." Science 275:1930-1933, 1997.
Clipstone, N. A. et al., "Molecular Analysis of the Interaction of Calcineurin with Drug-Immunophilin Complexes." J Biol Chem 269(42):26431-26437, 1994.
Courtois, G. et al., "A hypermorphic 1-kappa-B-beta mutation is associated with autosomal dominant anhidrotic ectodermal dysplasia and T cell immunodeficiency." J Clin Invest 112:1108-1115, 2003.
Crabtree, G. R. and Olson, E. N., "NFAT Signaling: Choreographing the Social Lives of Cells" Cell 9:S67-S79, 2002.
Cui, J. et al., "CaT1 Contributes to the Stores-operated Calcium Current in Jurkat T-lymphocytes" J Biol Chem 277 (49)47175-47183, 2002.
Döffinger, R. "X-linked anhidrotic ectodermal dysplasia with immunodeficiency is caused by impaired NF-kappa-B signaling." Nature Genetics 27:277-285, 2001.
Feske, S. et al., "The Duration of Nuclear Residence of NFAT Determines the Pattern of Cytokine Expression in Human SCID T Cells." J Immunol 165:297-305, 2000.
Feske, S. et al., "Gene regulation mediated by calcium signals in T lymphocytes." Nature Immunology 2(4):316-324, 2001.
Feske, S. et al., "A mutation in Orai 1 causes immune deficiency by abrogating CRAC channel function." Nature 441:179-185, 2006.
Feske, S. et al., "A severe defect in CRAC Ca2+ channel activation and altered K+ channel gating in T cells from immunodeficient patients." JEM 202(5):651-662, 2005.
Feske, S. et al., "Ca2+/calcineurin signalling in cells of the immune system." Biochemical and Biophysical Research Communications 311:1117-1132, 2003.
Gabriel, S. B. et al., "The Structure of Haptotype Blocks in the Human Genome." Science 296:2225-2229, 2002.
Gudbjartsson, D. F. et al., "Allegro, a new computer program for multipoint linkage analysis." Nature Genetics 25:12-13, 2000.
Gwack, Y. et al., "A genome-wide Drosophila RNAi screen identifies DYRK-family kinases as regulators of NFAT." Nature 441:646-650, 2006.
Hermosura, M. C. et al., "Dissociation of the store-operated calcium current Icrac and the Mg-nucleotide-regulated metal ion current MagNuM." J Physiol 539(2):445-458, 2002.
Hogan, P. G. et al., "Transcriptional regulation by calcium, calcineurin, and NFAT." Genes & Dev 17:2205-2232, 2003.
Horsley, V. And Pavlath, G. K., "NFAT: ubiquitous regulator of cell differentiation and adaptation." J Cell Biol 156 (5):771-774, 2002.
Im, S. and Rao A., "Activation and Deactivation of Gene Expression by Ca2+/Calcineurin-NFAT-mediated Signaling." Mol Cells 18(1):1-9, 2004.
The International HapMap Consortium, "The International HapMap Project." Nature 426:789-796, 2003.
Käll, L. et al., "A Combined Transmembrane Topology and Signal Peptide Prediction Method." J Mol Biol338:1027-1036, 2004.
Kanno, T. and Siebenlist, U., "Activation of Nuclear Factor-kappa-B via T Cell Receptor Requires a Raf Kniase and Ca2+ Influx." J Immunol 157:5277-5283, 1996.

Kim, E. and Sheng, M., "PDZ Domain Proteins of Synapses." Nature Reviews Neuroscience 5:771-781, 2004.
Kotturi, M. F. et al., "Identification and Functional Characterization of Voltage-dependent Calcium Channels in T Lymphocytes." J Biol Chem 278(47):46949-46960, 2003.
Krogh, A. et al., "Predicting Transmembrane Protein Topology with a Hidden Markov Model: Application to Complete Genomes." J Mol Biol 305:567-580, 2001.
Le Deist, F. et al., "A primary T-cell immunodeficiency associated with defective transmembrane calcium influx." Blood 85:1053-1062, 1995.
Lepple-Wienhues, A. and Cahalan. M. D., "Conductance and Permeation of Monovalent Cations through Depletion-Activated Ca2+ Channels (Icrac) in Jurkat T Cells." Biophysical Journal 71:787-794, 1996.
Lewis, R. S., "Calcium Signaling Mechanisms in T Lymphocytes." Annu Rev Immunol 19:497-521, 2001.
Leykin, I. et al., "Comparative linkage analysis and visualization of high-density oligonucleotide SNP array data." BMC Genetics 6(7):1-16, 2005.
Liou, J. et al., "STIM Is a Ca2+ Sensor Essential for Ca2+-Store-Depletion-Triggered Ca2+ Influx." Current Biology 15:1235-1241, 2005.
Liu, J., "FK506 and cyclosporin, molecular probes for studying intracellular signal transduction." Immunology Today 14(6):290-295, 1993.
Mácian, F., "NFAT Proteins: Key Regulators of T-Cell Development and Function." Nature 5:472-484, 2005.
Mácian, F., "Partners in transcription: NFAT and AP-1." Oncogene 20:2476-2489, 2001.
Mori, Y. et al., "Transient Receptor Potential 1 Regulates Capacitative Ca2+ Entry and Ca2+ Release from Endoplasmic Reticulum in B Lymphocytes." J Exp Med 195(6)673-681, 2002.
Myers, E. W. et al., "A Whole-Genome Assembly of Drosophila." Science 287:2196-2204, 2000.
Okamura, H. et al., "Concerted Dephosphorylation of the Transcription Factor NFAT1 Induces a Conformational Switch that Regulates Transcriptional Activity." Molecular Cell 6:539-550, 2000.
Okamura, H. et al., "A Conserved Docking Motif for CK1 Binding Controls the Nuclear Localization of NFAT1." Molecular and Cellular Biology 24(10):4184-4195, 2004.
Parekh, A. B. and Putney, Jr., J. W., "Store-Operated Calcium Channels" Physiol Rev 85:757-810, 2005.
Parekh, A. B. and Penner, R., "Store Depletion and Calcium Influx." Physiological Reviews 77(4):901-930, 1997.
Partiseti, M. et al., "The Calcium Current Activated by T Cell Receptor and Store Depletion in Human Lymphocytes is Absent in a Primary Immunodeficiency." J Biol Chem 269(51):32327-32335, 1994.
Philipp, S. et al., "TRPC3 Mediates T-cell Receptor-dependent Calcium Entry in Human T-lymphocytes." J Biol Chem 278(29):26629-26638, 2003.
Prakriya, M. and Lewis, R. S., "CRAC channels: activation, permeation, and the search for a molecular identity." Cell Calcium 33:311-321, 2003.
Feske et al., "A Mutation in Orai1 Causes Immune Deficiency by Abrogating CRAC Channel Function," Nature 441:179-185 (2006).
Parekh, A.B., "Cell Biology: Cracking the calcium entry code," Nature 441(11):163-165 (2006).
Robinson, L.C, and Marchant, J.S., "Calcium Influx: Beyond 'Current' Biology," Current Biology 16(14):R548-550 (2006).
Smyth et al., "Emerging perspective in store-operated Ca2+ entry: Roles Orai. Stim and TRP," Biochimica Biophysica Acta (2006) doi:10, 1016/j.bbamer.2006.08.050.
Vig et al., "CRACM1 is a plasma membrane protein essential for store-operated Ca2+ entry," Science 312(5777):1220-1223 (2006).
Zhang et al., "Genome Wide RNAi Screen of Ca2+ influx identifies Genes that Regulate Ca2+ Channel Activity," PNAS USA 103(4):9357-9362 (2006).
Prakriya, M. and Lewis, R. S., "Separation and Characterization of Currents through Store-operated CRAC Channels and Mg2+-inhibited Cation (MIC) Channels." J Gen Physiol 119(5):487-508, 2002.
Puel, A. et al., "Inherited disorders of NF-kappa-B-mediated immunity in man." Current Opinion in Immunology 16:34-41, 2004.

(56) References Cited

OTHER PUBLICATIONS

Roderick, H. L. and Bootman, M. D., "Calcium Influx: Is Homer the Missing Link?" Current Biology 13:R976-R978, 2003.
Roos, J. at el., "STIM1, an essential and conserved component of store-operated Ca2+ channel function." J Cell Biol 169(3):435-445, 2005.
Salazar, C. and Höfer, T., "Allosteric Regulation of the Transcription Factor NFAT1 by Multiple Phosphorylation Sites: A Mathematical Analysis." J. Mol. Biol. 327:31-45, 2003.
Schmidt-Ulrich, R. et al., "Requirement of NF-kappa-B/Rel for the development of hair follicles and other epidermal appendices." Development 128:3843-3653, 2001.
Smahi, A. et al., "The NF-kappa-B signalling pathway in human diseases: from incontinentia pigmenti to ectodermal dysplasias and immune-deficiency syndromes." Human Molecular Genetics 11(20):2371-2375, 2002.
Venkatachalam, K. et al., "The cellular and molecular basis of store-operated calcium entry." Nature Cell Biology 4:E263-E272, 2002.
Voets, T. et al., "CaT1 and the Calcium Release-activated Calcium Channel Manifest Distinct Pore Properties." J Biol Chem 276(51):47767-47770, 2001.
Winslow, M. M. et al., "Calcium signalling in lymphocytes." Current Opinion in Immunology 16:299-307, 2003.
Yeromin, A. V. et al., "A Store-operated Calcium Channel in Drosophila S2 Cells," J Gen Physiol 123:167-182, 2004.
Yue, L. et al., "CaT1 manifests the pore properties of the calcium-release-activated calcium channel." Nature 410:705-709, 2001.
Zhang, S. L. et al., "STIM1 is a Ca2+ sensor that activates CRAC channels and migrates from the Ca2+ store to the plasma membrane," Nature 437(7080):902-905, 2005.
Zweifach, A. and Lewis, R. S., "Rapid Inactivation of Depletion-activated Calcium Current (Icrac) Due to Local Calcium Feedback." J Gen Physiol 105:209-226, 1995.
Zweifach, A. and Lewis, R. S., "Calcium-dependent Potentiation of Store-operated Calcium Channels in T Lymphocytes." J Gen Physiol 107:597-610, 1996.
Markianos, K. et al., "Efficient Multipoint Linkage Analysis through Reduction of Inheritance Space." Am J Hum Genet 68:963-977, 2001.
Salzar, C. et al., "Activation of the Transcription Factor NFAT1: concerted or modular regulation?" FEBS Lett 579:621-626, 2005.
Eck et al., Goodman & Gilman's The Pharmacological Basis of Therapeutics, McGraw-Hill, New York, pp. 77-101.
Gorecki, D., 2001, Expert Opin. Emerging Drugs, 6(2): 187-198.
Kodama et al., 2006, Current Medicinal Chemistry, vol. 13, pp. 2155-2161.
Nishikawa et al., 2001, Human Gene Therapy, vol. 12, pp. 861-870.
Pan et al., 1997, Biochemical and Biophysical Research Communications, vol. 240, pp. 314-323.
International Search Report dated Jan. 18, 2008 for International App. No. PCT/US2007/000280.
Park et al., "STIM1 Clusters and Activates CRAC Channels via Direct Binding of a Cytosolic Domain to Orai1", Cell, 136:876-890 (2009).
Gwack et al., JBC, 282(22):16232-16243 (2007). "Biochemical and functional characterization of Orai proteins."
Tang et al., Viewing Sequences: 58, 182 of 412 for Document #20040219521, Publication Site for Issued and Published Sequences (PSIPS) online, Nov. 2004, United States Patent and Trademark Office, Alexandria, VA, USA (retrieved on Jun. 6, 2012). Retrieved from the Internet<URL:http://seqdata.uspto.gov/?pageRequest=viewSequence&DocID=20040219521&seqID=58%2C182>, SEQ ID No. 58, 182.
Clapham, Cell, 136:814-816 (2009). "A STIMulus Package Puts Orai Calcium Channels to Work."
Coury et al., Am J Physiol, 274:F34-F42 (1998). "Reconstitution of water channel function of aquaporins 1 and 2 by expression in yeast secretory vesicles."

Coury et al., Methods in Enzymology, 306:169-186 (1999). "[10] Use of Yeast sec6 Mutant for Purification of Vesicles Containing Recombinant Membrane Proteins."
Derler et al., The Journal of Biological Chemistry, 284(23):15903-15915 (2009). "Increased Hydrophobicity at the N Terminus/Membrane Interface Impairs Gating of the Severe Combined Immunodeficiency-related ORAI1 Mutant."
Eid et al., BMC Developmental Biology, 8:104 (2008). "The Drosophila STIM1 orthologue, dSTIM, has roles in cell fate specification and tissue patterning."
Heyman et al., The Journal of Cell Biology, 127(5):1259-1273 (1994). "Role of the PAS1 Gene of *Pichia pastoris* in Peroxisome Biogenesis."
Hogan et al., TRENDS in Biochemical Sciences, 32(5):235-245 (2007). "Dissecting ICRAC, a store-operated calcium current."
Huang et al., Nature Cell Biology, 8(9):1003-1010 (2006). "STIM1 carboxyl-terminus activates native SOC, Icrac and TRPC1 channels."
Ji et al., PNAS, 105(36):13668-13673 (2008). "Functional stoichiometry of the unitary calcium-release-activated calcium channel."
Kawasaki et al., Biochemical and Biophysical Research Communications, 385:49-54 (2009). "A minimal regulatory domain in the C terminus of STIM1 binds to and activates ORAI1 CRAC channels."
Koh et al., Developmental Biology, 330:368-376 (2009). "STIM1 regulates store-operated Ca2+ entry in oocytes."
Laize et al., FEBS Letters, 373:269-274 (1995). "Functional expression of the human CHIP28 water channel in a yeast secretory mutant."
Li et al., The Journal of Biological Chemistry, 282(40):29448-29456 (2007). "Mapping the Interacting Domains of STIM1 and Orai1 in Ca2+ Release-activated Ca2+ Channel Activation."
Liou et al., PNAS, 104(22):9301-9306 (2007). "Live-cell imaging reveals sequential oligomerization and local plasma membrane targeting of stromal interaction molecule 1 after Ca2+ store depletion."
Locke et al., Molecular and Cell Biology, 20(18):6686-6694 (2000). "A Homolog of Voltage-Gated Ca2+ Channels Stimulated by Depletion of Secretory Ca2+ in Yeast."
Lorin-Nebel et al., J Physiol, 580(1):67-85 (2007). "CRAC channel activity in *C. elegans* is mediated by Orai1 and STIM1 homologues and is essential for ovulation and fertility."
Luik et al., Nature, 454:538-542 (2008). "Oligomerization of STIM1 couples ER calcium depletion to CRAC channel activation."
Lyfenko et al., J Physiol, 586(20):4815-4824 (2008). "Differential dependence of store-operated and excitation-coupled Ca2+ entry in skeletal muscle on STIM1 and Orai1."
Muik et al., The Journal of Biological Chemistry, 283(12):8014-8022 (2008). "Dynamic Coupling of the Putative Coiled-coil Domain of ORAI1 with STIM1 Mediates ORAI1 Channel Activation."
Muik et al., The Journal of Biological Chemistry, 284(13):8421-8426 (2009). "A Cytosolic Homomerization and a Modulatory Domain within STIM1 C Terminus Determine Coupling to ORAI1 Channels."
Nakamoto et al., The Journal of Biological Chemistry, 266(12):7940-7949 (1991). "Expression of the Yeast PLasma Membrane [H+] ATPase in Secretory Vesicles."
Navarro-Borelly et al., J Physiol, 586(22):5383-5401 (2008). "STIM1-Orai1 interactions and Orai1 conformational changes revealed by live-cell FRET microscopy."
Ong et al., The Journal of Biological Chemistry, 282(16):12176-12185 (2007). "Relocalization of STIM1 for Activation of Store-operated Ca2+ Entry is Determined by the Depletion of Subplasma Membrane Endoplasmic Reticulum Ca2+ Store."
Penna et al., Nature, 456:116-120 (2008). "The CRAC channel consists of tetramer formed by Stim-induced Oral dimerization of Orai dimers."
Prakriya et al., Nature, 443:230-231 (2006). "Orai1 is an essential pore subunit of the CRAC channel."
Putney, Cell Calcium, 42:103-110 (2007). "Recent breakthroughs in the molecular mechanism of capacitative calcium entry (with thoughts on how we got here)."
Ruetz et al., Cell, 77:1071-1081 (1994). "Phosphatidylcholine Translocase: A Physiological Role for the mdr2 Gene."

(56) References Cited

OTHER PUBLICATIONS

Silverman-Gavrila et al., Journal of Cell Science, 115:5013-5025 (2002). "An IP3-activated Ca2+ channel regulates fungal tip growth."
Stathopulos et al., Cell, 135:110-122 (2008). "Structural and Mechanistic Insights into STIM1-Mediated Initiation of Store-Operated Calcium Entry."
Stiber et al., Nature Cell Biology, 10(6):688-697 (2008). "STIM1 signalling controls store-operated calcium entry required for development and contractile function in skeletal muscle."
Strayle et al., The EMBO Journal, 18(17):4733-4743 (1999). "Steady-state free Ca2+ in the yeast endoplasmic reticulum reaches only 10 µM and is mainly controlled by the secretory pathway pump Pmr1."
Terbush et al., The EMBO Journal, 15(23):6483-6494 (1996). "The Exocyst is a multiprotein complex required for exocytosis in *Saccharomyces cerevisiae*."
Varnai et al., J. Biol. Chem., 282:29678-29690 (2007). "Mechanisms of Signal Transduction: Visualization and Manipulation of Plasma Membrane-ENdoplasmic Reticulum Contact Sites Indicates the Presence of Additional Molecular Components within the STIM1-Orai1 Complex."
Vig et al., Current Biology, 16:2073-2079 (2006). "CRACM1 Multimers Form the Ion-Selective Pore of the CRAC Channel."
Wu et al., The Journal of Cell Biology, 174(6):803-813 (2006). "Ca2+ store depletion causes STIM1 to accumulate in ER regions closely associated with the plasma membrane."
Yeromin et al., Nature, 443:226-229 (2006). "Molecular identification of the CRAC channel by altered ion selectivity in a mutant of Orai."
Yuan et al., Nature Cell Biology, 11(3):337-343 (2009). "SOAR and the polybasic STIM1 domains gate and regulate Orai channels."
Zhang et al., The Journal of Biological Chemistry, 283(25):17662-17671 (2008). "Store-dependent and -independent Modes Regulating Ca2+ Release-activated Ca2+ Channel Activity of Human Orai1 and Orai3."
Feghali et al., Frontiers in Bioscience, 2:d12-d26 (1997). "Cytokines in Acute and Chronic Inflammation."
Huang et al., Molecular Biology of the Cell, 19:1717-1726 (2008). "Mammalian Septins are Required for Phagosome Formation."
Ishikawa et al., J. Immunol., 170:4441-4449 (2003). "A Pyrazole Derivative, YM-58483, Potently Inhibits Store-Operated Sustained Ca2+ Influx and IL-2 Production in T Lymphocytes."
Kloor et al., Biochimica et Biophysica Acta, 1579:219-224 (2002). "Identification and characterization of UEV3, a human cDNA with similarities to inactive E2 ubiquitin-conjugating enzymes."

Koonpaew et al., JEM, 203(1):119-129 (2006). "LAT-mediated signaling in CD4+CD25+ regulatory T cell development."
Mauri et al., Immunol. Res., 15(2):126-140 Abstract (1996). "Involvement of CD80 in the generation of CD4+ cytotoxic T cells."
Ohga et al., International Immunopharmacology, 8:1787-1792 (2008). "Characterization of YM-58483/BTP2, a novel store-operated Ca2+ entry blocker, on T cell-mediated immune responses in vivo."
Oh-Hora et al., Nature Immunology, 9(4):432-443 (2008). "Dual functions for the endoplasmic reticulum calcium sensors STIM1 and STIM2 in T cell activation and tolerance."
Oh-Hora et al., FASEB Summer Research Conferences, retrieved from the internet: https://secure.faseb.org/faseb/meetings/summrconf/programs/11643.pdf, Jun. 23, 2007.
Peterson et al., Clin Genet, 77:511-524 (2010). "Conquering the complex world of human septins: implications for health and disease."
Picard et al., N Engl J Med, 360(19):1971-1980 Author Manuscript (2009). "STIM1 Mutation Associated with a Syndrome of Immunodeficiency and Autoimmunity."
Ranger et al., Immunity, 9:627-635 (1998). "Inhibitory Function of Two NFAT Family Members in Lymphoid Homeostasis and Th2 Development."
Soboloff et al., Journal of Biological Chemistry, 281(30):20661-20665 (2006). "Orai1 and STIM Reconstitute Store-operated Calcium Channel Function."
Soboloff et al., Current Biology, 16:1465-1470 (2006). "STIM is an Inhibitor of STIM1-Mediated Store-Operated Ca2+ Entry."
Swanson et al., Proc. Natl. Acad. Sci., 89:3741-3745 (1992). "Cyclosporin-mediated inhibition of bovine calcineurin by cyclophilins A and B."
Trevillyan et al., The Journal of Biological Chemistry, 276(51):48118-48126 (2001). "Potent Inhibition of NFAT Activation and T Cell Cytokine Production by Novel Low Molecular Weight Pyrazole Compounds."
Wittmann et al., Journal of Leukocyte Biology, 80:75-86 (2006). "Critical involvement of IL-12 in IFN-y induction by calcineurin antagonists in activated human lymphocytes."
Wulff et al., PNAS, 97(14):8151-8156 (2000). "Design of a potent and selective inhibitor of the intermediate-conductance Ca2+-activated K+ channel, IKCa1: A potential immunosuppressant."
Eck et al., Goodman & Gilman's The Pharmacological Basis of Therapeutics, McGraw-Hill, New York, pp. 77-101, 1996.

\* cited by examiner

| | | | | | | | | | | | | | | | | | | | | | | | | |
|---|---|---|---|---|---|---|---|---|---|---|---|---|---|---|---|---|---|---|---|---|---|---|---|---|
| L | K | A | S | S | R | T | S | A | L | L | S | G | F | A | M | V | A | M | V | E | V | Q | L | D | A | D | Orai1 |
| | | | | 91 | | | | | | | 101 | | | | | | | | 111 | | | | | | | | |

| Sequence | Species | Accession |
|---|---|---|
| L K A S S R T S A L L S G F A M V A M V E V Q L D A D | H. sapiens | NP_116179 (SEQ ID NO: 36) |
| L K A S S R T S A L L S G F A M V A M V E V Q L D T D | M. musculus | NP_780632 (SEQ ID NO: 37) |
| L K A S S R T S A L L S G F A M V A M V E V Q L D T D | R. norvegicus | XP_222178 (SEQ ID NO: 38) |
| L K A S S R T S A L L S G F A M V A M V E V Q L D A D | B. taurus | XP_595862 (SEQ ID NO: 39) |
| L K A S S R T S A L L A G F A M V A M V E V Q L D A D | C. familiaris | XP_543386 (SEQ ID NO: 40) |
| L K A S S R T S A L L S G F A M V C L V E L Q Y D Q S | C. elegans | NP_497231 (SEQ ID NO: 41) |
| L K A S S R T S A L L S G F A M V C A M V E V Q L D A E | G. gallus | NP_001025829 (SEQ ID NO: 42) |
| L K A S S R T S A L L S G F A M V A M V E V Q L D N T | T. nigroviridis | CAF99270 (SEQ ID NO: 43) |
| L K A S S R T S A L L S G F A M V A M V E V Q L D T N | D. rerio | NP_991163 (SEQ ID NO: 44) |
| L K A S S R T S A L L S G F A M V A M V E V Q L E A D | X. tropicalis | ENSXETESTP00000016641 (SEQ ID NO: 45) |
| L K A S S K T S A L L A G F A M V A M V E V Q L D H D | D. melanogaster | NP_611273 (SEQ ID NO: 46) |
| L K A S S R T S A L L S G F A M V A M V E V Q L S A T | S. purpuratus | XP_780791 (SEQ ID NO: 47) |
| L K A S S R T S A L L S G F A M V A M V E V Q L E T Q | Orai2 H. sapiens | NP_116220 (SEQ ID NO: 48) |
| L K A S S R T S A L L S G F A M V A M V E V Q L E T D | Orai3 H. sapiens | NP_689501 (SEQ ID NO: 49) |

*FIG. 3a*

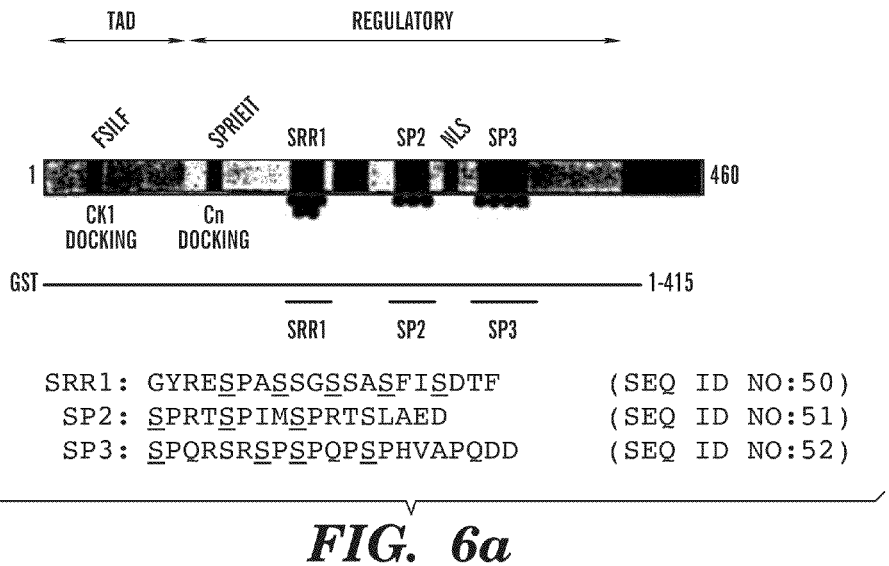
FIG. 6a
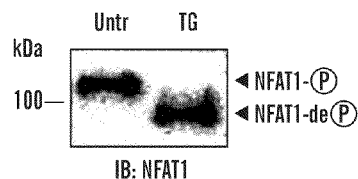
FIG. 6b
| | # WELLS |
|---|---|
| TOTAL SCREENED (EXCLUDING 293 INTERNAL CONTROLS) | 21,884 |
| UNTESTED FOR TECHNICAL REASONS | 813 |
| SCORED AS NEGATIVE | 19,844 |
| SCORED VISUALLY AS DEAD, OR HITS IN VIABILITY/SHAPE SCREENS | 489 |
| SCORED AS POSITVE | 738 |
| MISANNOTATED | 39 |
| OFF-TARGETS > 10 | 37 |
| TOTAL PUTATIVE POSITIVES | 662 (3%) |
| PERCENT POSITIVE UPON RETESTING | 272/326 (83%) |
FIG. 6c

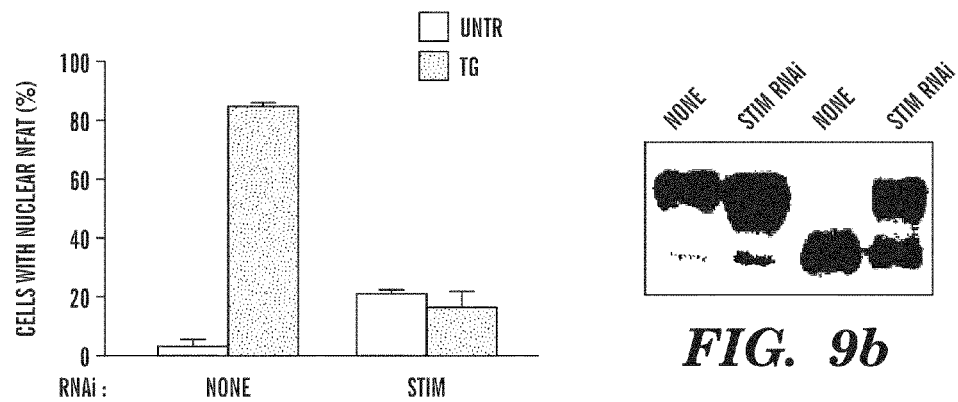
FIG. 9a
FIG. 9b
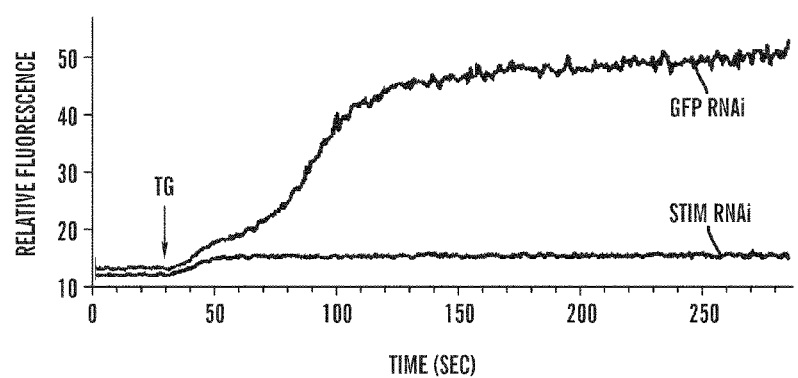
FIG. 9c

> ORAI1 NM_032790 (SEQ ID NO: 1)
AGCGGCGCCGCGGCCTTGCGTGCTGGGGCAGCGGGCACTTCTTCGACCTCGTCTCCTCGTCCTGTGCGGCCGGCCCGGCGGGTGAGGCGGCCCGGCGTAGGGGCGGCAGTCGGCGGCTGCTCCGGCGGAGGTGCCTCGCGGCG
CCCGGGCCGGCCTCCGCGCCTCGGCGGCGTCCTCCATGCATCCGGAGCCCCGGCCCGCAGCCCCAGCCGAGCTCCCCGAGCTTCCCCAAGCGGCGGCAGCCACCACCAGCGCGCTCCGGAGCCGCGCCGCCAGCGGGGA
CGGGGAGCCCCGCCCCGGGGCCCACCGCCCGTCCCCCGCCTACCCGGACTGACTCACCTGGCCATCGCCCGTGATCGGCCAGAGTTACTCCAGTGCATGGGATGAGCCTCAACGAGCACTCCATCAGGCGCCTCGTCCTGGGCAAGCTCTACTTGAGCC
GCGCCAAGCTTAAAGCCTCCAGCCGGACCTCGCTGCTCTCCGGCTTCGCCATGGTGGCAATGGTGGAGGTGCAGCTGGACCACGACGTTGACCACGTGACCGCTGACCACGACTACCCACCGGGGCTGCTCATCCTCAGTGCCTCAGTGCCTGACCACAGTG
CTGGTGGCTGCTGTGCACCTGTTTGCGCTCATGATCAGCACCTGCATCCTGCCCAACATCGAGGCCGTGAGCAACGTGCACAATCTCAACTCGGTCAAGGAGTCCCCCATGACGGCCATCACCCGCACCATCGAGCTGGCCTG
GGCCTTCTCCACCGTCATCGGCACGCTGCTCTTCCTAGCTGAGGTGGTGCTCCTGTGCTGGGTCAAGTTCTTGCCCCTCAAGAAGCAGCCAGGCCAGCCCCGCCCCACCAGCAAGCCCCCCGCCAGTGGCGCAGCAGCCA
ACGTCAGCACCAGCGGCATCACCCCGGGCCAGGCAGCTGCCATCGCCTCAACCACCATCATGGTGCCCTTCGGCCTGTTTATCGTCTTCGCCCTCTGACTTTATCGCCCCAGGAAGCCCCTCACTGGTTAGCCATAAGACTGACCGACAG
TTCCAGGAGCTCAACGAGCTGGCGGAGTTTGCCCGCCTGTACAGGACCAGCTGGACCACACAGAGGGGACCACCCCCTGACGCCCCGGCAGCCACTATGCCTAGGCCCACTGTGGTCTGGGCCCTTCCAGTGCTTTGCCTTACGC
CCTTCCCCTTGACCTTGTCCTGCCCCAGCTCACGGACAGCCTGCCGCAGGGGCTGGGCTTCAGCAGGGGCAGAGCATGGAGGGAAGAGATTTTATAAGAGAAATTTCTGCCACTTTGAAACTGTCCTCAAGAGAAT
AAGCATTTCCTGTTCTTCCAGCTCCAGTCCACTCTGCCAGTCCAGTCCAGGTTCCACTGGGGAGGCGGTGGGGGGCCACAAGTGGGGCCACACACTCGGTCTGTCCCCTCTCCCCCTGCACCAGTGCCAGTGCCACCTGGTGCCAGTGCCTCCTCCTCCTGTCCTGTCCGT
CTCAACCTCCCCTCCCCGTCCAGCATTGAGTGACATGTGTGTGACACATAAATATACTACTGTCAAAGTGCACACATCGGTCTGTCCCCTCTCCCCCTGCACCAGTGCCAGTGCCTCCTCCTCCTGTCCTGTCCGT
CTCAACCTCCCCTCCCCGTCCAGCATTGAGTGACATGTGTGTGACACATAAATATACTACTGTCAAAGAAAAAAAAAAAAAAAAAAAAAA

FIG. 11a

>ORAI2_BC069270 (SEQ ID NO: 2)
GGAGAGCCTGAGTTGGCATTCGTATAAATGACCTGCCTGCCTCCCACCATGAGTGCTGCTGAGCCTTAACGTGCCTATCGACCCCTGCTCCTGCCTGCCTGAGCCAGGCCATAAGGCCATGATTGATTACCGGGACTGGGTCCG
CCGCAGCTACCTGGAACTGGCAGTTCACCTCTAACCACCACAGCCCCTGTCGTCGGTACAGGCCCCTGCTACCTGGAAGCTCTACCTGACGGGCCAAGCTGAAGGCCTCCAGCAGGACCTCCCGCCTCCTCTCCGGCTTTGCCATGGTGGCCA
TGGTGGAGGTGCAGGTGGAGACGGCAGTAGCCGGCGGCCCTGCTGATTGCCTTCAGCGCCTGTGGTTGGCCGTGCACCTGTTCGCCTGCCACCTGTTCCTCCATCAGCACCTGCTCCTGCCGAGGTGGTCTGCTCTGCTGAT
GTGACAACATCCACAAACTGAACTCCATCAGCGAGTCCCCGGCATGAGCGCATCAGCCTGTCTCCACCCTACATCCAGCTGCCTGCCTCGGGGCTTCTCCTGGCATCATCATGTGCCCGTGGGCCTCATCTTCGTGTCTTCACCATCCACT
CAAGTTCCTCCTCCCGTGGATGCCCGCCAGCCTGGCCTCACACCTGTCACACGGCGGCCTGGCCAGGCCGCCCTGGGTGTCCACCATCATCATGTGCCCCTGGGCCCTCATCTTCGTGTCTTCACCATCCACT
TCTACCGCTCCTGGTGCGGCCACAAACGAGCGCCACACCGCGAGATCGAGGAGTCCACAAGTCCAAGGTCCAGCTGGACGGCATGAGCCAGCCTCAGGTCTTGTGAGGGCCGAGGGCTGGAGCGG
CCCTGTGCCCGGAGTCCGAGACGGGGGATTTGTCAGATGCAGACATTTTCAAGCTGCCGGGTAGTTCAAGAGACTGGATGACTTCCTGAGATAGAACCGTT
TGGTTCAATGAGGGACTGCTGTTGCTAAGACCGTTGGGGCAAAGCCAGCTGTTCCTTGGCCTCGGGTTCCTCGGGGTTCCCGGGGGCGTGAAGAGGCTCCAGCGGACCTGCCCATCAGTCCTGGCCAGGAGGGGCT
CCAAGCAGCAGCCACCAGCGGTCCGGGGAGTCCAGAGCCCGGCATGCGTGCCAGCGAGGATTGCCCAGAGACCCGTGTGGACTTCATGGGTGCTGAGTGGC
CCGTGTGACAGTGATGATGACAGAAGGCTTCGGCGTTTGAGTGGTGCAGTGCACGCAGGGCTGGTCCTGCCGGGTAGCTGGTGGCCTTCAGGGAAGACAGGAGCCAGGACACACGTCA
GCCCACCAGGTGTGGGGGTCCTGCAAAGTACGGCTAGGCTCAAATTCTCTTTTCCCAGCGTCTCCCTTGGCTGTGAGGACGGCCTGGAGCCAGGGCCGGCCGGCCCCAGGCCAAATGAGTGCCCTCCTTGTTATGACACCAAGTGACTACAAGGAGCCAAGACCCCTCCAGGCCTCTCAGCCG
TTATTTGAGGCTGTGGGGGTCCTGCAAAGTACGGCTAGGCTCAAATTCTCTTTTCCCAGCGTCTCCCTTGGCTGTGAGGACGGCCTGGAGCCAGGGCCGGCCGGCCCCAGGCCAAATGAGTGCCCTCCTTGTTATGACACCAAGTGACTACAAGGAGCCAAGACCCCTCCAGGCCTCTCAGCCG
TCGGCCACAGAATGGCCTAAGGCTGACTCAGCCGCTCTGGCCTGGGGCCTGGCTGTGGGGCCAGGAGCCGGCCCCAGGCCAAATGAGTGCCCTCCTTGTTATGACACCAAGTGACTACAAGGAGCCAAGACCCCTCCAGGCCTCTCAGCCG
TCCTGCCTAGGCAAGGTCATTGCCCGGGCCTCATTGCCCGGGCCTGCCTCTGGATAGTGGGGCAGGTTCTGGCCCTTTCCTTGAAGGACATCTGTAGTAGACCCGGACATCCGGCCCACCAGCTCTCCGGCCCGCCACCAGCTGCCCTGAGCTGCTTGT
ACACTGGCTCCACCACCACAGTGACTGCTGCCGTCAGTCGGCAGTTCTCGGCCGTCAGTTGCCTGTCAGTGGAGAGTCAGCACATGCTAACCGTGTAACCTGTAAAATAGTCACTGACTGACTCCAGCACTTGGAGGCCTAGGTG
ACAACCAAACCTTTCCCTCTTCTCCAGCTGTAACCTGGAGAGTCAGCACATGCTAACCGTGTAACCTGTAAAATAGTCACTGACTGACTCCAGCACTTGGAGGCCTAGGTG
GGCGGATCACTTGAGGTCAGGAGTTCGAGACCAGCTGGCCAACATGGTGAAACCTGTCTCTACTAAAAATACAAGAAATTAGCTGGGCGTGGTGGCGGCCGCCTGTAGCCCCCAGCTACTTGGGAGGCTGAGGTGGG
AGAATGGCAATGGCCGTGAACCCGGGAGGCAGAGCTTGCACTGCTGAGCTGAGCTGAGCTGAGCTGAGCCCAGACTTCAATCTCAAAAAAAAAAAAAAAAA

FIG. 11b

>ORAI3 NM_152288.1 (SEQ ID NO: 3)
CGCTCCGGCTCCTGGGGCTCCCCGCAGACGCTGCTTTTCTTGCTCCACTGGGGCGTGCCTCTTCCTGGGCGCCCGCCTGCCTGCATCCTCCGCCCTGTCTGGGAATGGGGCGCGCCCCGGGCTTGGGCCCGGCTGG
GGCCCCCGAGGCGCTTCCGCCCCTGGTGCCGCCTGGTGACCGTCAGTGACGCCCCCAGGATGAAGGGCGGCCAGGGGACCGGGGCCAGGCCCCTGGTTCTGGGCCGACGAACCTGAACCCTGAGCGCCGCCACGTACCGGG
AGTTCGTGCACCGCGGCGTACCCTGACCTCAGCACTCGCTGCGGGGCCAGTGCCGCCCCCTCAGCCTGGCCCTGCAAGCTCAAAGCTTCCAGCCCCACGTCTGCCTTGCTCTCGGGCTTCGCC
ATGTGGCCATGGTGGAGGTGCAGCTGACCATCCACAACTCTGTCCACCAGTCGCCACCAGAGACTGCACCAGTGAGCCTGCCCTGGGGCTTCTCCACTGCCCTGGGCACTTTCTTCCTTGTTGTGAAGTTGTCCTGG
CATTGAAAGCTGTGAGCAACATCACAACTCAACTCTGTCCCACCAGAGACTGCCACCAGTCGCCACCAGAGACTGCACCAGTGAGCCTGCCCTGGGGCTTCTCCACTGCCCTGGGCACTTTCTTCCTTGTTGTGAAGTTGTCCTGG
TTGGTTGGGTCAAGTTTGTGCCCATTGGGCTCTCCTTGGACACACCGACCATCCCGGTGCCCACATCCCCGGTGCCACCAGTGGCTACCTCCCTTAGTCCAGCTTCAGCTTCCCTTCCAGTCCCACCGCTCCTCTCCG
TCTGCAGCACCGTCCCAGGCTGAGCCAGCCTGCCCACCCCGGCAAGCAGCCCATCATCATGTACCCGTGGGGCTCGTGTTTGTGGCCTTT
TGCCCTGATTTCTACCCCTCCTTGGTGGCACACAAGACAGGAACTAGAGGAACTGAATCGCTGCAGGGGAGCTGTGTTAGCCACCCGCTCACTGCAAGCACTGCCT
CCCTCCGGGCTCTTAAGAGGCCCCAGGGGCCTACAGACCTCATCCCCATCCCCTCGCTGAGCCACTTCCAGTGCCCTCAGGACAGTTCTCCGCCCAGGGTCCTCTGGCCTCTGGGCAG
CTCCACATTCCCAGGGATTTTCCCCATCAGTCGTCCTCCCTTGGGTTCGGTTTTGCAACGTACTACTCCGACCTGCTGGCCTCAGTTGAAGGATCATCCAGTAGATAGAGGGAGCAGGAGAGCTTGTGTGGGACTTCAGTGCTG
ACTTTAGCCACCATTTCCATTCCTATACAGGATGTGAAGGTCAGCCAATTGTTGTTTAATTTTTTTTTTTTTGAGACTCGTTTCCCAGGCTGGAGTGCAGTGCGTGATCACAGCTCACTGTAGCCTC
GACCTTCAGGCTCAAAAGATGCTCCCACCACAGCTCTCCCACCACGAGATGTCGTGATCCCTCCCACCACCAGGATGTCTCTGCTGCTGACAGGGGTTGCGTCTGTTCCCAGGCTGTCTCAAACTCCT
GGGCTCAAGTGAACCTCCCGCTCGGCCTTCCAAAGTGCTGGGATTCCTTCTTTCTTTATTTCTGTAGAATCTATTTGGGGAAGAATTGCATTTGGGGAAGAATTCGATGGGTTCCACATTCTTGCTTAGTTGTTGTAGAGGG
ATTTGGGTGTTTCTACCCAAGGCATTGTGTCTAGCTTTTCCTACAATGAACCTATCTTTGGAGGTTAAGCTCCCACCTTCCCCACCTGTGGTGCCACTTGTGCCACTTCGACAAGGGATGGTGCCTGACCACTGCCCTA
GCCCACGCTATGCACCAAACTTGTTCTCCCCGTCCCAGGCCTGGGGTCTTTAGACACTGAGACTGAGACCCTCGCCCAGGCCTCGAGTCCTTAGCAAGGGTTGGGTAAGGAGGTTTTAAGGGAGAAGGTCCAGTCCTTA
GCCCTTGAAATACAAAGCTCTTCTTGACACTGAATTTGGATGCACCTTGTTTCACAGAAATAATAATCGTGTTTTCACAGAAAAAAAAAAAAAAAAAAAAAAAAAAAA

FIG. 11c

> DYRK1A NM_001396 (SEQ ID NO: 4)
GTTATAGTTTGCGCTGACTCTTCCCTCCCCTTCCCCACCCCATCAGGATCATATCAGACTTGAAAGAAGACGATCCATCAGGAGGAGACTTCAGCATGCAAACCTTCATCTGTTCGCTTCCACCGTTCATTTTC
ATTCCATCCTGCTCTGGGCCTCAGATGGCTGGACAGATGCCCCATTCACATCAGTACAGTGCCCCGATCACCCTCGCCAGCCAACACATAAGTGACCAACAGGTTTCTGCCTTATCATATTCTGACCAGATTCAGCAACCTCTAACTAACC
AGGTGATGCCTGATATTGTCATGTTACAGAGGCCGGATGCCCCAAAACCTTCCGTGACCCAGCAACTGCTCCTCTGAGAAAACTTCTGTTGACTTGATCAAAACATACAAGCATATTAATGAGGTTTACTATGCAAAAAAG
AAGCGAAGACACCAACAGGGCCAGGGAGACGATTCTAGTCATAAGAAGGAACGGAAGGTTTACAATGATGGTTATGATGATAACTATGATTATATTGTAAAAAACGGAGAAAAGTGGATGGATCGTTACGAAATTGA
CTCCCTTGATAGGCAAAAGTTCCTTTGGACAGGTTGTAAAGGATGAATGCTGTGGACCAAGAATGGGTTGCCATTAACAAGAACAAGAAGGCTTTTCGTCCTACACACCTCTATGACTTGCTGAGAAACACCAATTTCCGA
TCATGAACAAACATGACACTGAAATGAAATACTACATAGTGCATTTTGAAACGCCACTTCATTTGTTTAGTTTTTGAAAATGCTGTCCTGATCTAAAACCTGAATATCACTGTGATCATTCACTGTACTCTGAAAATATCCTTCTTTGAAACC
GGGTCTCTTTGAACCTAACACGAAGTTGCGCAACAGATGTGCACTACCAGTATATTGCCAACAGAGGATATACCAGTATATTCAGAGTGCTTCCAGAGTGTCTAGTCCTTATGACCTTGCCATTGATATGTGGCCCTCGGGT
AATCAAGATAGTTGACTTTGGCAGTTCTTGCAGTTGGGGCAGAGGATATACCAGTATATTGCCAATGAGTGCCCAATGAGTAGATAAAATAGTGGAAGTTCTGGGTATTCCACCTGCTCTATATTCTTGACCAAGCACCAAAAGCAAGAAAGTTCTTT
GTATTTTGGTTGAAATGCACACTGGAGAACCTCTGTTCAGTGGTGCAGAACCTCGTGCCAATGAGTGCCCAATGAGTAGATAAAATAGTGGAAGTTCTGGGTATTCCACCTGCTCTATATTCTTGACCAAGCACCAAAAGCAAGAAAGTTCTTT
GAGAAGTTGCCAGATGCGTCCAGATGCCCACTTGGAACTAAAGAACACCGGGAGTGACTAAAACGGGAGTGACTAAAACGTTCTCATAAACATTCTTGAGTGGAAACAGGAGGACCTGGTGGGCGACGTGCTGGGGAGTC
AGGTCATACGGTCGCTGACTACTTGAAGTTCAAAGACCTCATTTTGAAGTTCAAAGACCTCATTTAAGGATGCTTGATTATGACCCCAAAACTCAACCCTTATTATTGCTCGCAGACAAGCAACAGTGGGAGCCCGGTCGATCCGACGCGACTGAC
CAAGTAATAGTGTATCTACAAGCCCGCCATGAGCCCCAGCAGTCTCGGCACCAGCAGTCTTCGGGACACAGCAGTCAGGTTGGCTCATCGGGACAAGCAACAGTGGGAGCCCGGTCGATCCGACGCGACTGAC
CGGCACAGTGCTGGGCCACTTCAAGACCTTTCACGAGTTTCAAGATTCAGACGACTTCCTGCAGCAATTCCTGCCTCGCTCTCTCTTGGTTGGTCAGCAATTCCTGCCTCGCTCTCTCTTGGTTGGTCCAGCGGCTCAGCAGGTCACTGTTGAAACTCA
TCCTGTTCAAGAAACAACCTTTCATGTAGCCCAACGATTCATTCATCACAAGAATTGCATTCACCATCACCATGGTAACAGTTCCCATCAACCACCATCCTTGGACAAATCTTTCCTGACATCTCTACTGGTAACCGACCA
GGCCAAGGGTCTACAATTCTCCAACGAATAGCTCCCTACCCAAGATTCTATGGAGGTTGGCCACAGTCCCCACAGATTCTATGGACAGAGTCATGGACAGAATGAGCTATGACAGATGAGCTATGACATCCAAACAACAAAT
GGCAATCAGGCCTACCAGAATGCCCAGTGGCTGCTAATACCTTGGACTTTGGACTTGGACAGAATGAGCTATGACAGATGAGCTATGACATCCAAACAACAAAT
TTCTGCTAATACAGGCCTCTGCACATTACGATGACTGAAGACACCATCTGAACAATGAGGCAAGGGCTGATAGAGAAGAGTCCCATGTTGTGCAACGAGTCCTGTAGCTACGTACATCCAAACAACAACTGAAACT
TGAGTTTGTCTTCTTGTGTCTTTTTATAGAAGTGGTGGTTTTTTTCCAAAAACAAAGTCAAAGCTGCTTGAATCAGGAGGAGATTAACACACTGCTCCCCCATTTAACTTGCTCCCACATCCCAGTCACAGTGCCCACATCCCAGTCACAGTGCCCACATCCCAGTCACAGTGGGTGTTTTTTTTCTTTTGTCTTGGGTTTTTTCTTTTGTTTGAAAAG
ATTGCAAGGGACATTGAAGTGTTAAAGACTGTTTAAAACAGCCCATCTTCAACCCATCTTCATGATAGCTCAGAGTATCCTCTTTTTGCTCCCCATTTAACTTGCTGCCACATCCCAGTCACAGTGGGTGTTTTTTTTCTTTTGTCTTTCTTCATTC
AGCAAAAGTTAATATTCAGATGTGGTCTTGGTCATTTGCCAACTATGTTCCCAACTAATTTAAAGTAAAGGCACTGCACATAATTTTAAAGTAAAAGGCCCCATGAGGGTGTTTTTTTCTTTTGTCTTGGGGTTTTGTTTTGTCCCCCCATCCCCTTTTTT
TTTGTTTGTTGTTGTGGGTGGGTGGGTGGAGGTGCAGGGAAATTTGGTTTTTAAGTCCTCTAAAACAACTGGCCACGGAAATGCAGTAGTGTAAGGAAGAGGAGGGACCTTGAAGAGGGGACCTTGAAGAGGGGACCTTGTAAGGAAGAGGAGGGACCTTCACAAAACACCACCATTCTCAGCTGTAT

*FIG. 11d*

```
GAAAGGGACGGTTGTGTGTGAAGTTTGTCAGGCACACAGTAAGCATGCTGAGTGCGGGGATCAGAACTCTCCTATCTGAACCTACTGAGGAGCAAAGCAGCAAATTACAATGGATCCTGTGCTCTCCCGTTGCAGAGGCCAC
AGGAAGATAGAGATGGAACGTGACTGGTCTCCTAACCAAGGTGCACTGAGAACGGGTCGGTCTGCCAGTCGCTTGGGAGGTCTGAGTGGTGGTCTCTTTGGGATAACCTTTGCCTTATGGATTTGGACTCGAA
ATTAGAAGAGCCTACCATTTCAGATGCAATCACTTTGGACATGCTTTTGCAGACAGTCCTTAATGCTGAAACACAGAGAATTCAAGAGGCCTTTCTTCTTTTAAAAATAGACTTTGTGACCACTAATTGTAAG
GTATTGCAAGGTCACTTTGCGTGTGTCATAAAGTTGACTTCCTTATTGGTTCAAGGTCACAGAAGTAGTTGGTTTGCTTTGATGGAAATAGCTACAGCTGTGTCCTTCCTGCTTTTTCTTTTTGCTTTTTCTG
GCAACGTGGTATCTCCCACCATTTCTTCTGCACAAAGATGTCTCTTCGTTCATCCTGAACATTTTAAAAAATGCAGAATTTATGTGACTGCTTTTTGCCTCACAATTATGCTGAATTTACAAAAATTATTCTTT
TTTGATAATTTATTGTACCAAAGCTGTTTTATAGCACATAGAGTCTGTAACCAATCTGCTACCAATAATTAGCAGTTCTGCACTTTGACACAAGTTCTGCCACTTTTAAATGTCAGTGAAAATATGGCTGTACTATTGCT
TAAACAAAACTGGAACTGTTGTTGAATCCATAGCCAATCTGTACTGAACAATTACAGCAATCTAATTCAAGATTGACATCTAATTCAAGTGTGTTCAGGCTTCTGAAGGTAAAG
GGACACTGGATCCACAGAGCTATGGAACCAGCAGTTGCTCTTGTATTCCTGATTAATCCTGTAAACTTGTAAATGACCACCTTGATTGCACCAACAGGTCCAGAGTATGAGTGCAAGCAAAGCAGAACTCTCATGCGT
GACCTGAGCAGACAGGCTGGTATTTAACAGTGCCTCGTGTTAACAGCTCGGCAGTTGCTAAATTTGTGTTCCCATTTTAAATTGACCAATTTGGGGTGACACTTTGAGCGGT
TGAATTGGGAGAATGAAGATAAGTAATTTACCTGTCCAGGATCAAAAAGAAAGAAGCTAAATCTCGTCCCGATAACCTGTTTAAGATGACTCAGCAGAACACCGCCTTCATTCTATTGGTCAATTCC
ATGTGGCTGACTAGGTCAATTTTTTTCTGAACAAAAGCAGTTTTATATGTAAACAGTGAGAAAGAAGCTAAACACTATGTAAATGCAAACTTGGAAATACTCGTTTTTATAAACTACAAAAACTTTTT
GTTGCTTATCAGGAAATCCATATTTATTTGTAATTAACTGTCAAGCCTGTGGATGCATTTTTTTTTTTTCTGCTGTGTTGCCACATCTTAGCAAGCACCAAAAAAACTAAAGCAGTTTTTAACCGATATTACCTAAAGAAAATC
GTAGTTACTGCTGTTTAGGAATATAGGTTAAGATAATATGGGTCAGGTCATTTTTTTTTTTTTCTGCTGCGTTGCCATTGTACAGGACTTCTGTGCATTGTACACAGTTGGTTGCATTGTAAATCCTGTCTTCAGATTGTA
ATAAAATCCAATGCTTCTGCATACTGTGTTATGTTACAGTCCAGTTTGTGTGCTTTACCACACAGTTTGGTTACGAGGACTTCTGTGCATTGTACAGGACTTCTGTGCATTGTAAATCCTGTCTTCAGATTGTA
AGATCAGTCCGGACTTGCTGTGTATATTGTAACGTTAAAAATGAAAAAAGAACCCCCTTTGTATTATAGTCATGCGGTCTATGTGATGAATAATTGTCCTCAGAACTCTTTACTATGCTTTTTAAAAA
TTAATTTAAGAAAAATGTAAACATAGTAAAAAATCTTCCTATGCAATTAAACTTCGTCCAGGTCGGTAGGTATACTATGATCAAAGTTGAGTTAAATGTCTAAAAGCAAACTATTTGAGATACATTTGACATAGGCATCAGCAA
TCTCTCGAAAGTAAAAATTGGAGGTTTAACAGA
```

*FIG. 11d (cont'd.)*

> DYRK1B NM_004714 (SEQ ID NO: 5)
GGGATGGGGCGGGAGTCCAGGGCGTGGGGGGCCGGTTTGTTGTGGTCGGCCATTTTGCTGGTTGCATTACTGGGTAATGGGGCCGGTTGCCGCGTCCGCCGATACCCTCAGCCAGTGGGCAGTCTGAGCTCGGG
CTCCCCGAGCCAGTTTGAGTCCCCCTTGCCCGCTCCTTCTCAGGTCTTCAGGTCTCAGCCGCTGGCAGCCGAGGTGCAGGATGCAAGAAGGCGCCCCCGCTCCTCCCGCCGGGCTCCCGCTCCGCCCCTTCCCGCCGGGCCCCTCGAGCCCACC
ATGGCCGTCCCACCGGGCCATGGTCCCTTCCTGGCTTCCCAGGGCCCAGTGTATTGCCTGATGTGCGGCTACTGCGAGGCTGCCCTTCCGGATGCAACCTCAGCCGCCCTGCCTAA
GCTCTGTGGACCTCATCAAGACCTACAAGCACATCAATGAGGTATACTATGCGAAGAAGAAGCGGCGGCTCGATCCAGAGGATTCGAGCTGGTGAAAGCCTATGATCATCAGACCCAGGAGCTTGTGGCCATCAAG
ACGACAACCATGACTGACTACAGCTGCCAGTGGCAGCCCTGGCTGGGCCTACGAACGCGCTCAGTTCCAGGTCGTGAAAGCCTATGATCATCAGACGCCACGGAGCTTCATGTTCCGGAACCACCTGTG
ATCCTCAAGAACAAACAAAAAGGCTTTCCTGAACCAGGCCCAGATTGAGCTGCTGCGCTGCTGAGCTGATGAACCAGCATGACACGGAGTACTATATAGTACACCTGAAGCGGCCACTTCATGTTCCGGAACCACCTGTG
CCTGGTATTTGAGCTGCTGCCTACAACCTGTACGACACCCAAGGCGCAGCGCGCCCATCCAAGATTGTGTTGCCAGAGATGTACCAGTATATCCAGAGCCGCTTCTACCGC
GCATCATTCACTGCGACCTCAAGCCCGAAAACATCTTGCTGTGCAACCCAAGATTGTGCCCGATCCTGGGGCTCCATCTTTGGTGAGATGCACATGACATGTGGTCCAATGAGGTCGACCAGATGAACCGCATTGTGGA
GGTGTGGCATCCCACCGGCCGCCATGCTGGACAGCGGCCTGAAGCTGCTGGACAGCGCCCAAGCTACTTTTGAACGGCTCGTCAGCCTGTCCTCGGGGTGCCTCGAAGACCAGATGGACAGCCACCGCGACCCCTCCTTCCAGGACCTGGTGCTGCGAGTATGAGCCCGCCCCCATC
GGCCTGCAGGAGGTGCTGGGCCTCTGCAGCACGCGTCTTCCGCCCACGGGCCACGGCCCCGGCCAGGAGGCCACCAACAACCGGATGTGGGGCCCCGTGGCCCCCAGTACCCCCACGACTGAACAGCCCCCAGTTCCCACCTCCAGCCGTGC
AGCCCCCTGGGGGCTCGGGCTCTGAGCCTCCAGTGGCTCCTCCAGTGACACTGGCCTCTCCGCTTCCCACCCAGTGACAACCGATATTGGGCCCCGATAACAGCCCCCAGTTCCCACCTCCAGCCGTGC
GGCCCTGGGAGCTGATGGGGGTGATGCCCCACAGACAGCACATCAAGCCCCTTGGTGGGCCGCCCCTGGAGACGGCCCCAGCCGGACCCCGGCTCGATGCGCTGCGCGACTGGGAGTTGATGACTGGAGGTGTCCCCGACTCCCCGCCTCCTGA
CGGAGCTGATGATGGACCTGAGCCCCTGGTGGGCGCCCTGCTGACTGGTATCACCCCAGGATGACAGAGCACAGCAGCCAGCCATACCCCCTGAGACCATACCCCTCGGGGGCCCTGCTCCATC
TGACCCTGCCACTCTGGGCTCCTTGACTGACTGCGAATTGCTGCTCCAGCCAGGCGTGAGGCGTGGTGAGGCCTGCACTGAGCTCAACAAGAGGGGTTTGCCGCTCCCCTCCCCACTAAGGACTGGACCCTTGGCCCTC
TCATCTCTCCTCAGAAATTGCTGCTCCAGCCAGCTGCCTACCCGAGGGTGAGGGAAGACACCCCCCCACCCAGGACCCCACCCAGGACAACACAGTTGGTGGTCCGGTGAGCAGGTAGGGCGGCAGGTAGGGGGAGATGCCTTGCTCCTCCTCCTCGTGTACCCCAGTA
AAGAGCTTTCTCACAAAAAAA

> DYRK2 NM_003583 (SEQ ID NO: 6)

GGACTGTGTGTGTTGGCTGTAGCAGACGCGAGGCGGCGAGGGCGGCGAGGGCGGCGGGGCGGGGACCCGCGAGGCTAGCAGCAGGACCGGCGGCGACGGCAGCCCTGAAATG
CATTTTCCTCTCCAGCCATGTAACGAGGAAACCTTCGGCCGCGCCCACCGATTGCCGCAGTAAGCACACAATGATGATCACCTGCATGTCGCAGCCACCGCGTCACGGACAGATCCAGGT
TCAACAGTTCTTTGAGGATAACAGTAACAAGCGGACAGTGCTCACGACAGTGCTCAGAACAGTGGGCTACAACAGTGGGCAAAACGGGCCTGCCAGAGCCTGGACAGCGGCAGGGAGCT
CCACCTCTAAAGTCCATGGAAGCATGGGCAGGGAAGTGAAAGCCACCCATGACACCACCTGCAGGATCAATGTGACCAGGATCATATGTGCAGGTCCCCACGATCACGTGCTTACAGTGAGGTCCTCAAGGTCATTGGGAA
TTGGGTCTAAATGCTAAGAAGCGCCCAGGGCATGACAGTGGGCCTATGATGATGCACCAGGATCATATGTGAGAGCGCCTCCACCGGCAAGCAGCGGAGAGTCCGAATCCTGGACACCTGCGAAGCAGG
GGGGAGCTTTGGGCAGGTGGTCAAGGCCTACGATCACAAAGTCCACCACTGGCCCTAAAGATGTGCCGGAATGACAGAGAGCGCTTCCACCGGCAAGCAGCGGAGAGTCCGAATCCTGGACACCTGCGAAGCAGG
ACAAGGATAACACAATGAATGTCATCCATATGCTGGAGAATTTCACCTTCCGCAGCAAATTTGACATTTCCGCAGAATTTCACCTTCCGCACAAAAACAGAATAATTCACTGTGACCTTAAGCCCAGCATGAACCTCTATGAGCTCTATGAGCTCTATAGAAGCGGTATTAAGTAATTGATTTTGG
TTGGTTCGCAAGTTTTGCCCACTCCAGTCTCGCAGTTGCTTTGATGCTTTGATGCTTTGATGCTTTAAGCCCAGAACATTTTGTTAAGCACCAGGTAGAAGCGGTATTAAGTAATTGATTTTGG
CTCCAGTTGTTACGAGCATCAGCGTGCTGTCTACACGTACATCAGCGTGCTGTCCAGTGATCCTTGGGCTGCATTGATATGTGAGCCTGGCTGCATTTAGCCAGAGCTCCTGA
CGGGTTACCCCCTCTTTGCCTGGGAGAATGAAGGGACCAGCTTGGCCTGTATGATTGATTGAACTGTTGGGCATGCCCTCACAGAAACTGCTGATGCATCCAAAGAGCGCTGAAGGGGTCTGAAGGGTGTGATCATCCCCTTTTCTTTGA
TACTGCACTCGCTCCACCACTCGTTTAGAGTGGGATCCTGCAGTGCGCATGACCCAGGCCTTTGCGCGAACTGGAGCCTTTGCGCGAACTCAGGAGGGGAAACTCAGGGGTGGGGAACGGCGGCGGAAGCGCTCAGTGAACGCCGCTCCACCGGGGAGAAGCGTCAGTGAAAACGTCAGTGAAAACGATAACTGAGAGCA
CTTCTTAAAACAGTGCTTAGATCATCTTTAGAGTGCATCTATATCCAAGTTACCTCCACCTTCTAGCGTGGGTTGAAAGATAGCTAGCACGCTGTTTTCTGTAAAGCTGGTTGAAAGATAGCAGCAGAGACTAATTTCAGCACTCAATTGTATCTTTCAGCACTCATTAATTAAGCTGTTAATTAAGCTGTTTAAGTGGGGCGCTCTAGGCTGCAGGCCGTAAAAGGGACAGCGCAAAAACAGCGGCAAAAAACATTGTTCCTGCCACAGGCACCGCATCAATAACATCAGTGGCAGGCC
AAAGTTGTTCATTTGTTTTATAAAAATACATGAGGACAATGCTGTCAAAGAATGCATTACAGATTGTCAAAGACATTGTCATGTGTTGTCATGTGTTAGCGCTTTTGTGTTCTAAAAGTCAGACATGAACATCAGTCAGACATGAACATCAGTCAGACATGCAGCCC
ACTGATTACTTCATGACTGCCTCTGCCTGCCTGTTTCATTTCATAAATTACATTGCTGCAAAGACATTGCTGCAAAGACATTGCCAAGCACCATTGCAAAACGTCTTAAAGAACTGTTAACGAGCCCTCCCCATGCTCCAGGTGCTCCAGGTGCACTCTTCAGTGTCAAACAAATAC
CAGGTGTAGCATGCTCTGCTTCCGTTTTCATAAATTCATAATACTGGGTGTTGGGAGGAGGGAGGAGAGGAGAGAGAGAGAGAGTCAGAATCAAAAGTGTCAGAATCAAAGTGACATTCTAAGAAATCAAATTCAAATTCAAATTCAAATTCAAATTCAAATTCAAATTCAAATTCATAGTATGATCATCAGTATGATCATCAGTATGATCGTCAGCTGTTTT
AAAATAAGATCCCCAAGTTTAAACTGCCCAGTTAGCATTCTGACATTCTAAAATTAGAATTGAAATTGGAATTGGATAAATGGATAAATGGAAACGTGTGTGTTTCCTCGTTTGTTCCTCGTTTCTCGTTTCAAAATTTCAGCATCGATCCATACTGATCCATACCACACGCTCTGTCTGCTTGCATTAGTTTG
GTAAAGAAGCCTCATATTACAGATTGCTTTGCCACCTAAATTTAGAATTGTATTCCATGACGTCTTCCCCCTTTTCTGCTTTCTGCTTTTCATATTCCATGATCAACCATTGTCAACCATTGTCAACCATTGTTCATATTCATATTGTTCATATTGTTTCATATTTCATATTCCAATTAAAAAAGAACAGCCTACTTAAGGTGGGATTTCATAGTTCCAA
TCTTTTCCTTCAGCTGTGTATCCCAGACTGTTAATACAGAAAAGAGAGACATTTCAGCTGTGATTAACACGACGACCATTGTCAACTAGCAAATCCTCGGACCAACAGAAGTCACTTGGCTG
AGAAGATTTAGCAGATTAGAGTGAGTTGCACACTTTGCAGGTGCCACTGACCCTAATTCTAAAAGGGGATTTCTAATAGAAATCCTCGGACCAACAGAAGTCACTTGGCTG
TTCAGTAAGGCCAATGTCTTTTAAGACACGTTTAGAGGAGGAAAGTTCACCGGAGGAAAGTTCACCTCAAGTTAAATGGTTGACTATTCTTCGTATCATTAGAAGAACCCCAGAGATAGCATTCCTCTATTTTTACTTTCTTTTGGATTG
CACTGATTCGTTTCTGGAATGACACTTTATCCGCAAAGTAACTGCCAAAGTAACTGACAGTTTGGTAAAGAATAATTATTTCACAGTGAAAATTCAGTATATTTATCACTAATGTATGAGCAATGATC
TATATCAATTTCAAGGCACGTGAAAAAATTTTTTAGTATGTGCAAATTAATATAGAAGAATTCTGCCTGTTCTGCCTGTTTGGACAATAGGTTTTGGGTAGTACAGATTAGGATAGAATAAGCTTATATATGCACAGAGATTATGTA
TTACCTGTAAATTGATTTACAAGTACTTAAAGCGTGCTCCCCAGTGAGGCCCAAGAAGTTCCGGTTAAGTTCTTTAATAATACCTACAGTTTATCTTAAGAA

> DYRK3 NM_003582 (SEQ ID NO: 7)

ACTTCCCAGCCGGGGCCAGTCGGGGAGTCGGGAGCCGAAAGTGCCTGAGCTGTCTGGTCTCAGAGTACCCGTGGGACCGTCCGCGCCCGGGAGGCAGCCGTCCCGCGGAGGCAGGTGCCGTGGCCGGACCCCCAACTGGCCCT
CTCCCGCCCGGGGTCCCGAGCTGGGCTCGGGCCTCGGGGCCTGGGCCTGGGCCTGGGCGGGGCCCGGGCCTCCCAGCAGCCGGAGGTTGGGGGATGGTGTCTATGACACCTTCATGATGA
TAGATGAAACCAAATGTCCCCCCTGTTCAAATGTACTTCTGCAATCCTTCTGAACCACCTCCACCCAGAAGACTAAATATGACCACTGGAGTCATACTCAGACTCATATACTTTTTGGATGGAGGTGAGATGAAG
GTAGAACAGCCTGTTTCAAGAATTTGGCAACAGAAAATCCAATACTATTCAGTGACCTTGAAGACCCTCCCTACTGTTTCTCAGGTAAAAGTTCAGATTGCTTGAATACAGTAAAATCCAACAG
TTCATCCAAGGCACCCAAAGTGGTGCCTCTCAGAACAAGCCCTGACTCCAGAACAATATAAACACCACTGAAGCAATCGGAAATAATTATTATCAGAAATTACTTGTAGGTCCAAATGCCAAGAAAA
GACATGGAGTTATTGGTGGCTCCCAATAATGGAGGGTATGATGAGATGGGGCCCTATATTCATGTACCTCCAGACCATCAGTTCATGATATGAGGTGCTGAAAATTATTGGCAAGGGAGTTTTGGGCAGGTGCC
AGGGTCTATCGATCACAAACTTCGACAGTAAGTTGGCCCTAAAAATGTGCGCAATGAGAGCGCTTTCATCGTCAAGCACGTGAGGAGATCGGATTCTCAAGACAGGATAAAACTGTAGTATGAACGT
TATCCACATGCTGGAAAGTTTCACATTCCGGAACCATCGTTTGCATGGCCTTTTGAATTGCTGAGCATAGACCTTTATGAGCGTGATTAAAAAAAATAAGTTTCAGGGTTTTAGCGTCCAGTTGTACCCAAGTTTGCCCAGT
CCATCTTGCAATCTTTGGATGCCCTCCACAAATAAGATTATTCACTGCGAATCTGAAGCCAGAAGACATTCTCCTGAAACACCACGGCGCAGTTCAACCAAGTCATTGACTTTGGGTCCAGCTGTTTGAGTACCAG
AAGCTCTACACATATACCAGTCTCGGTTCTACAGAGACCTCCAGAAATCATCTTAGGAAGCGCTTGCATGATGAGCCTTGGCCTGCATGCCTGAGCAATCCTCTCGAGCAATCAAAACGGTCCAAGTACTTCTTATTATTCCAAGGGCATACCCCGCTGCTCTGTGACTACCCAGG
AGAGGATGAAGGAGGACCAGTTGGCCTGCATGATGGGGGGTCGCTCACGTAGGGGTAAAAAGCGGGGTCCCAGGCAGCAGAACTGGGGGACAGCACTGCAAAGACTGGGGACAGCACTGAAAGGGTGTGATGACTACTTGTTATAGAGTTCTTGAAAAGGTGTCTTCAC
CAGATGGAGGGTTTGCTTGTGGGGGTCGCTCACCTAGGGGTAAAAAGCGGGGTCCCCAGGCAGCAGAACTGGGGGACAGCACTGCAAAGACTGGGGACAGCACTCTGTCCCCAGACAAGTCTGTCTGCAAGTGTGCAGGTGTCAGGGAAACGGGTAGTAGTTCATCAGGGATT
TGGGACCCCCTCTGCCCGCTTGACCCGCTTGACCCCAGCTGAATTAAGACACCCTTGGATTAGGACACCCTTGGATTAAGACACCCTTGGATTAGCACATTAAGACACCCTTGGATTAGCAATAGCCAATAAGCTAACTAACTTAAGTCAGAAACCAATGGTAGTATACCCTATGCAGTGTATTGCCAAAACTGATTGGACAGAGATATGCCAGAGATGC
GGGTTCTAAGCTGCCTCCAGTTGTTGAATAGCCAATAAGCTAACTAACTTAAGTCAGAAACCAATGGTAGTATACCCTATGCAGTGTATTGCCAAAACTGATTGGACAGAGATATGCCAGAGATGC
ATATGTGTATATTTTTATGATCTTACAAACCTGCAAATGGAAAAAATGCAAGCCCATTGGTCGATGTTTTGTTAGAGTAGACATTTTTGTTAGAGTAGACATTTTTTAAACAAGACAAAACATTTTTATATGATTATAAAGAATTCTTCAAGGCT
AATTACCTAACCAGCTTGTATTGGCCATCTGAATATGCAATCGACTTTTTAAAATCACTTTTTTTAAGTGATCAATGCAAAAAAAAAAAAAAAAAAAAAAAAAAA

FIG. 11g

> DYRK4 NM_003845.1 (SEQ ID NO: 8)
AGTGTGAGCTGTTGAAAGCCTGCAGTGAAACACCAGTGTTACTTCACTCCCCTTTGTGACACCAAGGGGAAGAAGAATACGGTAAGCTTCCCACACATTAGCAAGAAAGTCCTGCTGAAGTCATCCCTGCTGTATCAGG
AGAATCAAGCTCACATCAGATGCCGGCCGCCTCAGAGCTGAAGGCTTCAAGGCTTCAGAGCTTCAGAAATACCTTTCCACCCTAGCATTGAACAAAGTTCACCAAAGAGAGAAGAAGTGACTCTGAACAGCGGCAGAG
GCCCTAAAGCTTTTAAGACCAGTGCTGTCTCCATATCAACAAAGTGAAATCCTGGGCTACCGGAGCTGTGGTTCTCTGGCTCTTGAAGCCAAGAGCTCGACACGGCTCTGAGAAATTTAGCAAGACCAGTTTTGATGA
TGAGCATGGCTTCTATCTGAAGGTTCTGCATGATCACATTGCCTACCGCTATGAAGTTCTGGAGACAATCGGGAAGGGGTCCTTTGGACAGGTGGCCAAGTGCTGATCACAAAACAATGAGCTGTGGCCCTGAAAA
TCATCAGGAACAAGAAGAGTTTCACCAGCAGGCCTGATGAGCCTGAAGATCCTGAAGCTCTTCAGAAGATCCTACACCTACAATGTGGTGCATATGAAGGACTTTTTCTACTTTCGCAATCACTTCTGC
ATCACCTTTGAGCTCCGGGAATCAACTGTATGAGTTGATGAAGAATAACAACTTTCAAGGCTTCAGTCTGTCCATAGTTCGGGGCCTTCACTCCTCTGTTTTGAAGTGCTTGCAGATGCTTTCGGTAGAGAAAATCAT
TCACTGTGATCTCAAGCCCGAAAATATAGTGCTATACCAAGGGCCAAGCCTCTGTTAAAGTCATTGACTTTGATCAGATCAGCTGTTATGAACACCAGAGAAAGTATACGTCATCCAAAGCCGGTTCTACCGATCCCAG
AAGTGATCCTGGGCCACCCCTACGACGTGGCCATTGACATGTGGAGCCTGGGCTGCATCACGGCGGAGTTGTACACGACGGAGAATGAGGTGGAGCAGCTGGCCTGCATCATGGAGGTGCTG
GGTCTGCCCAGCGGCCGGCTTCATTCAGACAGCCTCCAGGAGACAGACATTCTTGATCCTAAAAATATAACCAGGCCCCTCAAGATTCCAAGGACCTCACCATGGTGCTGAA
AACCTATGACACCAGCTTCCTGGACTTTCTCAGAAGGTGTTTGGTATGGAACCTTCTTCCTCCATGACCCCGACCAGATCCTGTCATCAGTTCCGGAACCTCAAGCCACCAGCCCCAGA
CCCTGAGGAAATCCAATTCCTTTTCCCCTCTGAGACAGGTTCAAGGTTCATCAGGACAAGGACAAGGTTCACAAAGACAGATGAGATTACCAAAGACTACAAGATAGCCCCAAGCATGTT
CAGCATTCAGTGATCAGCTGATCAGCAGGACTGCTGTCTCCAGCAGGCGAGCTGACACTGTTCAGCTCCAGTAGACGCTCCAAGAAGTCAGAGGCAGCTGTCGGGGCGGAGGTGTCCATGACCCCCCAGGACAGACAAAAA
CTTCCCCTCAAGAACACAAGTTTTACCCCCTATTGTATGACCCTTTGCTGAGGGTATGTCCTGCTCCTTTCCACCAGTGATTGTATTAAGACAGCACTTATATTGTACAATACTTCAGACTGTTTTTTTTAAATACA
TAAAACTTTATGTTAAAAAACTCTAAAAAAAAAAAAAAAA

*FIG. 11h*

> DYRK6 NM_005734.3 (SEQ ID NO: 9)
CCGGAAGGAGATGAGGGAGACGGGCCCGGCCTTAGCACCCAGAGCAGCAGCACCGGTCCGGGGAGGGTGTTTCGCCGTTTCCTCTCAGCCCCAGGACAAGATGCAGCCCCGGGAGGGGCTGA
GCCCCGGCCTGGCTGGTGCCGCTGCTGAAGCCCTGGCTCCTCCCCTGGCCGCCCCCTGCCGCCGCGGGGCCTCAGGGCTGCCGGCATGTGTCAGGCTCTAGGAAGGTATGGCCTCAC
AAGTCTTGGTCTACCACCATATGTTTATCAAACTCAGTCAAGTGCCTTTTGTAGTGTAGTAGAGCCAAGCAGTGTGTATTCCACGGACCTATGTGAATGTAGAAACTTT
GGAAATTCTCATCCTCCCCACTAAGGGTAGTGCTTTTCAGACAAGATACCATTTAATGAACTCTCGAGGACGACACAACTTTTCATTGCAGCAAGTGCTGCAGGTGCTACAAAGGTCATAGCAGC
TCAGGCACACCAAGCTCACCTGCAGCCACCTCAGAGATTGGGGCCTGGCGAAACAGATTCCATTCCTAGAAGGGCCCCCAGCCGATGTGATTGAAGCCCAAGAGTGAGGAGTTGATAATCATAGCAGCCGAATGCAGATTG
TCGATGAATTGTCCATACTTCCTGCAATGTCCAAACCAACATGGGAAATCCACTGACAGTTGTGACAGTTGTGACAGTTGTACCACTGAAGCAGGAAGCATCAGTGTTGATCAGAAGTCTTA
TGCCTCCATGAAAAAATACTTACGAAGTCCTTCATTGATTTTCTTGCTGCAGGCACGTTTGGCTCAGCAGTAGTTAAATGCTGGAAAAGAGGGACAATCAAAATTTGAAGAATCATCCTTCTTATGCCCGTCA
AGGTCAAATAGAAGTGAGCATATTAGCAAGGCTCAGTCTGATGAATATAACTTTGTACGAGCTTTCAGCACCGTAACCATACTTGTTTAGTCTTTGAGATGCTGGAACAAAACTTGTATG
ACTTTCTGAAACAAATAATTAGTCCCCTGCCACTAAAAGTCTTGGATCATTGCGCCCATTCTTGATTCTCAAGCCAGAGAATATTATGTTG
GTGGATCCTGTTCGGCAGCCTTACAGGGTTAAAGTAATAGACTTTGGGTCTCGGCCAGTCATGTAAAAGACTCTCAAAGATCTTGTTGTTCAACATATTCTACATACAATCTCGGTACTACAGAGCTCAGACTCAAGGTTTCCAGACTCAAGGTTGTTAA
TGAAGCCATAGACATGTGTCAGCCTTCATTGGGATCGTCATTGGATTAAACAGATTTTTCAAAGAACAGATATGCTTGGTTGGTCGCTGGTTGGTTGGCTGGAAGAAGCTGTCAACGCAGACCATGGAGCAGGGATGAAGTCTAAAGAAGCCAGAAAAATACATTTCAACAGT
ATGTGGGTACTAAATCCACAGATTTTTTGCAAAGAAACAGATATGCTTGGTTGGTCGCTGGTTGGTTGGCTGGAAGAAGCTGTCAACGCAGACCATGGAGCAGGGATGAAGTCTAAAGAAGCCAGAAAAATACATTTCAACAGT
CTGATGATGTAGCGCATGTGAACACAGTAGGATTTGGAACAACCATCTCTCTTCTCTTGTCCTGCTGATTCTCTGATTGCATGCAGATTGATTAAGAATTACTCCAGC
TGAGACCCTGAACCATCCTTTTGTTAATATGAAACATCTTCTAGATTTCCTCATAGCAACCATCTAAAGTCCTGTTTTCATATTATGGATATTTGTAAGTCCACACTAAATTCATGTGACACCAAGTCTGCTCCACCTAAATCATGTGACACCAAATAATCACAACAAAA
CTTCACTTTTAAGACCAGTTGCTTCAAGCAGTGCTTCACACTGCTACACATTGATTCAAGATCAAGTCAGGAACATTAAGAAGTCAGGACCATTGACACATCTGCTCATTCAGTTGTGCCACCATGGAAATACCTCTGCAGGCAGGA
ACTGCTCAGTTTTGGTTGTGGTGATGCTTTTCAGCAGACATTTCAGACAGACGACTTCTTCTCAGACGGACTTCTGGTAGAACACACACAGGTCACCCCTGGCAACAGGTGACACCCTGCCTCCTGCTACACTAACTTCTGAGA
GGCCCCAGCTGTGCTGTTCACAGGCCTTGGACTGGGGGAAGCAATGATTTCATCGCAGCAATCATTATAACTCAGTGATGCCGCAGCCTCTTCTGACCAATCAGATAACTTTATCTGCCCCTCAGCCAGTTGTGGATTGCA
GTGTGGCTGGTGTTCACAGAGCTGGACTGGGGGGAAGCAATGATGATTTCATCGCAGCAATCATTATAACTCAGTGATGCCGCAGCCTCTTCTGACCAATCAGATAACTTTATCTGCCCCTCAGCCAGTTGTGGATTGCA
CATGTGTCTGCTGGCCTGCAGCCTGCACTCACTCAGGAACAGTGCCCAAGAACAGTGCCCAGAACAGTGCCAGAACAGAGCAGAGAGTCTATTTTGGTAAAACTAATGGAATGGATGGAATGGAATAAATGCTTTCAGTTGGAGTAATTCATTACAGAATAC

*FIG. 11i*

```
CAATATCCCACATTCAGCATTTATTCTCCAAGATAATTAATGGGAAAGATGTCGAGGAAGTAAGTTGTATAGAAACCAGGACAATCAGAACTCAGAAGGAGAGGCAAGAAATTGCTGTGAAACATCTATCAGACAGG
ACTCTGATTCATCAGTTTCAGACAAACAGCGGCAAACCATCATTATTGAATATTGAATTGAATCGGATGTGTTCATTAAGTACTCTGATAGTCCTGATAGTCCTCAGGGCAGTCCAGCCTCCAAGAGACCGAATAGTAT
AAAGTAGTCTAGATTGTGAAGCTTGCCAGAGCACTTTGAATATTGATCGGATGTGTTCATTAAGTACTCTGATAGTCCTGATAGTCCTCAGGGCAGTCCAGCCTCCAAGAGACCGAATAGTAT
GTCAGATGAAGAGACAAGAAAGTAGTTGTGATACGGTCGATGCTGTGTCGTTCTGTTGTGCCACCAGTGAACTAGAAAAATGCTTAAATGCCGATGAGACATAGAGAGCATATGCCAGCCATTAATATGCCCCTGGAAGA
ACACAGAAAACCAAGCCAGCTGTCTGTTTCTGTTGTGCCACCAGTGAACTAGAAAAATGCCTTAAATGCCGATGAGACATAGAGCATATGCCAGCCATTAATAAGGACGATCTGCCCCTGGAAGA
TTAAACCAGCCTTCTGCAGTGGGTACTGTCGTCAGCAAAATTGACATCCAGCAGCATTCAGACTTGAACTTCAGTCAGGTTCAGCACTTGGGCATCAAGAGTTGAATGGAACTTTGGGCACAGAAGACA
GCAAGCTTATATTCCTACTAGTGTTACCAGTAGTGTCTCACAGTGGGCCCCTCCTTCTCATGGAAGCTCCAATGCAGCCTCCAATTAACACAGACCACCTGGCTGGAAATACACCTCGGAGGACAGCCTACTCTACTTCCATACCCATCAT
CAGCCACCCTCAGTAGTGCTGCTCCACCAGTGCCTCTCCGTTAGCCTCTCCGTGTACCTCAAGACCTATGTTACAGCATCCAACCTTATAATATCTCCCATCCCAGTGGCATAGTTCACCAAGTCCCCAGTGGCTTAAATCCC
CGTCTGTTACCATCCCAACCATTCATCAGACTCAGTACAACCAATCTTCCCACCACATTCTTACATTGCAGCATCGAGTCGAGTCCAACAAAACTCAGCCAGTATCCATATATGTGAAA
AACAGTATATTGGGAAGCTCAATGATACAAACATTTGATTAAAATAAAACATGGTATTTAATATTAGCAGTAACTCTAGACGTGACTTATGGAGACAGAAGTCCAGTTTGCTCCTGCTATTTTTATAAATTGCCTTCT
AACTCACTTTTGATCTGTCTTTGCACATTTGGTATAACTTGTCTTTGGTCATGTTATCTTCTTATGTAGTAACTCTAGACGTGACTTATGGAGACAGAAGTCCAGTTTGCTCCTGCTATTTTTATAAATTGCCTTCT
AACTAGTGCAAGACACGTCTACATTTGGGAGCCATTCCTGTGTACAAGACTTAGACCAACAGATCCAACAGTACAGCATACAGCAGTGATTGTATTATCCGTGCTTAGTGTATAAATGTTGGTCACTTACC
TAAGAAATTCAGCTATTGCTTCTTTACATTTGCATGTCTTTTGCATGGGCAAAATGTTGCCTAGACTTGCTCTTAAATGTTGTTCTAATAATCTCAGCTCCATTGTAAACCGTTCCTACACATAGTCCTTAAATATT
TGAGGTTGTTAATGTTATTACCTATATATAAATGTTCAGGACTGCAGCACTTAGGACTGCAGCACTTAAAATTCAGACTTAAAATTCAGACTTAAAATTCAGACTAATGTTCCTTTTGATAGGCGTAATTTCATTTTGTTTTTGTGGTATGATGATTCAGGTATGATTCAGGTAGTAGCTGTTT
TTTTCCTTATTAAGAGGGCAGCATGTTTGCTATAGCTGAATTCGCTGTCTGATTTTTCAGATGATCTAGCTTCAAGAAAAGCAAGCAGTAGTAGTGCTTAAGAAAAATTGATTCAGTATC
```

FIG. 11i (cont'd.)

SEQUENCE LISTING

<160> NUMBER OF SEQ ID NOS: 54

<210> SEQ ID NO 1
<211> LENGTH: 1497
<212> TYPE: DNA
<213> ORGANISM: Homo sapiens

<400> SEQUENCE: 1

| | | | | | |
|---|---|---|---|---|---:|
| agcggcgccg | cgggcctgcg | tgctggggca | gcgggcactt | cttcgacctc | gtcctcctcg | 60 |
| tcctgtgcgg | ccggccgggt | gaggccgggc | ccgcgtaggg | ggcagtcggc | ggctgcctcc | 120 |
| ggcggaggtg | cctcgcggcg | cccgggccgg | cccgcgcctc | ggcggcgtgc | tccatgcatc | 180 |
| cggagcccgc | cccgcccccg | agccgcagca | gtcccgagct | tcccccaagc | ggcggcagca | 240 |
| ccaccagcgg | cagccgccgg | agccgccgcc | gcagcgggga | cggggagccc | ccggggcccc | 300 |
| cgccaccgcc | gccgtccgcc | gtcacctacc | cggactggat | cggccagagt | tactccgagg | 360 |
| tgatgagcct | caacgagcac | tccatgcagg | cgctgtcctg | cgcaagctc | tacttgagcc | 420 |
| gcgccaagct | taaagcctcc | agccggacct | cggctctgct | ctccggcttc | gccatggtgg | 480 |
| caatggtgga | ggtgcagctg | gacgctgacc | acgactaccc | accggggctg | ctcatcgcct | 540 |
| tcagtgcctg | caccacagtg | ctggtggctg | tgcacctgtt | tgcgctcatg | atcagcacct | 600 |
| gcatcctgcc | caacatcgag | gcggtgagca | acgtgcacaa | tctcaactcg | gtcaaggagt | 660 |
| cccccatga | gcgcatgcac | cgccacatcg | agctggcctg | ggccttctcc | accgtcatcg | 720 |
| gcacgctgct | cttcctagct | gaggtggtgc | tgctctgctg | ggtcaagttc | ttgcccctca | 780 |
| agaagcagcc | aggccagcca | aggcccacca | gcaagccccc | cgccagtggc | gcagcagcca | 840 |
| acgtcagcac | cagcggcatc | accccgggcc | aggcagctgc | catcgcctcg | accaccatca | 900 |
| tggtgccctt | cggcctgatc | tttatcgtct | tcgccgtcca | cttctaccgc | tcactggtta | 960 |
| gccataagac | tgaccgacag | ttccaggagc | tcaacgagct | ggcggagttt | gcccgcttac | 1020 |
| aggaccagct | ggaccacaga | ggggaccacc | ccctgacgcc | cggcagccac | tatgcctagg | 1080 |
| cccatgtggt | ctgggccctt | ccagtgcttt | ggccttacgc | ccttcccctt | gaccttgtcc | 1140 |
| tgccccagcc | tcacggacag | cctgcgcagg | gggctgggct | tcagcaaggg | gcagagcatg | 1200 |
| gagggaagag | gattttata | agagaaattt | ctgcactttg | aaactgtcct | ctaagagaat | 1260 |
| aagcatttcc | tgttcttcca | gctccaggtc | cacctcctgt | tgggaggcgg | tgggggcca | 1320 |
| aagtggggcc | acacactcgc | tgtgtcccct | ctcctcccct | gtgccagtgc | cacctgggtg | 1380 |
| cctcctcctg | tcctgtccgt | ctcaacctcc | ctcccgtcca | gcattgagtg | tgtacatgtg | 1440 |
| tgtgtgacac | ataaatatac | tcataaggaa | aaaaaaaaa | aaaaaaaaa | aaaaaaa | 1497 |

<210> SEQ ID NO 2
<211> LENGTH: 2495
<212> TYPE: DNA
<213> ORGANISM: Homo sapiens

<400> SEQUENCE: 2

| | | | | | |
|---|---|---|---|---|---:|
| ggagagcctg | agttggcatt | cgtataaatg | acctgcctgg | ctcccaccat | gagtgctgag | 60 |
| cttaacgtgc | ctatcgaccc | ctctgctcct | gcctgccctg | agccaggcca | taagggcatg | 120 |
| gattaccggg | actgggtccg | ccgcagctac | ctggaactgg | tcacctctaa | ccaccactcg | 180 |
| gtacaggccc | tgtcgtggcg | gaagctctac | ctgagcaggg | ccaagctgaa | ggcctccagc | 240 |
| aggacctccg | ccctcctctc | cggctttgcc | atggtggcca | tggtggaggt | gcagctggag | 300 |
| acgcagtacc | agtacccgcg | gccgctgctg | attgccttca | gcgcctgcac | cacggtgctg | 360 |

```
gtggccgtgc acctgttcgc cctcctcatc agcacctgca tcctgcccaa tgtggaggcc    420
gtgagcaaca tccacaacct gaactccatc agcgagtccc cgcatgagcg catgcacccc    480
tacatcgagc tggcctgggg cttctccacc gtgcttggca tcctactctt cctggccgag    540
gtggtgctgc tctgctggat caagttcctc cccgtggatg cccggcgcca gcctggcccc    600
ccacctggcc ctgggagtca cacgggctgg caggccgccc tggtgtccac catcatcatg    660
gtgcccgtgg gcctcatctt cgtggtcttc accatccact tctaccgctc cctggtgcgc    720
cacaaaacgg agcgccacaa ccgcgagatc gaggagctcc acaagctcaa ggtccagctg    780
gacgggcatg agcgcagcct gcaggtcttg tgaggggccg agggccgggg ctgggagcgg    840
ccctgtgccc gggagtccgc agaggcgggg atttgtcaga tgcagacatt ttgcaaggct    900
gccgggtagt tcaagaccaa agttttcctc ttgtcttaat accataagga ctggatgact    960
tctcctgaga tagaaccgtt tggttcaatg agggactgtg ttgctaagag cgttgggggc   1020
aaagccaggc tggttccttg gcctcggggt ttcctgggtc ggggacacgg tgaagaggct   1080
ccagcgggac ctgcccatca gtcctgggcc aggaggggct ccaagcagca cccagcggtc   1140
cgggggagtc tcagacccgg catgcgtggc tggcagacct gggagagcca gggcagggtt   1200
ttgcgttcag agaaggattg ccccagagac ccgtggtgga cttcatgggt gctgagtggc   1260
ccgtgtgaca gtgatgacac gaaggcttcg gcgtttgagt gggtgcaggt gcacgccagg   1320
gcttggtgct ccctgcctg gccctggagg gagctgggtg gcctggcttc aggggaagac   1380
aggagccagg acacacgtca gcccagcagg tgtgggggt gctgcagccc tcggcagtgg   1440
ggtcaggccc tggggatgt ttccaatggt gggcagcctg gccaggccgg agaagacatg   1500
ttcacgggca tctatcagat gccccttga ggaggctgag ttatttgagg ctgctgcaa   1560 agtacgctag gctcaaattc tcttttccca gccagagccc tggccacacg gactcagagg   1620
ggccaccggg gtggggaaag gacccctccc cgacccccg cagccactgg cctccagctc   1680
tcggccacag aatggcctct aaggctgact cagccgctcc cttgggctgt ggcagcagga   1740
ggcgggggct ctggctcagg ccccggagcc tgtgcagctt gcccatggcc ctaggcagcg   1800
aggggacagc ctggggact tcctgcctag gcaaggtcat tggccgggcc tggcctgtgg   1860
atagtggggc caggggccgg cccaggccaa atgagtgccc tccttgttat gacaccaagt   1920
gactacaagg gaggcaagac ccctccaggc ctctcagccg acactgggtc ccaccacaca   1980
cagtgactgt gccgtgcagt gcaggttctg gccttttcct tgaaggcatc tggtagaccc   2040
gaagccacgc tctcgggccg cacatgcacg ccgcagcacc agctgccctg agctgcttgt   2100
acaaccaaac acctttcccc tcttctccag ctgtaacctg gagagtcagc catgccttgt   2160
cttttgttct cataaatagt cactgggcc gggcgcagtg actcacgcct gtaatcccag   2220
cactttggga ggcctaggtg gcggatcac ttgaggtcag gagttcgaga ccagcctggc   2280
caacatggtg aaaccctgtc tctactaaaa aatacagaa aattagctgg gcgtggtggc   2340
gggcgcctgt agccccagct acttgggagg ctgaggtggg agaatggcaa tggcgtgaac   2400 ccggaggca gagcttgcag tgagctgaga tggcgccact gcactccagc ctgggcgaca   2460
gagccagact caatctcaaa aaaaaaaaa aaaa                                2495

<210> SEQ ID NO 3
<211> LENGTH: 2239
<212> TYPE: DNA
<213> ORGANISM: Homo sapiens
```

<400> SEQUENCE: 3

```
cgctccggct cctggggctc cccgcagacg ctgcttttct tgctccactg ggggtgcctc    60
ttcctgggcg cccgccgcct gcatcctgct cgccctgtct gggaatgggg ccgcccccgg   120
gcttgggccg gcccggctgg ggccccgag gcgcttccgc cccgtagtga ccgcctggtg    180
ccgccccccc ccaggatgaa gggcggcgag ggggacgcgg gcgagcaggc cccgctgaac   240
cctgagggcg agagccctgc aggctcggcc acgtaccggg agttcgtgca ccgcggctac   300
ctggacctca tggggccag tcagcactcg ctgcgggcgc tcagctggcg ccgcctctac   360
ctcagccggg ccaagctcaa agcttccagc cgcacgtctg ccttgctctc gggcttcgcc   420
atggtggcca tggtggaggt gcagctggag agtgaccacg agtacccacc aggcctgctg   480
gtggccttca gtgcctgcac caccgtgctg gtggctgtgc acctctttgc actcatggtc   540
tccacgtgtc tgctgcccca cattgaagct gtgagcaaca tccacaacct caactctgtc   600
caccagtcgc acaccagag actgcaccgc tacgtggagc tggcctgggg cttctccact   660
gccctgggca cctttctctt ccttgctgaa gttgtcctgg ttggttgggt caagtttgtg   720
cccattgggg ctccccttgga cacaccgacc ccatggtgc ccacatcccg ggtgcccggg   780
actctggcac cagtggctac ctcccttagt ccagcttcca atctcccacg gtcctctgcg   840
tctgcagcac cgtcccaggc tgagccagcc tgcccacccc ggcaagcctg tggtggtggt   900
ggggcccatg ggccaggctg gcaagcagcc atggcctcca cagccatcat ggtacccgtg   960
gggctcgtgt ttgtggcctt tgccctgcat ttctaccgct ccttggtggc acacaagaca  1020
gaccgctaca gcaggaact agaggaactg aatcgcctgc aggggagct gcaggctgtg   1080
tgagactggt gttagccacc gctcactgca agcactgcct ccctccgggg tctgtaagag  1140
gccgcagggg cctacagacc tcatccccccc atcccctggc tggagccact tccagtggcc  1200
actctcaggc agagttcaga ttcctgcccg cagggtcctc tgggctgggc cttggggcag  1260
ctcccacatt cccagggatt ttccccatca gtctgtccct tgggttttgc aagctactct  1320
gcacctgggc tggcctcagt tgaaggatca tgcagtagat agaggggagg cagggagagc  1380
ttgtgggacc ttcagtgctg actttagcca ccatttccat tcctatacag gatgtgaagg  1440
tcagaaggca gccaattgtt ggtttaattt ttttttttt tgagacagtc tgtttcccag  1500
gctggagtgt agtgatacag tcacagctca ctgtagcctc gaccttccag gctcaaaaga  1560
tgctcccacc acagcctccc aggtagtgag tagctggtac tacaggtgtg tgctgccaca  1620
cccgactaat ttttttgtag agacgggtt tcgctgttcc caggctggtc tcaaactcct  1680
gggctcaagt gaacctcccg cctcggcctc ccaaagtgct gggattcctt tctttatttc  1740
tgtagaatct atttatggt tggcattttg ggggaagatt tcgatgggtt ccacattctt  1800
gctttagttg ttgtagaggg atttgggtgt ttctacccaa ggcattggtc tagcttttcc  1860
tacaatgaac ctatctttgg aggtttaagc tccccacctt cccccactgt ggtgacctgt  1920
ggccacttgc agaagggatg gtgcctgacc cactgcccta gccccacgct atgcaccaaa  1980
cttgttctcc ccgtcctggt ccagggctgg ggtctttaga gactgacagc ctctgcccca  2040
ggcctgagtc cttagcaagg gttgggtaag gaggttttaa gggagaaggt ccagtcctta  2100
gcccttgaaa tacaaagctc ttctgacact gaatttggat gcaccttgtt ttatataata  2160
aatcgtgttt cacagaaaaa aaaaaaaaa aaaaaaaaa aaaaaaaaa aaaaaaaaa     2220
aaaaaaaaaa aaaaaaaaa                                             2239
```

<210> SEQ ID NO 4
<211> LENGTH: 5212
<212> TYPE: DNA
<213> ORGANISM: Homo sapiens

<400> SEQUENCE: 4

```
gttatagttt tgccgctgga ctcttccctc ccttccccca ccccatcagg atgatatgag      60
acttgaaaga agacgatgca tacaggagga gagacttcag catgcaaacc ttcatctgtt     120
cggcttgcac cgtcattttc attccatgct gctggccttc agatggctgg acagatgccc     180
cattcacatc agtacagtga ccgtcgccag ccaaacataa gtgaccaaca ggtttctgcc     240
ttatcatatt ctgaccagat tcagcaacct ctaactaacc aggtgatgcc tgatattgtc     300
atgttacaga ggcggatgcc ccaaaccttc cgtgacccag caactgctcc cctgagaaaa     360
ctttctgttg acttgatcaa aacatacaag catattaatg aggtttacta tgcaaaaaag     420
aagcgaagac accaacaggg ccagggagac gattctagtc ataagaagga acggaaggtt     480
tacaatgatg gttatgatga tgataactat gattatattg taaaaaacgg agaaaagtgg     540
atggatcgtt acgaaattga ctccttgata ggcaaaggtt cctttgggca ggttgtaaag     600
gcatatgatc gtgtggagca agaatggggt gccattaaaa taataagaa caagaaggct     660 tttctgaatc aagcacagat agaagtgcga cttcttgagc tcatgaacaa acatgacact     720
gaaatgaaat actacatagt gcatttgaaa cgccacttta tgtttcgaaa ccatctctgt     780 ttagttttg aaatgctgtc ctacaacctc tatgacttgc tgagaaacac caatttccga     840
ggggtctctt tgaacctaac acgaaagttt gcgcaacaga tgtgcactgc actgcttttc     900
cttgcgactc cagaacttag tatcattcac tgtgatctaa aacctgaaaa tatccttctt     960
tgtaacccca acgcagtgc aatcaagata gttgactttg gcagttcttg tcagttgggg    1020
cagaggatat accagtatat tcagagtcgc ttttatcggt ctccagaggt gctactggga    1080
atgccttatg accttgccat tgatatgtgg tccctcgggt gtattttggt tgaaatgcac    1140
actggagaac ctctgttcag tggtgccaat gaggtagatc agatgaataa aatagtggaa    1200
gttctgggta ttccacctgc tcatattctt gaccaagcac caaaagcaag aaagttcttt    1260
gagaagttgc cagatggcac ttggaactta agaagacca agatggaaa cgggagtac     1320 aaaccaccag gaaccccgtaa acttcataac attcttggag tggaaacagg aggacctggt    1380
gggcgacgtg ctggggagtc aggtcatacg gtcgctgact acttgaagtt caaagacctc    1440 atttttaagga tgcttgatta tgaccccaaa actcgaattc aaccttatta tgctctgcag    1500
cacagtttct tcaagaaaac agctgatgaa ggtacaaata caagtaatag tgtatctaca    1560
agccccgcca tggagcagtc tcagtcttcg ggcaccacct ccagtacatc gtcaagctca    1620
ggtggctcat cggggacaag caacagtggg agagcccggt cggatccgac gcaccagcat    1680
cggcacagtg gtgggcactt cacagctgcc gtgcaggcca tggactgcga gacacacagt    1740
ccccaggtgc gtcagcaatt tcctgctcct cttggttggt caggcactga agctcctaca    1800
caggtcactg ttgaaactca tcctgttcaa gaaacaacct ttcatgtagc ccctcaacag    1860
aatgcattgc atcatcacca tggtaacagt tcccatcacc atcaccacca ccaccaccat    1920
caccaccacc atgacaaca agccttgggt aaccggacca ggccaagggt ctacaattct    1980
ccaacgaata gctcctctac ccaagattct atggaggttg gccacagtca ccactccatg    2040 acatcccctgt cttcctcaac gacttcttcc tcgacatctt cctcctctac tggtaaccaa    2100
ggcaatcagg cctaccagaa tcgcccagtg gctgctaata ccttggactt tggacagaat    2160
```

-continued

```
ggagctatgg acgttaattt gaccgtctac tccaatcccc gccaagagac tggcatagct    2220
ggacatccaa cataccaatt ttctgctaat acaggtcctg cacattacat gactgaagga    2280
catctgacaa tgaggcaagg ggctgataga gaagagtccc ccatgacagg agtttgtgtg    2340
caacagagtc ctgtagctag ctcgtgacta cattgaaact tgagtttgtt tcttgtgtgt    2400
ttttatagaa gtggtgtttt ttttccaaaa acaaagtgca aagctgcttg aatcaggagg    2460
agattaacac actgaaccgc tacaagaggg caaagctgat tttttttta acttgaaaag    2520 attgcaaagg gacattgaag tgtttaaaag agccatgtcc aaacccatct tcatggatag    2580
ctcagaggta tcctcttttt gctcccccat tttaacttgc cacatcccag tcacagtggg    2640 gttttttttgt ctttctattc agcaaaagtt aatattcaga tgttggtctt ggtcatttgc    2700
caactaattt taaagtaaaa ggcactgcac ataatttgca taaagggccc catgagggtg    2760 ttttttttttt ttcttttttgt ccccccatc ccccttttttt tttgttttgt tctgttttgt    2820
tttgggtggg agggtgggaa atttgggttt ttaagtcctc taaacacact tgggcacgga    2880
aatgcagtac tgtaaggaag agggacctcc agcttccaca acaccatct tcagctgtat    2940 gaaagggacg gttgtggtga agtttgtcag gcacagtaag catgctgagt ggcggggatc    3000
agaactctcc tatctgaacc tactgaggag caaagcagca attacatggg atcctgtggc    3060
tctcccgttg cagaggccac aggaagatag gatggaacgt gactggtctc ctaaccaagg    3120
tgcactgaga agcaatcaac gggtcggtcg tggccagtcc tggggaggtc tgagtggtgg    3180 tcttttgggat aacctttggc cttatggatt tggactcgaa attagaagag cctaccattt    3240
cagatgcaat cacttttgga catgcttttg cagacagtcc ttaatgctga aaacacagag    3300
aatgggtaat tcaagaggcc tttcttttaa aatagacttt tgtgacccac taattgtaag    3360
gtattgcaag gtcactttgc gtgtgtcata agttgactt ccttattggt tgaaggtcac    3420
agaagtagtg gtttgctttg atggaaatag ctacagctgt gtccttcct gcttttact    3480 ttttcttttg cttttctcg gcacgtggta tctccaccat ttcttctgca caaagatgtc    3540
ttctgttcat cctgaacatt tttaaaaaat gcagaatttt atgtgactgc ttttttgcct    3600
cacaattatg ctgtgaattt tacaaaaatt tattttcttt tttgataatt tattgtacca    3660
aagctgtttt tatagcacat agatgtctgt aaccaataat gtagcagttc tgcactttga    3720
cacaaggtgt aactagacca tttttaaatg tcagttgaaa attatggctg tactattgct    3780
taaacaaaac tggaactgtt gttgaatcca tagccaatac atttacagca atctgtgtac    3840
tgaacatagt agattgacat ctaattcaag attacaacat ctgttacatt ctaagtgtgt    3900
tcaggcttct gaaggtaaag ggacactgga tccagaagct atggaaccag cagttgattc    3960
ttgtattcct gattaaccta cttgtaaact tgaaagcaag accttgattg caccaacagg    4020
tccagagtat gagtgcaagc aaagcagaac tctcatgcgt gacctgagca gacaggctgg    4080
tatttaacag gtgcctcgtg ttgagattac gctgccttaa tgtaacacag tctggcagtt    4140
gctaaatttg tgttcccatt ttaaattgac caattttggg gtgtgacact tttgagcggt    4200
tgaattggga gaatgaagat aagtaattta cctgtccagg atcaaaagaa gcctagaaaa    4260
gaagcagtaa tctacctctg ccgataacct gtttaagatg actcagcaga acaccgcgtt    4320
tcattctatt ggtcaattcc atgtggctga ctaggtcaat tttttttctg aacaaaagca    4380 ggttttttata tgtaaacagt gagaaaagaa aggctaaaca ctatgtaaat gtgaatggaa    4440
acttggaaat actcgttttt ataaactaca aaaacttttt gttgtttatc aggaaatcca    4500
tatttatttt gtaattaact gtcaagcctg tggatgattt ttttgaactt ggtagttcat    4560
```

```
aaaggtttac agtgaataaa aggatatcat cttgagtata gcaatatcaa aaggaattca    4620
gtagttactg ctgtttagga atataaggtt aagatatcat atgggtcagg tcattttttt    4680
tttctgtgct ggttgccaca tcttagcaag caccaaaaaa ctaaagcagt ttttaaaccg    4740
atatttacgt aaagaaaatc ataaaatcca atgcttctgc atactgtgtt atgttacagt    4800
ccagttttgt gtgctttact acacagtttg gttacaggac ttctgtgcat tgtaaacata    4860
aacagcatgg aaaaggttaa atacctgtgt tcagattgta agatctagtc cggacttgct    4920
gtgtatattg taacgttaaa tgaaaaaaga acccccttt gtattatagt catgcggtct    4980
tatgtatgat aaacagttga ataatttgtc ctcagactct ttactatgct tttttaaaaa    5040
ttaatttaag aaaaatgtaa acatagtaaa aatcttccta tgcaattaaa ctggtccagg    5100
tctggtaggt atagtatcaa agttgagtta aatgtgtaaa aaggaaacta tttgagatac    5160
attgacatag gcatcagcaa tctctgaaag taaaaattgg aggtttaaca ga            5212
```

<210> SEQ ID NO 5
<211> LENGTH: 2540
<212> TYPE: DNA
<213> ORGANISM: Homo sapiens

<400> SEQUENCE: 5

```
gggatggggg cggagtccag ggcgtggggg ggccggtttg ttgtggtcgc cattttgctg      60
gttgcattac tgggtaatcg gggccctggc ttgccgcgtc cgccggatac cctcagccag     120
tgggcaggtc tgagctcggg ctccccgagc agtttgagtc cccttgcccg ctccttcagg     180
tctcagcggc ggtggcagcc gaggtgcagg atgcaagaag gcgcccccg gccgggctcc      240 cgctccaggc ctcgctcccc tgcggccctc tgagcccacc atggccgtcc caccgggcca     300
tggtcccttc tctggcttcc cagggcccca ggagcacacg caggtattgc ctgatgtgcg     360
gctactgcct cggaggctgc ccctggcctt ccgggatgca acctcagccc cgctgcgtaa     420
gctctctgtg gacctcatca agacctacaa gcacatcaat gaggtatact atgcgaagaa     480
gaagcggcgg gcccagcagg cgccacccca ggattcgagc aacaagaagg agaagaaggt     540
cctgaaccat ggttatgatg acgacaacca tgactacatc gtgcgcagtg gcgagcgctg     600
gctggagcgc tacgaaattg actcgctcat tggcaaaggc tcctttggcc aggtggtgaa     660
agcctatgat catcagaccc aggagcttgt ggccatcaag atcatcaaga caaaaaggc      720 tttcctgaac caggcccaga ttgagctgcg gctgctggag ctgatgaacc agcatgacac     780
ggagatgaag tactatatag tacacctgaa gcggcacttc atgttccgga ccacctgtg      840 cctggtattt gagctgctgt cctacaacct gtacgacctc ctgcgcaaca cccacttccg     900
cggcgtctcg ctgaacctga cccggaagct ggcgcagcag ctctgcacgg cactgctctt     960
tctggccacg cctgagctca gcatcattca ctgcgacctc aagcccgaaa acatcttgct    1020
gtgcaacccc aagcgcagcg ccatcaagat tgtggacttc ggcagctcct gccagcttgg    1080
ccagaggatc taccagtata tccagagccg cttctaccgc tcacctgagg tgctcctggg    1140 cacacccctac gacctggcca ttgacatgtg gtccctgggc tgcatccttg tggagatgca    1200
caccggagag cccctcttca gtggctccaa tgaggtcgac cagatgaacc gcattgtgga    1260
ggtgctgggc atcccaccgg ccgccatgct ggaccaggcg cccaaggctc gcaagtactt    1320 tgaacgctg cctgggggtg gctggaccct acgaaggacg aaagaactca ggaaggatta    1380
ccagggcccc gggacacggc ggctgcagga ggtgctgggc gtgcagacgg gcgggcccgg    1440
```

-continued

| | |
|---|---|
| gggccggcgg gcgggggagc cgggccacag ccccgccgac tacctccgct tccaggacct | 1500 |
| ggtgctgcgc atgctggagt atgagcccgc cgcccgcatc agcccctggg ggctctgca | 1560 |
| gcacggcttc ttccgccgca cggccgacga ggccaccaac acgggcccgg caggcagcag | 1620 |
| tgcctccacc tcgcccgcgc ccctcgacac ctgcccctct tccagcaccg ccagctccat | 1680 |
| ctccagttct ggaggctcca gtggctcctc cagtgacaac cggacctacc gctacagcaa | 1740 |
| ccgatattgt gggggccctg gccccctat cacagactgt gagatgaaca gcccccaggt | 1800 |
| cccaccctcc cagccgctgc ggccctgggc aggggtgat gtgccccaca agacacatca | 1860 |
| agccctgcc tctgcctcgt cactgcctgg gaccggggcc cagttacccc ccagccccg | 1920 |
| ataccttggt cgtccccat caccaacctc accaccaccc ccggagctga tggatgtgag | 1980 |
| cctggtgggc ggccctgctg actgctcccc acctcaccca gcgcctgccc cccagcaccc | 2040 |
| ggctgcctca gccctccgga ctcggatgac tggaggtcgt ccaccccctcc cgcctcctga | 2100 |
| tgaccctgcc actctgggc ctcacctggg cctccgtggt gtaccccaga gcacagcagc | 2160 |
| cagctcgtga ccctgccccc tccctggggc ccctcctgaa gccataccct cccccatctg | 2220 |
| ggggccctgg gctcccatcc tcatctctct ccttgactgg aattgctgct acccagctgg | 2280 |
| ggtgggtgag gcctgcactg attggggcct ggggcagggg ggtcaaggag agggttttgg | 2340 |
| ccgctccctc cccactaagg actggaccct tgggcccctc tccccctttt tttctattta | 2400 |
| ttgtaccaaa gacagtggtg gtccggtgga gggaagaccc cccctcaccc caggaccta | 2460 |
| ggaggggtg ggggcaggta gggggagatg gccttgctcc tcctcgctgt accccagta | 2520 |
| aagagctttc tcacaaaaaa | 2540 |

<210> SEQ ID NO 6
<211> LENGTH: 3466
<212> TYPE: DNA
<213> ORGANISM: Homo sapiens

<400> SEQUENCE: 6

| | |
|---|---|
| ggactgtgtg tgtctggctg tagcagacgc gaggcggcga cgaggcgccg gggacccgcg | 60 |
| cgaggggcgg ccgggaggcg gcggcggcgg ccgccagaag tagcagcagg accggcggcg | 120 |
| gcgacggcag ccctgaaatg cattttcctc tccagcggcc atgttaacca ggaaaccttc | 180 |
| ggccgccgct cccgccgcct acccgaccga ttggcggcag taagcacaca atgaatgatc | 240 |
| acctgcatgt cggcagccac gctcacggac agatccaggt tcaacagttg tttgaggata | 300 |
| acagtaacaa gcggacagtg ctcacgcaca aaccaaatgg gcttacaaca gtgggcaaaa | 360 |
| cgggcttgcc agtggtgcca gagcggcagc tggacagcat tcatagacgg caggggagct | 420 |
| ccacctctct aaagtccatg gaaggcatgg ggaaggtgaa agccaccccc atgacacctg | 480 |
| aacaagcaat gaagcaatac atgcaaaaac tcacagcctt cgaacaccat gagatttca | 540 |
| gctaccctga atatatttc ttgggtctaa atgctaagaa gcgccagggc atgacaggtg | 600 |
| ggcccaacaa tggtggctat gatgatgacc agggatcata tgtgcaggtg ccccacgatc | 660 |
| acgtggctta caggtatgag gtcctcaagg tcattgggaa ggggagcttt gggcaggtgg | 720 |
| tcaaggccta cgatcacaaa gtccaccagc acgtggccct aaagatggtg cggaatgaga | 780 |
| agcgcttcca ccggcaagca gcggaggaga tccgaatcct ggaacacctg cggaagcagg | 840 |
| acaaggataa cacaatgaat gtcatccata tgctggagaa tttcaccttc cgcaaccaca | 900 |
| tctgcatgac gtttgagctg ctgagcatga acctctatga gctcatcaag aagaataaat | 960 |
| tccagggctt cagtctgcct ttggttcgca gtttgcccca ctcgattctg cagtgcttgg | 1020 |

```
atgctttgca caaaaacaga ataattcact gtgaccttaa gcccgagaac attttgttaa    1080
agcagcaggg tagaagcggt attaaagtaa ttgattttgg ctccagttgt tacgagcatc    1140
agcgtgtcta cacgtacatc cagtcgcgtt tttaccgggc tccagaagtg atccttgggg    1200
ccaggtatgg catgcccatt gatatgtgga gcctgggctg cattttagca gagctcctga    1260
cgggttaccc cctcttgcct ggggaagatg aaggggacca gctggcctgt atgattgaac    1320
tgttgggcat gccctcacag aaactgctgg atgcatccaa acgagccaaa attttgtga    1380 gctccaaggg ttatccccgt tactgcactg tcacgactct ctcagatggc tctgtggtcc    1440
taaacggagg ccgttcccgg agggggaaac tgagggccc accggagagc agagagtggg    1500
ggaacgcgct gaagggtgt gatgatcccc ttttccttga cttcttaaaa cagtgtttag    1560
agtgggatcc tgcagtgcgc atgacccag gccaggcttt gcggcacccc tggctgagga    1620
ggcggttgcc aaagcctccc accggggaga aacgtcagt gaaaaggata actgagagca    1680
ccggtgctat cacatctata tccaagttac ctccaccttc tagctcagct tccaaactga    1740
ggactaattt ggcgcagatg acagatgcca atgggaatat tcagcagagg acagtgttgc    1800
caaaacttgt tagctgagct cacgtcccct gatgctggta acctgaaaga tacgacattg    1860
ctgagcctta ctgggttgaa aaggagtagc tcagacctgt ttttatttgc tcaataactc    1920
tactcatttg tatcttttca gcacttaatt ttaatgtaag aaagttgttc attttgtttt    1980
tataaaatac atgaggacaa tgctttaagt ttttatactt tcagaaactt tttgtgttct    2040
aaaagtacaa tgagccttac tgtatttagt gtggcagaat aataacatca gtggcaggcc    2100
actgattact tcatgactgc cacgcattta cagattggtg tcaaagacat tcactatgtt    2160
tttatggttc atgttatatc ctccccaggg tgacagcccc ttaaggccct ccttttccct    2220
ccatgctcca ggtccatgca caggtgtagc atgtcctgct tccgttttc ataaattaat    2280 ctgggtgttg ggggtagtgg gaggagaacg gtcagaatca agtgacatt ctaagaaaaa    2340 ctgtaccta gagattttcc tctagtgctc aaacaaatac aaaataagat ccccaaggtt    2400
taaactgccc agttagcatt ctgacattct aaaagccggc aaagcagctt ttagtggata    2460
aatgggaatg gaaacgtgtg tgttcctcca aattttctag tatgatcggt gagctgtttt    2520
gtaaagaagc tcatattac agagttgctt ttgcacctaa atttagaatt gtattccatg    2580
aactgttcct ccctttctc tgcttttctc ctctctgttc ctcttttaat accacacgtc    2640
tgttgcttgc atttagtttg tcttcttcct tcagctgtgt atcccagact gttaatacag    2700
aaaagagaca tttcagctgt gattatgacc attgtttcat attccaatta aaaaagaac    2760 agcagcctag ctacttaagg tggggatttc atagttccaa agaagattta gcagattaga    2820
gtgagttcac acttttcagg tgccactgta aggttctctc agcctgggaa actatcaact    2880
ctttctttaa aagaaagag ggttgaaaat cctctggacg aacagaagtc actttggctg    2940
ttcagtaagg ccaatgttaa caacacgttt agaggaggaa aagttcaacc tcaagttaaa    3000
tggtttgact tattcttcgt atcattagaa gaaccccaga gatagcattc ctctatttta    3060
ttttactttc ttttggattg cactgattgt ttttgtggga atgacacttt atctggcaaa    3120
gtaactgaga gtttggtaaa agaatatttt cttctctgaa taataattat tttcacagtg    3180
aaaatttcag tattttatca ctaatgtatg agcaatgatc tatatcaatt tcaaggcacg    3240
tgaaaaaaat ttttttagtat gtgcaattta atatagaaag atttctgcct gtttggacaa    3300
taggttttgg gtagtacaga ttaggataag taagcttata tatgcacaga gattattgta    3360
```

<210> SEQ ID NO 7
<211> LENGTH: 2207
<212> TYPE: DNA
<213> ORGANISM: Homo sapiens

<400> SEQUENCE: 7

| | | | | | | |
|---|---|---|---|---|---|---|
| acttcccagc | cggggccagt | cgggagcgaa | agtgcgctga | gctgcagtgt | ctggtcgaga | 60 |
| gtacccgtgg | gagcgtcgcg | ccgcggaggc | agccgtcccg | gcgtaggtgg | cgtggccgac | 120 |
| cggacccccca | actggcgcct | ctcccgcgc | ggggtcccga | gctaggagat | gggaggcaca | 180 |
| gctcgtgggc | ctgggcggaa | ggatgcgggg | ccgcctgggg | ccgggctccc | gccccagcag | 240 |
| cggaggttgg | gggatggtgt | ctatgacacc | ttcatgatga | tagatgaaac | caaatgtccc | 300 |
| ccctgttcaa | atgtactctg | caatccttct | gaaccacctc | cacccagaag | actaaatatg | 360 |
| accactgagc | agtttacagg | agatcatact | cagcacttt | tggatggagg | tgagatgaag | 420 |
| gtagaacagc | tgtttcaaga | atttggcaac | agaaaatcca | atactattca | gtcagatggc | 480 |
| atcagtgact | ctgaaaaatg | ctctcctact | gtttctcagg | gtaaaagttc | agattgcttg | 540 |
| aatacagtaa | aatccaacag | ttcatccaag | gcacccaaag | tggtgcctct | gactccagaa | 600 |
| caagccctga | agcaatataa | acaccacctc | actgcctatg | agaaactgga | ataattaat | 660 |
| tatccagaaa | tttactttgt | aggtccaaat | gccaagaaaa | gacatggagt | tattggtggt | 720 |
| cccaataatg | gagggtatga | tgatgcagat | ggggcctata | ttcatgtacc | tcgagaccat | 780 |
| ctagcttatc | gatatgaggt | gctgaaaatt | attggcaagg | ggagttttgg | gcaggtggcc | 840 |
| agggtctatg | atcacaaact | tcgacagtac | gtggccctaa | aaatggtgcg | caatgagaag | 900 |
| cgctttcatc | gtcaagcagc | tgaggagatc | cggattttgg | agcatcttaa | gaaacaggat | 960 |
| aaaactggta | gtatgaacgt | tatccacatg | ctggaaagtt | tcacattccg | gaaccatgtt | 1020 |
| tgcatggcct | ttgaattgct | gagcatagac | ctttatgagc | tgattaaaaa | aaataagttt | 1080 |
| cagggtttta | gcgtccagtt | ggtacgcaag | tttgcccagt | ccatcttgca | atctttggat | 1140 |
| gccctccaca | aaaataagat | tattcactgc | gatctgaagc | cagaaaacat | tctcctgaaa | 1200 |
| caccacgggc | gcagttcaac | caaggtcatt | gactttgggt | ccagctgttt | cgagtaccag | 1260 |
| aagctctaca | catatatcca | gtctcggttc | tacagagctc | cagaaatcat | cttaggaagc | 1320 |
| cgctacagca | caccaattga | catatggagt | tttggctgca | tccttgcaga | acttttaaca | 1380 |
| ggacagcctc | tcttccctgg | agaggatgaa | ggagaccagt | tggcctgcat | gatggagctt | 1440 |
| ctagggatgc | caccaccaaa | acttctggag | caatccaaac | gtgccaagta | ctttattaat | 1500 |
| tccaagggca | taccccgcta | ctgctctgtg | actacccagg | cagatgggag | ggttgtgctt | 1560 |
| gtgggggtc | gctcacgtag | gggtaaaaag | cggggtcccc | caggcagcaa | agactgggg | 1620 |
| acagcactga | aagggtgtga | tgactacttg | tttatagagt | tcttgaaaag | gtgtcttcac | 1680 |
| tgggacccct | ctgcccgctt | gaccccagct | caagcattaa | gacacccttg | gattagcaag | 1740 |
| tctgtcccca | gacctctcac | caccatagac | aaggtgtcag | ggaacgggt | agttaatcct | 1800 |
| gcaagtgctt | tccagggatt | gggttctaag | ctgcctccag | ttgttggaat | agccaataag | 1860 |
| cttaaagcta | acttaatgtc | agaaaccaat | ggtagtatac | ccctatgcag | tgtattgcca | 1920 |
| aaactgatta | gctagtggac | agagatatgc | ccagagatgc | atatgtgtat | attttttatga | 1980 |
| tcttacaaac | ctgcaaatgg | aaaaaatgca | agcccattgg | tggatgtttt | tgttagagta | 2040 |

```
gacttttttt aaacaagaca aaacattttt atatgattat aaaagaattc ttcaagggct    2100
aattacctaa ccagcttgta ttggccatct ggaatatgca ttaaatgact ttttataggt    2160
caatgcaaaa aaaaaaaaaa aaaaaaaaaa aaaaaaaaaa aaaaaaa                  2207
```

<210> SEQ ID NO 8
<211> LENGTH: 1860
<212> TYPE: DNA
<213> ORGANISM: Homo sapiens

<400> SEQUENCE: 8

```
agtgtgagct gttgaaagcc tgcagctaaa caccagtgtt acttcactcc cctttgtgga      60
caccaagggg aagaagaata cggtaagctt cccacacatt agcaagaaag tcctgctgaa     120
gtcatccctg ctgtatcagg agaatcaagc tcacaatcag atgccggcct cagagctcaa     180
ggcttcagaa ataccttcc accctagcat aaaacccag gatcccaagg cagaggagaa       240
gtcaccaaag aagcaaaagg tgactctgac agcggcagag ccctaaagc ttttaagaa       300 ccagctgtct ccatatgaac aaagtgaaat cctgggctac gcggagctgt ggttcctggg     360
tcttgaagcc aagaagctcg acacggctcc tgagaaattt agcaagacga ttttgatga     420 tgagcatggc ttctatctga aggttctgca tgatcacatt gcctaccgct atgaagttct     480
ggagacaatc gggaaggggt cctttggaca ggtggccaag tgcttggatc acaaaaacaa     540
tgagctggtg gccctgaaaa tcatcaggaa caagaagagg tttcaccagc aggccctgat     600
ggagctgaag atcctggaag ctctcagaaa aaggacaaa acaacacct acaatgtggt       660 gcatatgaag gactttttct actttcgcaa tcacttctgc atcacctttg agctcctggg     720
aatcaacttg tatgagttga tgaagaataa caactttcaa ggcttcagtc tgtccatagt     780
tcggcgcttc actctctctg ttttgaagtg cttgcagatg ctttcggtag agaaaatcat     840
tcactgtgat ctcaagcccg aaaatatagt gctataccaa aagggccaag cctctgttaa     900
agtcattgac tttggatcaa gctgttatga acaccagaaa gtatacacgt acatccaaag     960
ccggttctac cgatccccag aagtgatcct gggccacccc tacgacgtgg ccattgacat    1020
gtggagcctg ggctgcatca cggcggagtt gtacacgggc taccccctgt tccccgggga    1080
gaatgaggtg gagcagctgg cctgcatcat ggaggtgctg ggtctgccgc agccggctt     1140 cattcagaca gcctccagga gacagacatt ctttgattcc aaaggttttc ctaaaaatat    1200
aaccaacaac aggggggaaaa aaagataccc agattccaag gacctcacga tggtgctgaa    1260
aacctatgac accagcttcc tggacttct cagaaggtgt ttggtatggg aaccttctct     1320
tcgcatgacc ccggaccagg ccctcaagca tgcttggatt catcagtctc ggaacctcaa    1380
gccacagccc aggccccaga ccctgaggaa atccaattcc ttttttcccct ctgagacaag    1440 gaaggacaag gttcaaggct gtcatcactc gagcagaaaa gcagatgaga tcaccaaaga    1500
gactacagag aaaacaaaag atagcccac gaagcatgtt cagcattcag gtgatcagca     1560
ggactgtctc cagcacggag ctgacactgt tcagctgcct caactggtag acgctcccaa    1620
gaagtcagag gcagctgtcg gggcggaggt gtccatgacc tccccaggac agagcaaaaa    1680
cttctccctc aagaacacaa acgttttacc ccctattgta tgacctttgc tgagggtatg    1740
tcctgctcct ttccaccagt gatttgtatt aagacagcac ttatattgta caatacttca    1800
gactgttttt tttaaataca taaaacttta tgttaaaaaa ctctaaaaaa aaaaaaaaaa    1860
```

<210> SEQ ID NO 9

<211> LENGTH: 4743
<212> TYPE: DNA
<213> ORGANISM: Homo sapiens

<400> SEQUENCE: 9

```
ccgggaagga agatgaggga gacgggcccg gcgcttagca gccagagcag cagcagcagc       60
agcagcggtc gggggagggt gtttcgccgt ttcctctcag ccgccaggac aagatggcag      120
cggccgcgga gaggggctga gcccgggctg ggtggtgccg cctgctgaag cgcctggctc      180
ccggtccccg gcacggccct gcgccccacc ccggacatgc tcagggctgc ggccgcccga      240
agaggagaga gcgcgggcct ctaggaaggt atggcctcac aagtcttggt ctacccacca      300
tatgtttatc aaactcagtc aagtgccttt tgtagtgtga agaaactcaa agtagagcca      360
agcagttgtg tattccagga agaaactat ccacggacct atgtgaatgg tagaaacttt       420
ggaaattctc atcctcccac taagggtagt gcttttcaga caaagatacc atttaataga      480
cctcgaggac acaactttc attgcagaca agtgctgttg ttttgaaaaa cactgcaggt       540
gctacaaagg tcatagcagc tcaggcacag caagctcacg tgcaggcacc tcagattggg      600
gcgtggcgaa acagattgca tttcctagaa ggccccagc gatgtggatt gaagcgcaag       660
agtgaggagt tggataatca tagcagcgca atgcagattg tcgatgaatt gtccatactt      720
cctgcaatgt tgcaaaccaa catgggaaat ccagtgacag ttgtgacagc taccacagga      780
tcaaaacaga attgtaccac tggagaaggt gactatcagt tagtacagca tgaagtctta      840
tgctccatga aaaatactta cgaagtcctt gattttcttg tcgaggcac gtttggccag       900 gtagttaaat gctggaaaag agggacaaat gaaattgtag caatcaaaat tttgaagaat      960
catccttctt atgcccgtca aggtcaaata gaagtgagca tattagcaag gctcagtact     1020
gaaaatgctg atgaatataa ctttgtacga gcttatgaat gctttcagca ccgtaaccat     1080
acttgtttag tctttgagat gctggaacaa aacttgtatg actttctgaa acaaaataaa     1140
tttagtcccc tgccactaaa agtgattcgg cccattcttc aacaagtggc cactgcactg     1200
aaaaaattga aaagtcttgg tttaattcat gctgatctca gccagagaa tattatgttg     1260 gtggatcctt tcggcagcc ttacagggtt aaagtaatag actttgggtc ggccagtcat     1320
gtatcaaaga ctgtttgttc aacatatcta caatctcggt actacagagc tccagagatt     1380
atattggggt tgccattttg tgaagccata gacatgtggt cattgggatg tgtgattgca     1440
gaattatttc ttgatggcc gctctaccca ggagccttgg agtatgatca gattcgatac     1500
atttctcaga ctcaaggttt gccaggagaa cagttgttaa atgtgggtac taaatccaca     1560 agatttttt gcaaagaaac agatatgtct cattctggtt ggagattaaa gacattggaa     1620
gagcatgagg cagagacagg aatgaagtct aaagaagcca gaaatacat tttcaacagt     1680 ctggatgatg tagcgcatgt gaacacagtg atggatttgg aaggaagtga tcttttggct     1740
gagaaagctg atagaagaga atttgttagt ctgttgaaga aatgttgct gattgatgca     1800 gatttaagaa ttactccagc tgagaccctg aaccatcctt ttgttaatat gaaacatctt     1860
ctagatttcc ctcatagcaa ccatgtaaag tcctgttttc atattatgga tatttgtaag     1920
tcccacctaa attcatgtga cacaaataat cacaacaaaa cttcactttt aagaccagtt     1980
gcttcaagca gtactgctac actgactgca aattttacta aaatcggaac attaagaagt     2040
caggcattga ccacatctgc tcattcagtt gtgcaccatg gaatacctct gcaggcagga     2100
actgctcagt ttggttgtgg tgatgctttt cagcagacat tgattatctg tcccccagct     2160
attcaaggta ttcctgcaac acatggtaaa cccaccagtt attcaataag ggtagataat     2220
```

```
acagttccac ttgtaactca ggccccagct gtgcagccac tacagatccg accaggagtt    2280
ctttctcaga cgtggtctgg tagaacacag cagatgctgg tgcctgcctg gcaacaggtg    2340
acacccctgg ctcctgctac tactacacta acttctgaga gtgtggctgg ttcacacagg    2400
cttggagact gggggaagat gatttcatgc agcaatcatt ataactcagt gatgccgcag    2460
cctcttctga ccaatcagat aactttatct gcccctcagc cagttagtgt ggggattgca    2520
catgttgtct ggcctcagcc tgccactacc aagaaaaata aacagtgcca gaacagaggt    2580
attttggtaa aactaatgga atgggagcca ggaagagagg aaataaatgc tttcagttgg    2640
agtaattcat tacagaatac caatatccca cattcagcat ttatttctcc aaagataatt    2700
aatgggaaag atgtcgagga agtaagttgt atagaaacac aggacaatca gaactcagaa    2760
ggagaggcaa gaaattgctg tgaaacatct atcagacagg actctgattc atcagtttca    2820
gacaaacagc ggcaaaccat cattattgcc gactccccga gtcctgcagt gagtgtcatc    2880
actatcagca gtgacactga tgaggaagag acttcccaga gacattcact cagagaatgt    2940
aaaggtagtc tagattgtga agcttgccag agcactttga atattgatcg gatgtgttca    3000
ttaagtagtc ctgatagtac tctgagtacc agctcctcag gcagtccagc ccatccccc    3060 tgcaagagac cgaatagtat gtcagatgaa gagcaagaaa gtagttgtga tacggtggat    3120
ggctctccga catctgactc ttccgggcat gacagtccat ttgcagagag cacttttgtg    3180
gaggacactc atgaaaacac agaattggta tcctctgctg acacagaaac caagccagct    3240
gtctgttctg ttgtggtgcc accagtgaaa ctagaaaatg gcttaaatgc cgatgagcat    3300
atggcaaaca cagattctat atgccagcca ttaataaaag gacgatctgc ccctggaaga    3360
ttaaaccagc cttctgcagt gggtactcgt cagcaaaaat tgacatcagc attccagcag    3420
cagcatttga acttcagtca ggttcagcac tttggatctg ggcatcaaga gtggaatgga    3480
aactttgggc acagaagaca gcaagcttat attcctacta gtgttaccag taatccattc    3540
actctttctc atggaagtcc caatcacaca gcagtgcatg cccacctggc tggaaataca    3600
cacctcggag acagcctac tctacttcca tacccatcat cagccaccct cagtagtgct    3660
gcaccagtgg cccacctgtt agcctctccg tgtacctcaa gacctatgtt acagcatcca    3720
acttataata tctcccatcc cagtggcata gttcaccaag tcccagtggg cttaaatccc    3780
cgtctgttac catccccaac cattcatcag actcagtaca aaccaatctt cccaccacat    3840
tcttacattg cagcatcacc tgcatatact ggatttccac tgagtccaac aaaactcagc    3900
cagtatccat atatgtgaaa aacagtatat tggggaagct caatgataca acatttgat    3960 taaaaataaa aacatggtat ttaatattag ccatggcaca agaaaattat ttttgaatca    4020
tgtagacttg ggtgcaattt aaacaacttt gagctttaaa aactcacttt tgatgtgttt    4080
tgcacatttg gtataacttg tctttggtca tgttatcttc ttatgtagta actctagaca    4140
ggtgacttat gggagcagaa gtccagtttt gctcctgcta ttttttataa attgccttct    4200
aactagtgca agacacgtct acatttggga agccattctg tgtacagact tagagcaaca    4260
gatgcacata tgtcagaatt acagcataca agtgaattgt attatccgtg tcttagtgta    4320
taaatgttgg gtcacttacc taagaaattg agctattgtt ctttacattt gcatgtgtct    4380
tttgcatggg caaatgttg cctagacttt gctcttaaat gttgttctaa taatctcagc    4440
tgcattgtaa accgttccta cacatagtgc cttaaatatt tgaggttgtt aatgttatta    4500
cctatatata aatgttgagg actgcagcac ttaaaattca gacctactat ttagtttcct    4560
```

```
tttgatagcg taatgttcat ttttgttttt gtgtggtatg atttcaggta gtagctgttt    4620
ttttccttat taagagggca gcatgtttgc tatagctgaa ttctgctgtc tgattttca     4680 gaatgatcta gcttcaagaa aagcaagcag ttagtagtgc ttaagaaaaa ttgattcagt    4740
atc                                                                 4743
```

```
<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agttctgggt attccacctg ctca                                            24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgaagtttac gggttcctgg tggt                                            24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tccaccttct agctcagctt ccaa                                            24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggcaacact gtcctctgct gaat                                            24

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gccagctcca tctccagttc t                                               21

<210> SEQ ID NO 15
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 15
cacaatatcg gttgctgtag cggt                                              24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgcaatcctt ctgaaccacc tcca                                              24

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gctgttctac cttcatctca cctcca                                            26

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aggctgtcat cactcgagca gaaa                                              24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agtcctgctg atcacctgaa tgct                                              24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gccgatgagc atatggcaaa caca                                              24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
```

```
                              primer

<400> SEQUENCE: 21
tacccactgc agaaggctgg ttta                                              24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acaacaacgc ccacttcttg gtgg                                              24

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgctcacgtc cagcacctc                                                    19

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcttgctttc tgtagggctt tctg                                              24

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tctcaaagga gctggaagtg c                                                 21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agcatgcaaa acagcccagg                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 27
acggtttctc ccagctcttc                                               20

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgacaggagg agagctagg                                                19

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aagagatcct cctgccttgg                                               20

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Ile Val Ile Thr
1               5

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
agguggaggu gcaauauua                                                19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
cuuuaagccu cgagauaua                                                19

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 33

Ser Pro Arg Ile Glu Ile Thr
1               5

<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Pro Gln Arg Ser Arg Ser Pro Ser Pro Gln Pro Ser Pro His Val
1               5                   10                  15

Ala Pro Gln Asp Asp
            20

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Pro Arg Thr Ser Pro Ile Met Ser Pro Arg Thr Ser Leu Ala Glu
1               5                   10                  15

Asp

<210> SEQ ID NO 36
<211> LENGTH: 27
<212> TYPE: PRT
<213> ORGANISM: Homo sapiens

<400> SEQUENCE: 36

Leu Lys Ala Ser Ser Arg Thr Ser Ala Leu Leu Ser Gly Phe Ala Met
1               5                   10                  15

Val Ala Met Val Glu Val Gln Leu Asp Ala Asp
            20                  25

<210> SEQ ID NO 37
<211> LENGTH: 27
<212> TYPE: PRT
<213> ORGANISM: Mus musculus

<400> SEQUENCE: 37

Leu Lys Ala Ser Ser Arg Thr Ser Ala Leu Leu Ser Gly Phe Ala Met
1               5                   10                  15

Val Ala Met Val Glu Val Gln Leu Asp Thr Asp
            20                  25

<210> SEQ ID NO 38
<211> LENGTH: 27
<212> TYPE: PRT
<213> ORGANISM: Rattus norvegicus

<400> SEQUENCE: 38

Leu Lys Ala Ser Ser Arg Thr Ser Ala Leu Leu Ser Gly Phe Ala Met
1               5                   10                  15

Val Ala Met Val Glu Val Gln Leu Asp Thr Asp
```

<210> SEQ ID NO 39
<211> LENGTH: 27
<212> TYPE: PRT
<213> ORGANISM: Bos taurus

<400> SEQUENCE: 39

Leu Lys Ala Ser Ser Arg Thr Ser Ala Leu Leu Ser Gly Phe Ala Met
1               5                   10                  15

Val Ala Met Val Glu Val Gln Leu Asp Ala Asp
            20                  25

<210> SEQ ID NO 40
<211> LENGTH: 27
<212> TYPE: PRT
<213> ORGANISM: Canis familiaris

<400> SEQUENCE: 40

Leu Lys Ala Ser Ser Arg Thr Ser Ala Leu Leu Ser Gly Phe Ala Met
1               5                   10                  15

Val Ala Met Val Glu Val Gln Leu Asp Ala Asp
            20                  25

<210> SEQ ID NO 41
<211> LENGTH: 27
<212> TYPE: PRT
<213> ORGANISM: Caenorhabditis elegans

<400> SEQUENCE: 41

Leu Lys Ala Ser Ser Arg Thr Ser Ala Leu Leu Ala Gly Phe Ala Met
1               5                   10                  15

Val Cys Leu Val Glu Leu Gln Tyr Asp Gln Ser
            20                  25

<210> SEQ ID NO 42
<211> LENGTH: 27
<212> TYPE: PRT
<213> ORGANISM: Gallus gallus

<400> SEQUENCE: 42

Leu Lys Ala Ser Ser Arg Thr Ser Ala Leu Leu Ser Gly Phe Ala Met
1               5                   10                  15

Val Ala Met Val Glu Val Gln Leu Asp Ala Glu
            20                  25

<210> SEQ ID NO 43
<211> LENGTH: 27
<212> TYPE: PRT
<213> ORGANISM: Tetraodon nigroviridis

<400> SEQUENCE: 43

Leu Lys Ala Ser Ser Arg Thr Ser Ala Leu Leu Ser Gly Phe Ala Met
1               5                   10                  15

Val Ala Met Val Glu Val Gln Leu Asp Asn Thr
            20                  25

<210> SEQ ID NO 44
<211> LENGTH: 27
<212> TYPE: PRT
<213> ORGANISM: Danio rerio

<400> SEQUENCE: 44

Leu Lys Ala Ser Ser Arg Thr Ser Ala Leu Leu Ser Gly Phe Ala Met
1               5                   10                  15

Val Ala Met Val Glu Val Gln Leu Asp Thr Asn
            20                  25

<210> SEQ ID NO 45
<211> LENGTH: 27
<212> TYPE: PRT
<213> ORGANISM: Xenopus tropicalis

<400> SEQUENCE: 45

Leu Lys Ala Ser Ser Arg Thr Ser Ala Leu Leu Ser Gly Phe Ala Met
1               5                   10                  15

Val Ala Met Val Glu Val Gln Leu Glu Ala Asp
            20                  25

<210> SEQ ID NO 46
<211> LENGTH: 27
<212> TYPE: PRT
<213> ORGANISM: Drosophila melanogaster

<400> SEQUENCE: 46

Leu Lys Ala Ser Ser Lys Thr Ser Ala Leu Leu Ser Gly Phe Ala Met
1               5                   10                  15

Val Ala Met Val Glu Val Gln Leu Asp His Asp
            20                  25

<210> SEQ ID NO 47
<211> LENGTH: 27
<212> TYPE: PRT
<213> ORGANISM: Strongylocentrotus purpuratus

<400> SEQUENCE: 47

Leu Lys Ala Ser Ser Arg Thr Ser Ala Leu Leu Ala Gly Phe Ala Met
1               5                   10                  15

Val Ala Met Val Glu Val Gln Leu Ser Ala Thr
            20                  25

<210> SEQ ID NO 48
<211> LENGTH: 27
<212> TYPE: PRT
<213> ORGANISM: Homo sapiens

<400> SEQUENCE: 48

Leu Lys Ala Ser Ser Arg Thr Ser Ala Leu Leu Ser Gly Phe Ala Met
1               5                   10                  15

Val Ala Met Val Glu Val Gln Leu Glu Thr Gln
            20                  25

<210> SEQ ID NO 49
<211> LENGTH: 27
<212> TYPE: PRT
<213> ORGANISM: Homo sapiens

<400> SEQUENCE: 49

Leu Lys Ala Ser Ser Arg Thr Ser Ala Leu Leu Ser Gly Phe Ala Met
1               5                   10                  15

Val Ala Met Val Glu Val Gln Leu Glu Thr Asp
            20                  25

<210> SEQ ID NO 50

```
<211> LENGTH: 20
<212> TYPE: PRT
<213> ORGANISM: Drosophila melanogaster

<400> SEQUENCE: 50

Gly Tyr Arg Glu Ser Pro Ala Ser Ser Gly Ser Ser Ala Ser Phe Ile
1               5                   10                  15

Ser Asp Thr Phe
            20

<210> SEQ ID NO 51
<211> LENGTH: 17
<212> TYPE: PRT
<213> ORGANISM: Drosophila melanogaster

<400> SEQUENCE: 51

Ser Pro Arg Thr Ser Pro Ile Met Ser Pro Arg Thr Ser Leu Ala Glu
1               5                   10                  15

Asp

<210> SEQ ID NO 52
<211> LENGTH: 21
<212> TYPE: PRT
<213> ORGANISM: Drosophila melanogaster

<400> SEQUENCE: 52

Ser Pro Gln Arg Ser Arg Ser Pro Ser Pro Gln Pro Ser Pro His Val
1               5                   10                  15

Ala Pro Gln Asp Asp
            20

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Pro Arg Ile Glu Ile Thr Pro Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

His Pro Val Ile Val Ile Thr Gly Pro
1               5
```

REGULATORS OF NFAT

CROSS-REFERENCED TO RELATED APPLICATIONS

This application is a Continuation application of U.S. Utility application Ser. No. 12/160,030 filed Oct. 28, 2008, which is a 35 U.S.C. §371 National Phase Entry Application of International Application No. PCT/US2007/000280 filed Jan. 5, 2007, which designates the U.S. and which claims benefit under 35 U.S.C. §119(e) to U.S. Provisional Application 60/756,934, filed, Jan. 5, 2006, the entire contents of which are incorporated by reference herein.

GOVERNMENT SUPPORT

This invention was supported, in part, by National Institutes of Health (NIH) Grant Nos. RO1 AI40127, HD39685, R21 AI054933, and GM 075256. The government of the United States has certain rights to the invention.

FIELD OF THE INVENTION

The invention relates to the field of regulation of a family of calcium regulated transcription factors known as NFAT proteins.

BACKGROUND OF THE INVENTION

Hyperactivity or inappropriate activity of the immune system is a serious and widespread medical problem. It contributes to acute and chronic immune diseases, e.g., allergic and atopic diseases, e.g., asthma, allergic rhinitis, allergic conjunctivitis and atopic dermatitis, and to autoimmune diseases, e.g., rheumatoid arthritis, insulin-dependent diabetes, inflammatory bowel disease, autoimmune thyroiditis, hemolytic anemia and multiple sclerosis. Hyperactivity or inappropriate activity of the immune system is also involved in transplant graft rejections and graft-versus-host disease.

A certain family of transcription factors, the NFAT proteins (nuclear factor of activated T cells), are expressed in immune cells and play a key role in eliciting immune responses. The NFAT proteins are activated by an increase in intracellular calcium levels, e.g., by means of store-operated calcium entry. The activated NFAT proteins, in turn, induce transcription of cytokine genes which are required for an immune response. The immunosuppressive drugs cyclosporin A and FK506 are potent inhibitors of cytokine gene transcription in activated immune cells, and have been reported to act by inhibiting calcineurin such that calcineurin is not able to activate NFAT. These drugs, however, can display nephrotoxic and neurotoxic effects after long term usage. Since calcineurin is ubiquitously expressed in many tissues, the drugs' inhibition of calcineurin activity toward substrates other than NFAT may contribute to the observed toxicity.

There is a need for immunosuppressive agents which selectively inhibit the store-operated calcium entry activation of NFAT.

SUMMARY OF THE INVENTION

The present invention provides a method for identifying an agent that modulates NFAT activity. In one embodiment, the agent modulates NFAT activity by means of modulating intracellular calcium levels. In one preferred embodiment, the agent modulates at least one component of the CRAC channel, e.g., an ORAI protein, e.g., proteins encoded by ORAI1 (NM_032790; SEQ ID NO: 1), ORAI2 (BC069270; SEQ ID NO: 2), and/or ORAI3 (NM_152288; SEQ ID NO: 3). In one embodiment, the agent modulates phosphorylation of NFAT, e.g., via modulation of a DYRK protein, e.g., proteins encoded by DYRK1A (NM_001396; SEQ ID NO:4), DYRK1B (NM_004714; SEQ ID NO:5), DYRK2 (NM_003583; SEQ ID NO:6), DYRK3 (NM_003582; SEQ ID NO:7), DYRK4 (NM_003845; SEQ ID NO:8) and/or DYRK6 (NM_005734; SEQ ID NO:9).

The present invention provides a method of identifying an agent that modulates an NFAT regulator protein, comprising contacting at least one test agent with a recombinant cell comprising at least one NFAT regulator protein or fragment or derivative thereof; assessing the effect of the test agent on an activity, interaction, expression, or binding to the NFAT regulator protein or fragment or derivative thereof; and identifying the test agent that has an effect on an activity, interaction, expression, or binding to the NFAT regulator protein or fragment or derivative thereof, whereby the identified test agent is characterized as an agent that modulates an NFAT regulator protein.

In one embodiment, the NFAT regulator protein is encoded by at least one NFAT regulator selected from the group consisting of ORAI1 (SEQ ID NO:1), ORAI2 (SEQ ID NO:2), ORAI3 (SEQ ID NO:3), DYRK1A (SEQ ID NO:4), DYRK1B (SEQ ID NO:5), DYRK2 (SEQ ID NO:6), DYRK3 (SEQ ID NO:7), DYRK4 (SEQ ID NO:8) and DYRK6 (SEQ ID NO:9). In one embodiment, the NFAT regulator protein is encoded by at least one of the genes listed in Table I.

In one embodiment, assessing the effect of the test agent comprises using an antibody which specifically binds to a NFAT regulator protein encoded by ORAI1 (SEQ ID NO: 1), ORAI2 (SEQ ID NO: 2), ORAI3 (SEQ ID NO: 3), DYRK1A (SEQ ID NO:4), DYRK1B (SEQ ID NO:5), DYRK2 (SEQ ID NO:6), DYRK3 (SEQ ID NO:7), DYRK4 (SEQ ID NO:8), or DYRK6 (SEQ ID NO:9).

In one embodiment, the method further comprises assessing the effect of the test agent on electrical current across the plasma membrane of the cell. In one embodiment, the electrical current is due to flux of monovalent cations or divalent cations across the cell. In one embodiment, the method further comprises assessing the effect of the test agent on intracellular calcium within the cell. In one embodiment, the method further comprises identifying the test agent that has an effect on intracellular calcium within the cell, whereby the identified test agent is characterized as an agent that modulates intracellular calcium and an agent that modulates NFAT regulator protein.

In one embodiment, the cell comprises at least one heterologous NFAT regulator proteins or a fragment or derivative thereof. In one embodiment, the cell comprises heterologous nucleic acid encoding at least one NFAT regulator protein or a fragment or derivative thereof. In one embodiment, the cell overexpresses, or underexpresses at least one NFAT regulator protein or fragment or derivative thereof.

The present invention further provides a method of identifying an agent that modulates intracellular calcium, comprising contacting at least one test agent with a recombinant cell comprising at least one NFAT regulator protein or fragment or derivative thereof; assessing the effect(s) of the test agent on intracellular amounts, or concentrations, of cations or divalent cations within the cell, or on ion influx into the cell; and identifying the test agent that has an effect on intracellular amounts or concentrations of cations or divalent cations within the cell, or on ion influx into the cell, whereby the identified test agent is characterized as an agent that modulates intracellular calcium. In one embodiment, the intracellular cation is calcium. In one embodiment, assessing the effect of the test agent comprises monitoring calcium levels in the cytoplasm, monitoring calcium levels in an intracellular calcium store, monitoring calcium movement, or monitoring a calcium-entry mediated event. In one embodiment, the method further comprises assessing the effect of the test agent on an activity, interaction, expression, or binding to the NFAT regulator protein or fragment or derivative thereof. In one embodiment, the NFAT regulator protein is encoded by at least one NFAT regulator selected from the group consisting of ORAI1 (SEQ ID NO: 1), ORAI2 (SEQ ID NO: 2), or ORAI3 (SEQ ID NO: 3), DYRK1A (SEQ ID NO:4), DYRK1B (SEQ ID NO:5), DYRK2 (SEQ ID NO:6), DYRK3 (SEQ ID NO:7), DYRK4 (SEQ ID NO:8) or DYRK6 (SEQ ID NO:9). In one embodiment, the agent that modulates intracellular calcium is further characterized as an agent that modulates NFAT regulator protein. In one embodiment, the recombinant cell comprises at least one heterologous NFAT regulator proteins or a fragment or derivative thereof. In one embodiment, the recombinant cell comprises a heterologous nucleic acid encoding at least one NFAT regulator proteins or fragment or derivative thereof. In one embodiment, the recombinant cell overexpresses at least one NFAT regulator protein or fragment or derivative thereof. In one embodiment, the recombinant cell exhibits dyshomeostasis. In one embodiment, the recombinant cell exhibits calcium dyshomeostasis The present invention further provides a method to screen for an agent that modulates NFAT regulator function, comprising administering at least one test agent to a recombinant cell comprising at least one vector that comprises heterologous nucleic acid encoding at least one NFAT regulatory domain or a fragment or derivative thereof, operably linked to a sequence encoding a reporter protein; and monitoring intracellular localization of at least one expression product encoded by the vector, whereby a test agent that has an effect on intracellular localization of the expression product is characterized as an agent that modulates NFAT regulator function. In one embodiment, the agent that modulates NFAT regulator function is associated with cytoplasmic or nuclear localization of the expression product. In one embodiment, the cell is under resting conditions. In one embodiment, the cell is stimulated with a calcium modulating agent. In one embodiment, the cell is stimulated with thapsigargin or ionomycin. In one embodiment, the cell is further administered a vector that comprises a heterologous nucleic acid encoding at least one NFAT regulator protein, or a fragment or derivative thereof. In one embodiment, the vector that comprises the heterologous nucleic acid encoding at least one NFAT regulator protein, or fragment or derivative thereof, is the same vector that comprises heterologous nucleic acid encoding at least one NFAT regulatory domain or a fragment or derivative thereof, operably linked to a sequence encoding a reporter protein.

The present invention further provides a method to diagnose unexplained immunodeficiency in a subject comprising sequencing at least 25 contiguous nucleotides in a gene from the subject corresponding to ORAI1 (SEQ ID NO:1), ORAI2 (SEQ ID NO:2), ORAI3 (SEQ ID NO:3), DYRK1A (SEQ ID NO:4), DYRK1B (SEQ ID NO:5), DYRK2 (SEQ ID NO:6), DYRK3 (SEQ ID NO7), DYRK4 (SEQ ID NO:8), DYRK6 (SEQ ID NO:9), or any of the genes listed in Table I; and comparing the sequence of the subject's gene to the wild type sequence of the gene, wherein a variation between the gene from the wild type sequence indicates the subject's gene is responsible for the immunodeficiency. In one embodiment, the comparison comprises obtaining a biological sample from the subject, sequencing the DNA in the biological sample, and electronically aligning the DNA sequence obtained from the biological sample to a wild type sequence. In one embodiment, the variation comprises a nucleotide mutation from C to T at position 271 of the coding sequence of ORAI1 (SEQ ID NO: 1). In one embodiment, the unexplained immunodeficiency is associated with defects in regulation of NFAT activity. In one embodiment, the variation comprises a mutation in a splice site. In one embodiment, the variation comprises a nonsynonymous mutation.

The present invention further provides a method for identifying an agent for treating or preventing a disease or disorder associated with a NFAT regulator protein, comprising assessing the effects of a test agent on an organism exhibiting a disease or disorder associated with NFAT regulator protein; and identifying the test agent as an agent for treating or preventing a disease or disorder associated with NFAT regulator protein if it has an effect on a phenotype of the organism associated with the disease or disorder, wherein the test agent modulates an activity, interaction, expression, or binding of, at least one NFAT regulator protein or fragment or derivative thereof. In one embodiment, the organism comprises one or more cells that exhibit calcium dyshomeostasis. In one embodiment, the organism exhibits calcium dyshomeostasis. In one embodiment, the phenotype on which the test agent has an effect is associated with the disease or disorder. This method is particularly useful, for diseases or conditions associated with altered regulation of intracellular calcium. In one embodiment, the disease or disorder is primarily attributable to deranged calcium signaling. In one embodiment, the disease or disorder associated with NFAT regulator protein is rheumatoid arthritis, inflammatory bowel disease, allogeneic or xenogeneic transplantation rejection, graft-versus-host disease, aplastic anemia, psoriasis, lupus erytematosus, inflammatory disease, MS, type I diabetes, asthma, pulmonary fibrosis, scleroderma, dermatomyositis, Sjogren's syndrome, postpericardiotomy syndrome, Kawasaki disease, Hashimoto's thyroiditis, Graves' disease, myasthenia gravis, pemphigus vulgaris, autoimmune hemolytic anemia, idiopathic thrombopenia, chronic glomerulonephritis, Goodpasture's syndrome, Wegner's granulomatosis, multiple sclerosis, cystic fibrosis, chronic relapsing hepatitis, primary biliary cirrhosis, uveitis, allergic rhinitis, allergic conjunctivitis, atopic dermatitis, Crohn's disease, ulcerative colitis, colitis/inflammatory bowel syndrome, Guilllain-Barre syndrome, chronic inflammatory demyelinating polyradiculoneuropathy, eczema, and autoimmune thyroiditis. Transplant graft rejections, acquired immunodeficiencies, common variable immunodeficiency, myocardial hypertrophy, severe combined immunodeficiency, dilated cardiomyopathy, excessive or pathological bone resorption, excessive adipocyte differentiation, obesity, or reactivation of latent viruses.

The present invention further provides an antibody which specifically binds to a NFAT regulator protein encoded by ORAI1 (SEQ ID NO: 1), ORAI2 (SEQ ID NO: 2), or ORAI3 (SEQ ID NO: 3), DYRK1A (SEQ ID NO:4), DYRK1B (SEQ ID NO:5), DYRK2 (SEQ ID NO:6), DYRK3 (SEQ ID NO:7), DYRK4 (SEQ ID NO:8) or DYRK6 (SEQ ID NO:9), or a homolog thereof.

The NFAT regulator protein of the invention can be produced by a variety of means known in the art, e.g. automated peptide synthesis or culturing a host cell comprising a recombinant vector, the recombinant vector comprising a nucleic acid sequence, the nucleic acid sequence comprising/encoding the NFAT regulator or a fragment or derivative thereof, wherein the host cell is cultured under conditions suitable for expression of the NFAT regulator.

The present invention further provides a system comprising an isolated cell comprising at least one heterologous NFAT regulator protein or fragment or derivative thereof, and/or at least one heterologous nucleic acid encoding a NFAT regulator protein or fragment or derivative thereof; and a monitoring agent used to monitor, detect, or measure electrical current across the plasma membrane of the cell. In one embodiment, the monitoring agent is an apparatus. In one embodiment, the electrical current is due to flux of cations or divalent ions across the cell. In one embodiment, the monitoring agent is used to monitor the effect of a test agent on intracellular calcium within the cell. In one embodiment, the monitoring agent is used to monitor, detect, or measure a calcium-entry mediated event.

The present invention further provides a system comprising a recombinant cell overexpressing at least one mammalian NFAT regulator protein or fragment or derivative thereof; and a monitoring agent used to monitor, detect, or measure a calcium-entry mediated event. In one embodiment, the NFAT regulator is encoded by ORAI1 (SEQ ID NO: 1), ORAI2 (SEQ ID NO: 2), or ORAI3 (SEQ ID NO: 3), DYRK1A (SEQ ID NO: 4), DYRK1B (SEQ ID NO: 5), DYRK2 (SEQ ID NO: 6), DYRK3 (SEQ ID NO: 7), DYRK4 (SEQ ID NO: 8) or DYRK6 (SEQ ID NO: 9).

The present invention further provides a recombinant cell comprising at least one heterologous NFAT regulator protein or fragment or derivative thereof, and/or at least one heterologous nucleic acid encoding a NFAT regulator protein or fragment or derivative thereof. In one embodiment, the recombinant cell overexpresses at least one mammalian NFAT regulator protein or fragment or derivative thereof.

The present invention further provides a recombinant cell overexpressing at least on mammalian NFAT regulator protein or fragment or derivative thereof.

The present invention further provides a method for identifying an agent for treating or
preventing a disease or disorder associated with calcium signaling. The method comprises assessing the effects of a test agent on an organism exhibiting the disease or disorder, and identifying the test agent as an agent for treating or preventing the disease or disorder if it modulates an activity, interaction, expression, or binding of at least one NFAT regulator protein or fragment thereof. In one embodiment, the disease or disorder is rheumatoid arthritis, inflammatory bowel disease, allogeneic or xenogeneic transplantation rejection, graft-versus-host disease, aplastic anemia, psoriasis, lupus erytematosus, inflammatory disease, MS, type I diabetes, asthma, pulmonary fibrosis, scleroderma, dermatomyositis, Sjogren's syndrome, postpericardiotomy syndrome, Kawasaki disease, Hashimoto's thyroiditis, Graves' disease, myasthenia gravis, pemphigus vulgaris, autoimmune hemolytic anemia, idiopathic thrombopenia, chronic glomerulonephritis, Goodpasture's syndrome, Wegner's granulomatosis, multiple sclerosis, cystic fibrosis, chronic relapsing hepatitis, primary biliary cirrhosis, uveitis, allergic rhinitis, allergic conjunctivitis, atopic dermatitis, Crohn's disease, ulcerative colitis, colitis/inflammatory bowel syndrome, Guilllain-Barre syndrome, chronic inflammatory demyelinating polyradiculoneuropathy, eczema, and autoimmune thyroiditis. Transplant graft rejections, acquired immunodeficiencies, common variable immunodeficiency, myocardial hypertrophy, severe combined immunodeficiency, dilated cardiomyopathy, excessive or pathological bone resorption, excessive adipocyte differentiation, obesity, or reactivation of latent viruses.

BRIEF DESCRIPTION OF THE DRAWINGS

FIG. 1A shows a pedigree of patients with a defect in SOCE and CRAC channel function. Two male SCID patients (subject ID numbers 8 and 11; filled black squares) were born to consanguineous parents (subject ID numbers 35 and 36). For functional and genetic analysis, DNA and blood samples were obtained from all individuals shown in yellow or black. Half black squares or circles indicate heterozygous disease carriers as determined by phenotypic analysis. Double horizontal bars indicate consanguineous marriages, black boxes SCID disease, diagonal bars death of individuals. FIG. 1B shows reduced SOCE in T cells of both parents of CRAC deficient SCID patients that defines them as heterozygous carriers of the disease trait. T cells were stimulated with thapsigargin (TG) in the absence of extracellular $Ca^{2+}$. The peak (upper panel) and rate (bottom panel) of $Ca^{2+}$ influx were measured after readdition of 0.5 mM extracellular $Ca^{2+}$. FIG. 1C shows reduced SOCE that phenotypically identifies 12/21 family members of the SCID patients as heterozygous disease trait carriers. $Ca^{2+}$ influx was measured as described in B but using 0.2 mM extracellular $Ca^{2+}$. Shown are the averages of $Ca^{2+}$ influx rates from 4-5 experiments. Individual ID numbers correspond to those shown in FIG. 1A. Stars indicate heterozygous carriers as defined by influx rates below 2 nM/s (dotted red line). Co, healthy control; P, patient.

FIG. 2A shows that RNAi of dSTIM or dOrai inhibits dephosphorylation of NFAT. S2R+ cells stably transfected with NFAT1(1-460)-GFP were incubated for 4 days with double-stranded (ds) RNAi against dSTIM, dOrai or an irrelevant DNA sequence (mock). Cells were left unstimulated (−TG) or stimulated with thapsigargin (+TG) for 10 min, then lysed after stimulation with TG, and cell extracts were separated by SDS-PAGE and immunoblotted with antibodies against NFAT1. Dephosphorylation of NFAT is evidenced by more rapid migration (lower band) on SDS-PAGE. FIG. 2B shows that RNAi of either dSTIM or dOrai inhibits $Ca^{2+}$ influx in S2R+ cells. Cells were left unstimulated (−TG) or stimulated with thapsigargin (+TG) for 10 min, then loaded with Fluo-4 and Fura-Red and analyzed for $Ca^{2+}$ influx by flow cytometry. 1 μM thapsigargin was added at the indicated time. The top line in each panel shows RNAi for Gfp and the bottom line RNAi for dSTIM or dOrai. Decreased $Ca^{2+}$ influx is indicated by the much reduced change in emission ratio following addition of thapsigargin.

FIGS. 3A-3C show that Orai1 is a transmembrane protein. FIG. 3A shows that Orai1 is highly conserved in eukaryotes. Shown is the sequence conservation in the first of four putative transmembrane regions (M1, underlined) of Orai1, which contains the R>W mutation (bold) found in the SCID patients. FIG. 3B shows membrane topology of Orai1. Hydropathy plots were calculated from the full-length amino acid sequence of human Orai1 (301 a.a., NP_116179) using the Kyte-Doolittle algorithm with a window size of 19 amino acids. Three transmembrane domains (M2-M4) are predicted with a score >1.8; M1 has a score of ~1.3. FIG. 3C shows schematic representation of the predicted membrane topology of Orai1, based on the hydropathy plot and immunocytochemistry data. The site of the R>W mutation in the SCID patients is indicated by a dark box. FIG. 4A shows activation of an inward current in an $Orai^{WT}$-complemented SCID T cell by passive store depletion with a pipette solution containing 8 mM BAPTA. At the indicated times, the 20 mM $Ca^{2+}_o$ solution was replaced with a divalent free (DVF) solution. Enhanced current in the absence of divalent cations is a characteristic of CRAC channels and certain other Ca$^{2+}$-selective channels. FIG. 4B shows the current-voltage (I-V) relation of currents in 20 mM Ca$^{2+}_o$ (left) and in DVF solution (right) measured during voltage ramps from −100 to +100 mV. Data were collected at the times indicated by the arrows in 4A. Note that the Ca$^{2+}$ current I-V relation is inwardly rectifying with a reversal potential >+90 mV. In DVF solution, the current reversed at ~+50 mV. FIG. 4C shows that SCID T cells expressing mutant Orai1$^{R>W}$, inward Ca$^{2+}$ and Na$^+$ currents fail to develop during passive store depletion by 8 mM BAPTA. FIG. 4D shows noise characteristics of the depotentiating Na$^+$ current. Top graph shows the mean current at a constant holding potential of −100 mV. The dotted line indicates the zero current level (measured in 20 mM Ca$^{2+}$+2 μM La$^{3+}$). Variance was calculated from 100-ms segments of the Na$^+$ current and plotted against mean current in lower panel. The data are fit by a straight line with a slope of 26 fA, giving a lower limit to the unitary current. FIG. 4E shows fast inactivation of the Ca$^{2+}$ current in a SCID T cell expressing Orai$^{WT}$. Fast inactivation was measured during 300-ms steps to −100 mV from a holding potential of +30 mV with 20 mM Ca$^{2+}_o$. FIG. 4F shows blockade of the Ca$^{2+}$ current by 2 μM La$^{3+}$. After passive induction of the inward current in a SCID T cell expressing Orai$^{WT}$, 2 μM La$^{3+}$ was applied. The dotted line indicates the zero current level, determined from traces collected at the beginning of the experiment immediately following whole-cell break-in. FIG. 4G shows potentiation and blockade of I$_{CRAC}$ by application, respectively, of low (5 μM) and high (40 μM) doses of 2-APB. FIG. 4H shows the summary of peak current densities in the indicated cell categories. Peak currents were measured during steps to −100 mV. Reconstitution with wild-type Orai1 thus reconstitutes a current with the expected characteristics of native CRAC channels. Cells transduced with Orai1$^{WT}$ or Orai1$^{R>W}$ were visually selected based on GFP-fluorescence; untransduced cells were GFP-negative.

FIG. 5A shows inhibition of Ca$^{2+}$ influx in Orai1$^{WT}$ expressing SCID fibroblasts by 75 μM 2-APB. FIG. 5B shows potentiation of Ca$^{2+}$ influx in Orai1$^{WT}$-expressing SCID fibroblasts by 3 μM 2-APB. FIGS. 5C-5D shows inhibition of Ca$^{2+}$ influx in Orai1$^{WT}$-expressing SCID fibroblasts by 2 μM La$^{3+}$ added before (FIG. 5C) or after (FIG. 5D) readdition of 20 mM Ca$^{2+}$. For each experiment, ~15-20 GFP-positive fibroblasts were analyzed. Experiments were repeated at least three times for each protocol.

FIGS. 6A-6C show the NFAT regulatory domain and results of the genome-wide RNAi screen in Drosophila. FIG. 6A shows a schematic diagram of the N-terminal regulatory domain of NFAT1, showing the conserved phosphorylated serine motifs which are dephosphorylated upon stimulation (circles). Peptides corresponding to the SRR1, SP2 and SP3 motifs used for in vitro kinase assays are represented. Serine residues shown underlined have been identified to be phosphorylated in NFAT1 in vivo, and these are the residues mutated to alanine in the mutant SP2 and SP3 motifs. FIG. 6B shows that heterologously expressed NFAT is correctly regulated by Ca$^{2+}$ and calcineurin in Drosophila S2R+ cells. Drosophila S2R+ cells were transfected with NFAT1-GFP expression vector. 48 hrs later, the cells were left untreated (Untr) or treated with thapsigargin (TG, 1 μM) for 30 min and lysates from the cells were analysed by immunoblotting (IB) with anti-NFAT1. P and deP refer to the migration positions of phosphorylated and dephosphorylated NFAT-GFP, respectively. FIG. 6C shows the tabulation of the results of the primary screen.

FIG. 7A shows the ability of overexpressed mammalian homologs of the candidate kinases to directly phosphorylate the NFAT regulatory domain. FLAG-tagged mammalian homologues of selected Drosophila kinases were expressed in HEK293 cells, and immunopurified kinases were tested using an in vitro kinase assay for phosphorylation of GST-NFAT1(1-415). Phosphorylation levels were assessed by autoradiography with either short (top panel) or long (middle panel) exposures. Expression of each kinase was verified by immunoblotting (IB) using an anti-FLAG antibody. Kinases tested are as follows: lane 1, CK1α; lane 2, CK1ε; lane 3, Bub1; lane 4, STK38; lane 5, STK38L; lane 6, CDC42BPA; lane 7, ARAF; lane 8, PRKG1; lane 9, SGK; lanes 10 and 11, CSNKA1 and CSNKA2 (CKII isoforms); lane 12, SRPK1; lane 13, DYRK2; lane 14, ALS2CR7; lane 15, IRAK4. Bub1 was later dropped from our candidate list because of >10 predicted off-targets (Example 3). FIG. 7B shows overexpression of DYRK2 blocks calcineurin-mediated dephosphorylation of NFAT1. Each kinase was co-transfected with NFAT-GFP into HEK293 cells; after 18 hrs cells were stimulated with 1 μM ionomycin in the presence of 2 mM CaCl$_2$. Lysates were immunoblotted using NFAT1 antibody. Relative expression levels of the kinases were determined by immunoblot using anti-FLAG antibody, and were identical to those represented in FIG. 6A (bottom panel). FIG. 7C shows depletion of endogenous DYRK1A potentiates NFAT activation. HeLa cells stably expressing Ha-tagged NFAT1-GFP were transfected with control siRNA or DYRK1A-specific siRNA. After 4 days cells were stimulated with 1 μM thapsigargin (TG) or 1 μM thapsigargin (TG) followed by 20 nM CsA for indicated times; lysates were immunoblotted for NFAT-GFP using anti-HA antibody (left). DYRK1A mRNA levels (right) were assessed after 3 and 4 days by real-time PCR. siControl, scrambled control siRNA; siDYRK1A, DYRK1A-specific siRNA. Results show the average and standard deviation of three independent experiments.

FIG. 8A shows that overexpression of DYRK2 inhibits IL2 promoter-driven luciferase activity in stimulated Jurkat T cells. (The IL2 promoter is an example of a cytokine promoter whose activation exhibits a strong requirement for NFAT.) Exponentially growing Jurkat T cells were co-transfected with pRLTK (renilla luciferase, internal control), IL-2-pGL3 (IL-2-promoter driven firefly luciferase, experimental promoter) and empty vector or increasing amounts of wild type (WT) or kinase dead (KD) DYRK2 expression plasmids (5, 10, 15 and 20 μg). After 24 h cells untreated or stimulated with PMA and ionomycin for 6 h were analyzed for IL-2-promoter-driven luciferase activity. Firefly luciferase was normalized to renilla luciferase and fold induction calculated relative to IL-2 promoter activity measured in untreated cells. Results show the average and standard deviation of three independent experiments. FIG. 8B shows that overexpression of DYRK2 inhibits endogenous IL-2 expression in stimulated Jurkat T cells. Exponentially-growing Jurkat T cells were co-transfected with GFP and empty vector or increasing amounts of wild type (WT) or kinase dead (KD) DYRK2 expression plasmids (10, 20 and 30 μg). After 24 h cells untreated or stimulated with PMA and ionomycin for 6 h were evaluated for IL-2 expression in GFP+ cells by intracellular cytokine staining and flow cytometry. FIG. 8C shows quantification of the results shown in 8B. Results show the average and standard deviation of three independent experiments.

FIGS. 9A-9C shows that STIM proteins affect NFAT localization by altering store-operated $Ca^{2+}$ influx. FIG. 9A shows the percent of cells with nuclear NFAT was quantified in three independent experiments after mock treatment or treatment with dsRNAs against dSTIM. Mean and standard deviations are plotted. 50-100 cells were analyzed for each experiment. FIG. 9B shows the effect of RNAi-mediated depletion of *Drosophila* STIM (dSTIM) on NFAT phosphorylation status. Lysates made from unstirnulated or thapsigargin (TG)-stimulated S2R+ cells were examined by immunoblotting with antibody against NFAT1. The cells were mock-treated or treated for 4 days with dsRNAs targeting dSTIM. FIG. 9C shows intracellular $Ca^{2+}$ levels, analyzed by flow cytometry, in S2R+ cells depleted with dSTIM or novel gene candidates from the confirmatory screen. GFP dsRNA was used as a control for non-specific effects caused by dsRNA treatment. After 30 sec of basal $[Ca^2]_I$ measurement, 1 μM thapsigargin was added (arrow) and $[Ca^2]_I$ measurements were continued for a further 5 min. Depletion of dSTIM almost completely abolishes thapsigargin-triggered, that is store-operated, $Ca^{2+}$ influx.

FIG. 10A shows the phylogenetic tree of DYRK family kinases using distance-based methods (neighbour joining). The left-hand side figures show the homology relationships between *Drosophila* CG40478 and human DYRK 2, 3; *Drosophila* CG4551 (smi35A) and human DYRK 4; *Drosophila* CG7826 (mnb) and human DYRK1A, B (top); as computed by the program Tcoffee. In the right-hand side figures, the orthologue bootstrap value for CG40478-DYRK2 is higher than for CG40478-DYRK3 (top). Therefore, DYRK2 is an orthologue of CG40478 (the genes diverged by a speciation event), while DYRK3 may be a paralogue (the genes diverged by a duplication event). The calculations of the ortholog bootstrap values were performed with Orthostrapper. FIG. 10B shows expression of DYRK family members in Jurkat T cells. Expression level of mammalian DYRK mRNAsin Jurkat T cells was estimated by RT-PCR analysis. Primers correspond to:

Figure 1A:
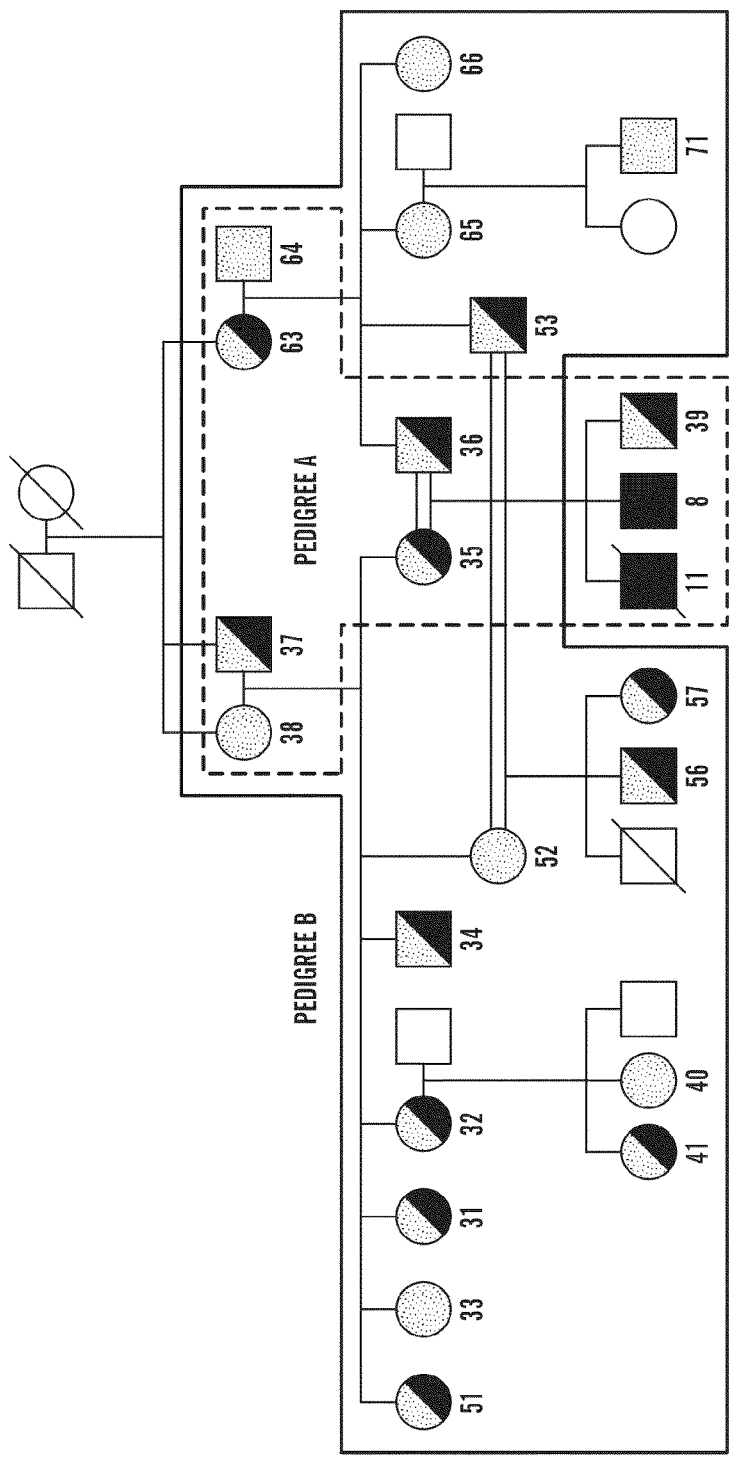
FIGS. 1A-1C show gene-dosage effect in store-operated $Ca^{2+}$ entry (SOCE).

```
DYRK1A sense:
                                     (SEQ ID NO: 10)
AGTTCTGGGTATTCCACCTGCTCA DYRK1A anti-sense:
                                     (SEQ ID NO: 11)
TGAAGTTTACGGGTTCCTGGTGGT;

DYRK2 sense:
                                     (SEQ ID NO: 12)
TCCACCTTCTAGCTCAGCTTCCAA, DYRK2 anti-sense:
                                     (SEQ ID NO: 13)
TGGCAACACTGTCCTCTGCTGAAT;

DYRK1B sense:
                                     (SEQ ID NO: 14)
GCCAGCTCCATCTCCAGTTCT, DYRK1B anti-sense:
                                     (SEQ ID NO: 15)
CACAATATCGGTTGCTGTAGCGGT;
```

```
-continued
DYRK3 sense:
                                     (SEQ ID NO: 16)
TGCAATCCTTCTGAACCACCTCCA, DYRK3 anti-sense:
                                     (SEQ ID NO: 17)
GCTGTTCTACCTTCATCTCACCTCCA;

DYRK4 sense:
                                     (SEQ ID NO: 18)
AGGCTGTCATCACTCGAGCAGAAA, DYRK4 anti-sense:
                                     (SEQ ID NO: 19)
AGTCCTGCTGATCACCTGAATGCT;

DYRK6 sense:
                                     (SEQ ID NO: 20)
GCCGATGAGCATATGGCAAACACA, DYRK6 anti-sense:
                                     (SEQ ID NO: 21)
TACCCACTGCAGAAGGCTGGTTTA.
```

FIGS. 11A-11I show the nucleotide sequences for NFAT regulator genes. FIG. 11A shows the nucleotide sequence ORAI1 (NM_032790; SEQ ID NO:1). FIG. 11B shows the nucleotide sequence for ORAI2 (BC069270; SEQ ID NO:2). FIG. 11C shows the nucleotide sequence for ORAI3 (NM_152288; SEQ ID NO:3). FIG. 11D shows the nucleotide sequence for DYRK1A (NM_001396; SEQ ID NO:4). FIG. 11E shows the nucleotide sequence for DYRK1B (NM_004714; SEQ ID NO:5). FIG. 11F shows the nucleotide sequence for DYRK2 (NM_003583; SEQ ID NO:6). FIG. 11G shows the nucleotide sequence for DYRK3 (NM_003582; SEQ ID NO:7). FIG. 11H shows the nucleotide sequence for DYRK4 (NM_003845; SEQ ID NO:8). FIG. 11I shows the nucleotide sequence for DYRK6 (NM_005734; SEQ ID NO:9).

DETAILED DESCRIPTION OF THE INVENTION

Aspects of the present invention relate to the characterization of genes regulating NFAT activity, for example, via Store-Operated Calcium Entry (SOCE) or via modulation of NFAT phosphorylation. In particular, to the discovery of an essential component of the $Ca^{2+}$ release-activated $Ca^{2+}$ (CRAC) channel. Accordingly, aspects of the invention relate to novel regulators of NFAT activity, particularly with regard to modulation of NFAT activity in T cells. Aspects of the invention also relate to methods to screen for novel agents that modulate NFAT activity. Aspects of the invention further relate to methods to screen for agents that modulate the activity of the NFAT regulators of the present invention. The invention further provides methods to screen for agents that modulate the NFAT regulators of the present invention by means of modulating intracellular calcium.

NFAT Genes and Proteins

By NFAT protein (nuclear factor of activated T cells) is meant a member of a family of transcription factors comprising the members NFAT1, NFAT2, NFAT3 and NFAT4, with several isoforms. Any other NFAT protein whose activation is calcineurin dependent is also meant to be included. NFAT proteins can be, e.g., mammalian proteins, e.g., human or murine. NFAT1, NFAT2 and NFAT4 are expressed in immune cells, e.g., T lymphocytes, and play a role in eliciting immune responses. NFAT proteins are involved in the transcriptional regulation of cytokine genes, e.g., IL-2, IL-3, IL-4, TNF-alpha and IFN-gamma, during the immune response.

The conserved regulatory domain of NFAT is an N-terminal region of NFAT which is about 300 amino acids in length. The conserved regulatory domain of murine NFAT1 is a region extending from amino acid residue 100 through amino acid residue 397, of human NFAT1 is a region extending from amino acid residue 100 through 395, of human NFAT2 is a region extending from amino acid residue 106 through 413, of human NFAT2b is a region extending from amino acid residue 93 through 400, of human NFAT3 is a region extending from amino acid residue 102 through 404, and of human NFAT4 is a region extending from amino acid residue 97 through 418. The conserved regulatory domain is moderately conserved among the members of the NFAT family, NFAT1, NFAT2, NFAT3 and NFAT4. The conserved regulatory region binds directly to calcineurin. The conserved regulatory region is located immediately N-terminal to the DNA-binding domain (amino acid residues 398 through 680 in murine NFAT1, amino acid residues 396 through 678 in human NFAT1, amino acid residues 414 through 696 in human NFAT2, amino acid residues 401 through 683 in human NFAT2b, amino acid residues 405 through 686 in human NFAT3, and amino acid residues 419 through 700 in human NFAT4).

Store Operated Calcium Entry

SOCE is one of the main mechanisms to increase intracellular cytoplasmic free $Ca^{2+}$ concentrations ($[Ca^{2+}]i$) in electrically non-excitable cells. $Ca^{2+}$ elevations are a crucial signal transduction mechanism in virtually every cell. The tight control of intracellular $Ca^{2+}$, and its utility as a second messenger, is emphasized by the fact that $[Ca^2]i$ levels are typically 70-100 nM while extracellular $Ca^{2+}$ levels ($[Ca^{2+}]ex$) are $10^4$-fold higher, ~1-2 mM. The immediate source of $Ca^{2+}$ for cell signaling can be either intracellular or extracellular (FIG. 1). Intracellular $Ca^{2+}$ is released from ER stores by inositol 1,4,5-triphosphate (IP3), or other signals, while extracellular $Ca^{2+}$ enters the cell through voltage-gated, ligand-gated, store-operated or second messenger-gated $Ca^{2+}$ channels in the plasma membrane. In electrically non-excitable cells such as lymphocytes, the major mechanism for $Ca^{2+}$ entry is store-operated $Ca^{2+}$ entry, a process controlled by the filling state of intracellular $Ca^{2+}$ stores. Depletion of intracellular $Ca^{2+}$ stores triggers activation of membrane $Ca^{2+}$ channels with specific electrophysiological characteristics, which are referred to as calcium release-activated $Ca^{2+}$ (CRAC) channels (Parekh and Putney, Jr. 2005, Physiol Rev 85:757).

$Ca^{2+}$ release activated $Ca^{2+}$ (CRAC) channels. The electrophysiological characteristics of CRAC channels have been studied intensively, but the molecular nature of the channel itself and the mechanisms of its activation remain unknown. One definition of CRAC channels holds that depletion of intracellular $Ca^{2+}$ stores is both necessary and sufficient for channel activation without direct need for increases in $[Ca^{2+}]$i, inositol phosphates IP3 or IP4, cGMP or cAMP (Parekh and Penner. 1997, Physiol Rev. 77:901). Biophysically, CRAC current is defined, amongst other criteria, by its activation as a result of ER $Ca^{2+}$ store depletion, its high selectivity for $Ca^{2+}$ over monovalent ($Cs^+$, $Na^+$) cations, a very low single channel conductance, a characteristic I-V relationship with pronounced inward rectification and its susceptibility to pharmacological blockade for instance by $La^{3+}$ and 2-APB (100 μM), respectively (Parekh and Putney, Jr. 2005, Physiol Rev 85:757; Lewis, 2001, Annu Rev Immunol 19:497).

Candidate genes for SOCE and CRAC. The molecular nature of the CRAC channel remains completely unknown. The most widely investigated candidate genes for the CRAC channel have been the >25 mammalian homologues of the Drosophila photoreceptor TRP (Transient Receptor Potential) gene. But most TRP proteins form non-specific cation channels and even those that show some preference for divalent cations do not exhibit all of the key biophysical hallmarks of the CRAC channel when heterologously expressed (Clapham, 2003. Nature 426:517). Until recently, TRPV6 was the most promising CRAC channel candidate gene because some of its biophysical features overlapped with that of CRAC. But while TRPV6, like CRAC, selectively conducts $Ca^{2+}$, it is not activated by store depletion, a defining characteristic of the CRAC channel. Knockdown studies using RNAi to suppress TRPV6 expression and our studies using T cells from TRPV6-/- mice showed no defect in SOCE or ICRAC in the absence of TRPV6 (Kahr, et al. 2004. J Physiol 557:121; Kepplinger, et al. Neither CaT1 nor TRPC3 proteins contribute to CRAC of T lymphocytes. Manuscript in preparation). Thus, neither TRPV6 nor any other gene has been confirmed to be involved in SOCE or CRAC channel activity.

Mechanisms of SOCE and CRAC Channel Activation.

The mechanism by which CRAC channels are activated is equally unclear. Depletion of intracellular $Ca^{2+}$ stores is necessary for CRAC activation but how the information about reduced $Ca^{2+}$ concentrations in the ER is conveyed to the CRAC pore is not known. Three main models have been proposed but no consensus has been reached (Parekh and Putney, Jr. 2005, Physiol Rev 85:757). (i) The "conformational coupling model" postulates a conformational change of a molecule at the surface of the ER which then binds to the CRAC channel; (ii) The "secretion coupling model" suggests that (constitutively active) CRAC channels reside in intracytoplasmic vesicles that fuse to the plasma membrane upon store depletion; (iii) The "Calcium influx factor (CIF) model" predicts a soluble small molecule, which activates $Ca^{2+}$ influx through CRAC channels when CIF is released into the cytoplasm of stimulated cells.

Stromal interaction molecule 1 (STIM1). Recent evidence suggests that STIM1 plays an important role in store operated $Ca^{2+}$ entry and CRAC channel function. Three independent RNAi screens by Roos et al. (2005, J Cell Biol 169:435), Liou et al. (2005, Curr Biol 15:1235) and by our group (see Example 2 below) have found that suppression of STIM expression by RNAi impairs $Ca^{2+}$ influx in Drosophila melanogaster S2 cells as well as mammalian cells (FIG. 5). STIM1 is a type I transmembrane protein which was initially characterized as a stromal protein promoting the expansion of pre-B cells and as a putative tumor suppressor (Oritani, et al. 1996. J Cell Biol 134:771; Sabbioni, et al. 1997. Cancer Res 57:4493). The human gene for STIM1 is located on chromosome 11p15.5 which is believed to contain genes associated with a number of pediatric malignancies, including Wilms tumor (Parker et al. 1996, Genomics 37:253). STIM1 contains a $Ca^{2+}$ binding EF hand motif and a sterile α-motif (SAM) domain in its ER/extracellular region, a single membrane-spanning domain, and two predicted cytoplasmic coiled-coil regions (Manji et al. 2000, Biochim Biophys Acta 1481:147). Domain structure and genomic organization are conserved in a related gene called STIM2, which differs from STIM1 mainly in its C-terminus (Williams et al. 2002, Biochim Biophys Acta 1596:131). STIM1 is able to homodimerize or heterodimerize with STIM2 (Williams et al. 2002 supra). Expressed in the ER, its C-terminal region is located in the cytoplasm whereas the N-terminus resides in the lumen of the ER, as judged by glycosylation and phosphorylation studies (Maji et al. 2000 supra; Williams et al. 2002 supra). A minor fraction of STIM1 is located in the plasma membrane. Although RNAi mediated suppression of STIM1 expression interferes with SOCE and CRAC channel function, STIM1 is unlikely to be a $Ca^{2+}$ channel itself. Rather it is thought that STIM1 may sense $Ca^{2+}$ levels in the ER via its EF hand (Putney, Jr. 2005. J Cell Biol 169:381; Marchant, 2005, Curr Biol 15:R493). Consistent with the conformational coupling model of store-operated $Ca^{2+}$ influx, STIM1 could act as a key adapter protein, which physically bridges the space between ER and plasma membrane, and thus directly connects sensing of depleted $Ca^{2+}$ stores to store-operated $Ca^{2+}$ channels in the plasma membrane (Putney, Jr. 2005. supra; Putney, Jr. 1986, Cell Calcium 7:1).

NFAT Regulators

As used herein, the term "NFAT regulators" is used to refer to the proteins (NFAT regulator proteins), and the encoding genes (NFAT regulator genes) which regulate NFAT activity. The methods of the present invention are intended to include use of homologues, analogues, isoforms (e.g. alternative splice variants), derivatives, and functional fragments of the NFAT regulators described herein. Preferably, homologues of NFAT regulator proteins have at least 70%, more preferably, 80%, and more preferably 90% amino acid identity to those specifically identified herein.

NFAT Regulator Proteins

In one preferred embodiment, the NFAT regulator proteins of the present invention are encoded by the ORAI genes. Previous to the discoveries upon which the present invention is based, the function of the ORAI genes was unknown. ORAI1 nucleic acid sequence corresponds to GenBank accession number NM_032790, ORAI2 nucleic acid sequence corresponds to GenBank accession number BC069270 and ORAI3 nucleic acid sequence corresponds to GenBank accession number NM_152288. As used herein, ORAI refers to any one of the ORAI genes, e.g., ORAI1, ORAI2, ORAI3.

In one embodiment, the NFAT regulator proteins of the present invention are encoded by the DYRK genes. Previous to the discoveries upon which the present invention is based, the DYRK genes were not known to regulate NFAT activity or function. DYRK1A is encoded by several nucleic acid isoforms including GenBank accession numbers NM_001396, NM_101395, NM_130436, NM_130437, and NM_130438. DYRK1B is encoded by multiple nucleic acid isoforms including GenBank accession numbers NM_004714, NM_006483, and NM_006484. DYRK2 is encoded by GenBank accession numbers including NM_003583 and NM_006482. DYRK3 is encoded by GenBank accession numbers including NM_001004023 and NM_003582. DYRK4 is encoded by GenBank accession number NM_003845. DYRK6, also known as HIPK3, is encoded by GenBank accession number NM_005734.

In one embodiment, the NFAT regulator proteins of the present invention are encoded by the genes listed in Table I.

The term "fragment" or "derivative" when referring to a NFAT regulator protein means proteins or polypeptides which retain essentially the same biological function or activity in at least one assay as the native NFAT regulator proteins. For example, the NFAT regulator fragments or derivatives of the present invention maintain at least about 50% of the activity of the native proteins, preferably at least 75%, more preferably at least about 95% of the activity of the native proteins, as determined e.g. by a calcium influx assay described in Example 1.

Fragments or derivatives as the term is used herein can include competitors of the native NFAT regulators with respect to a particular NFAT regulator domain activity. However, the fragment or derivative shows an overall similarity to NFAT regulators in other areas as explained herein.

The term fragment, as used herein, refers to a fragment of the NFAT regulator protein, or nucleic acid sequence, wherein the (encoded) protein retains at least one biological activity of the full length NFAT regulator protein. The term fragment and functional fragment are used herein interchangeably. A fragment of a sequence contains less nucleotides or amino acids than the corresponding full length sequences, wherein the sequences present are in the same consecutive order as is present in the full length sequence. As such, a fragment does not contain internal insertions or deletions of anything (e.g. nucleic acids or amino acids) in to the portion of the full length sequence represented by the fragment. This is in contrast to a derivative, which may contain internal insertions or deletions within the nucleic acids or amino acids that correspond to the full length sequence, or may have similarity to full length coding sequences.

A derivative may comprise the same or different number of nucleic acids or amino acids as full length sequences. The term derivative, as used herein with respect to an NFAT regulator protein, includes NFAT regulator proteins, or fragments thereof, which contain one or more modified amino acids. e.g. chemically modified, or modification to the amino acid sequence (substitution, deletion, or insertion). Such modifications should substantially preserve at least one biological activity of the NFAT regulator protein. Such biological activity is readily determined by a number of assays known in the art, for example, a calcium influx assay described below in Example 1. By way or nonlimiting example, a derivative may be prepared by standard modifications of the side groups of one or more amino acid residues of the NFAT regulator protein, its analog, or a functional fragment thereof, or by conjugation of the NFAT regulator protein, its analogs or fragments, to another molecule e.g. an antibody, enzyme, receptor, etc., as are well known in the art. Accordingly, "derivatives" as used herein covers derivatives which may be prepared from the functional groups which occur as side chains on the residues or the N- or C-terminal groups, by means known in the art, and are included in the invention. Derivatives may have chemical moieties such as carbohydrate or phosphate residues. Such a derivativization process should preserve at least one biological activity of the NFAT regulator protein. Derivatives can be made for convenience in expression, for convenience in a specific assay, to enhance detection, or for other experimental purposes. Derivatives include dominant negatives, dominant positives and fusion proteins.

Antibodies

In one embodiment, the invention provides antibodies to the NFAT regulators of the present invention. Antibodies can be prepared that will bind to one or more particular domains of a peptide of the invention and can be used to modulate NFAT regulator gene or protein activity.

Moreover, administration of an antibody against an NFAT regulator protein or fragment or derivative thereof, preferably monoclonal or monospecific, to mammalian cells (including human cells) can reduce or abrogate NFAT induced transcription of immune system associated genes, thus serving to treat hyperactivity or inappropriate activity of the immune system. Administration of an activating antibody against an NFAT regulator protein or fragment or derivative thereof, e.g. an Orai protein, may serve to treat hypoactivity of the immune system by activating NFAT and thereby inducing transcription of immune response associated genes. Administration of an antibody against an NFAT regulator protein or fragment or derivative thereof, e.g., a DYRK protein, may serve to treat hypoactivity of the immune system by activating NFAT and thereby inducing transcription of immune response associated genes.

The present invention also relates to antibodies that bind a protein or peptide encoded by all or a portion of the NFAT regulator nucleic acid molecule, as well as antibodies which bind the protein or peptide encoded by all or a portion of a variant nucleic acid molecule. For instance, polyclonal and monoclonal antibodies which bind to the described polypeptide or protein, or fragments or derivatives thereof, are within the scope of the invention.

Antibodies of this invention can be produced using known methods. An animal, such as a mouse, goat, chicken or rabbit, can be immunized with an immunogenic form of the protein or peptide (an antigenic fragment of the protein or peptide which is capable of eliciting an antibody response). Techniques for conferring immunogenicity on a protein or peptide include conjugation to carriers or other techniques well known in the art. The protein or peptide can be administered in the presence of an adjuvant. The progress of immunization can be monitored by detection of antibody titers in plasma or serum. Standard ELISA or other immunoassays can be used with immunogen as antigen to assess the levels of antibody. Following immunization, anti-peptide antisera can be obtained, and if desired, polyclonal antibodies can be isolated from the serum. Monoclonal antibodies can also be produced by standard techniques which are well known in the art (Kohler and Milstein, Nature 256:4595-497 (1975); Kozbar et al., Immunology Today 4:72 (1983); and Cole et al., Monoclonal Antibodies and Cancer Therapy, Alan R. Liss, Inc., pp. 77-96 (1985)). Such antibodies are useful as diagnostics for the intact or disrupted gene, and also as research tools for identifying either the intact or disrupted gene.

As an alternative to preparing monoclonal antibody-secreting hybridomas, a monoclonal antibody to NFAT regulator proteins may be identified and isolated by screening a recombinant combinatorial immunoglobulin library (e.g., an antibody phage display library) to thereby isolate immunoglobulin library members that bind to NFAT regulator proteins. Kits for generating and screening phage display libraries are commercially available from, e.g., Dyax Corp. (Cambridge, Mass.) and Maxim Biotech (South San Francisco, Calif.). Additionally, examples of methods and reagents particularly amenable for use in generating and screening antibody display libraries can be found in the literature.

Polyclonal sera and antibodies may be produced by immunizing a suitable subject, such as a rabbit, with NFAT regulator proteins (preferably mammalian; more preferably human) or an antigenic fragment thereof. The antibody titer in the immunized subject may be monitored over time by standard techniques, such as with ELISA, using immobilized marker protein. If desired, the antibody molecules directed against NFAT regulator proteins may be isolated from the subject or culture media and further purified by well-known techniques, such as protein A chromatography, to obtain an IgG fraction.

Fragments of antibodies to NFAT regulator proteins may be produced by cleavage of the antibodies in accordance with methods well known in the art. For example, immunologically active F(ab') and F(ab')$_2$ fragments may be generated by treating the antibodies with an enzyme such as pepsin. Additionally, chimeric, humanized, and single-chain antibodies to NFAT regulator proteins, comprising both human and non-human portions, may be produced using standard recombinant DNA techniques. Humanized antibodies to NFAT regulator proteins may also be produced using transgenic mice that are incapable of expressing endogenous immunoglobulin heavy and light chain genes, but which can express human heavy and light chain genes.

NFAT Associated Diseases

The methods of the present invention can also be utilized to treat, or identify agents useful in treatment of, conditions and diseases associated with NFAT disregulation/disfunction and/or Calcium signaling. Such diseases include, without limitation, immune system diseases involving hyperactivity or inappropriate activity of the immune system, e.g., acute immune diseases, chronic immune diseases and autoimmune diseases Examples of such diseases include rheumatoid arthritis, inflammatory bowel disease, allogeneic or xenogeneic transplantation rejection (organ, bone marrow, stem cells, other cells and tissues), graft-versus-host disease, aplastic anemia, psoriasis, lupus erytematosus, inflammatory disease, MS, type I diabetes, asthma, pulmonary fibrosis, scleroderma, dermatomyositis, Sjogren's syndrome, postpericardiotomy syndrome, Kawasaki disease, Hashimoto's thyroiditis, Graves' disease, myasthenia gravis, pemphigus vulgaris, autoimmune hemolytic anemia, idiopathic thrombopenia, chronic glomerulonephritis, Goodpasture's syndrome, Wegner's granulomatosis, multiple sclerosis, cystic fibrosis, chronic relapsing hepatitis, primary biliary cirrhosis, uveitis, allergic rhinitis, allergic conjunctivitis, atopic dermatitis, Crohn's disease, ulcerative colitis, colitis/inflammatory bowel syndrome, Guilllain-Barre syndrome, chronic inflammatory demyelinating polyradiculoneuropathy, eczema, and autoimmune thyroiditis. Transplant graft rejections can result from tissue or organ transplants. Graft-versus-host disease can result from bone marrow or stem cell transplantation. Immune system diseases involving hypoactivity of the immune system include, e.g., immunodeficiency diseases including acquired immunodeficiencies, such as HIV disease, and common variable immunodeficiency (CVID).

The methods of the present invention can also be utilized to treat or identify agents useful in treatment of conditions and diseases that are not immune mediated, but which nevertheless involve the $Ca^{2+}$-calcineurin-mediated activation of NFAT, e.g. a protein-protein interaction between calcineurin and NFAT. Examples include myocardial hypertrophy, dilated cardiomyopathy, excessive or pathological bone resorption, excessive adipocyte differentiation, obesity, and reactivation of latent human herpesvirus-8 or other viruses. Further, the methods of the present invention can be utilized to treat, or identify agents useful in the treatment of, conditions that involve a dysfunction of cellular $Ca^{2+}$ signaling, attributable to altered function of an NFAT regulator protein, wherein, the dysfunction of $Ca^{2+}$ signaling causes a disease or disorder at least in part through its effects on other $Ca^{2+}$ dependent pathways in addition to the $Ca^{2+}$-calcineurin-NFAT pathway, or wherein the dysfunction of $Ca^{2+}$ signaling acts largely through such other pathways and the changes in NFAT function are ancillary.

Severe Combined Immunodeficiency

One NFAT associated disease/disorder is Severe Combined Immunodeficiency (SCID). SCID is a group of congenital immune disorders caused by failed or impaired development and/or function of both T and B lymphocytes. A rare disease with an estimated prevalence of 1 per 100,000 population, SCID can be caused by mutations in more than 20 different genes. Mutations in the common γ chain (cγ) of the interleukin 2 (IL-2), IL-4, -7, -9 and -15 receptors leading to X-linked SCID account for 50% of all cases. Approximately 10% of all SCID cases are due to a variety of rare mutations in genes important for T and B cell development or function, especially signal transduction (CD3ε and γ, ZAP-70, p56lck, CD45, JAK3, IL-7Rα chain). Due to the low incidence of these mutations and small family sizes, classical positional cloning is usually not possible for most of these SCID diseases and mutations were often found in known signal transducing genes by functional analysis of T cells followed by sequencing of candidate genes. Scientifically, SCID disease has been of extraordinary value for the elucidation of T cell and B cell function, highlighting the consequences of gene dysfunction in the immune system.

In one embodiment, the invention relates to a method to diagnose unexplained immunodeficiency in a subject comprising comparison of a nucleotide sequence corresponding to a gene from the subject comprising the NFAT regulators of the present invention to wild type sequence of that gene, wherein alteration of the nucleotide sequence of the gene from the wild type sequence indicates that the alteration in the gene is responsible for the immunodeficiency. In one embodiment, the alteration in the gene is a mutation in a splice site. In one embodiment, the alteration in the gene is a nonsynonymous mutation. In one embodiment, the unexplained immunodeficiency is associated with defects in regulation of NFAT activity.

In one embodiment, the comparison is accomplished by way of obtaining a biological sample from the subject, sequencing the DNA in the biological sample, and electronically aligning the DNA sequence obtained from the biological sample to a wild type sequence.

In one embodiment, a comparison is accomplished by way of obtaining a DNA sample, processing the DNA sample such that the DNA is available for hybridization, combining the DNA with nucleotide sequences complementary to the nucleotide sequence of a NFAT regulator of the present invention under conditions appropriate for hybridization of the probes with complementary nucleotide sequences in the DNA sample, thereby producing a combination; and detecting hybridization in the combination, wherein absence of hybridization in the combination is indicative of alteration in the nucleotide sequence in the gene.

Method to Screen for Agents that Modulate NFAT Regulator Function

In one embodiment, the present invention relates to methods to screen for agents that alter NFAT regulator expression or function. In one embodiment, the present invention relates to methods to screen for agents that alter the function of the NFAT regulator proteins of the present invention. NFAT regulator function may be altered as to the modulation of CRAC channel activation. NFAT regulator function may be altered as to the modulation of NFAT phosphorylation. NFAT regulator function may be altered as to modulation of NFAT subcellular localization. NFAT regulator function may be altered as to modulation of free intracellular calcium levels. NFAT regulator function may be altered as to modulation of calcineurin activity. In one embodiment, alter or modulate refers to upregulation or enhancement of activity. In one embodiment, alter or modulate refers to downregulation or inhibition.

As used herein, the term "NFAT regulator genes" is used to refer to the genes identified by the methods of the present invention that regulate NFAT activity, including by way of SOCE, by way of direct phosphorylation of NFAT or by other means as described in example 2. The NFAT regulator genes of the present invention include: ORAI1, ORAI2, ORAI3, the DYRK genes including DYRK1A, DYRK1B, DYRK2, DYRK3 DYRK4 and DYRK6 and the genes disclosed in Table I in Example 3. In one preferred embodiment, the NFAT regulator genes of the present invention are ORAIs, e.g., ORAI1, ORAI2, and ORAI3. The NFAT regulator genes and/or their encoded protein products, modulate the activity of NFAT either directly or indirectly.

As used herein, the term "modulates" refers the effect an agent, including a gene product, has on another agent, including a second gene product. In one embodiment, an agent that modulates another agent upregulates or increases the activity of the second agent. In one embodiment, an agent that modulates another agent downregulates or decreases the activity of the second agent.

One example of an NFAT regulator detected through the RNAi screening described herein is calcineurin. The role of calcineurin in NFAT signaling was previously known. Specifically, calcineurin dephosphorylates and activates NFAT, and therefore is a positive regulator.

Calcineurin serves to illustrate the relationship between altered expression of a regulator and altered NFAT signaling: Overexpression of calcineurin leads to increased activation of NFAT in standard assays; conversely, diminished expression of calcineurin, as in the RNAi screen detailed below in Example 1, leads to a decrease in NFAT activation. Calcineurin also illustrates that altered activity of a regulator, by an agent, is reflected in altered NFAT signaling. Thus, cyclosporin A and FK506 are calcineurin inhibitors when complexed with their cytoplasmic binding proteins (cyclophilin A and FKBP12, respectively), and the inhibitory action of these compounds on calcineurin can be detected, for example, by examining the effect of cyclosporin A or FK506 on NFAT localization in cells stimulated with thapsigargin, or in T cells stimulated physiologically through the T cell receptor.

An assay for an agent that affects an NFAT regulator need not directly involve NFAT. Thus, a number of agents that alter the activity of calcineurin, for example, the PVIVIT peptide and its derivatives, the CsA-cyclophilin A complex, and the FK506-FKBP12 complex, can be assayed by examining their binding to calcineurin; and the calcineurin autoinhibitory peptide can be assayed by examining its effect on dephosphorylation of substrates other than NFAT.

Positive regulators of NFAT are known to act at other stages of the $Ca^{2+}$-calcineurin-NFAT signaling pathway. For example, Orai1 and STIM1 contribute to the elevation of cytoplasmic $[Ca^{2+}]$, and thereby elicit activation of calcineurin and subsequently of NFAT. Here again, agents that decrease expression of Orai1 or STIM1 (e.g., RNAi reagents, as shown herein for both Orai1 and STIM1; and as shown for dStim and STIM1 in Roos et al (2005) J Cell Biol 169, 435-445; Liou et al (2005) Current Biology 15, 1235-1241) can be recognized either by their effects on NFAT activation (e.g., NFAT dephosphorylation or intracellular localization) or on other parameters diagnostic of the function of the NFAT regulators in question (e.g., cytoplasmic $Ca^{2+}$ levels).

Agents that inhibit function of the $Ca^{2+}$-calcineurin-NFAT signaling pathway by affecting one or more NFAT regulator proteins, for example agents that inhibit $Ca^{2+}$ influx through the CRAC channel (e.g., $La^{3+}$, $Gd^{3+}$, 2-APB) are likewise readily detected. The inhibitory agents that are known at present, however, are not entirely selective, which is the reason that the assays described herein constitute a valuable tool for the discovery of agents that target the NFAT modulator proteins of this pathway more selectively.

The present invention is also inclusive of negative regulators of $Ca^{2+}$-calcineurin-NFAT signaling. These include, for example, DYRK-family kinases, casein kinase-1 isoforms, and glycogen synthase kinase (GSK-3). Inhibition of the expression of these negative regulators, for example by RNAi treatment, or inhibition of their activity, for example by treatment with an agent that inhibits enzyme activity (e.g., the casein kinase inhibitor CKI-7; Li+ as a GSK-3 inhibitor), in each case can be detected using an assay that monitors an aspect of NFAT activation.

The invention relates to screening methods (also referred to herein as "assays") for identifying modulators, i.e., candidate compounds or agents (e.g., proteins, peptides, peptidomimetics, peptoids, oligonucleotides (such as siRNA or anti-sense RNA), small non-nucleic acid organic molecules, small inorganic molecules, or other drugs) that bind to NFAT regulator proteins, or to NFAT, have an inhibitory (or stimulatory) effect on, for example, NFAT regulator gene expression or protein activity, NFAT gene expression or protein activity, or have a stimulatory or inhibitory effect on, for example, the expression or activity of an NFAT regulator-interacting protein (e.g. a NFAT regulator substrate) or a NFAT-interacting protein (e.g. a NFAT substrate). Such interacting proteins can include $Ca^{2+}$ and other subunits of calcium channels, proteins that interact with one or more Orai proteins, e.g., additional CRAC channel subunits or CRAC channel modulatory proteins. Compounds thus identified can be used to modulate the activity of target gene products (e.g., NFAT regulator polypeptides, NFAT polypeptides) either directly or indirectly in a therapeutic protocol, to elaborate the biological function of the target gene product, or to identify compounds that disrupt the normal interactions of the target gene or gene product. Identification of a blocking agent or inhibitor of an NFAT regulator gene or an encoded product can be carried out using the screening methods of this invention and other methods known in the art.

Compounds that affect NFAT regulator expression or activity can be identified as described herein or using other methods known in the art. The modulator compounds can be novel, compounds not previously identified as having any type of activity as a calcium channel modulator, or a compound previously known to modulate calcium channels, but that is used at a concentration not previously known to be effective for modulating calcium influx. The modulator can also be a modulator compound for NFAT regulators other than CRAC channel components.

The term "agent" or "compound" as used herein and throughout the specification means any organic or inorganic molecule, including modified and unmodified nucleic acids such as antisense nucleic acids, RNAi, such as siRNA or shRNA, peptides, peptidomimetics, receptors, ligands, and antibodies.

Compounds that inhibit the activity or expression of an NFAT regulator are useful in the treatment of disorders involving cells that express an NFAT regulator. Particularly relevant disorders are those involving hyperactivity or inappropriate activity of the immune system or hypoactivity of the immune system, as further described herein.

Cells or tissues affected by these disorders can be used in screening methods, e.g., to test whether an agent that modulates expression or activity of an NFAT regulator can reduce proliferation of affected cells, alleviate abnormal SOCE function, or alleviate abnormal NFAT activity. Other cells useful in the screening methods of the present invention are cells that exhibit store-operated calcium entry, which include insect cells, e.g., *Drosophila* cells (e.g., Schneider 2 or S2 cells), human embryonic kidney (HEK) cells, neuronal or nervous system cells, e.g., SHSY5Y neuroblastoma cells and PC12 cells, rat basophilic leukemia (RBL) cells, and immune system cells, e.g., primary T cells from mammals such as human or mouse, lymphocytes such as T lymphocytes, including Jurkat cells. Cells derived from the knock out or transgenic animals described below may be useful. Cells derived from immunodeficient patients, e.g., patients described in Example 1, including T cells and fibroblasts, may be useful in the methods of the present invention.

As used herein, the term "recombinant cell" is used to refer to a cell with exogenous and/or heterologous nucleic acid incorporated within, either incorporated stably so as to remain incorporated in clonal expansion of the cells, or introduced transiently into a cell (or a population of cells). The nucleic acid may contain, for example, an NFAT regulator gene or it's mRNA, or its complementary (antisense) strand, or an shRNA or siRNA, or any fragment or derivative of the foregoing. The nucleic acid may comprise genomic DNA of NFAT regulator proteins, fragments, or derivative thereof. The nucleic acid can comprise corresponding coding and non-coding mRNA or its complementary (anticoding) strand, which can be employed to regulate expression of the corresponding mRNA, e.g. corresponding short nucleotides of shRNA or siRNA. The nucleic acid can result in altered expression (e.g. over expression or underexpression) of at least one NFAT regulator protein or its mRNA or antisense. It may also result in the expression of a NFAT regulator protein functional fragment or derivative otherwise not expressed in the recipient cell.

Test Compounds

The test compounds of the present invention can be obtained using any of the numerous approaches in combinatorial library methods known in the art, including: biological libraries; peptoid libraries (libraries of molecules having the functionalities of peptides, but with a novel, non-peptide backbone, which are resistant to enzymatic degradation but that nevertheless remain bioactive; see, e.g., Zuckermann, et al., 1994 J. Med. Chem. 37: 2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., 1993, Proc. Natl. Acad. Sci. USA. 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Biotechniques 13:412-421), or on beads (Lam (1991) Nature 354:82-84), chips (Fodor, 1993, Nature 364:555-556), bacteria (Ladner, U.S. Pat. No. 5,223,409), spores (Ladner, U.S. Pat. No. 5,223,409), plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. 87:6378-6382; Felici, 1991, J. Mol. Biol. 222:301-310; and Ladner supra.).

The compounds that can be screened by the methods described herein include, but are not limited to, any small molecule compound libraries derived from natural and/or synthetic sources, small non-nucleic acid organic molecules, small inorganic molecules, peptides, peptoids, peptidomimetics, oligonucleotides (e.g., siRNA, antisense RNA, aptamers such as those identified using SELEX), and oligonucleotides containing synthetic components.

The test compounds can be administered, for example, by diluting the compounds into the medium wherein the cell is maintained, mixing the test compounds with the food or liquid of a test animal (see below), topically administering the compound in a pharmaceutically acceptable carrier on the test animal, using three-dimensional substrates soaked with the test compound such as slow release beads and the like and embedding such substrates into the test animal, intracranially administering the compound, parenterally administering the compound.

A variety of other reagents may also be included in the mixture. These include reagents such as salts, buffers, neutral proteins, e.g. albumin, detergents, etc. which may be used to facilitate optimal protein-protein and/or protein-nucleic acid binding and/or reduce non-specific or background interactions, etc. Also, reagents that otherwise improve the efficiency of the assay, such as protease inhibitors, nuclease inhibitors, antimicrobial agents, etc. may be used.

The language "pharmaceutically acceptable carrier" is intended to include substances capable of being coadministered with the compound and which allow the active ingredient to perform its intended function of preventing, ameliorating, arresting, or eliminating a disease(s) of the nervous system. Examples of such carriers include solvents, dispersion media, adjuvants, delay agents and the like. The use of such media and agents for pharmaceutically active substances is well known in the art. Any conventional media and agent compatible with the compound may be used within this invention.

The compounds can be formulated according to the selected route of administration. The addition of gelatin, flavoring agents, or coating material can be used for oral applications. For solutions or emulsions in general, carriers may include aqueous or alcoholic/aqueous solutions, emulsions or suspensions, including saline and buffered media. Parenteral vehicles can include sodium chloride, potassium chloride among others. In addition intravenous vehicles can include fluid and nutrient replenishers, electrolyte replenishers among others.

Preservatives and other additives can also be present. For example, antimicrobial, antioxidant, chelating agents, and inert gases can be added (see, generally, Remington's Pharmaceutical Sciences, 16th Edition, Mack, 1980).

Test Assays for Agents that Modulate NFAT Activity

Another aspect of the invention relates to a method to screen for regulators of free intracellular $Ca^{2+}$ levels, calcineurin activation and NFAT localization in cells as described in Examples 1 through 3. In one embodiment, a recombinant vector encoding a fusion protein comprising the entire NFAT regulatory domain or a functional fragment or derivative thereof, and an operably linked reporter protein (for determining subcellular localization of the regulatory domain, e.g. GFP or an antigenic epitope) is transfected into cells, i.e. test cells. Test cells transfected with the vector are contacted with the test agent. After a period of time, e.g., 48-72 hours, the test cells are scored for subcellular localization of the NFAT-reporter fusion protein. Scoring may be accomplished by way of automated microscopy, as in the examples, or by way of manual microscopy, e.g., fluorescent microscopy, confocal microscopy. Secondary test assays include calcium influx detection assays. If the test agent has an effect on intracellular localization of the expression product of the recombinant vector, this is indicative that it modulates NFAT regulator function.

In one embodiment, the cells also express an exogenous (e.g. heterologous or homologous) NFAT regulator protein, or fragment or derivative thereof, and/or exhibit altered expression of a NFAT regulatory protein or fragment or derivative thereof, achieved with the tools/methods described herein.

In one embodiment, the test cells are resting cells wherein NFAT is normally localized to the cytoplasm. Nuclear localization, or partial nuclear localization in excess of that observed in untreated control cells, of the NFAT-reporter fusion protein in the resting test cell indicates that the test agent successfully activated NFAT activity.

In one embodiment, the test cells are stimulated cells, wherein intracellular $Ca^{2+}$ stores are depleted and store-operated $Ca^{2+}$ entry is activated and NFAT is localized to the nucleus. $Ca^{2+}$ store depletion may be accomplished, for example, by means of contacting the test cells with thapsigargin or ionomycin. The test cells may be stimulated prior to, concurrently with or subsequent to contacting the test cells with the test agent. Cytoplasmic localization, or a reduction in nuclear localization compared to that observed in control cells, of the NFAT-reporter fusion protein in the stimulated test cell indicates that the test agent successfully inhibited NFAT activation.

A reporter gene which encodes a reporter protein to be operably linked to nucleotide sequences encoding the NFAT regulatory domain, any reporter gene for general use is satisfactory provided that its localization in the cell can be assessed either directly or indirectly in the context of the fusion protein. For example, the reporter can be any protein whose localization can be detected by staining with a labeled antibody, or a protein epitope such as a haemagglutinin or myc epitope, or green fluorescent protein (GFP) or one of its variants. In one preferred embodiment, the reporter protein is GFP. The NFAT protein in the fusion protein may be full length or may comprise the regulatory domain, particularly the calcineurin and CK1 docking sites and the conserved serine rich regions (SRR) and serine-proline (SP) repeat motifs.

Another aspect of the invention relates to methods for identifying an agent for treating or preventing a disease or disorder associated with calcium signaling. In one embodiment, the method comprises assessing the effects of a test agent on an organism that exhibits the disease or disorder, or exhibits at least one phenotype associated with the disease or disorder. The test agent is identified as an agent for treating or preventing the disease or disorder if it modulates an activity, interaction, expression or binding of at least one NFAT regulator protein, fragment, or derivative thereof. In one embodiment, the NFAT regulator protein, fragment, or derivative thereof is expressed either endogenously or exogenously in cells of the organism. Appropriate methods of administration of the test agent and assessment of effects can be determined by the skilled practitioner.

Test Assays for Agents that Modulate Calcium Levels

In monitoring the effect of a test agent on intracellular calcium in any of the screening/identification methods provided herein, a direct or indirect evaluation or measurement of cellular (including cytosolic and intracellular organelle or compartment) calcium and/or movement of ions into, within or out of a cell, organelle, or portions thereof (e.g., a membrane) can be conducted. A variety of methods are described herein and/or known in the art for evaluating calcium levels and ion movements or flux. The particular method used and the conditions employed can depend on whether a particular aspect of intracellular calcium is being monitored. For example, as described herein, reagents and conditions are known, and can be used, for specifically evaluating store-operated calcium entry, resting cytosolic calcium levels and calcium levels and uptake by or release from intracellular organelles. The effect of test agent on intracellular calcium can be monitored using, for example, a cell, an intracellular organelle or storage compartment, a membrane (including, e.g., a detached membrane patch or a lipid bilayer) or a cell-free assay system.

Generally, monitoring the effect of a test agent on intracellular calcium involves contacting a test agent with or exposing a test agent to (1) a protein (and/or nucleic acid, or portion(s) thereof, encoding a protein) involved in modulating intracellular calcium (in particular, a protein provided herein) and/or (2) a cell, or portion(s) thereof (e.g., a membrane or intracellular structure or organelle) that may or may not contain a protein (and/or nucleic acid, or portion(s) thereof, encoding a protein) involved in modulating intracellular calcium. A cell can be one that exhibits one or more aspects of intracellular $Ca^{2+}$ modulation, such as, for example, store-operated calcium entry. Before, during and/or after the contacting of test agent, a direct or indirect assessment of intracellular calcium can be made. An indirect assessment can be, for example, evaluation or measurement of current through an ion transport protein (e.g., a store-operated calcium channel or a $Ca^{2+}$-regulated ion channel), or transcription of a reporter protein operably linked to a calcium-sensitive promoter. A direct assessment can be, for example, evaluation or measurement of intracellular (including cytosolic and intracellular organelle) calcium.

The assessment of intracellular calcium is made in such a way as to be able to determine an effect of an agent on intracellular calcium. Typically, this involves comparison of intracellular calcium in the presence of a test agent with a control for intracellular calcium. For example, one control is a comparison of intracellular calcium in the presence and absence of the test agent or in the presence of varying amounts of a test agent. Thus, one method for monitoring an effect on intracellular calcium involves comparing intracellular calcium before and after contacting a test agent with a test cell containing a protein that modulates intracellular calcium, or comparing intracellular calcium in a test cell that has been contacted with test agent and in a test cell that has not been contacted with test agent (i.e., a control cell). Generally, the control cell is substantially identical to, if not the same as, the control cell, except it is the cell in the absence of test agent. A difference in intracellular calcium of a test cell in the presence and absence of test agent indicates that the agent is one that modulates intracellular calcium.

Another method for monitoring an effect on intracellular calcium involves comparing intracellular calcium of a test cell and a control cell that is substantially similar to the test cell (e.g., comparing a cell containing a protein (and/or nucleic acid encoding a protein) involved in intracellular calcium signaling, such as the proteins provided herein), and a cell that does not contain, or that contains lower levels of, the particular protein involved in modulating intracellular calcium signaling. Thus, for example, if the test cell containing the protein involved in intracellular calcium modulation is a recombinant cell generated by transfer of nucleic acid encoding the protein into a host cell, then one possible control cell is a host cell that has not been transfected with nucleic acid encoding the protein or that has been transfected with vector alone. Such a cell would be substantially similar to the test cell but would differ from the test cell essentially only by the absence of the introduced nucleic acid encoding the protein. Thus, a control cell may contain, e.g., endogenously, the particular protein involved in modulating intracellular calcium, in which case the test cell would contain higher levels of (or overexpress) the particular protein.

It may also be useful to experimentally reduce the endogenous expression or functional levels of a particular protein (e.g. by inhibition of protein expression or function) to identify an agent that modulates intracellular calcium by targeting that particular protein. Expression of an NFAT regulator protein can be reduced in a cell by known experimental methods such as by targeting expression at the nucleic acid level, e.g. siRNA or shRNA treatment, to thereby reduce expression of functional protein. Systems which comprise such a cell which have reduced, or completely inhibited, expression of NFAT regulator are included in this invention. Such systems may further contain an exogenous (e.g. homologous or heterologous) nucleic acid molecule encoding one or more mammalian NFAT regulator proteins, or a portion thereof, in expressible form.

The type of control comparison described above, where endogenous expression/functional levels of a particular protein are reduced in a cell, is particularly useful when trying to identify an agent that specifically modulates intracellular calcium via an effect on, or modulation of, a particular protein (and/or nucleic acid, or portion(s) thereof, encoding a particular protein). Thus, for example, if there is no detectable or substantial difference in intracellular calcium in the test (non-modified) versus control (reduced endogenous expression/function) cells in the presence of the agent, the agent likely does not mediate its effect on intracellular calcium via the particular protein (or nucleic acid encoding the protein). A detectable or substantial difference in intracellular calcium in the test versus control cells in the presence of the test agent, indicates the test agent may be a candidate agent that specifically modulates intracellular calcium via an effect on or modulation of the particular protein. A candidate agent can be subjected to further control assays to compare intracellular calcium in test cells in the presence and absence of test agent or to compare intracellular calcium in control cells in the presence and absence of test agent, which can aid in determination of whether a candidate agent is an agent that modulates intracellular calcium.

An assessment of intracellular calcium conducted to monitor the effect of test compound on intracellular calcium can be made under a variety of conditions. Conditions can be selected to evaluate the effect of test compound on a specific aspect of intracellular calcium. For example, as described herein, reagents and conditions are known, and can be used, for specifically evaluating store-operated calcium entry, resting cytosolic calcium levels and calcium levels of and calcium uptake by or release from intracellular organelles. For example, as described herein, calcium levels and/or calcium release from the endoplasmic reticulum can directly be assessed using mag-fora 2, endoplasmic reticulum-targeted aequorin or cameleons. One method for indirect assessment of calcium levels or release is monitoring intracellular cytoplasmic calcium levels (for example using fluorescence-based methods) after exposing a cell to an agent that effects calcium release (actively, e.g., $IP_3$, or passively, e.g., thapsigargin) from the organelle in the absence of extracellular calcium. Assessment of the effect of the test agent/compound on concentrations of cations or divalent cations within the cell, or of ion influx into the cell, can also be used to identify a test agent as an agent that modulates intracellular calcium.

Resting cytosolic calcium levels, intracellular organelle calcium levels and cation movement may be assessed using any of the methods described herein or known in the art (see, e.g., descriptions herein of calcium-sensitive indicator-based measurements, such as fluo-3, mag-furs 2 and ER-targeted aequorin, labeled calcium (such as $^{45}Ca^{2+}$)-based measurements, and electrophysiological measurements). Particular aspects of ion flux that may be assessed include, but are not limited to, a reduction (including elimination) or increase in the amount of ion flux, altered biophysical properties of the ion current, and altered sensitivities of the flux to activators or inhibitors of calcium flux processes, such as, for example, store-operated calcium entry. Reagents and conditions for use in specifically evaluating receptor-mediated calcium movement and second messenger-operated calcium movement are also available.

In particular embodiments of the methods for screening for or identifying agents that modulate intracellular calcium, the methods are conducted under conditions that permit store-operated calcium entry to occur. Such conditions are described herein and are known in the art. Test agents can be contacted with a protein and/or nucleic acid encoding a protein (such as the proteins and nucleic acids provided herein) involved in modulating intracellular calcium and/or a cell (or portion thereof) containing such a protein (or nucleic acid) under these appropriate conditions. For example, in conducting one method for screening for an agent that modulates intracellular calcium under conditions selected for evaluating store-operated calcium entry, intracellular calcium levels of test cells are monitored over time using a fluorescent calcium indicator (e.g., FLUO-4). Store-operated calcium entry into the cells is detected depending on the specific indicator used as, e.g. an increase in fluorescence, a decrease in fluorescence, or a change in the ratio of fluorescence intensities elicited by excitation using light of two different wavelengths. in response to conditions under which store-operated calcium entry occurs. The methods for eliciting the fluorescence signal for a specific calcium indicator and for interpreting its relation to a change in free calcium concentration are well known in the art. The conditions include addition of a store-depletion agent, e.g., thapsigargin (which inhibits the ER calcium pump and allows discharge of calcium stores through leakage) to the media of cell that has been incubated in $Ca^{2+}$-free buffer, incubation with thapsigargin for about 5-15 minutes, addition of test compound (or vehicle control) to the media and incubation of the cell with test agent for about 5-15 minutes, followed by addition of external calcium to the media to a final concentration of about 1.8 mM. By adding thapsigargin to the cell in the absence of external calcium, it is possible to delineate the transient increase in intracellular calcium levels due to calcium release from calcium stores and the more sustained increase in intracellular calcium levels due to calcium influx into the cell from the external medium (i.e., store-operated calcium entry through the plasma membrane that is detected when calcium is added to the medium). Because the fluorescence-based assay allows for essentially continuous monitoring of intracellular calcium levels during the entire period from prior to addition of thapsigargin until well after addition of calcium to the medium, not only can "peak" or maximal calcium levels resulting from store-operated calcium entry be assessed in the presence and absence of test agent, a number of other parameters of the calcium entry process may also be evaluated, as described herein. For example, the kinetics of store-operated calcium entry can be assessed by evaluation of the time required to reach peak intracellular calcium levels, the up slope and rate constant associated with the increase in calcium levels, and the decay slope and rate constant associated with the decrease in calcium levels as store-operated calcium entry discontinues. Any of these parameters can be evaluated and compared in the presence and absence of test agent to determine whether the agent has an effect on store-operated calcium entry, and thus on intracellular calcium. In other embodiments, store-operated calcium entry can be evaluated by, for example, assessing a current across a membrane or into a cell that is characteristic of a store-operated calcium entry current (e.g., responsiveness to reduction in calcium levels of intracellular stores) or assessing transcription of a reporter construct that includes a calcium-sensitive promoter element. In particular embodiments, a test agent is identified as one that produces a statistically significant difference. E.g., at least a 30% difference in any aspect or parameter of store-operated calcium entry relative to control (e.g., absence of compound, i.e., vehicle only).

Generally, a test agent is identified as an agent, or candidate agent, that modulates intracellular calcium if there is a detectable effect of the agent on intracellular calcium levels and/or ion movement or flux, such as a detectable difference in levels or flux in the presence of the test agent. In particular embodiments, the effect or differences can be substantial or statistically significant.

Test Assays for Agents that Modulate NFAT Regulator Activity

In one embodiment, an assay is a cell-based assay in which a cell that expresses an NFAT regulator protein or biologically active portion thereof is contacted with a test compound, and the ability of the test compound to modulate NFAT regulator activity is determined. Determining the ability of the test compound to modulate NFAT regulator activity can be accomplished by monitoring, for example, changes in calcium flux in the cell or by testing downstream effects of modulating calcium flux such activation or IL-2 expression. Methods of testing such downstream effects are known in the art and include modulation of cell proliferation and cell growth. For example, a compound that decreases the number of NFAT regulator molecules in a cell or affects the function of an NFAT regulator channel may decrease cellular proliferation. Alternatively, transcription of genes requiring NFAT transactivation may be monitored.

U.S. Pat. Application No. 20040002117 discloses known gene targets of NFAT and teaches methods to identify further genes transcribed due to activity of NFAT. Detection of transcription or protein expression of NFAT target genes may be useful in the methods of the present invention. Ablation of induced expression of NFAT target genes in the presence of a test agent indicates that the test agent is effective in inhibiting NFAT regulator activity, where the NFAT regulator is a positive regulator of NFAT. Conversely, expression of NFAT target genes above basal levels in the presence of a test agent, in otherwise unstimulated conditions, indicates that the test agents is effective in inhibiting a negative regulator of NFAT.

In some cases, the cell used in such assays does not normally express the NFAT regulator of interest (e.g. a channel protein). By way of non-limiting example, a cell such as a *Xenopus* oocyte or immune system cell or derivative thereof can be engineered to expresses a recombinant NFAT regulator protein, biologically active portion or derivative thereof. In general, recombinant expression that results in increased expression of the NFAT regulator compared to a corresponding cell that does not express recombinant NFAT regulator, is referred to as "overexpression" of the NFAT regulator. Alternatively, the cell can be of mammalian origin. The cell can also be a cell that expresses the NFAT regulator of interest (e.g. a calcium channel) but in which such NFAT regulator activity can be distinguished from other NFAT regulator (e.g. calcium channel) activity, for example, by comparison with controls. The ability of the test compound to modulate NFAT regulator binding to a compound, e.g., an NFAT regulator substrate, or to bind to NFAT regulator can also be evaluated. This can be accomplished, for example, by coupling the compound, e.g., the substrate, with a radioisotope or enzymatic label such that binding of the compound, e.g., the substrate, to NFAT regulator can be determined by detecting the labeled compound, e.g., substrate, in a complex. Alternatively, NFAT regulator could be coupled with a radioisotope or enzymatic label to monitor the ability of a test compound to modulate NFAT regulator binding to an NFAT regulator substrate in a complex. For example, compounds (e.g., NFAT regulator substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

An example of a screening assay for a compound that specifically modulates activity of an NFAT regulator polypeptide is as follows. Incubate a cell that expresses the NFAT regulator polypeptide of interest (e.g., a Jurkat cell or an 14E1(293 cell) with a test compound for a time sufficient for the compound to have an effect on transcription or activity (e.g., for at least 1 minute, 10 minutes, 1 hour, 3 hours, 5 hours, or 24 or more hours. Such times can be determined experimentally. The concentration of the test compound can also be varied (e.g., from 1 nM-100 µM, 10 nM to 10 µM or, 1 nM to 10 µM). Inhibition of calcium influx in the presence and absence of the test compound is then assayed using methods known in the art. For example, fura-2, Indo-1, Fluo-3, or Rho-2 can be used to assay calcium flux. Other methods can be used as assays of inhibition. For example, a test compound is considered to have, or suspected of, having a significant impact on influx if any one or more of the following criteria are met:
  a. there is direct inhibition of increased $[Ca^{2+}]i$ as measured by a calcium indicator.
  b. there is a direct inhibition of $I_{CRAC}$ as measured by patch clamp;
  c. there is inhibition of downstream signaling functions such as calcineurin activity, NFAT subcellular localization, NFAT phosphorylation, and/or cytokine, e.g., IL-2, production; or
  d. there are modifications in activation-induced cell proliferation, differentiation and/or apoptotic signaling pathways.

Direct testing of the effect of a test compound on an activity of a specific NFAT regulator polypeptide can be accomplished using, e.g., patch clamping to measure $I_{CRAC}$. This method can be used in screening assays as a second step after testing for general effects on calcium influx or as a second step after identifying a test compound as affecting expression of an NFAT regulator mRNA or polypeptide. Alternatively, direct testing can be used as a first step in a multiple step assay or in single step assays.

The ability of a compound (e.g., an NFAT regulator substrate) to interact with the NFAT regulator with or without the labeling of any of the interactants can be evaluated. For example, a microphysiometer can be used to detect the interaction of a compound with NFAT regulator without the labeling of either the compound or the NFAT regulator (McConnell et al., 1992, Science 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and NFAT regulator polypeptide.

In yet another embodiment, a cell-free assay is provided in which a NFAT regulator protein or biologically active portion thereof is contacted with a test compound and the ability of the test compound to bind to the NFAT regulator protein or biologically active portion thereof is evaluated. Preferred biologically active portions of the NFAT regulator proteins to be used in assays of the present invention include fragments or derivatives that participate in interactions with other signaling molecules, or fragments or derivatives that interact directly with NFAT.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence resonance energy transfer (FRET) (see, for example, Lakowicz et al., U.S. Pat. No. 5,631,169; Stavrianopoulos et al., U.S. Pat. No. 4,868,103). A fluorophore label is selected such that a first 'donor' label's emission spectrum overlaps with the absorption spectrum of a second, 'acceptor' molecule, which then fluoresces on excitation of the donor, if the labels are in close proximity, due to transfer of energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay is increased over the emission when binding does not occur, or when, e.g., binding is prevented by the excess of unlabelled competitor protein. A FRET binding event can be conveniently measured, in comparison to controls, through standard fluorometric detection means well known in the art (e.g., using a fluorimeter).

Assays which monitor assembly of the protein complex in cells or in cell free assays may also be used.

In another embodiment, determining the ability of the NFAT regulator protein to bind to a target molecule can be accomplished using real-time Biomolecular Interaction Analysis (BIA) (see, e.g., Sjolander and Urbaniczky, 1991, Anal. Chem. 63:2338-2345 and Szabo et al., 1995. Curr. Opin. Struct. Biol. 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product, e.g., NFAT regulator polypeptide or the test substance, is anchored onto a solid phase. The target gene product/test compound complexes anchored on the solid phase can be detected at the end of the reaction. In general, the target gene product can be anchored onto a solid surface, and the test compound, (which is not anchored), can be labeled, either directly or indirectly, with detectable labels discussed herein.

It may be desirable to immobilize an NFAT regulator, an anti-NFAT regulator antibody or its target molecule to facilitate separation of complexed from non-complexed forms of one or both of the proteins, as well as to accommodate automation of the assay. Binding of a test compound to an NFAT regulator protein, or interaction of an NFAT regulator protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/NFAT regulator fusion proteins or glutathione-S-transferase/target fusion proteins can be adsorbed onto glutathione Sepharose™ beads (Sigma Chemical, St. Louis, Mo.) or glutathione-derivatized microtiter plates, which are then combined with the test compound or the test compound and either the non-adsorbed target protein or NFAT regulator protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of NFAT regulator binding or activity determined using standard techniques.

Other techniques for immobilizing either NFAT regulator protein or a target molecule on matrices include using conjugation of biotin and streptavidin. Biotinylated NFAT regulator protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemicals).

To conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

This assay is performed utilizing antibodies reactive with NFAT regulator protein or target molecules but which do not interfere with binding of the NFAT regulator protein to its target molecule. Such antibodies can be derivatized to the wells of the plate, and unbound target or NFAT regulator protein trapped in the wells by antibody conjugation. Methods for detecting such complexes, in addition to those described above for the GST-immobilized complexes, include immunodetection of complexes using antibodies reactive with NFAT regulator protein or target molecule, as well as enzyme-linked assays which rely on detecting an enzymatic activity associated with the NFAT regulator protein or target molecule.

Alternatively, cell free assays can be conducted in a liquid phase. In such an assay, the reaction products are separated from unreacted components, by any of a number of standard techniques, including, but not limited to: filtration; differential centrifugation (see, for example, Rivas and Minton, 1993, Trends Biochem. Sci. 18:284-7); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (see, e.g., Heegaard, 1998, J. Mol. Recognit. 11:141-8; Hage and Tweed, 1997, J. Chromatogr. B. Biomed. Sci. Appl. 699:499-525). Further, fluorescence resonance energy transfer may also be conveniently utilized, as described herein, to detect binding without further purification of the complex from solution.

The assay can include contacting the NFAT regulator protein or biologically active portion thereof with a known compound that binds NFAT regulator to form an assay mixture, contacting the assay mixture with a test compound, and determining the ability of the test compound to interact with an NFAT regulator polypeptide, wherein determining the ability of the test compound to interact with an NFAT regulator protein includes determining the ability of the test compound to preferentially bind to NFAT regulator or biologically active portion thereof, or to modulate the activity of a target molecule, as compared to the known compound.

To the extent that NFAT regulator can, in vivo, interact with one or more cellular or extracellular macromolecules, such as proteins, inhibitors of such an interaction are useful. Such interacting molecules include $Ca^{2+}$ and subunits of the calcium channel complex as well as signaling molecules that directly interact with the channel, such as kinases, phosphatases and adapter proteins, can be used to identify inhibitors. For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, an NFAT regulator polypeptide can be used as a "bait protein" in a two-hybrid assay or three-hybrid assay (see, e.g., U.S. Pat. No. 5,283,317; Zervos et al., 1993, Cell 72:223-232; Madura et al., 1993, J. Biol. Chem. 268: 12046-12054; Bartel et al., 1993, Biotechniques 14:920-924; Iwabuchi et al., 1993, Oncogene 8:1693-1696; and Brent WO94/10300), to identify other proteins, that bind to or interact with NFAT regulator ("NFAT regulator-binding proteins" or "NFAT regulator-bp") and are involved in NFAT regulator activity. Such NFAT regulator-bps can be activators or inhibitors of signals by the NFAT regulator proteins or NFAT regulator targets as, for example, downstream elements of an NFAT regulator-mediated signaling pathway, e.g., NFAT target gene expression or activity.

Modulators of NFAT regulator expression can also be identified. For example, a cell or cell free mixture is contacted with a candidate compound and the expression of an NFAT regulator mRNA or protein evaluated relative to the level of expression of an NFAT regulator mRNA or protein in the absence of the candidate compound. Methods to detect expression or evaluate expression level are well known to the skilled artisan. When expression of an NFAT regulator mRNA or protein is greater in the presence of the candidate compound than in its absence, the candidate compound is identified as a stimulator of NFAT regulator mRNA or protein expression. Alternatively, when expression of NFAT regulator mRNA or protein is less (i.e., statistically significantly less) in the presence of the candidate compound than in its absence, the candidate compound is identified as an inhibitor of NFAT regulator mRNA or protein expression. The level of NFAT regulator mRNA or protein expression can be determined by methods described herein for detecting an NFAT regulator mRNA or protein.

A modulating agent can be identified using a cell-based or a cell-free assay, and the ability of the agent to modulate the activity of a NFAT regulator protein can be confirmed in vivo, e.g., in an animal such as an animal model for a disease (e.g., an animal with leukemia or autoimmune disease or an animal harboring a xenograft from an animal (e.g., human) or cells from a cancer resulting from a leukemia or other lymphocytic disorder, or cells from a leukemia or other lymphocytic disorder cell line.

This invention further pertains to novel agents identified by the above-described screening assays. Accordingly, it is within the scope of this invention to further use an agent identified as described herein (e.g., a NFAT regulator-modulating agent, an antisense NFAT regulator nucleic acid molecule, a NFAT regulator-specific antibody, or a NFAT regulator-binding partner) in an appropriate animal model (such as those described above) to determine the efficacy, toxicity, side effects, or mechanism of action, of treatment with such an agent. Furthermore, novel agents identified by the above-described screening assays can be used for treatments as described herein.

Animal models that are useful include animal models of leukemia and autoimmune disorders. Examples of such animal models are known in the art and can be obtained from commercial sources, e.g., the Jackson Laboratory (Bar Harbor, Me.) or generated as described in the relevant literature. Examples of animals useful for such studies include mice, rats, dogs, cats, sheep, rabbits, and goats. Other useful animal models include, without limitation, those for other disorders of $Ca^{2+}$-NFAT signaling or of $Ca^{2+}$ signaling, e.g., for myocardial hypertrophy, dilated cardiomyopathy, excessive or pathological bone resorption, excessive adipocyte differentiation, obesity, and reactivation of latent human herpesvirus-8 or other viruses, as discussed elsewhere in this document.

Systems

Also provided herein are systems for use in identifying an agent that modulates one or more of the following: a NFAT protein, a NFAT regulator protein, and intracellular or cytoplasmic calcium. Such a system includes a cell, or portion(s) thereof, containing one or more proteins, e.g., NFAT regulator proteins of the present invention, or fragments or derivative thereof, e.g., ORAI proteins or fragments or derivatives thereof. In one embodiment, the proteins are exogenous (heterologous or homologous) to the cell. In one embodiment, the cell contains an exogenous (e.g. heterologous or homologous) nucleic acid encoding a NFAT regulator protein or fragment or derivative thereof. In one embodiment, the system further contains a monitoring agent used to monitor, detect or measure electrical current across the plasma membrane of the cell. Many such monitoring agents are known in the art. The term "monitoring agent" is also meant to include any apparatus used for such monitoring.

In particular embodiments of the systems, the protein(s) involved in modulating intracellular calcium are contained in cells. The cells can be isolated cells or cell cultures that endogenously express such protein(s) or recombinantly express such proteins as described above with respect to the methods for identifying agents, e.g. a recombinant cell overexpressing at least one NFAT regulator protein or fragment or derivative thereof. Systems in which the cells recombinantly express the proteins can be such that the cells are isolated cells or cell cultures or are contained within an animal, in particular, a non-human animal, e.g., a non-human mammal.

The proteins (and/or nucleic acids encoding proteins) or cells (or portions thereof) of the system can be contained in a medium that contains an agent that provides for passive or active intracellular calcium store reduction or depletion (e.g., thapsigargin and other agents described herein or known in the art) and/or that contains a molecule or molecules that facilitate monitoring or measurement of intracellular calcium and/or calcium movement. Such molecules include fluorescent (or otherwise labeled) calcium indicators, trivalent cations, divalent cations other than calcium and calcium-buffering agents, e.g., calcium chelators.

Recombinant Cells

Aspects of the invention further relate to recombinant cells used in the assays described in the methods discussed herein. In one aspect, the invention also encompasses any recombinant cells described herein. In one embodiment, the recombinant cell comprises at least one exogenous (heterologous or homologous) NFAT regulator protein or fragment or derivative thereof. The recombinant cell may also further comprise at least one exogenous (heterologous or homologous) nucleic acid encoding a NFAT regulator protein or fragment or derivative thereof. The NFAT regulator protein may be of mammalian origin. The recombinant cell may over express the NFAT regulator protein or fragment or derivative thereof. This overexpression may result from expression of an exogenous (heterologous or homologous) NFAT regulator protein (e.g. from an exogenous nucleic acid) or may result from over expression of native/endogenous NFAT regulator protein.

Transgenic Animals

The invention provides non-human transgenic animals that are engineered to overexpress an NFAT regulator, ectopically express an NFAT regulator, express reduced levels of an NFAT regulator, express a mutant NFAT regulator, or be knocked out for expression of an NFAT regulator. Such animals and cell lines derived from such animals are useful for studying the function and/or activity of an NFAT regulator protein and for identifying and/or evaluating modulators of NFAT regulator activity. An animal that overexpresses an NFAT regulator polypeptide is useful, e.g., for testing the effects of candidate compounds for modulating the activity of the NFAT regulator polypeptide and assessing the effect of the compound in vivo.

As used herein, a "transgenic animal" is a non-human animal, in general, a mammal, for example, a rodent such as a rat or mouse, in which one or more of the cells of the animal include a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which is in most cases integrated into or occurs in the genome of the cells of a transgenic animal. A transgene can direct the expression of an encoded gene product in one or more cell types or tissues of the transgenic animal; other transgenes, e.g., a knockout, reduce expression. Thus, a transgenic animal can be one in which an endogenous NFAT regulator gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of an NFAT regulator protein to particular cells. A transgenic founder animal can be identified based upon the presence of an NFAT regulator transgene in its genome and/or expression of NFAT regulator mRNA in tissues or cells of the animals. A transgenic founder animal can then be used to breed additional animals carrying the transgene. Moreover, transgenic animals carrying a transgene encoding an NFAT regulator protein can further be bred to other transgenic animals carrying other transgenes.

NFAT regulator proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

In one non-limiting example, a mouse is engineered to express an NFAT regulator polypeptide using a T cell-specific promoter such as an LCK promoter using methods known in the art (e.g., Zhang et al., 2002, Nat. Immunol. 3:749-755). In an alternative example, a mouse is engineered with a tissue-specific knockdown of an NFAT regulator mRNA and protein, e.g., by Cre-lox mediated recombination, where expression of the recombinase is under control of a tissue-specific promoter. Engineered animals can be identified using known methods of identifying the presence of a transgene in cells and by assaying a cell sample (e.g., T cells) for the overexpression or underexpression of the NFAT regulator (for example, using immunocytochemistry) or by assaying calcium flux in a cell from the sample. Such transgenic animals are useful, e.g., for testing compounds for their ability to inhibit NFAT regulator-mediated cell proliferation.

The invention also includes a population of cells from a transgenic animal. Methods of developing primary, secondary, and immortal cell lines from such animals are known in the art.

Pharmaceutical Compositions

For therapeutic applications, peptides and nucleic acids of the invention, the antibodies to the NFAT regulators or the agents identified by the screening methods of the present invention, e.g., small molecules, siRNAs, shRNAs, may be suitably administered to a subject such as a mammal, particularly a human, alone or as part of a pharmaceutical composition, comprising the peptide, nucleic acid, antibody or agent together with one or more acceptable carriers thereof and optionally other therapeutic ingredients. The carrier(s) must be "acceptable" in the sense of being compatible with the other ingredients of the formulation and not deleterious to the recipient thereof.

The pharmaceutical compositions of the invention include those suitable for oral, rectal, nasal, topical, e.g, including buccal and sublingual, mucosal or parenteral, e.g., including subcutaneous, intramuscular, intravenous and intradermal administration. The formulations may conveniently be presented in unit dosage form, e.g., tablets and sustained release capsules, and in liposomes, and may be prepared by any methods well know in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and nonaqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Application of the subject therapeutics often will be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way. Systemic administration of a nucleic acid using lipofection, liposomes with tissue targeting (e.g. antibody) may also be employed.

It will be appreciated that actual preferred amounts of a given peptide or nucleic acid of the invention, or of an antibody or agent identified by the screening methods of the present invention, used in a given therapy will vary to the particular active peptide or nucleic acid or agent being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests.

Various embodiments of the invention are further illustrated in the following examples. All references made to other publications or disclosures throughout this document are incorporated by reference herein.

EXAMPLE 1

Identification of Ca$^{2+}$ Release Activated Ca$^{2+}$ (CRAC) Channel Gene, ORAI1, in SCID Patients Materials and Methods:
Case Reports Detailed case reports of the two SCID patients investigated in this study have been described (Feske 1996, 2000).

Cell Lines and Reagents

T cell lines were established from peripheral blood lymphocytes of two patients and 21 family members and grown as described[48]. Foreskin fibroblasts from the newborn SCID patient 2 and a healthy newborn (Hs27 cell line, ATCC, Manassas, Va.) were immortalized by retroviral transduction with a telomerase expression plasmid (hTERT, generous gift of S. Lessnick, DFCI, Boston, Mass.). The macrophage-hemocyte-like *Drosophila* cell line S2R$^+$ was grown in Schneider's medium with 10% fetal calf serum (Invitrogen) according to standard protocols. Thapsigargin was purchased from LC Biochemicals (Woburn, Mass.), Charybdotoxin (CTX) and 2-aminoethoxydiphenylborate (2-APB) from Sigma (St. Louis, Mo.).

Single Nucleotide Polymorphism (SNP) Array Based Linkage Analysis

Genomic DNA of SCID patients and 21 relatives was prepared from peripheral blood mononuclear cells using genomic DNA Maxi prep kits (Qiagen). Genotyping was performed at the SNP Genotyping Center (Broad Institute, Cambridge, Mass.) and the Harvard Partners Center for Genetics and Genomics (Boston, Mass.), using "GeneChip" Human Mapping 10K Arrays (Xba 142 2.0, Affymetrix, Santa Clara, Calif.) with an average SNP heterozygosity of 0.38 and a mean intermarker density of 258 kb. This platform allowed for simultaneous genotyping of more than 10,000 SNPs in the human genome. For parametric linkage analysis, data were converted into "Linkage" format using "Compare Linkage"[49]. Mendelian genotype errors inconsistent with the parental genotypes were detected and set to missing genotypes. Multipoint parametric linkage analysis was performed to compute LOD scores at each SNP position using Allegro[50]. To confirm linkage, we reanalyzed the SNP data using Genehunter 2.1r6[51] and Merlin[52] obtaining very similar results. For parametric analysis, a disease allele frequency of 0.001, a penetrance value of 0.99 and a phenocopy of 0.01 were used for all the pedigrees. Parametric linkage analyses were carried out using recessive and dominant models of inheritance, respectively. For the "recessive" model, haplotypes from both patients, their parents, unaffected brother and grandparents (individuals 8, 11, 35, 36, 37, 38, 39, 63, 64 in FIG. 1A) were analyzed assuming an autosomal recessive mode of inheritance for the SCID disease with both SCID patients being homozygous for a common disease-causing mutation. The predicted maximum $\log_{10}$ of the odds ratio (LOD) score from this analysis was ~1.9 (i.e. $-\log_{10}$ [0.25×0.25×0.25×0.75]). For the "dominant" model, 12 family members with reduced store-operated Ca$^{2+}$ entry were defined as "affected", i.e. carriers of a dominantly acting mutation, and their SNP haplotypes compared to those of 8 healthy family members with normal store-operated Ca$^{2+}$ entry. The predicted maximum LOD score from this analysis was ~3.8 (i.e. $-\log_{10}$ [0.5$^{12}$]).

Genomic DNA Sequencing

Genomic DNA of two patients, 21 family members and three independent controls was sequenced for mutations in exons 1 and 2 of Orai1 using the following oligonucleotide primers: Orai1ex1for1 5' ACAACAACGCCCACTTCTTG-GTGG (SEQ ID NO: 22) (exon 1); Orai1ex1rev1 5' TGCT-CACGTCCAGCACCTC (SEQ ID NO: 23) (exon 1); Orai1ex2for1 5' TCTTGCTTTCTGTAGGGCTTTCTG (SEQ ID NO: 24) (exon 2); Orai1ex2rev1 5' TCTCAAAG-GAGCTGGAAGTGC (SEQ ID NO: 25) (exon 2). DNA was amplified using AmpliTaq Gold polymerase and separated on 1% agarose gels. PCR products were gel-purified and sequenced directly using the following primers: Orai1ex1for2 5' AGCATGCAAAACAGCCCAGG (SEQ ID NO: 26) (exon 1); Orai1ex1rev2 5' ACGGTTTCTC-CCAGCTCTTC (SEQ ID NO: 27) (exon 1); Orai1ex2for2 5' TGACAGGAGGAGAGCTAGG (SEQ ID NO: 28) (exon 2); Orai1ex2rev2 5' AAGAGATCCTCCTGCCTTGG (SEQ ID NO: 29). Sequencing was done at the DF/HCC DNA Resource Core (DFCI) and DNA sequences analyzed using Xplorer Lite (dnaTools, Ft. Collins, Colo.).

Sequenom Analysis of HapMap DNA

To exclude the possibility that the C>T point mutation at position 271 in the coding sequence of Orai1 (NM_032790) is a SNP, we examined DNA from a panel of 270 individuals of diverse geographical origin assembled for the International HapMap project[30,31]. Genotyping was performed using a high-throughput primer extension method with detection by mass spectrometry (MALDI-TOF) on the Sequenom platform as previously described[53]. A detailed description of this method can be found at http://www.hapmap.org/downloads/genotyping_protocols.html under "Sequenom platform". 89% of samples were genotyped successfully and all were identified as CC homozygotes.

dsRNA Mediated Knockdown in *Drosophila* Cells

PCR fragments (size up to 600 bp) were used as templates for in vitro transcription reactions, followed by DNase I treatment to remove the template DNA. After purification, dsRNA (5 μg) was co-transfected together with the NFAT-GFP expression plasmid into S2R+ cells in 8-chamber slides (10 μg for 12 well plate). After 72 hrs of incubation, cells were treated with the Ca$^{2+}$ influx inducers, 1 μM ionomycin or 1 μM thapsigargin for localization assays and were trypsinized for the measurement of [Ca$^{2+}$]$_i$ levels.

Genome-Wide RNAi Screen

The RNAi screen was performed essentially as described (Armknecht S. et al., 2005, Methods Enzymol 392, 55-73; Btros M. et al. 2004 Science 303, 832-835). The macrophage-hemocyte-like *Drosophila* cell line S2R+ was stably transfected with the coding sequence for the NFAT1 (1-460)-GFP fusion protein subcloned into the expression plasmid pAc5.1 (Invitrogen). Transfection was achieved using Effectene (Qiagen) with a 19:1 ratio of the expression plasmid to pCo-Hygro (Invitrogen), which encodes a hygromycin resistance gene under the control of a constitutively active promoter. The cells were selected for 3-4 weeks with 300 μg/ml hygromycin, and stable clones were selected by visual inspection. 10$^4$ S2R$^+$ cells stably expressing NFAT1(1-460)-GFP were added onto each well of a 384 well plate containing 0.25 μg of dsRNAs (in 10 μl of serum-free medium) against *Drosophila* mRNAs and incubated for 1 h at 26° C. and incubated for 48-72 hrs at 26° C. to achieve RNAi. S2R$^+$ cells were stimulated with 1 μM thapsigargin in Schneider medium containing 5 mM CaCl$_2$ at room temperature for 10 min, fixed and stained with DAPI. Coincident GFP and DAPI images were acquired by an automated camera from three different locations in each well, and scored by visual inspection. A total of fifty-eight 384-plates were analysed, containing a total of 21,884 wells into which individual dsRNAs had been arrayed. For this study, we note that the dsRNA amplicons for both dStim and dOrai had no predicted off-targets with exact matches of 19 nucleotides or greater.

Plasmids and Retroviral Transduction

Full-length cDNA for Orai1 (BC015369) was purchased from OpenBiosystems (Huntsville, Ala.) and subcloned into pENTR11 ("Gateway" system, Invitrogen, Carlsbad, Calif.) in frame with an N- or C-terminal sequence encoding the myc epitope. Orai1 was then moved to the bicistronic retroviral expression vector pMSCV-CITE-eGFP-PGK-Puro (kind gift of Masatsugu Oh-hora), which allows for simultaneous expression of Orai1, GFP and a puromycin resistance gene. gp293 packaging cell lines were co-transfected with plasmids encoding Orai1, gag-pol and env to produce amphotropic, replication-incompetent retrovirus. Virus containing supernatant was collected for 24 h, filtered (0.45 microm, low protein binding) and concentrated by centrifugation at 6000×g for 16 h. T cells and fibroblasts were transduced by addition of viral supernatant for 4 d and 1 d, respectively. Transduction efficiency was evaluated by GFP expression using flow cytometry and myc-Orai1 expression using immunoblotting and immunocytochemistry. In some cases, transduced T cells were further selected with 1 μg/ml puromycin for 3 days.

Bioinformatic Prediction of Membrane Topoplogy

The hydropathy plot of Orai1 was generated using the Kyte-Doolittle algorithm[29]. Membrane topology was further evaluated using the Phobius algorithm based on the hidden Markov model[26]. Sequence alignment was performed using MegAlign (DNAStar, Madison, Wis.).

Confocal Imaging

Immunocytochemistry for Orai1 was done as described[11]. Briefly, retrovirally transduced T cells and fibroblasts were fixed with 3% paraformaldehyde, left unpermebealized or permeabilized with wash buffer containing 0.5% NP-40, incubated with anti-myc antibodies (9E10) and Cy3-labeled secondary antibodies. Immunofluorescence was analyzed by confocal imaging using a Radiance 2000 Laser-scanning confocal system (Bio-Rad Laboratories) on a BX50BWI Olympus microscope using a 63× water immersion objective.

Single-Cell $Ca^{2+}$ Imaging

T cells were loaded at $1\times10^6$ cells/ml with 1 μM fura-2/AM (Molecular Probes) in loading medium (RPMI+10% FBS) for 30 min at 22-25° C., resuspended in loading medium and attached to poly-L-lysine-coated coverslips for 15 min. Fibroblasts were grown directly on UV-sterilized coverslips and loaded with 3 μM fura-2/AM for 45 min at 22-25° C. For $[Ca^{2+}]_i$ measurements, cells were mounted in a RC-20 closed-bath flow chamber (Warner Instrument Corp., Hamden, Conn.) and analyzed on an Axiovert S200 epifluorescence microscope (Zeiss) with OpenLab imaging software (Improvision). Cells were perfused in $Ca^{2+}$-free Ringer solution and $Ca^{2+}$ stores were passively depleted with 1 μM thapsigargin. Active depletion of stores was induced by incubation with 10 μg/ml anti-CD3 antibody (OKT3, eBioscience, San Diego, Calif.) for 10 min at 22-25° C. Fura-2 emission was detected at 510 nm with excitation at 340 and 380 nm and Fura-2 emission ratios (340/380) were calculated for each 5-s interval after subtraction of background. For each experiment, approximately 100 individual cells were analyzed for 340/380 ratios using Igor Pro (Wavemetrics, Lake Oswego, Oreg.) analysis software. $[Ca^2]_i$ was estimated from the relation $[Ca^{2+}]_i=K*(R-R_{min})/(R_{max}-R)$. $K*$, $R_{min}$, and $R_{max}$ were measured in control human T cells in situ as previously described[54]. $Ca^{2+}$ influx rates were calculated from the maximal rate of rise in $Ca^{2+}$ concentrations ($d[Ca^{2+}]_i/dt$) after readdition of 0.2 mM extracellular $Ca^{2+}$.

$Ca^{2+}$ influx in S2R+ cells was measured by flow cytometry after detaching cells from the dish with trypsin (CellGro, Herndon, Va.). Cells were loaded with the $Ca^{2+}$ indicator dyes Fluo4-AM and Fura-Red (2 μM each, Molecular Probes, Eugene, Oreg.) for 45 min at room temperature and then resuspended in loading medium (Schneider's medium+10% FCS). Immediately before the flow cytometric $Ca^{2+}$ measurements, cells were resuspended in Ringer solution containing 2 mM $Ca^{2+}$ and analyzed on a FACSCalibur (BD Biosciences, San Jose, Calif.). After 30 sec, thapsigargin (3 μM) in $Ca^{2+}$ free Ringer to deplete intracellular $Ca^{2+}$ stores, 4 mM $Ca^{2+}$ Ringer solution was added and cellular $Ca^{2+}$ levels were monitored for 300 sec. The ratio of Fluo-4 and Fura-Red emission was analyzed using FloJo software (Tree Star, Inc., Ashland, Oreg.).

Solutions and Chemicals

The standard extracellular Ringer's solution contained (in mM): 155 NaCl, 4.5 KCl, 20 $CaCl_2$, 1 $MgCl_2$, 10 D-glucose, and 5 Na-Hepes (pH 7.4). The standard divalent-free (DVF) Ringer's solutions contained (in mM): 155 Na, 10 HEDTA, 1 EDTA and 10 Hepes (pH 7.4). Charybdotoxin (CTX) was included in all external solution to block Kv1.3 channels to prevent contamination of $I_{CRAC}$ recordings in DVF solutions. The standard internal solution contained (in mM): 150 Cs-aspartate, 8 $MgCl_2$, 8 BAPTA, and 10 Cs-Hepes (pH 7.2).

Thapsigargin (LC Biochemicals, Woburn, Mass.) was diluted from a 1 mM stock in DMSO, CTX (Sigma, St. Louis, Mo.) was diluted 1:1000 from 50 μM stock solution in water. 2-aminoethyoxydiphenylborate (2-APB, Sigma) was diluted from stock solutions in DMSO. The drugs were diluted to the concentrations indicated in the legends and applied to the cells using a multi-barrel local perfusion pipette with a common delivery port. The time for 90% solution exchange was measured to be <1 s, based on the rate at which the $K^+$ current reversal potential changed when the external $[K^+]$ was switched from 2 mM to 150 mM.

Patch-Clamp Measurements

Patch-clamp experiments were conducted in the standard whole-cell recording configuration at 22-25° C. using an Axopatch 200 amplifier (Axon Instruments, Foster City, Calif.) interfaced to an ITC-16 input/output board (Instrutech, Port Washington, N.Y.) and a Macintosh G3 computer. Recording electrodes were pulled from 100-ml pipettes, coated with Sylgard, and fire-polished to a final resistance of 2-5 MΩ. Stimulation and data acquisition and analysis were performed using in-house routines developed on the Igor Pro platform (Wavemetrics, Lake Oswego, Oreg.). The holding potential was +30 mV unless otherwise indicated. Voltage stimuli usually consisted of a 100-ms step to −100 mV followed by a 100-ms ramp from −100 to +100 mV, applied every 1.3 s. Currents were filtered at 2 kHz with a 4-pole Bessel filter and sampled at 5 kHz. Data are corrected for the liquid junction potential of the pipette solution relative to Ringer's in the bath (−10 mV) and for the bath DVF solution relative to Ringer's in the bath-ground agar bridge (+5 mV). For noise analysis, 200-ms sweeps were acquired at the rate of 3 Hz at a holding potential of −100 mV, digitized at 5 kHz, and low-pass filtered using the Axopatch 200 amplifier's internal Bessel filter at 2 kHz. The mean and variance were calculated from 100-ms segments of the digitized data.

Data Analysis

Unless noted otherwise, all data were corrected for leak currents collected either with 2 μM $La^{3+}$ or with traces collected prior to $I_{CRAC}$ induction during passive dialysis with BAPTA. Permeability ratios ($P_{Cs}/P_{Na}$) was calculated from the biionic reversal potential using the equation:

$$\frac{P_{Cs}}{P_{Na}} = \left(\frac{[Na]_o}{[Cs]_i}\right) e^{\left(\frac{E_{rev}F}{RT}\right)}$$

where R, T, and F have their usual meanings and $E_{rev}$, is the reversal potential.

Introduction $Ca^{2+}$ is an essential second messenger in almost all cell types. In particular, sustained $Ca^{2+}$ influx across the plasma membrane is crucial for lymphocyte activation and the adaptive immune response. Antigen recognition by the surface antigen receptors of T and B lymphocytes triggers an elaborate signal transduction cascade, involving the activation of multiple tyrosine kinases and the assembly of large scaffolded complexes containing diverse adapters and signaling proteins. An early biochemical consequence is the activation of PLCγ, which releases $Ca^{2+}$ from the endoplasmic reticulum (ER) by generating $IP_3$; the resulting decrease in lumenal ER $Ca^{2+}$ opens a class of "store-operated" $Ca^{2+}$ channels with very specific electro-physiological characteristics, which have been termed $Ca^{2+}$ release-activated $Ca^{2+}$ (CRAC) channels[1-3]. CRAC channel opening results in sustained influx of $Ca^{2+}$ ions across the plasma membrane, promoting a sustained elevation of intracellular free $Ca^{2+}$ ($[Ca^{2+}]_i$) levels and activating diverse $Ca^{2+}$/calmodulin-dependent enzymes including the protein phosphatase calcineurin; an ultimate consequence is the activation of $Ca^{2+}$-dependent transcriptional pathways required for proliferation and effector immune function[4,5]. One of the major $Ca^{2+}$-regulated transcription factors is NFAT, a family of heavily-phosphorylated proteins that resides in the cytoplasm of resting cells[5]. Sustained $Ca^{2+}$ influx results in the dephosphorylation of NFAT by calcineurin and promotes its translocation to the nucleus, where it turns on the expression of a large number of activation-associated genes[4,6].

A great deal of pharmacological, electrophysiological, and genetic evidence supports the notion that CRAC channels are the principal pathway for $Ca^{2+}$ influx in both developing and mature T cells, thus orchestrating essentially all aspects of lymphocyte development and function[1,7]. Analysis of two families of patients with hereditary severe combined immune deficiency (SCID), who presented as infants with a marked propensity to bacterial and viral infections, revealed that the primary defect is lack of store-operated $Ca^{2+}$ entry in the patients' lymphocytes[8-10]. Detailed analysis of T cell lines derived from one family of patients revealed severe impairment of NFAT dephosphorylation, nuclear translocation and activation of NFAT-dependent genes, secondary to a correspondingly severe impairment of store-operated $Ca^{2+}$ influx in cells activated through the T cell receptor or treated with thapsigargin, an inhibitor of the SERCA $Ca^{2+}$ pump[10]. Electrophysiological analysis of the patients' T cells confirmed an almost complete absence of CRAC channel function[11]. Together these data highlight the crucial importance of CRAC channels and store-operated $Ca^{2+}$ entry for lymphocyte activation and immune defense.

Although the pharmacological and electrophysiological properties of the CRAC channel have been described in some detail[1,12,13], its molecular identity has remained elusive to date. The key biophysical hallmarks of the channel include high selectivity for $Ca^{2+}$ over monovalent cations, low single-channel conductance (<1 pS), an inwardly rectifying I-V relationship, a lack of significant voltage-dependent gating, rapid inactivation by intracellular $Ca^{2+}$, extracellular blockade by submicromolar $La^{3+}$, and modulation of channel properties by 2-APB[1,13,14]. Several candidate genes belonging to the TRP family of ion channels have been proposed to encode the CRAC channel, including TRPC1[15], TRPC3[16], and TRPV6[17,18], as well as voltage-gated $Ca^{2+}$ (Cav) channels[19,20]. However, evidence that TRPs are store-dependent following heterologous expression in several cell lines is inconsistent[21,22], and none of the candidates exhibit all of the biophysical properties of the CRAC channel. Previous sequence analyses and complementation studies in the SCID patients' cells had failed to establish a role for several TRP family members including TRPC3, TRPV5 and TRPV6 in the defect in CRAC channel function[11]. More recently, the type I membrane proteins STIM1 and STIM2 were shown to be essential for store-operated $Ca^{2+}$ entry and CRAC channel function[23,24]. STIM1 has been suggested to "sense" the filling state of the ER $Ca^{2+}$ stores via its EF hand domain, thus coupling store depletion to the opening of CRAC channels. However neither STIM1 nor STIM2 were mutated in the SCID patients, and expression of STIM1 in SCID T cells did not result in complementation of the $Ca^{2+}$ entry defect[11].

Here we describe the identification of a novel protein crucial for store-operated $Ca^{2+}$ entry and CRAC channel function. The protein, here termed Orai1, was identified using two unbiased genetic approaches: a modified linkage analysis to identify the gene mutated in the SCID patients, and a genome-wide RNAi screen in *Drosophila* to identify regulators of store-operated $Ca^{2+}$ entry and NFAT nuclear import. The combination of these two approaches pinpointed a single candidate gene. We show that RNAi-mediated depletion of *Drosophila* Orai abrogates store-operated $Ca^{2+}$ entry as effectively as RNAi against *Drosophila* Stim. We further show that a point mutation in Orai1 is responsible for the $Ca^{2+}$ influx defect in the SCID patients, and that complementation of SCID T cells and fibroblasts with wild type Orai1 reconstitutes store-operated $Ca^{2+}$ influx and CRAC channel current ($I_{CRAC}$). The pharmacological and electrophysiological properties of the reconstituted currents are indistinguishable from those of endogenous $I_{CRAC}$ in control T cells. The primary sequence of Orai1 predicts four transmembrane domains, and immunocytochemistry of epitope-tagged Orai1 shows that the protein is localized at or near the plasma membrane.

Results

Phenotypic Identification of Heterozygous Disease Carriers

Figure 1B:
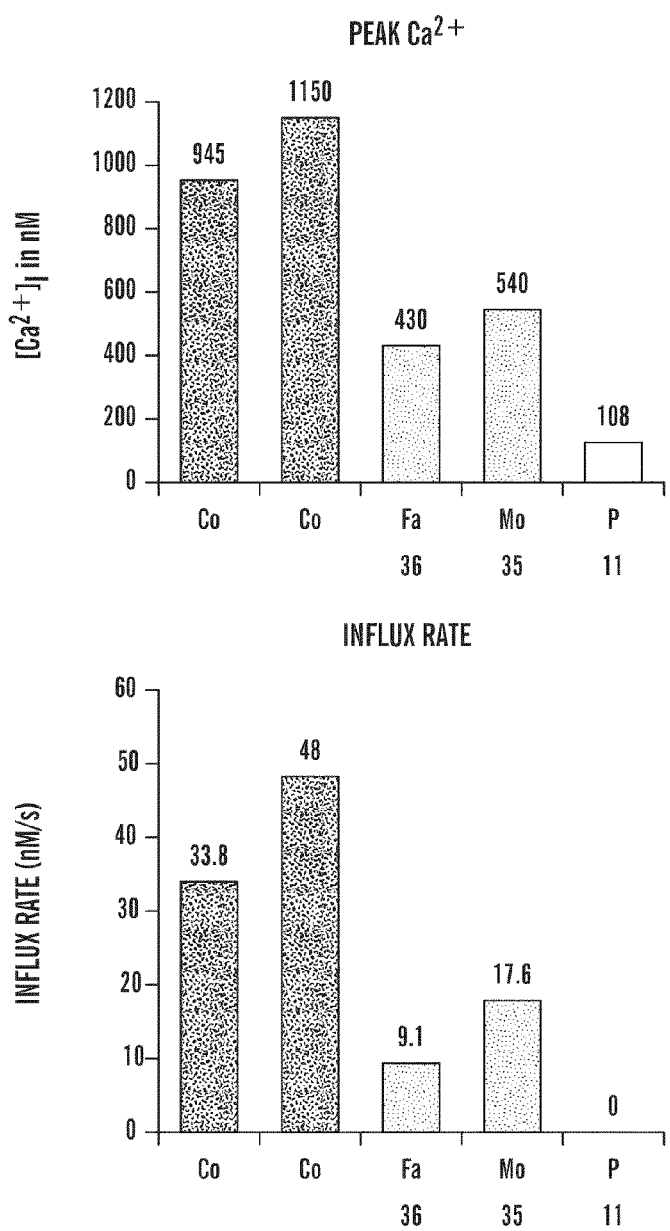

The two SCID patients were born to consanguineous parents, suggesting an autosomal recessive mode of inheritance as neither the parents of the SCID patients nor any other members of the SCID patients' family showed clinical symptoms of immunodeficiency (FIG. 1A). Furthermore, T cells derived from the parents of the SCID patients showed almost normal store-operated $Ca^{2+}$ entry in the presence of 2 mM extracellular $Ca^{2+}$ [10]. To unmask a potential defect in $Ca^{2+}$ entry in the parental T cells, we measured the initial rate of $Ca^{2+}$ influx (here defined as the initial rate of change of intracellular free $Ca^{2+}$ concentration, $d[Ca^{2+}]_i/dt$) after thapsigargin-mediated store depletion, but decreased the driving force for $Ca^{2+}$ entry by reducing the extracellular $Ca^{2+}$ concentration from 2 mM to 0.2-0.5 mM $CaCl_2$. Under these conditions, peak $Ca^{2+}$ levels and $Ca^{2+}$ influx rates in T cells from both parents were ~50% or less of those observed in wild-type control T cells (FIG. 1B). We hypothesized that this finding reflected a potential gene-dosage effect, resulting from the fact that the parents were heterozygous carriers of the causal mutation in the SCID patients.

Figure 1C:
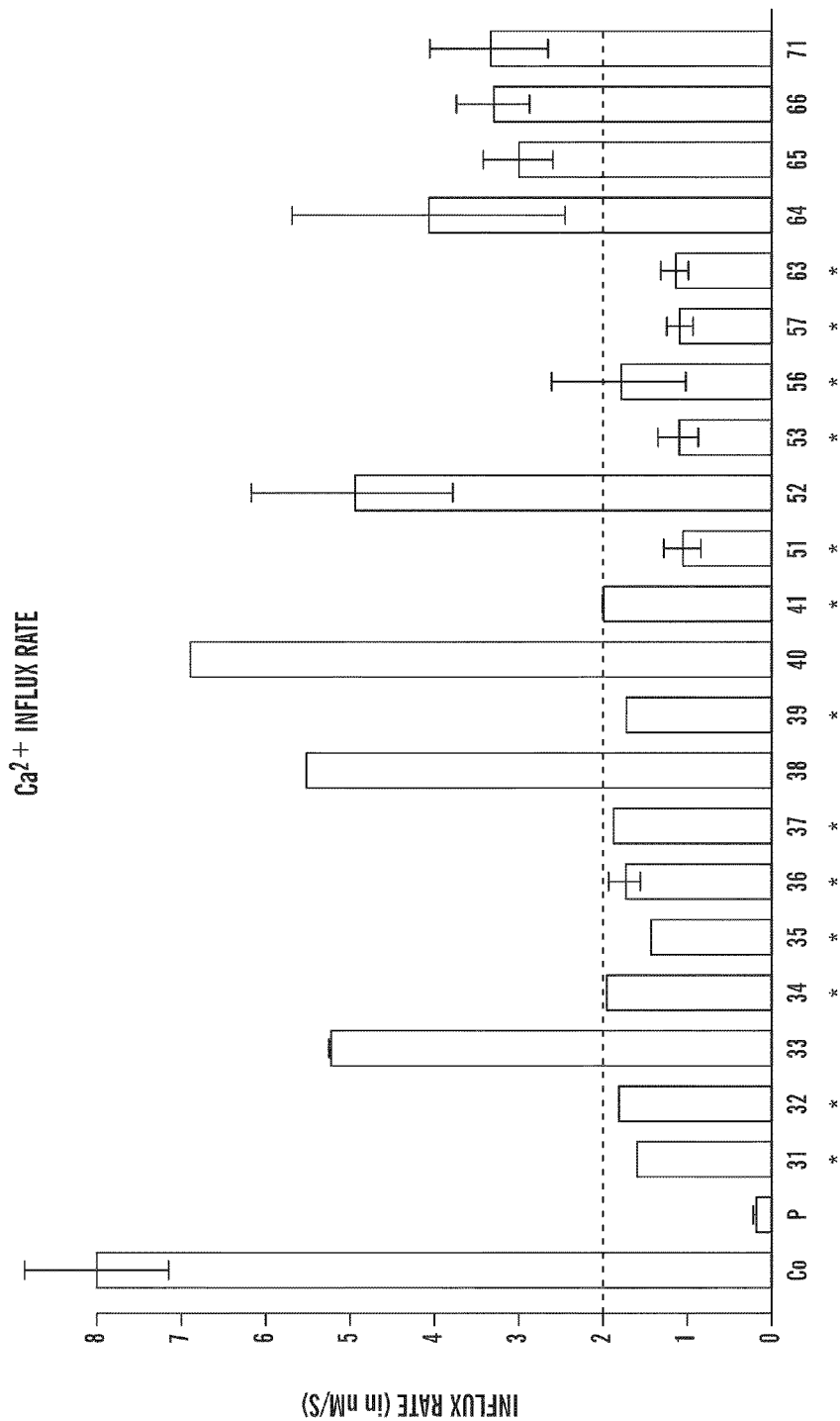

We used this assay to identify other potential heterozygous carriers of such a mutation in the more extended pedigree. Blood samples were obtained from 19 additional family members (FIG. 1A), T cell lines were generated, and $Ca^{2+}$ entry phenotype was evaluated by phenotypic analysis in vitro. Thirteen family members consistently showed reduced peak $Ca^{2+}$ influx and decreased initial rate of $Ca^{2+}$ influx, compared to T cells from 8 other family members and unrelated controls (FIG. 1C). An arbitrary cutoff of $Ca^{2+}$ influx rate below 2 nM/s was used to distinguish potential heterozygous disease carriers from unaffected (homozygous wild-type) individuals (FIG. 1C). With this cutoff, the distribution of putative heterozygous carriers within the family appears fully compatible with an autosomal dominant mode of inheritance (FIG. 1A).

Linkage Manning by Genome-Wide SNP Array Screen

Genomic DNA from the 23 members of the SCID family was used for genotyping using genome-wide SNP arrays. SNP data were evaluated using two independent linkage analyses. The first analysis assumed an autosomal recessive mode of inheritance based on the clinical phenotype, and DNA from the two patients, their parents, their unaffected brother and their grandparents was analysed (Pedigree A, indicated by the grey shaded area in FIG. 1A). In contrast, the second analysis utilized the remainder of the pedigree in a completely independent analysis. Here, an autosomal dominant mode of inheritance was assumed, based on our ability to identify heterozygous carriers of the disease mutation by phenotypic analysis in vitro (Pedigree B, indicated by the green box in FIG. 1A). Importantly, the first analysis (standard homozygosity mapping) was performed without consideration of the heterozygous phenotype status of individuals, and the second (dominant inheritance) was performed on the large pedigree as two unrelated halves (the relatives of parent 35 and 36 being treated independently) such that the results of these two analyses are fully independent. Thus we can consider the analyses of these two runs to emerge from three independent pedigrees (one homozygosity mapping run and two unrelated dominant pedigrees) and can simply add the parametric LOD scores from these to acquire a statistically robust combined LOD score (see Materials and Methods).

Parametric linkage analysis for a recessive trait (Pedigree A) identified six regions on six chromosomes with LOD scores of 1.5-1.9—while one of these is almost certain to harbor the gene, it is fully expected that this maximum LOD score would be achieved several times by chance and thus the homozygosity mapping is not sufficient alone to map this gene. Satisfyingly, the dominant analysis identified a unique region on chromosome 12q24, clearly overlapping with one of the 6 regions identified in the homozygosity mapping analysis, with a LOD score of ~3.8. The combination of these two linkage analyses defines an overlapping ~9.8 Mb candidate region with a highly significant cumulative LOD score of 5.7, representing odds of ~500,000:1 in favor of linkage—overwhelmingly likely to contain the true gene. This region is located between SNP_A-1514003 and SNP_A-1510776 (115.49 Mb-125.27 Mb). In support of this conclusion, no other region in the genome had a cumulative LOD score exceeding zero. Because incorrect assignment of heterozygous disease carrier status based on phenotypic analysis would decrease overall LOD scores rather than yielding false positives of this magnitude, our novel combination of recessive and dominant analyses successfully identifies a genomic region with a very high probability of linkage to the mutant gene.

Genomic sequencing of six known genes in this region with a potential role in $Ca^{2+}$ signaling or $Ca^{2+}$ binding (PLA2G1B, CABP1, P2RX7, P2RX4, CAMKK2, PITPNM2) did not reveal any mutations in exons or immediately adjacent genomic regions. It did however allow us to narrow down the candidate homozygous region from ~9.8 Mb to ~6.5 Mb, on the basis of several SNPs in PITPNM2 for which the patients were heterozygous. The ~6.5 Mb interval contains ~74 genes, of which 16 were annotated as "hypothetical proteins" or potential gene loci (Human genome assembly, NCBI build 35.1). Of these, 2 were predicted to contain transmembrane domains (KIAA0152 and FLJ14466) using TMHMM and Phobius algorithms[25,26].

A Genome-Wide RNAi Screen in *Drosophila* Identifies olf186F (dOrai) as a Novel Regulator of Store-Operated $Ca^{2+}$ Entry In parallel with the positional cloning effort, we conducted a genome-wide RNAi screen for NFAT regulators in *Drosophila*, as an independent method of identifying components of the CRAC channel and the signalling pathway leading to CRAC activation. *Drosophila* S2R+ cells, stably-expressing an NFAT-GFP fusion protein, were incubated for 3 days with arrayed dsRNAs against each of ~21,000 *Drosophila* genes to achieve knockdown of gene expression. The cells were then stimulated for 10 min with thapsigargin to deplete $Ca^{2+}$ stores, thus activating store-operated $Ca^{2+}$ entry and nuclear translocation of NFAT-GFP. The cells were then fixed, wells containing the cells were photographed robotically, and the subcellular distribution of NFAT-GFP was assessed by visual inspection. Among the positive candidates whose depletion interfered with NFAT nuclear translocation were several expected regulators of the $Ca^{2+}$/calcineurin/NFAT signalling pathway, including Calcineurin B (CanB), Calcineurin A (CanA-14F) and *Drosophila* Stim[24,27].

Figure 2A:
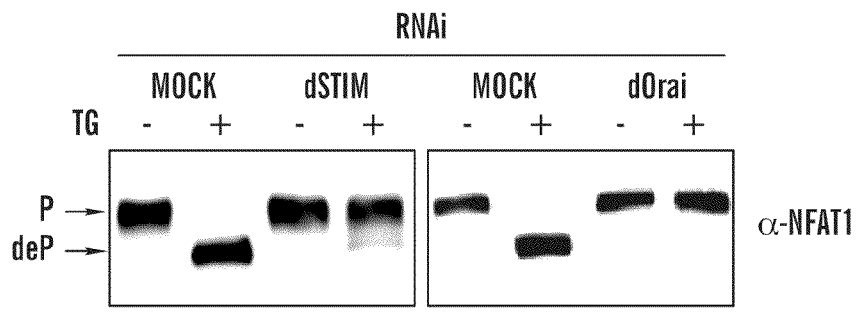
FIGS. 2A-2B show that a genome-wide RNAi screen identifies Drosophila Orai as a protein regulating NFAT translocation and store-operated $Ca^{2+}$ entry.
Figure 2B:
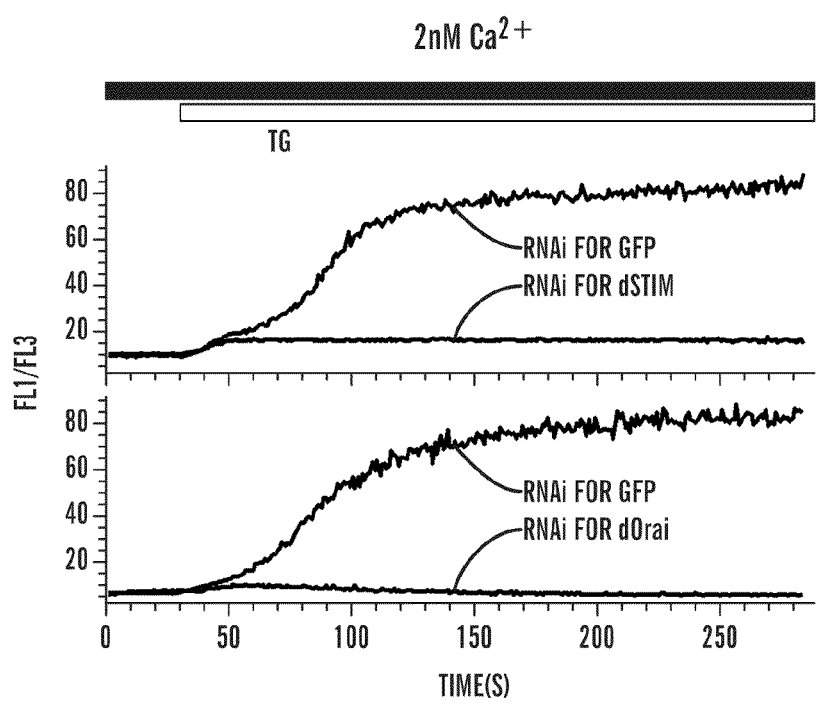

One positive candidate, olf186F, was notable because the gene encoding one of its three human homologues was located within the 6.5 Mb homozygous genomic region linked to the SCID mutation at 12q24 (hypothetical protein FLJ14466, NM_032790, NP_116179). For reasons discussed below, olf186F and its human homologue at 12q24 have been designated *Drosophila* Orai (dOrai) and human Orai1 respectively; the other two human homologues, C7Orf19 located on chromosome 7 and MGC13024 located on chromosome 16, have been designated Orai2 and Orai3 (FIG. 3A). In *Drosophila* S2R+ cells, RNAi-mediated depletion of either dStim or dOrai blocked nuclear translocation and dephosphorylation of NFAT-GFP (FIG. 2B). Likewise, knockdown of either dSTIM or dOrai completely inhibited thapsigargin-induced $Ca^{2+}$ influx in S2R+ cells (FIG. 2B). These data confirm previous reports that dSTIM and human STIM1 are essential for store-operated $Ca^{2+}$ entry and CRAC channel activation in *Drosophila* and mammalian cells[23,24,28], and identify dOrai as a second novel regulator of store-operated $Ca^{2+}$ entry in *Drosophila* cells.

Orai1 is Mutated in the SCID Patients

Figure 3B:
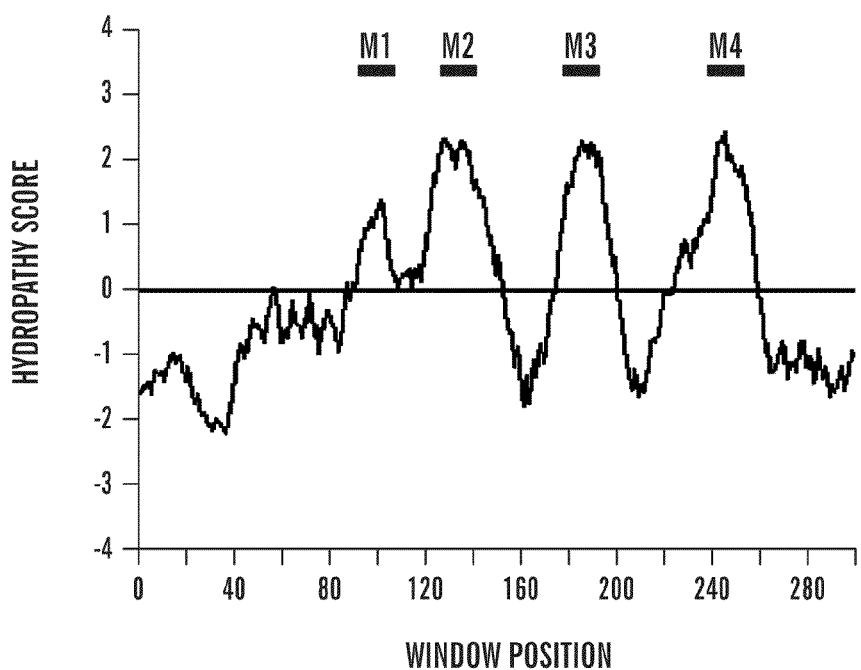
Figure 3C:
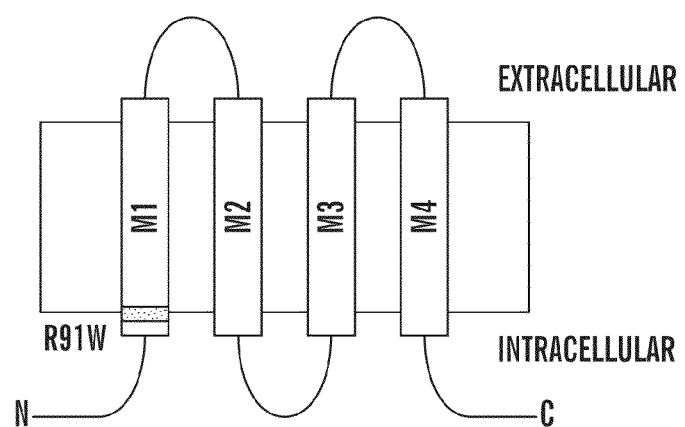

Since our data implicated dOrai as a second novel regulator of store-operated $Ca^{2+}$ entry (FIG. 2), and since the gene for human Orai1 was located in the 12q24 region that is homozygous in the SCID patients, we asked whether the SCID defect was associated with a mutation in human Orai1 (FIG. 3). By sequencing genomic DNA from the 23 individuals (patients and their relatives) shown in FIG. 1A, we found that both SCID patients were homozygous for a missense mutation in exon 1 of Orai1. The mutation at position 271 of the coding sequence of Orai1 (position 444 of NM_032790), a C>T transition, leads to substitution of tryptophan for a highly-conserved arginine residue at position 91 (R91W) of the protein (NP_116179, FIG. 3B). The mutated residue is located at the beginning of the first of four potential transmembrane segments in Orai1, predicted by calculating the hydrophobicity of Orai1 using the Kyte-Doolittle method[29] (FIG. 3B, 3C). All 13 phenotypically predicted heterozygous disease carriers (FIG. 1) were genotypically heterozygous for the mutation (C/T), while healthy controls and unaffected family members were homozygous for the wild-type allele (C/C). The mutation at this position is not an annotated SNP (dbSNP Build 124), rendering it unlikely this is simply a common polymorphism. To confirm this hypothesis, we typed this polymorphism in the entire HapMap panel (270 individuals in total from Utah, Ibadan (Nigeria), Tokyo and Beijing) and did not find a single copy of the putatively causal "T" allele in this panel (Materials and Methods, and data not shown)[30,31]. These data demonstrate unequivocally that the C>T transition is not a common sequence variant in the general population; thus the mutation is likely to have occurred spontaneously in the ancestors of the SCID patients and is strongly associated with disease.

Expression of Orai1 Restores Store-Operated $Ca^{2+}$ Influx in the SCID T Cells We asked whether Orai1 would complement the $Ca^{2+}$ influx defect in the SCID T cells (and fibroblasts) by expressing N- and C-terminally epitope-tagged versions of wild type and mutant Orai1 in T cells and fibroblasts from the SCID patients. Retroviral expression of Myc-Orai1$^{WT}$ in SCID T cells or fibroblasts using a bicistronic IRES-GFP vector restored $Ca^{2+}$ influx in response to thapsigargin treatment in GFP-positive but not GFP-negative cells, whereas retroviral expression of mutant R91>W Orai1 (Myc-Orai1$^{R>W}$) did not restore $Ca^{2+}$ influx. The inability of Myc-Orai1$^{R>W}$ to restore $Ca^{2+}$ influx in the SCID T cells and fibroblasts was not due to aberrant expression of Myc-Orai1$^{R>W}$ compared to Myc-Orai1$^{WT}$, because mutant and wild-type proteins are present at equivalent levels and appear to be similarly localized at or near the plasma membrane as judged by immunoblotting (data not shown) and immunocytochemistry. We were unable to stain non-permeabilized cells with the anti-myc antibody, consistent with a topology in which both the N- and C-termini are cytoplasmically oriented and so inaccessible to the antibody (FIG. 3C).

Notably, $Ca^{2+}$ influx in SCID T cells (and fibroblasts) reconstituted with Myc-Orai1$^{WT}$ did not occur in unstimulated T cells (or fibroblasts) when 2-20 mM extracellular $Ca^{2+}$ was present but was only observed after store-depletion with thapsigargin (FIG. 5A-5D). This is an important finding because it demonstrates that restoration of $Ca^{2+}$ influx in Orai1-expressing cells is dependent on store depletion, a defining feature of store-operated $Ca^{2+}$ entry through CRAC channels, and is not due to expression or activation of constitutively-open $Ca^{2+}$ channels. Myc-Orai1$^{WT}$ also restored store-operated $Ca^{2+}$ entry in SCID T cells in response to TCR crosslinking. The pharmacological characteristics of thapsigargin- and TCR-induced $Ca^{2+}$ entry in SCID T cells and fibroblasts complemented with Orai1 were exactly those expected for $Ca^{2+}$ influx through CRAC channels[12,32]. Treatment with 75 μM 2-APB or 2 μM La$^{3+}$ inhibited $Ca^{2+}$ influx (FIG. 5A,5C,5D), whereas treatment with a low dose of 2-APB (3 μM) caused a distinct further increase in $[Ca^{2+}]_i$ (FIG. 5B), although the increase in the Orai1$^{WT}$ expressing SCID T cells was slightly lower than that in control T cells (~15% vs. ~23%). Taken together, these results show clearly that Orai1 is the gene responsible for the $Ca^{2+}$ influx defect in the SCID patients' T cells and fibroblasts.

Expression of Orai1 Restores $I_{CRAC}$ in the SCID T Cells

The recovery of $Ca^{2+}$ influx seen in the previous experiments could reflect reconstitution of active CRAC channels in the patients' cells, or could arise from expression (or activation) of store-operated, $Ca^{2+}$ permeable ion channels distinct from CRAC. To distinguish between these possibilities, we characterized in detail the current arising from store-depletion in the SCID cells reconstituted with wild type or mutant (R91W) Orai1, using the whole-cell patch-clamp configuration. SCID T cells were retrovirally transduced with Orai1 in a bicistronic IRES-GFP vector, and cells expressing Orai1 were identified by GFP fluorescence as described above. In the experiments shown here, store depletion was accomplished either by including 8 mM BAPTA in the patch pipette or by treatment with thapsigargin.

Figure 4A:
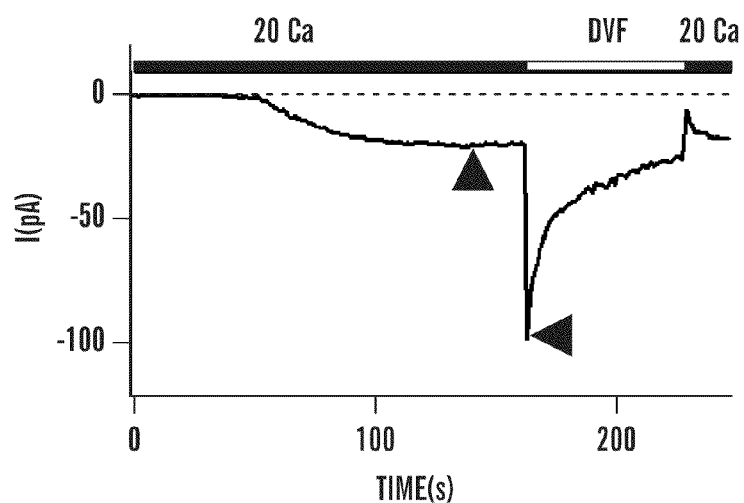
FIGS. 4A-4H show that expression of Orai1 restores CRAC channel function in SCID T cells.
Figure 4B:
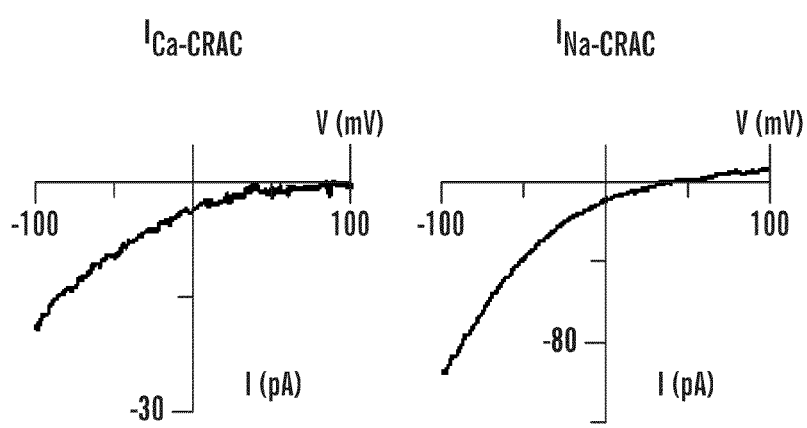
Figure 4C:
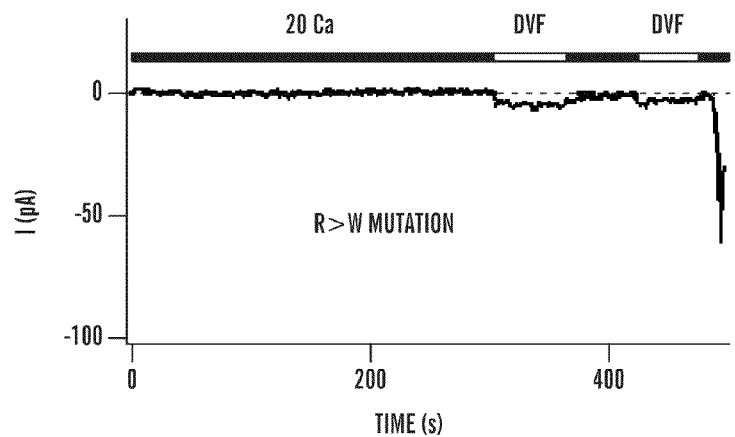
Figure 4D:
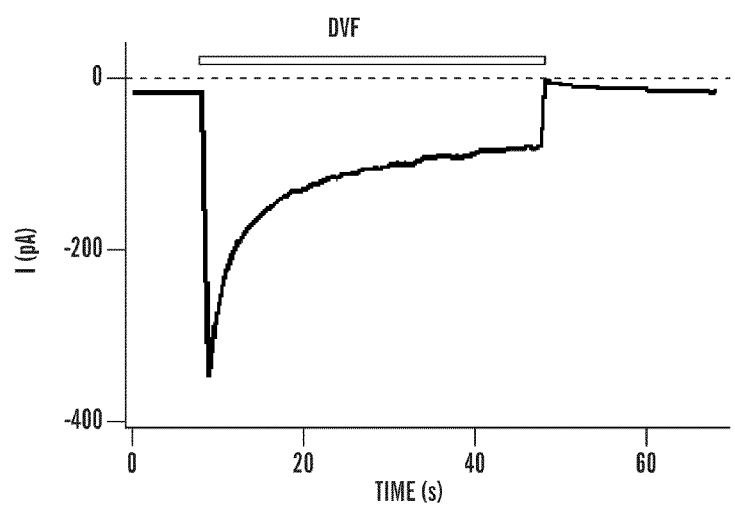
Figure 4D:
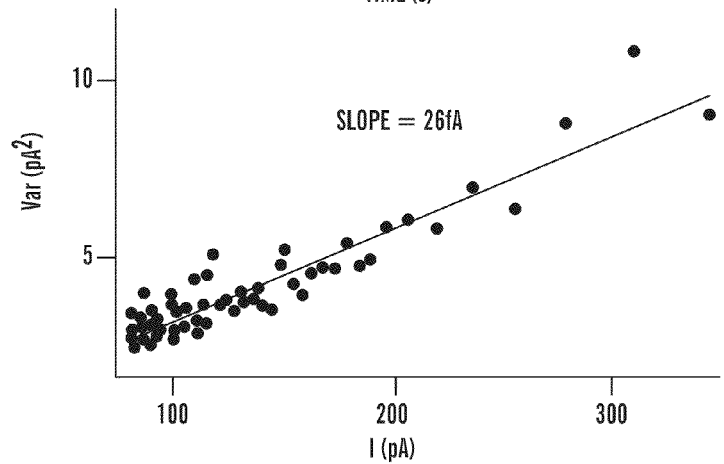
Figure 4E:
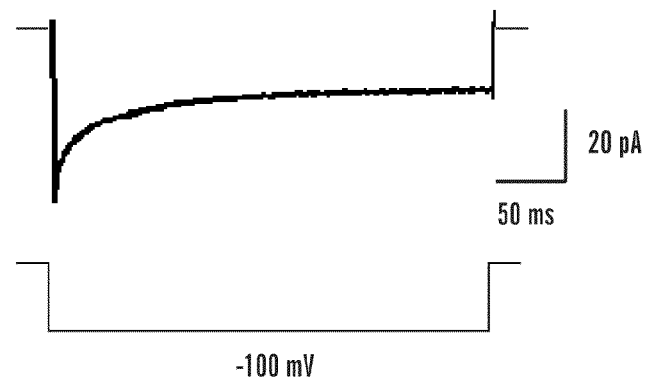
Figure 4F:
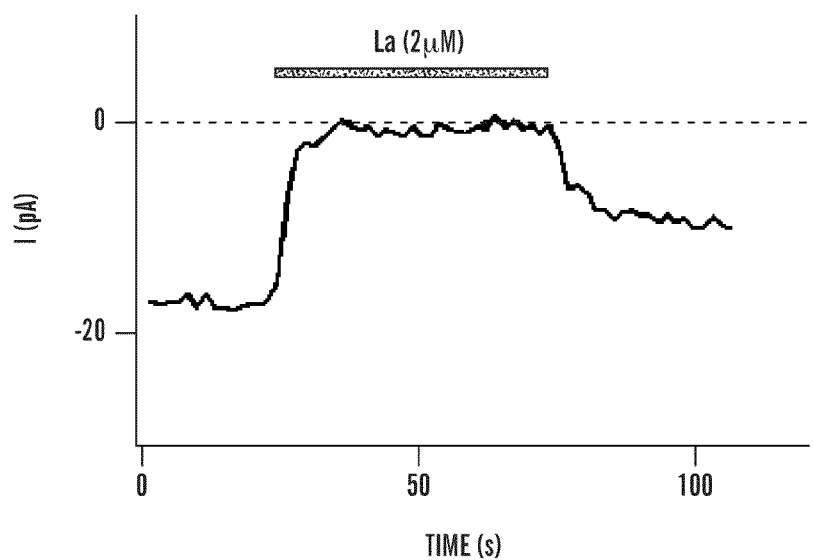
Figure 4G:
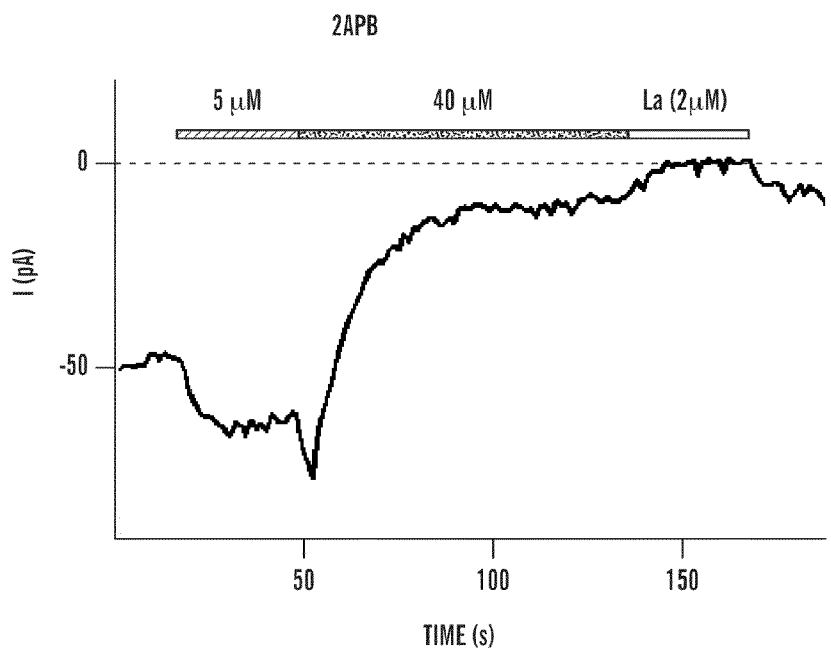
Figure 4H:
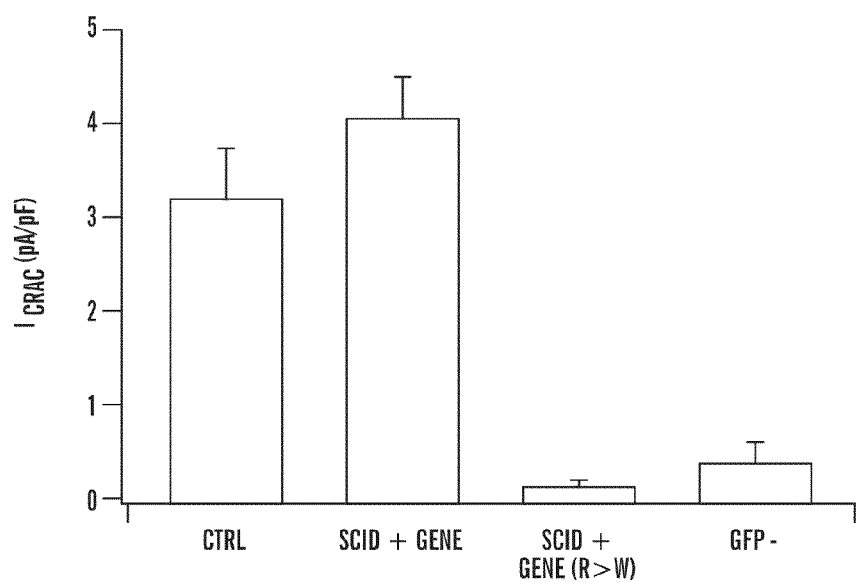
Figure 5A:
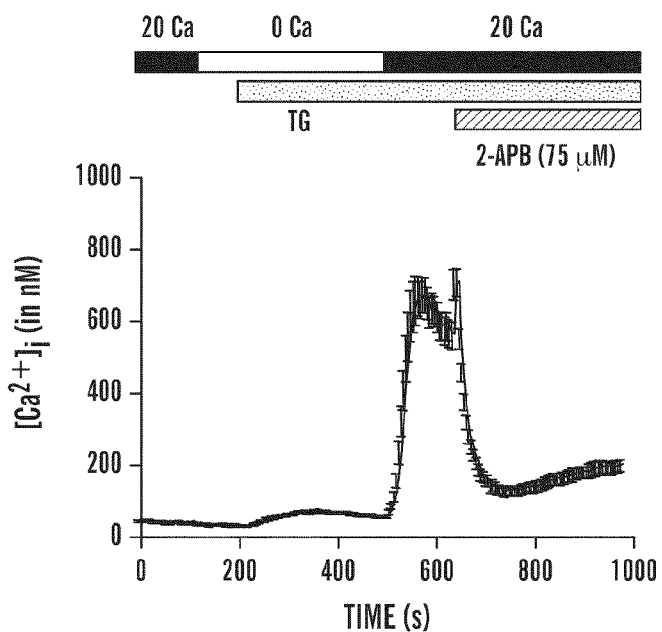
FIGS. 5A-5D show that expression of Orai1 in fibroblasts from SCID patients restores store-operated Ca$^{2+}$ influx.
Figure 5B:
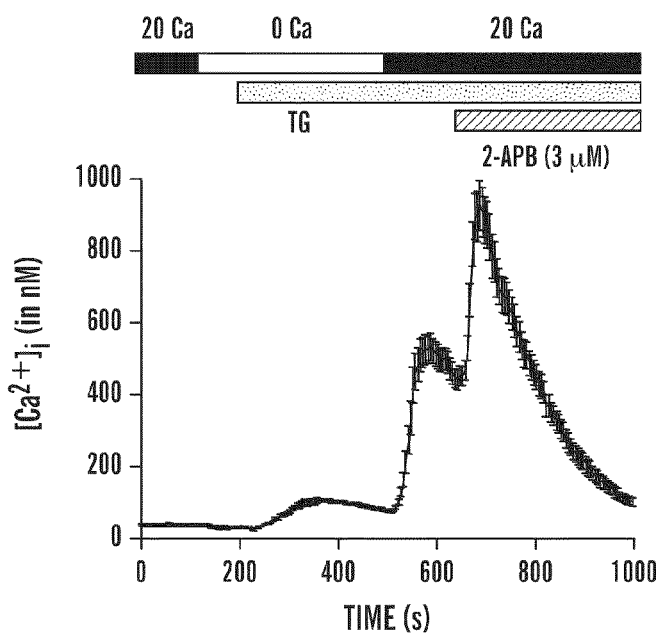
Figure 5C:
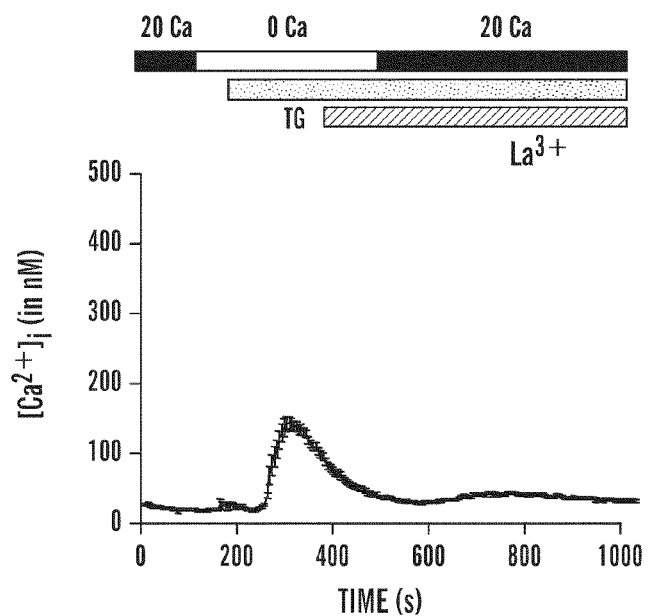
Figure 5D:
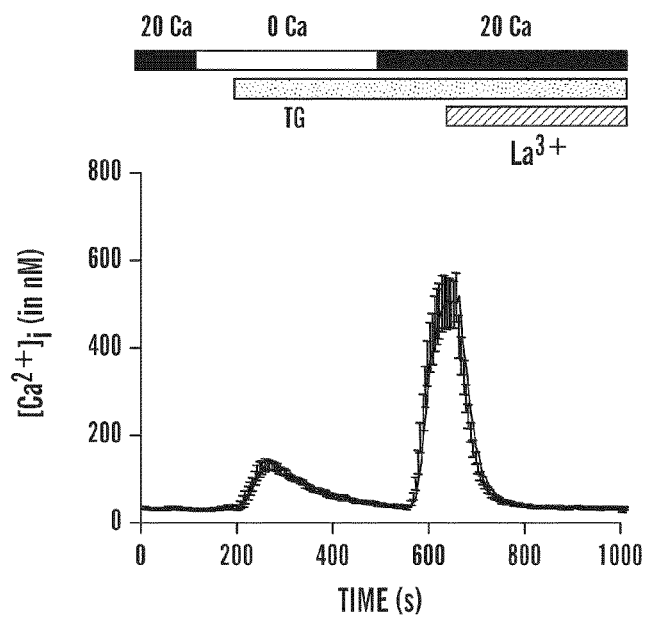

In SCID cells reconstituted with wild type Orai1, inclusion of 8 mM BAPTA in the patch pipette caused the slow development of an inward current in 20 mM $Ca^{2+}_o$, following whole-cell break-in, reminiscent of the development of $I_{CRAC}$ in response to store depletion (FIG. 4A)[2,3]. By contrast, SCID T cells expressing the R91W mutant of Orai1 failed to manifest any inward $Ca^{2+}$ currents following store depletion either with BAPTA (FIG. 4C) or with thapsigargin (data not shown), as expected from the inability of this mutant protein to reconstitute store-operated $Ca^{2+}$ entry. The current observed in Orai1-reconstituted SCID T cells displayed many key hallmarks of the $I_{CRAC}$[11,33,34]. First, when a divalent-free (DVF) solution lacking $Ca^{2+}$ and $Mg^{2+}$, in which the only current carrier is Na$^+$, was applied after full development of the current in 20 mM $Ca^{2+}_o$, an inward Na$^+$ current was observed that was initially much larger than the $Ca^{2+}$ current but that declined over tens of seconds (FIG. 4A). This decline of the Na$^+$ current, known as depotentiation, is characteristic of CRAC channels in Jurkat T cells, RBL cells and human T cell lines[11,33,34]. Second, both the $Ca^{2+}$ and Na$^+$ currents showed an inwardly rectifying current-voltage (I-V) relationship (FIG. 4B). The reversal potential of the inward current in 20 mM $Ca^{2+}$ was >+90 mV, consistent with the known high selectivity of CRAC channels for $Ca^{2+}$, whereas the reversal potential in divalent-free solution was 49±2 mV (n=4 cells), indicating that the channels are only weakly permeable to the Cs$^+$ ions in the patch pipette ($P_{Cs}/P_{Na}$=0.14) and consistent with the selectivity of CRAC channels for monovalent ions[33,35]. Third, the noise characteristics of the Orai1 complemented current were consistent with those of CRAC channels in wild-type T cells (FIG. 4D)[33]. During depotentiation of the Na$^+$ current, variance declined linearly with mean current with an average slope of 29±4 fA (n=4 cells), providing a lower limit estimate of the unitary current similar to that of previous measurements of $I_{CRAC}$. Furthermore, the $Ca^{2+}$ current resulting from complementation with Orai1 exhibited fast inactivation in 20 mM $Ca^{2+}_o$ (FIG. 4E); the extent and time course of inactivation was similar to that previously reported for CRAC channels in Jurkat T cells (current inactivates by 54±5% at −100 mV within 200 ms; $\tau_{fast}$: 9±2 ms; $\tau_{slow}$: 84±12 ms)[36]. And lastly, the pharmacological hallmarks of the reconstituted current included complete block by 2 μM La$^{3+}$ (FIG. 4F), inhibition by high doses of 2-APB (FIG. 4G) and potentiation by low doses of 2-APB (FIG. 4G); moreover the block observed with high doses of 2-APB was accompanied by the loss of fast inactivation[32]. The discrepancy between full complementation of CRAC currents by expression of Orai1 (FIG. 4H) and the partial complementation of $Ca^{2+}$ influx observed by $Ca^{2+}$ imaging may be explained by the fact that for measurements of $I_{CRAC}$, we selected T cells with high GFP/Orai1 levels, whereas for the single-cell $Ca^{2+}$ imaging, we averaged responses of all GFP/Orai 1-positive cells (both bright and dim).

In summary, reconstitution of SCID T cells with Orai1 restores not only store-operated $Ca^{2+}$ entry but also a current that is identical to $I_{CRAC}$ with regard to store dependence, ion selectivity and unitary conductance, gating properties, and pharmacological profile. Thus, we conclude that Orai1 is essential for CRAC channel function in T cells. The pore properties and pharmacological characteristics of the channel observed in SCID T cells complemented with Orai1 are indistinguishable from those of bonafide CRAC channels.

Discussion

Here we identify Orai1 as an evolutionarily-conserved component of store-operated $Ca^{2+}$ entry and an essential contributor to $I_{CRAC}$. We show that a point mutation in Orai1 is responsible for the genetic defect in store-operated $Ca^{2+}$ entry and $I_{CRAC}$ function in two patients with a rare form of severe combined immune deficiency (SCID)[10,11]. Identification of Orai1 as the defective gene was accomplished through the synergistic combination of two independent genetic analyses, both involving unbiased genome-wide screens.

Our first screen employed genome-wide SNP analysis to identify the chromosomal region linked to the SCID disease. Because only two diseased individuals exist, the theoretically-attainable LOD score from traditional linkage analysis is ~1.9, significantly below the 3.0 value necessary to establish linkage. Indeed, analysis of a small pedigree including the two SCID patients, their parents and their grandparents identified 6 regions on 6 separate chromosomes with maximum LOD scores of 1.9 (Pedigree A). To extend the amount of genetic information available, we devised a method of identifying heterozygous carriers of the mutant allele. This was accomplished through a simple modification of our in vitro method of measuring store-operated $Ca^{2+}$ influx, in which the driving force for $Ca^{2+}$ entry was decreased by reducing the extracellular $Ca^{2+}$ concentration. When this assay was applied to T cell lines derived from 21 additional family members of the SCID patients (Pedigree B), 13 members showed a significantly reduced initial rate of $Ca^{2+}$ influx, which we interpret as reflecting a gene-dosage effect consistent with heterozygosity for the mutant allele. A second, completely independent linkage analysis, in which the haplotype of these 13 putatively heterozygous individuals was compared to that of the remaining 8 homozygous healthy family members, yielded experimental LOD scores that identified a unique region on 12q24 with a LOD score of 3.8. This region overlapped with one of the regions identified by linkage analysis of Pedigree A. Because the individuals used for each analysis and the phenotypes used to classify them were distinct, allele sharing and thus linkage results were completely independent in these analyses; hence we could combine LOD scores from the two analyses to obtain an unbiased cumulative and highly significant LOD score of ~5.7 for an ~9.8 Md region at 12q24. In principle, this novel and powerful combination of linkage mapping approaches may be applied to elucidate the genetic causes of other rare autosomal-recessive diseases, even if only a very few diseased individuals are available and conventional homozygosity mapping fails to establish linkage. Prerequisites are that other family members are available and that mutation of one allele can be detected as a quantifiable trait in vitro.

In the hope of rapidly identifying a gene in the 12q24 region that was involved in store-operated $Ca^{2+}$ entry, we conducted a parallel genome-wide RNAi screen in *Drosophila*, taking advantage of the fact that *Drosophila* S2R cells contain a store-operated $Ca^{2+}$ channel with characteristics very similar to CRAC[37]. Rather than focusing solely on $Ca^{2+}$ entry, we designed the screen to identify evolutionarily-conserved regulators of the $Ca^{2+}$-regulated transcription factor NFAT; although $Ca^{2+}$-regulated NFAT proteins are not themselves represented in *Drosophila*, there is strong evolutionary conservation of the pathways which regulate its nuclear-cytoplasmic shuttling, through effects on $Ca^{2+}$ homeostasis, store-operated $Ca^{2+}$ entry, calcineurin activity and kinase-phosphatase balance[27]. The screen was used to identify candidates whose RNAi-mediated depletion interfered with nuclear localization of an NFAT-GFP fusion protein in response to stimulation with thapsigargin. Among the positive candidates was olf186F (here renamed *Drosophila* Orai), which has three human homologues, FLJ14466, C7Orf19 and MGC13024. Since these are novel proteins without known function, we named them Orai1-3, respectively. In Greek mythology, the Orai are the keepers of the gates of heaven: Eunomia (Order or Harmony), Dike (Justice) and Eirene (Peace)[38-40]; in Japan, Orai is in part derived from the sound of "all right" in English and also refers to comings and goings, communication, streets and traffic in Japanese. In a satisfying validation of our dual strategy, the gene encoding Orai1 (hypothetical protein FLJ14466) is located on chromosome 12q24, exactly the region identified by our SNP analysis as linked genetically to the SCID syndrome. DNA sequencing rapidly revealed the genetic basis for the SCID defect as a point mutation (C>T) in exon 1 of Orai1, which resulted in an arginine to tryptophan substitution at residue 91. This mutation is not a known polymorphism, as confirmed by sequencing DNA from 270 individuals of mixed ethnic backgrounds assembled for the international HapMap project[31]. This number of samples is sufficient to find almost all haplotypes with frequencies of 5% or higher. Although there is a small chance that the C>T mutation is a SNP confined to a small ethnic population not represented in the HapMap panel, this possibility can be ruled out with reasonable certainty based on the fact that complementation with Orai1 restores store-operated $Ca^{2+}$ entry and $I_{CRAC}$ in SCID patient cells. Furthermore, arginine 91 which is mutated in the SCID patients is located in a putative transmembrane region that is highly conserved across species (FIG. 3A), highlighting its potential importance in the function of Orai1.

The characteristics of $Ca^{2+}$ influx and $Ca^{2+}$ current in Orai1-complemented SCID T cells were indistinguishable from those observed in control T cells. In particular, both processes were strictly regulated by store depletion, and the electrophysiological and pharmacological properties of the restored current were fully consistent with those of $I_{CRAC}$. These properties include: an extremely high selectivity for $Ca^{2+}$ over monovalent cations, inwardly rectifying I-V relation, depotentiation under divalent-free conditions, current noise characteristics, rapid $Ca^{2+}$-dependent inactivation, blockade by low micromolar $La^{3+}$ and positive and negative modulation by 2-APB. We therefore conclude that Orai1 reconstituted $I_{CRAC}$ in the SCID patients' T cells, and thus that the C>T transition and resulting R91W mutation in the Orai1 coding region and protein are responsible for the SCID defect. While its specific role has not yet been determined, the available data are consistent with the possibility that Orai1 encodes a channel subunit or a closely-associated channel regulator in the plasma membrane. First, the hydropathy profile of Orai1 predicts a membrane protein with three, or potentially four, hydrophobic membrane domains (FIG. 3B). Second, immunocytochemistry of myc-tagged Orai1 is consistent with localization at the plasma membrane under resting conditions; this distribution differs from that of STIM1, which is predominantly located in the ER where it is thought to sense $Ca^{2+}$ store depletion via its luminal EF hand domain (Feske 2005, Liou 2005, Ref). Notably, both N- and C-terminal epitope tags on Orai1 are inaccessible to antibody staining in non-permeabilised cells; this finding is consistent with the prediction of four transmembrane domains and predicts a topology compatible with a channel subunit, in which both N- and C-termini are cytoplasmically oriented (FIG. 3C). Further studies will be necessary to determine whether Orai1 is part of the CRAC channel itself, or whether it encodes a regulator of the channel.

Orai1 is widely expressed at the mRNA level, potentially explaining our previous observations that not only T cells but also B cells and fibroblasts from the SCID patients show a substantial defect in store-operated $Ca^{2+}$ entry. Surprisingly, however, the clinical phenotype of the SCID patients is predominantly one of immunodeficiency, associated in the single surviving patient with ectodermal dysplasia and anhydrosis (EDA) and a mild, congenital, non-progressive myopathy. EDA is characterized by defective tooth enamel and hair follicle function, and complete absence of sweat glands, and many previous studies have linked it to hypoactivation of NF-κB[41-45]. $Ca^{2+}$ mobilization is thought to contribute to NFκB activation in T cells and other cell types under certain conditions of stimulation[46], thus the EDA syndrome may well reflect defective NFκB activation, either during development or acutely in specific cell types. In contrast the myopathy could potentially be a direct consequence of defective NFAT activation, given that NFAT has a major role in certain aspects of skeletal muscle development and function (reviewed in[7,47]).

In conclusion, our studies establish a critical role for Orai1 in T cell function and the in vivo immune response. A single point mutation in Orai1, a novel protein conserved from *C. elegans* to humans, disrupts store-operated $Ca^{2+}$ entry and CRAC channel function in patients with an inherited immune deficiency. Future studies will address the relation between Orai and Stim proteins and the mechanism by which store depletion couples to CRAC channel opening.

REFERENCES

1. Lewis, R. S. Calcium signaling mechanisms in T lymphocytes. Annu Rev Immunol 19, 497-521 (2001).
2. Hoth, M. & Penner, R. Depletion of intracellular calcium stores activates a calcium current in mast cells. Nature 355, 353-6 (1992).
3. Zweifach, A. & Lewis, R. S. Mitogen-regulated Ca2+ current of T lymphocytes is activated by depletion of intracellular Ca2+ stores. Proc Natl Acad Sci USA 90, 6295-9 (1993).
4. Feske, S., Okamura, H., Hogan, P. G. & Rao, A. Ca2+/calcineurin signalling in cells of the immune system. Biochem Biophys Res Commun 311, 1117-32 (2003).
5. Macian, F. NFAT proteins: key regulators of T-cell development and function. Nat Rev Immunol 5, 472-84 (2005).
6. Winslow, M. M., Neilson, J. R. & Crabtree, G. R. Calcium signalling in lymphocytes. Curr Opin Immunol 15, 299-307 (2003).
7. Hogan, P. G., Chen, L., Nardone, J. & Rao, A. Transcriptional regulation by calcium, calcineurin, and NFAT. Genes Dev 17, 2205-32 (2003).
8. Partiseti, M. et al. The calcium current activated by T cell receptor and store depletion in human lymphocytes is absent in a primary immunodeficiency. J Biol Chem 269, 32327-35 (1994).
9. Le Deist, F. et al. A primary T-cell immunodeficiency associated with defective transmembrane calcium influx. Blood 85, 1053-62 (1995).
10. Feske, S., Giltnane, J., Dolmetsch, R., Staudt, L. & Rao, A. Gene regulation by calcium influx in T lymphocytes. Nature Immunology 2, 316-324 (2001).
11. Feske, S., Prakriya, M., Rao, A. & Lewis, R. S. A severe defect in CRAC Ca2+ channel activation and altered K+ channel gating in T cells from immunodeficient patients. J Exp Med 202, 651-62 (2005).
12. Parekh, A. B. & Putney, J. W., Jr. Store-operated calcium channels. Physiol Rev 85, 757-810 (2005).
13. Parekh, A. B. & Penner, R. Store depletion and calcium influx. Physiol Rev. 77, 901-930 (1997).
14. Prakriya, M. & Lewis, R. S. CRAC channels: activation, permeation, and the search for a molecular identity. Cell Calcium 33, 311-21 (2003).
15. Mori, Y. et al. Transient receptor potential 1 regulates capacitative Ca(2+) entry and Ca(2+) release from endoplasmic reticulum in B lymphocytes. J Exp Med 195, 673-81 (2002).
16. Philipp, S. et al. TRPC3 mediates T-cell receptor-dependent calcium entry in human T-lymphocytes. J Biol Chem 278, 26629-38 (2003).
17. Yue, L., Peng, J. B., Hediger, M. A. & Clapham, D. E. CaT1 manifests the pore properties of the calcium-release-activated calcium channel. Nature 410, 705-9 (2001).
18. Cui, J., Bian, J. S., Kagan, A. & McDonald, T. V. CaT1 contributes to the stores-operated calcium current in Jurkat T-lymphocytes. J Biol Chem 277, 47175-83 (2002).
19. Badou, A. et al. Requirement of voltage-gated calcium channel beta4 subunit for T lymphocyte functions. Science 307, 117-21 (2005).
20. Kotturi, M. F., Carlow, D. A., Lee, J. C., Ziltener, H. J. & Jefferies, W. A. Identification and functional characterization of voltage-dependent calcium channels in T lymphocytes. J Biol Chem 278, 46949-60 (2003).
21. Voets, T. et al. CaT1 and the calcium release-activated calcium channel manifest distinct pore properties. J Biol Chem 276, 47767-70. (2001).
22. Venkatachalam, K., Van Rossum, D. B., Patterson, R. L., Ma, H. T. & Gill, D. L. The cellular and molecular basis of store-operated calcium entry. Nat Cell Biol 4, E263-72 (2002).
23. Liou, J. et al. STIM is a Ca2+ sensor essential for Ca2+-store-depletion-triggered Ca2+ influx. Curr Biol 15, 1235-41 (2005).
24. Roos, J. et al. STIM1, an essential and conserved component of store-operated Ca2+ channel function. J Cell Biol 169, 435-45 (2005).
25. Krogh, A., Larsson, B., von Heijne, G. & Sonnhammer, E. L. Predicting transmembrane protein topology with a hidden Markov model: application to complete genomes. J Mol Biol 305, 567-80 (2001).
26. Kall, L., Krogh, A. & Sonnhammer, E. L. A combined transmembrane topology and signal peptide prediction method. J Mol Biol 338, 1027-36 (2004).
27. Gwack, Y. S., S. et al. A genome-wide *Drosophila* RNAi screen identifies DYRK as a novel regulator of NFAT. Nature (submitted; see example 2) (2005).
28. Zhang, S. L. et al. STIM1 is a Ca2+ sensor that activates CRAC channels and migrates from the Ca2+ store to the plasma membrane. Nature 437, 902-5 (2005).
29. Kyte, J. & Doolittle, R. F. A simple method for displaying the hydropathic character of a protein. J Mol Biol 157, 105-32 (1982).
30. Altshuler, D. et al. A haplotype map of the human genome. Nature 437, 1299-320 (2005).
31. Consortium, T. I. H. The International HapMap Project. Nature 426, 789-96 (2003).
32. Prakriya, M. & Lewis, R. S. Potentiation and inhibition of Ca(2+) release-activated Ca(2+) channels by 2-aminoethyldiphenyl borate (2-APB) occurs independently of IP(3) receptors. J Physiol 536, 3-19 (2001).
33. Prakriya, M. & Lewis, R. S. Separation and characterization of currents through store-operated CRAC channels and Mg(2+)-inhibited cation (MIC) channels. J Gen Physiol. 119, 487-507 (2002).

34. Hermosura, M. C., Monteilh-Zoller, M. K., Scharenberg, A. M., Penner, R. & Fleig, A. Dissociation of the store-operated calcium current I(CRAC) and the Mg-nucleotide-regulated metal ion current MagNuM. J Physiol 539, 445-58 (2002).
35. Lepple-Wienhues, A. & Cahalan, M. D. Conductance and permeation of monovalent cations through depletion-activated Ca2+ channels (ICRAC) in Jurkat T cells. Biophys J 71, 787-94 (1996).
36. Zweifach, A. & Lewis, R. S. Rapid inactivation of depletion-activated calcium current (ICRAC) due to local calcium feedback. J Gen Physiol 105, 209-26 (1995).
37. Yeromin, A. V., Roos, J., Stauderman, K. A. & Cahalan, M. D. A store-operated calcium channel in Drosophila S2 cells. J Gen Physiol 123, 167-82 (2004).
38. Stewart, M. "The Hours", Greek Mythology: From the Iliad to the Fall of the Last Tyrant. http://messagenet.com/myths/bios/hours.html (2005).
39. Homer. Iliad (Book 5) pp. 749-50.
40. Homer. Iliad (Book 8), pp. 393-394.
41. Doffinger, R. et al. X-linked anhidrotic ectodermal dysplasia with immunodeficiency is caused by impaired NF-kappaB signaling. Nat Genet 27, 277-85 (2001).
42. Courtois, G. et al. A hypermorphic IkappaBalpha mutation is associated with autosomal dominant anhidrotic ectodermal dysplasia and T cell immunodeficiency. J Clin Invest 112, 1108-15 (2003).
43. Schmidt-Ullrich, R. et al. Requirement of NF-kappaB/Rel for the development of hair follicles and other epidermal appendices. Development 128, 3843-53 (2001).
44. Puel, A., Picard, C., Ku, C. L., Smahi, A. & Casanova, J. L. Inherited disorders of NF-kappaB-mediated immunity in man. Curr Opin Immunol 16, 34-41 (2004).
45. Smahi, A. et al. The NF-kappaB signalling pathway in human diseases: from incontinentia pigmenti to ectodermal dysplasias and immune-deficiency syndromes. Hum Mol Genet 11, 2371-5 (2002).
46. Kanno, T. & Siebenlist, U. Activation of nuclear factor-kappaB via T cell receptor requires a Raf kinase and Ca2+ influx. Functional synergy between Raf and calcineurin. J Immunol 157, 5277-83 (1996).
47. Horsley, V. & Pavlath, G. K. NFAT: ubiquitous regulator of cell differentiation and adaptation. J Cell Biol 156, 771-4 (2002).
48. Feske, S., Draeger, R., Peter, H. H., Eichmann, K. and Anjana Rao. The Duration of Nuclear Residence of NFAT Determines the Pattern of Cytokine Expression in human SCID T Cells. J Immunol 165, 297-305 (2000).
49. Leykin, I. et al. Comparative linkage analysis and visualization of high-density oligonucleotide SNP array data. BMC Genet 6, 7 (2005).
50. Gudbjartsson, D. F., Jonasson, K., Frigge, M. L. & Kong, A. Allegro, a new computer program for multipoint linkage analysis. Nat Genet 25, 12-3 (2000).
51. Markianos, K., Daly, M. J. & Kruglyak, L. Efficient multipoint linkage analysis through reduction of inheritance space. Am J Hum Genet 68, 963-77 (2001).
52. Abecasis, G. R., Cherny, S. S., Cookson, W. O. & Cardon, L. R. Merlin—rapid analysis of dense genetic maps using sparse gene flow trees. Nat Genet 30, 97-101 (2002).
53. Gabriel, S. B. et al. The structure of haplotype blocks in the human genome. Science 296, 2225-9 (2002).
54. Zweifach, A. & Lewis, R. S. Calcium-dependent potentiation of store-operated calcium channels in T lymphocytes. J Gen Physiol 107, 597-610 (1996).

EXAMPLE 2

A Genome-Wide *Drosophila* RNAi Screen Identifies DYRK as a Novel Regulator of NFAT Materials and Methods
The Genome-Wide Primary Screen Methods were adapted from refs[12,13]. $10^4$ S2R+ cells were added into each well containing 0.25 µg of dsRNAs in 10 µl of serum-free medium and incubated for 1 h at 26° C. The cells were then transiently transfected with NFAT1(1-460)-GFP expression plasmid[9,17] (10 ng) in Schneider's medium (Invitrogen) (30 µl). After incubation for 48-72 hrs at 26° C., the cells were fixed and stained with DAPI, and the coincident GFP and DAPI images were acquired by an automated camera from three different locations in each well. A total of fifty-eight 384-plates were analysed, containing a total of 21,884 wells into which individual dsRNAs had been arrayed.

Control wells (no dsRNA, dsRNA against GFP, and dsRNA against a gene (thread-anti-apoptotic) causing cell death) were present on each plate and served as an internal control for knockdown efficiency of each plate. All three photographs of GFP fluorescence in each assay well were manually scored using MetaMorph 6.1 Software (Universal Imaging Corporation). To identify even weak effectors of NFAT localization non-stringent criteria were used in the primary screen, such that wells were scored positive even if only one cell in each of three fields showed complete nuclear localization of NFAT-GFP. Since the RNAi library was constructed before the *Drosophila* genome was completely annotated, 39 of the 738 positives did not correspond to known genes and were eliminated. Another 37 candidates were eliminated because the dsRNAs used to identify them had more than 10 predicted "off-targets" with exact matches of 21 nucleotides (nt) (see Bioinformatics and Classification below).

The Confirmatory Screen

The confirmatory screening on the 699 potentially positive candidates from the primary screen was performed essentially as described for the primary screen, except that S2R+ cells stably transfected with NFAT1(1-460)-GFP were used, and candidates were tested for whether their depletion altered NFAT subcellular localization in both resting and stimulated S2R+ cells. Wells in which all cells contained cytoplasmic NFAT-GFP got the lowest score (0) while wells with >90% of the cells showing nuclear NFAT-GFP scored the highest (3). The summed scores from all three experiments are presented in Table I. Note that the highest possible score is 9, but because we scored conservatively in the confirmatory screen, the highest actual score obtained by any candidate is 6. All candidates were also tested for whether they prevented NFAT nuclear localization in cells treated with thapsigargin (1 µM, 30 min); only *Drosophila* STIM (dSTIM) scored positive in this assay.

To generate the stably-expressing cell line, the coding sequence for the NFAT1(1-460)-GFP fusion protein was subcloned into the expression plasmid pAc5.1 (Invitrogen), and the macrophage-hemocyte-like *Drosophila* cell line S2R+ was transfected in a 6-well format using Effectene (Qiagen) with a 19:1 ratio of the expression plasmid to pCoHygro (Invitrogen), which encodes a hygromycin resistance gene under the control of a constitutively active promoter. The cells were selected for 3-4 weeks with 300 µg/ml hygromycin, and stable clones were selected by visual inspection.

Bioinformatics and Classification

Scores were consolidated and formatted for submission to the DRSC (*Drosophila* RNAi Screening Center at Harvard Medical School), which then provided the identity of the genes assayed (FlyBase identifier; *Drosophila* gene name, where known; some Gene Ontology (GO) identifiers; and some human homologues). Gene Ontology (GO) annotation was retrieved in two ways. First, we employed Ensembl's EnsMart tool using the FlyBase identifier for each gene to get the GO description. Second, we used the GO identifiers provided by the screening center to get descriptions from the "GO terms and IDs" file from the Gene Ontology Consortium. Functional categories of genes were constructed by keyword searches of the positives followed by manual curation. Positive genes were also examined for involvement in common pathways using tools such as those at the KEGG Pathway Database.

For each candidate that was positive in the primary screen, the number of off-targets was determined using the off-target sequence search tool on the DRSC website (http://www.flymai.org/RNAi_primer_design.html). This bioinformatic tool is based on an algorithm similar to that in ref[37] except that it does not have a built-in primer design component (Flockhart et al., submitted). Amplicon (dsRNA) sequences are searched for predicted off-targets by considering all possible fragments, of length 16-50 bp with a default value of 21 bp, that perfectly match sequences in fly transcripts in release 4.0. Ideally, only 1 match corresponding to the targeted mRNA should be found, but some amplicons have matches with other mRNAs which are not the intended target. For the genes in Table I, a default length of 21 nt was used to compute the number of off-targets for each positive candidate, and candidates with >10 off-targets were eliminated. For the genes in Table II (calcineurin) and III (candidates used for additional experiments), shorter fragments of 19 nt and 20 nt were considered as well. The identity of off-targets was determined using BLASTN against *Drosophila* NCBI RefSeq database. Mammalian orthologues of *Drosophila melanogaster* proteins in Table I were retrieved from the NCBI Homologene database (http://www.ncbi.nlm.nih.gov/entrez/query.fcgi?db=homologene). The human homologues of the fly kinases were obtained by reciprocal blast method using BLASTP; Altschul, et al. 1990, J. Mol. Biol. 215:403-410), as described[38,39]. Phylogenetic analysis was performed using TCoffee[40], and the reliability of the ortholog assignments was assessed with the bootstrap method implemented in Orthostrapper[41].

DsRNA Mediated Knockdown in *Drosophila* Cells

PCR fragments (size up to 600 bp) were used as templates for in vitro transcription reactions, followed by DNase I treatment to remove the template DNA. After purification, dsRNA (5 μg) was co-transfected together with the NFAT-GFP expression plasmid into S2R+ cells in 8-chamber slides (10 μg for 12 well plate). After 72 hrs of incubation, cells were left untreated or were treated with the $Ca^{2+}$ influx inducers, 1 μM ionomycin or 1 μM thapsigargin for localization assays and were trypsinized for the measurement of [Ca2+]i levels.

In Vitro Kinase Assays

FLAG-tagged human kinases were immunoprecipitated from whole cell lysates of transiently-transfected HEK293 cells using anti-FLAG antibody-coupled protein G beads (Sigma), and immunoprecipitates were analysed for phosphorylation of either the entire NFAT1 regulatory domain (GST-NFAT1[1-415]) expressed in bacterial cells, or GST-fused peptides corresponding to the SRR-1 (amino acids 149-183), SP-2 (amino acids 206-237) and SP-3 (amino acids 264-295) motifs of NFAT1 (both wild-type and Ser→Ala mutants in serines phosphorylated in vivo)[10]. Immunocomplexes were washed twice with lysis buffer (1.0% NP-40, 50 mM HEPES pH 7.4, 150 mM NaCl, 5 mM EDTA, 5 mM EGTA, 1 mM dithiothreitol [DTT], 20 mM β-glycerol-phosphate, 10 mM sodium pyrophosphate, 0.1 mM sodium orthovanadate, 10 mM NaF, 1 mM phenylmethylsulfonyl fluoride [PMSF], 10 μg/ml aprotinin, 10 μg/ml leupeptin) and twice with kinase buffer (20 mM HEPES, pH 7.4, 20 mM $MgCl_2$, 1 mM DTT, 0.1 mM sodium orthovanadate, 20 mM β-glycerol-phosphate), and incubated at 30° C. for 20 minutes in a 40 μl final volume of kinase buffer in the presence of 20 μM ATP, 2 μCi [$\gamma^{32}P$]-ATP and 10 μg of wild-type or mutant GST-peptide substrate. Peptides were isolated on glutathione-sepharose and phosphorylation was assessed by SDS gel electrophoresis and autoradiography.

The ability of DYRK1A and DYRK2 to phosphorylate GST-NFAT1 fusion peptides was examined using 20 ng of recombinant protein kinase (Upstate Biotechnology) in a 40 μl final volume of kinase buffer in the presence of 20 μM ATP, 2 μCi [-$^{32}P$]-ATP and 10 μg of GST-peptide substrate. The ability of GSK3 to phosphorylate NFAT1 was examined by first pre-phosphorylating GST fusion proteins pre-bound to glutathione sepharose beads using 1 U of recombinant protein kinase A (PKA) (New England Biolabs [NEB]), 20 ng DYRK1A or DYRK2 in the presence of 1 mM cold ATP for 16 h at 30° C. After cold priming fusion proteins were washed repeatedly to remove recombinant kinase and ATP. Phosphorylated fusion proteins were then incubated with 1 U of GSK3 (NEB) in a 40 μl final volume of kinase buffer in the presence of 20 μM ATP, 2 μCi [$\gamma^{32}P$]-ATP for 45 minutes.

Reporter Assays and IL-2 Expression Assays

Exponentially growing ($10^7$) Jurkat T cells stably expressing HA-tagged full-length NFAT1 in the pOZ vector[42] were transfected by electroporation at 250 V and 960 μF. For luciferase experiments, cells were transfected with 0.5 μg pRLTK reporter (Renilla luciferase for internal control), 5.0 μg pGL3 reporter (firefly luciferase, experimental promoter) and expression plasmids encoding empty vector, wild type or kinase dead DYRK2. At 24 h post transfection cells left untreated or stimulated with PMA (20 nM), ionomycin (1 μM) and 2 mM $CaCl_2$ for 6 hours were measured for reporter gene activity using the Dual-Luciferase Reporter Assay (Promega) as recommended by the manufacturer. For intracellular cytokine staining, cells were co-transfected with GFP-encoding plasmid and empty vector plasmids, wild type or kinase-dead DYRK2. At 24 h post transfection cells left untreated or stimulated with PMA (20 nM), ionomycin (1 μM) and 2 mM $CaCl_2$ for 6 hours in the presence of Brefeldin A (2 μg/mL) for the last 4 hours were fixed with 4% paraformaldehyde in PBS for 20 min at 25° C., washed twice with PBS, permeabilized in saponin buffer (PBS, 0.5% saponin [Sigma], 1% BSA and 0.1% sodium azide) and stained with phycoerythrin-conjugated rat anti-human IL-2 (PharMingen) for 30 min at 25° C. Cells were washed twice in PBS and analyzed with a FACSCalibur flow cytometer (Becton Dickinson) and FlowJo software.

siRNA-Mediated Knockdown of DYRK1A $0.5 \times 10^6$ HeLa cells stably expressing NFAT1(1-460)-GFP were seeded in 6-well plates and transfected the next day with siRNAs (Dharmacon, Inc., Lafayette, Colo.) corresponding to control siRNA or human DYRK siRNA using lipofectamine 2000 transfection reagent (Invitrogen, Carlsbad, Calif.) according to the manufacturer's protocol. Cells were reseeded and the transfection procedure was repeated after 24 h to increase the efficiency of knockdown. Cells were harvested for immunoblot analysis or immunocytochemistry 4 days post transfection. DYRK transcript levels were measured by real-time RT-PCR. Threshold cycles ($C_T$) for DYRKIA were normalized to GAPDH housekeeping gene expression levels (ΔCT) and plotted as $0.5^{\Delta Ct}*10^4$ (arbitrary units). The siRNA sequences correspond to DYRK1A: AGGUGGAGGUGCAAUAUUA (SEQ ID NO: 31); scrambled control: CUUUAAGCCUCGAGAUAUA (SEQ ID NO: 32). The RT-PCR primer sequences correspond to DYRKIA sense: AGTTCTGGGTATTCCACCTGCTCA (SEQ ID NO: 10), DYRKIA anti-sense: TGAAGTT-TACGGGTTCCTGGTGGT (SEQ ID NO: 11).

Intracellular Calcium Measurements by Time-Lapse Video Imaging

HEK 293T cells were grown directly on UV-sterilized coverslips, loaded with $Ca^{2+}$ indicator dye Fura-2 AM (3 μM, Molecular Probes, Eugene, Oreg.) for 45 min at room temperature, washed and resuspended in loading medium (RPMI+10% FCS). For ratiometric $Ca^{2+}$ videoimaging, coverslips were mounted on a closed bath RC-20 flow chamber (Warner Instrument Corp., Hamden, Conn.) and perfused in 2 mM Calcium Ringer solution (155 mM NaCl, 4.5 mM KCl, 10 mM D-glucose, 5 mM Hepes (pH 7.4), 1 mM $MgCl_2$, 2 mM $CaCl_2$). After switching to $Ca^{2+}$ free Ringer solution (2 mM $Ca^{2+}$ replaced with 2 mM $MgCl_2$), intracellular $Ca^{2+}$ stores were depleted with 1 μM thapsigargin, and store-operated Ca2+ influx was measured after perfusing cells with Ringer solution containing 2 mM CaCl2. Single cell video imaging was performed on a S200 inverted epifluorescence microscope (Zeiss, Thornwood, N.Y.) using OpenLab imaging software (Improvision, Lexington, Mass.). Fura-2 emission was detected at 510 nm following excitation at 340 and 380 nm, respectively, with ratios of 340/380 being calculated for each 5 sec interval after background subtraction. Calibration values ($R_{min}$, $R_{max}$, $S_f$) were derived from cuvette measurements as previously described[43]. For each experiment, approximately 50-100 cells were analyzed. For simultaneous measurements of $[Ca^{2+}]i$ and DYRK2 expression, Jurkat T cells were cotransfected with DYRK2 cDNA and eGFP at a ratio of 10:1. 48 hrs post transfection, cells were used for $Ca^{2+}$ imaging as described above. For single cell analysis of [Ca2+] i, GFP⁻ (that is, DYRK2⁻) and GFP⁺ (that is, DYRK2⁺) cells were gated and plotted separately.

Intracellular Calcium Measurements by Flow Cytometry

S2R+ cells were detached from the dish with trypsin (Cell-Gro, Herndon, Va.) and loaded with the $Ca^{2+}$ indicator dye Fluo4-AM (2 μM Molecular Probes, Eugene, Oreg.) for 45 min at room temperature and then resuspended in loading medium (RPMI+10% FCS). Immediately before the flow cytometric $Ca^{2+}$ measurements, cells were resuspended in $Ca^{2+}$ free Ringer solution and analyzed on a FACSCalibur (BD Biosciences, San Jose, Calif.). 180 sec after addition of thapsigargin (3 μM) in $Ca^{2+}$ free Ringer to deplete intracellular $Ca^{2+}$ stores, 4 mM $Ca^{2+}$ Ringer solution was added to the cells to achieve a final concentration of 2 mM $Ca^{2+}$. Cellular $Ca^{2+}$ levels were then analyzed using FloJo software (Tree Star, Inc., Ashland, Oreg.).

Subcloning of Human Orthologues of the Candidate Kinases

Full-length cDNAs encoding human orthologues of the kinase candidates were obtained from Flexgene Kinase Repository (Harvard Institute of Proteomics)[36] or the Mammalian Gene Collection (MGC, Open Biosystems), subcloned into pENTRY.11 (Invitrogen) vectors with insertion of Flag-tag at the N-terminus, and then recombined into pDEST12.2 (Invitrogen). Kinase-dead DYRK2 was constructed by introducing a K251R point mutation in the ATP binding pocket of the active site using the PCR-based method (QuikChange Site-Directed Mutagenesis, Stratagene) and sequenced to ensure polymerase fidelity.

Introduction and Results

The subcellular localization of NFAT is determined by a complex process of signal integration that involves inputs from diverse signalling pathways[3-5]. In resting cells, NFAT proteins are heavily phosphorylated and reside in the cytoplasm; in cells exposed to stimuli that raise intracellular free $Ca^{2+}$ ($[Ca^{2+}]_i$) levels they are dephosphorylated by the calmodulin-dependent phosphatase calcineurin and translocate to the nucleus[3,6]. Dephosphorylation of NFAT by calcineurin is countered by distinct NFAT kinases, among them CK1, GSK3, and various members of the MAP kinase family[3,7-10]. The transcriptional activity of NFAT is regulated by additional inputs, including phosphorylation of the N-terminal transactivation domain, recruitment of co-activators and co-repressors, and choice of partner proteins in the nucleus[3,9,11].

We used a strategy, based on genome-wide RNAi screening in Drosophila S2R+ cells[12-14], to identify regulators of intracellular free $Ca^{2+}$ ($[Ca^{2+}]_i$) levels, calcineurin activation and NFAT localization in cells. The strategy relies on the fact that although $Ca^{2+}$-regulated NFAT proteins are not represented in Drosophila, the pathways of $Ca^{2+}$ homeostasis, $Ca^{2+}$ influx, and calcineurin activity that regulate NFAT localization are evolutionarily conserved[15,16]. To validate this point, we used the GFP fusion protein NFAT1(1-460)-GFP (here termed NFAT-GFP)[17]. NFAT-GFP contains the entire regulatory domain of NFAT, including the calcineurin and CK1 docking sites, the nuclear localization signal (NLS), and the conserved serine-rich regions (SRR) and serine-proline repeat (SP) motifs which control NFAT1 subcellular localization and DNA-binding affinity[3,9,10,17] (FIG. 6A). NFAT-GFP was correctly regulated in Drosophila S2R+ cells: it was phosphorylated and properly localized to the cytoplasm under resting conditions and became dephosphorylated and translocated to the nucleus in response to $Ca^{2+}$ store depletion with the SERCA inhibitor thapsigargin (FIG. 6B); it was imported into the nucleus with similar kinetics in S2R+ cells and mammalian HeLa cells and was sensitive to the calcineurin inhibitor CsA in both cell types. S2R+ cells treated with limiting amounts of thapsigargin displayed intermediate phosphorylated forms of NFAT-GFP, most likely reflecting progressive dephosphorylation of serines within the individual conserved motifs of the regulatory domain[9,10]. Finally, depletion of the primary NFAT regulator, calcineurin, by RNAi in S2R+ cells inhibited thapsigargin-dependent dephosphorylation and nuclear import of NFAT-GFP (Table II). Together these experiments confirmed that the major pathways regulating NFAT phosphorylation and subcellular localization—store-operated $Ca^{2+}$ influx, calcineurin activation, and NFAT phosphorylation—are conserved in Drosophila and appropriately regulate vertebrate NFAT.

We performed a genome-wide RNAi screen[12,13] on unstimulated S2R+ cells, and scored visually for aberrant nuclear localization of NFAT-GFP (see Methods and Example 3). Of 21,884 screened wells, 662 were scored as potentially positive using non-stringent criteria; in a confirmatory screen, 271/325 (83%) retested candidates were confirmed as positive, attesting to the reproducibility of our initial assessment of NFAT nuclear localization (FIG. 6C). Positive candidates included $Na^+/Ca^{2+}$ exchangers and SERCA $Ca^{2+}$ ATP-ases whose knockdown would be expected to increase basal $[Ca^{2+}]_i$, and the scaffold protein Homer which has been linked to $Ca^{2+}$ influx and $Ca^{2+}$ homeostasis[18,19] (Table I). The screen also identified Stim, a recently-identified regulator of store-operated $Ca^{2+}$ influx[20-22] as causing nuclear localization of NFAT-GFP in resting S2R+ cells, possibly because its depletion resulted in minor dysregulation of NFAT kinases or small increases in basal $[Ca^{2+}]_i$ levels (FIGS. 9A-9C).

Finally, the screen identified a large number of protein kinases which could potentially influence basal $[Ca^{2+}]_I$ levels or calcineurin activity, directly phosphorylate the NFAT regulatory domain, or indirectly influence the activity of direct NFAT kinases (Table I).

We were interested in kinases that directly phosphorylate the NFAT regulatory domain. In the family member NFAT1, the regulatory domain bears>14 phosphorylated serines, 13 of which are dephosphorylated by calcineurin[9] (FIG. 6A). Five of these serines are located in the SRR-1 motif, which controls exposure of the NLS and is a target for phosphorylation by CK1[3,10]; three are located in the SP-2 motif, which can be phosphorylated by GSK3 after a priming phosphorylation by protein kinase A (PKA)[7,10]; and four are located in the SP-3 motif, for which a relevant kinase had yet to be identified at the time this study was initiated. The SP-2 and SP-3 motifs do not directly regulate the subcellular localization of NFAT1, but their dephosphorylation increases both the probability of NLS exposure and the affinity of NFAT for DNA[3,10,23]. It was not known how distinct SRR-1, SP-2 and SP-3 kinases acted together to promote the full phosphorylation of NFAT; nevertheless, we expected that depletion of individual NFAT kinases in S2R+ cells would result in varying degrees of nuclear accumulation of NFAT, depending on kinase expression level, the particular motif phosphorylated, and whether or not other related kinases were redundantly expressed. We therefore tested at least one mammalian homologue (where available) of all constitutively-active kinases identified in the screen, regardless of their score in the secondary screen. Some inducible kinases were included, but others (e.g. protein kinases C and D) will be investigated as part of a separate study.

Figure 7A:
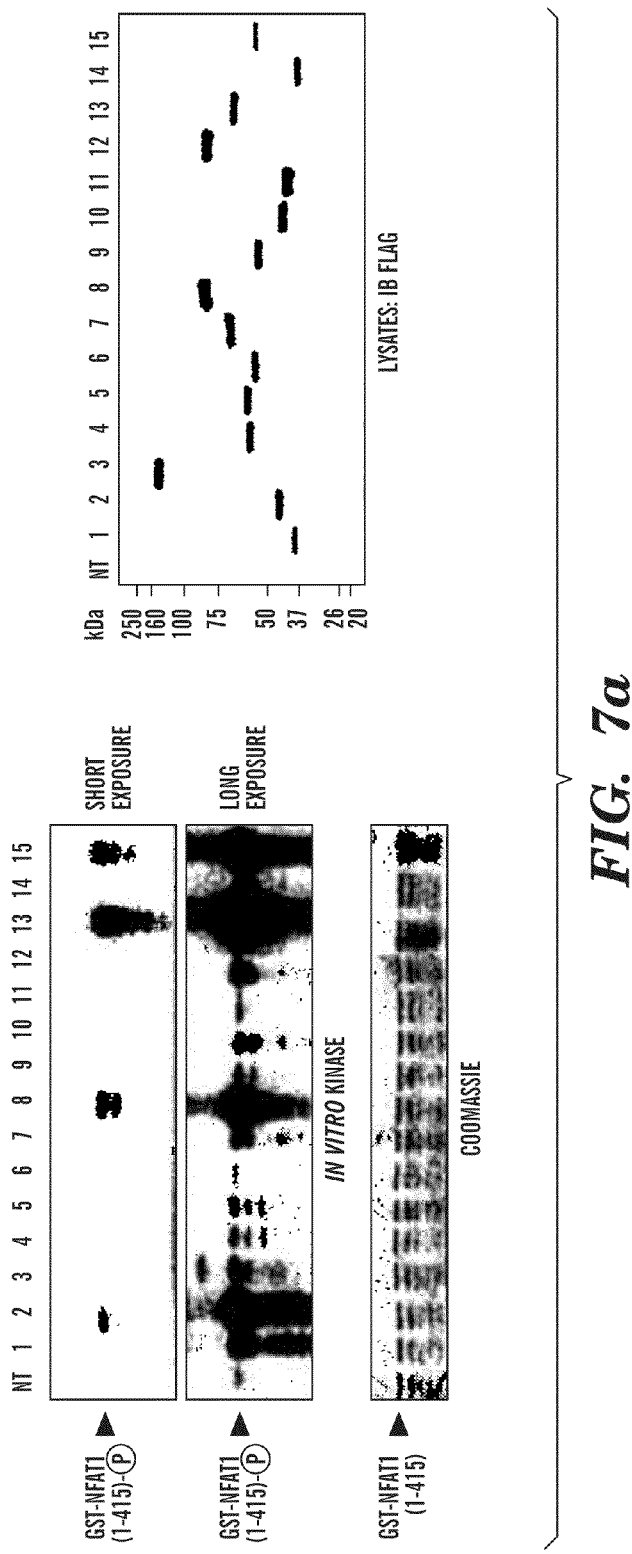
FIGS. 7A-7C shows screening of candidate kinases identified in the Drosophila S2R+ cell RNAi screen, for NFAT phosphorylation and identification of DYRK as a negative regulator of NFAT.
Figure 7B:
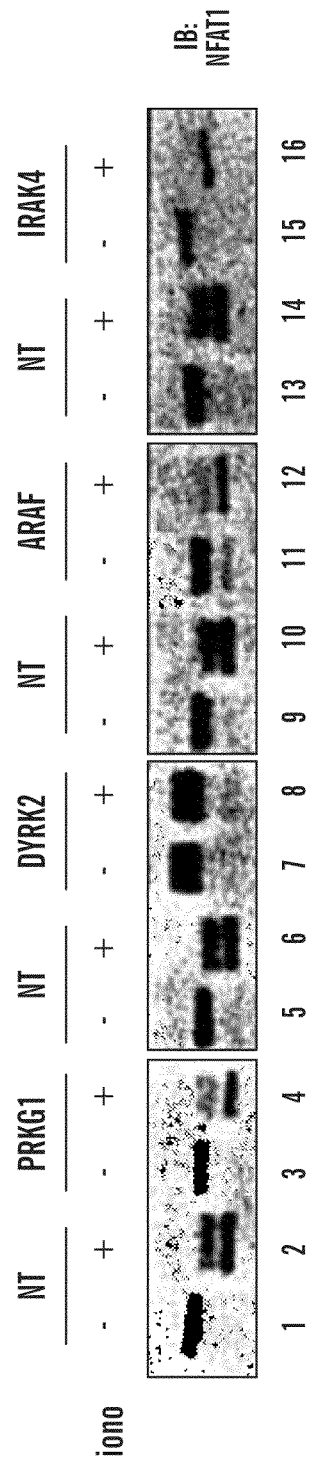
Figure 7C:
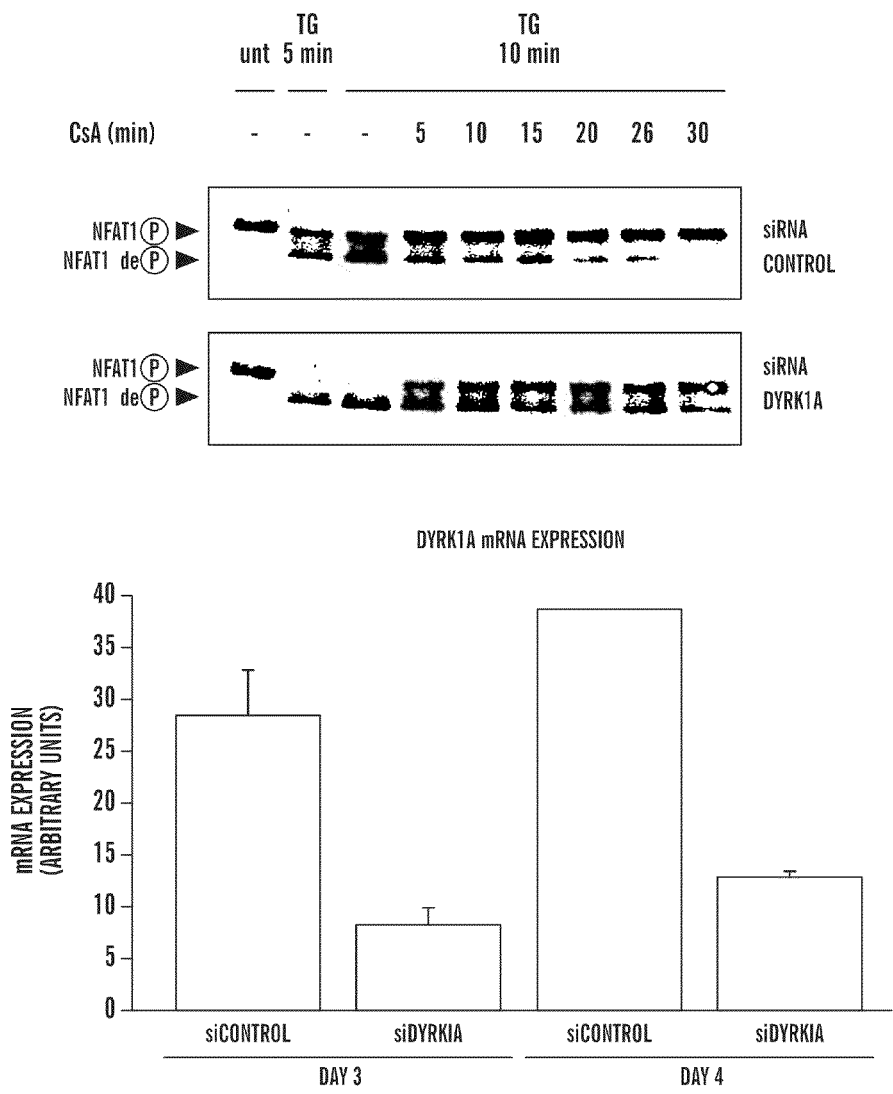

FLAG-tagged mammalian homologues of selected *Drosophila* kinases were expressed in HEK293 cells, and anti-FLAG immunoprecipitates were tested in an in vitro kinase assay for their ability to phosphorylate the GST-NFAT1(1-415) fusion protein (FIG. 7A). Three novel candidates—PRKG1, DYRK2 and IRAK4—showed strong activity in this assay (FIG. 7A, lanes 8, 13 and 15; CK1 isoforms CK1α and CK1ε were included as positive controls in lanes 1 and 2). PRKG1 was expressed at equivalent or higher levels than DYRK2 (FIG. 7A, bottom panel, lanes 8 and 13), but only DYRK2 could counter the dephosphorylation of NFAT-GFP by calcineurin (FIG. 7B, lanes 3, 4; 7, 8; 11, 12). IRAK4 was poorly expressed (FIG. 7A, bottom panel, lane 15); however CD4+ Th1 cells isolated from IRAK4−/− mice showed normal NFAT1 dephosphorylation, rephosphorylation and nuclear transport compared to control cells. For these reasons, neither PRKG1 nor IRAK4 were further investigated.

We focused on the role of DYRK-family kinases as direct regulators of NFAT. Overexpression of DYRK2 maintained NFAT-GFP in its phosphorylated form after ionomycin treatment (FIG. 7B, lanes 5-8); similarly, overexpression of wild type (WT) DYRK2 but not a kinase-dead (KD) mutant of DYRK2, prevented NFAT nuclear localization in thapsigargin-treated cells. DYRK overexpression yielded a slower-migrating form of NFAT (FIG. 7B, lanes 7, 8), leading to the concern that DYRK (a serine/proline-directed kinase[24]) phosphorylated SPRIEIT (SEQ ID NO: 33), the calcineurin docking sequence on NFAT1[3,6], preventing NFAT:calcineurin interaction. However, DYRK2 inhibited the ionomycin-induced dephosphorylation of NFAT-GFP containing a SPRIEITPS (SEQ ID NO: 53)>HPVIVITGP (SEQ ID NO: 54) (VIVIT) (SEQ ID NO: 30) substitution[17], which eliminates the SP and TP sequences that could be targeted by DYRK. The ability of DYRK to inhibit dephosphorylation of the VIVIT (SEQ ID NO: 30)-substituted NFAT-GFP is particularly impressive, given the higher affinity (~40-50-fold) of the VIVIT (SEQ ID NO: 30) docking site for calcineurin compared to the affinity of the wild type SPRIEIT (SEQ ID NO: 33) docking site[17]. Consistent with direct phosphorylation of NFAT, $Ca^{2+}$ mobilization in response to thapsigargin was unaffected by depletion of the DYRK-family candidate CG40478 in S2R+ cells, and only slightly diminished by DYRK2 overexpression in Jurkat T cells.

Figure 10A:
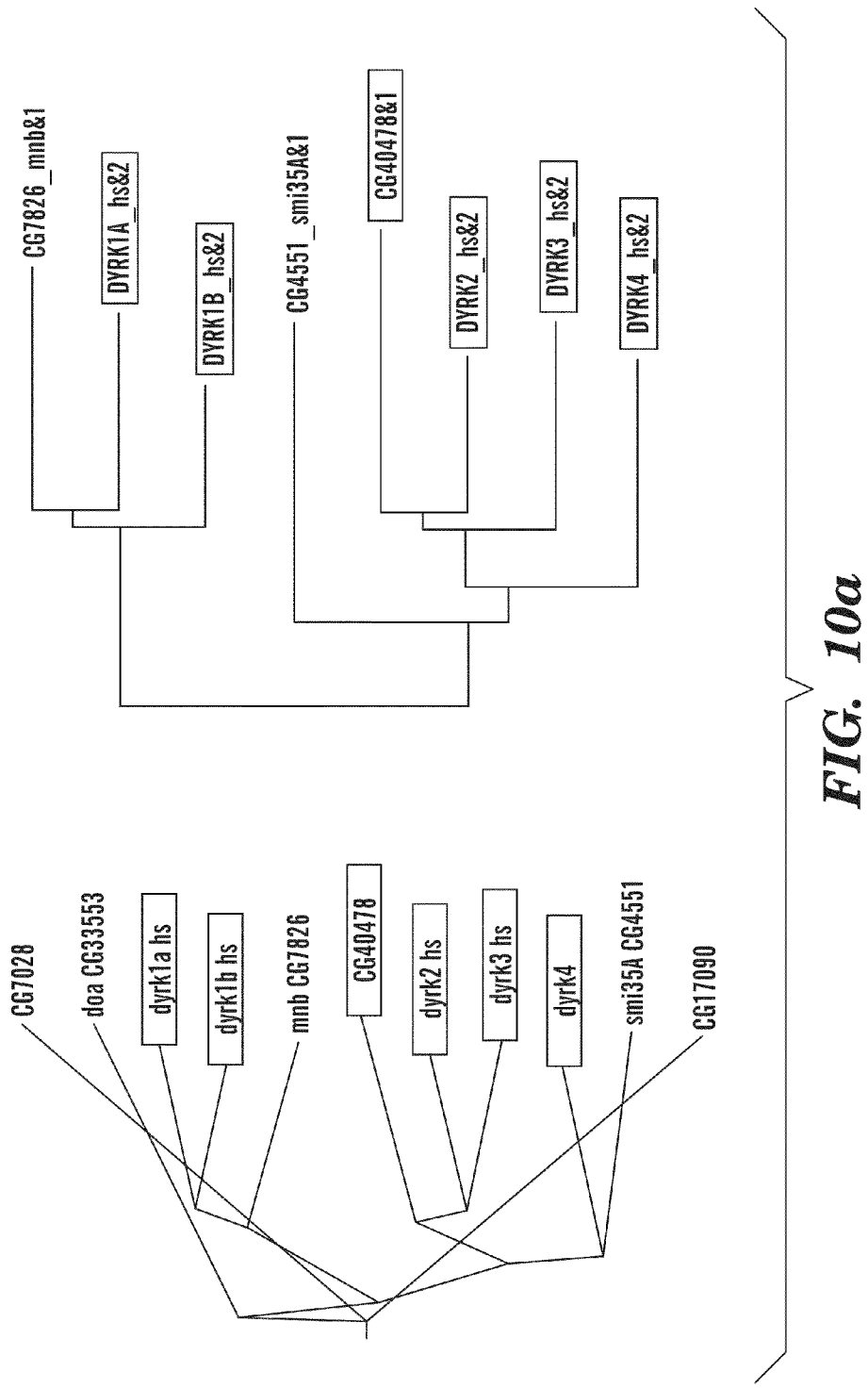
FIGS. 10A-10B shows the phylogenetic relation between different members of the DYRK family in *Drosophila* and in humans, and the expression pattern of human DYRKs in Jurkat T cells.
Figure 10B:
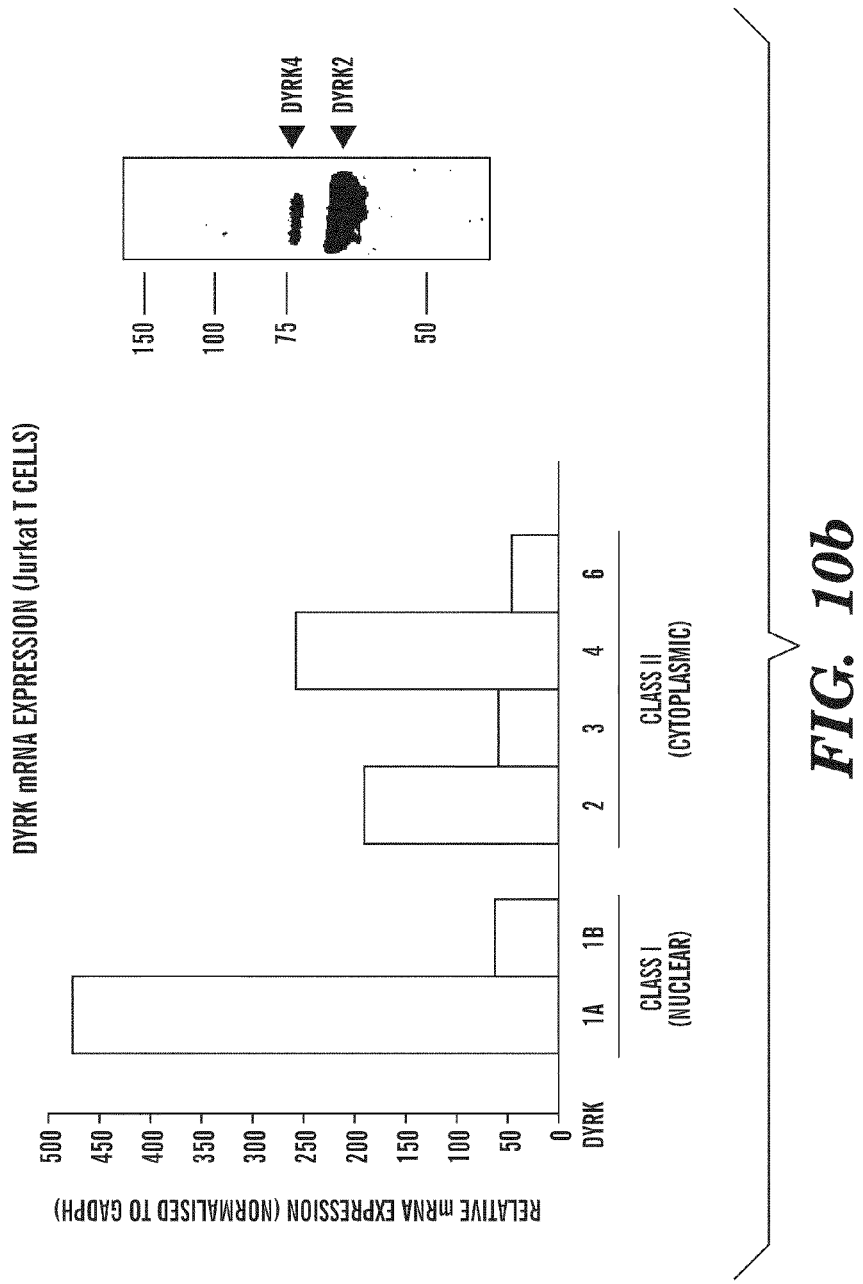

DYRKs constitute an evolutionarily-conserved family of proline or arginine-directed protein kinases distantly related to cyclin-dependent kinases (CDK), mitogen-activated protein kinases (MAPK), glycogen synthetase kinases (GSK), and CDK-like (CLK) kinases (CMGC kinases[24]. The DYRK family has multiple members (FIG. 11A) which have been designated class I (nuclear, DYRK1A and DYRK1B) or class II (cytoplasmic, DYRK2-6), depending on their subcellular localisation[25,26]. RT-PCR and western blotting suggested that DYRK1A and DYRK2 were major representatives of nuclear and cytoplasmic DYRKs in Jurkat T cells, respectively (FIG. 11B). Depletion of endogenous DYRK1A using DYRK1A-specific siRNA in HeLa cells stably expressing NFAT-GFP increased the rate and extent of NFAT1 dephosphorylation and nuclear import while slowing rephosphorylation and nuclear export, in response to treatment with thapsigargin for 10 min (to induce dephosphorylation and nuclear import) followed by CsA addition for 5 to 30 min (to inactivate calcineurin and permit rephosphorylation by NFAT kinases for nuclear export) (FIG. 10C left panel). Results obtained using endogenous DYRK1A depletion, which reflect a knockdown efficiency of approximately 70% of mRNA levels (FIG. 10C right panel), indicate that DYRK represent physiological negative regulators of NFAT activation in cells.

Further experiments showed that DYRK specifically targeted the SP-3 motif of NFAT1. FLAG-tagged DYRK2 was expressed in HEK 293 cells, immunoprecipitated with anti-FLAG antibodies, and phosphorylated peptides corresponding to the conserved SP-3 but not the SP-2 motif of the NFAT regulatory domain in vitro. To rule out the possibility that the NFAT kinase was not DYRK itself but rather a DYRK-associated kinase, we tested bacterially-expressed recombinant DYRK1A and DYRK2 for in vitro phosphorylation of peptides corresponding to three conserved serine-rich motifs of NFAT1 phosphorylated in cells (SRR-1, SP-2 and SP-3 motifs[9]). DYRK2 and DYRK1A both displayed strong and selective kinase activity towards the SP-3 motif of NFAT1, but neither kinase phosphorylated an SP-3 peptide with Ser>Ala substitutions in the specific serine residues known to be phosphorylated in cells[9]. At least 2 serine residues (bold and underlined) in the SP-3 motif (SPQRSRSPSPQP SPHVAPQDD) (SEQ ID NO: 34) fit the known sequence preference of DYRK kinases for serine/threonine residues with arginine at the −2 or −3 position, and proline (or valine) at the +1 position[27-29], and both are known to be phosphorylated in cells[9] (see FIG. 6A). Additional studies will be needed to establish whether the two other phosphorylated serine residues (underlined) in the SP-3 motif are targets for DYRK or other NFAT kinases in vivo.

Phosphorylation at the SP-2 and SP-3 motifs are the primary determinants for upward mobility shift of phosphorylated NFAT1, and we have shown here and previously that they are phosphorylated by GSK3 and DYRK, respectively[9]. Because DYRK kinases have been reported to prime for GSK3-mediated phosphorylation of protein-synthesis initiation factor eIF2Bε and the microtubule-associated protein tau[29], we asked whether DYRK kinases could similarly prime for GSK3-mediated phosphorylation of NFAT. The SP2 motif of NFAT1 can be phosphorylated by GSK3[10], and GSK3 recognition of the target sequence requires a priming phosphorylation that can be mediated by PKA. In contrast to the strong priming by PKA, neither DYRK2 nor DYRK1A could efficiently prime for phosphorylation of the SP-2 motif by GSK3.

As DYRK2 phosphorylated only the SP-3 motif of NFAT in vitro, and because it was not a priming kinase for GSK3 at the SP-2 motif, we expected that it would cause only half the expected mobility shift of NFAT1 when expressed in cells. However, overexpression of DYRK2 resulted in complete phosphorylation of NFAT1 (FIG. 7B). To resolve this paradox, we asked whether prior phosphorylation of the entire NFAT regulatory domain by DYRK would facilitate further phosphorylation by GSK3. The GST-NFAT1(1-415) fusion protein was prephosphorylated to completion by PKA or DYRK2 using the recombinant kinases, then washed and incubated briefly (45 min) in the absence or presence of recombinant GSK3 and radiolabelled [γ-$^{32}$P] ATP. As shown previously, GSK3 does not phosphorylate GST-NFAT1(1-415) without priming, but does phosphorylate after pre-phosphorylation with either PKA or DYRK2. Pre-phosphorylation with DYRK2 caused an upward mobility shift of the GST-NFAT1(1-415) substrate as judged by Coomassie blue staining, as expected from the fact that DYRK2 phosphorylates the SP-3 motif; moreover, pre-phosphorylation with DYRK2 yielded a radioactive GSK3-phosphorylated band of slower mobility compared to the band observed after pre-phosphorylation with PKA. These results suggest that while PKA primes for GSK3 by phosphorylating the fourth serine (bold) in the SP-2 motif (SPRTSPIMSPRTSLAED) (SEQ ID NO: 35) and permitting processive N-terminal phosphorylation of the underlined serines by GSK3, while DYRK2 potentiates GSK3-mediated phosphorylation of the regulatory domain motif by phosphorylating a separate motif, the SP-3 motif. Indeed, the serine targeted by PKA in the SP-2 motif is not found phosphorylated in cells[10], providing further evidence for physiological regulation of NFAT by DYRK.

Figure 8A:
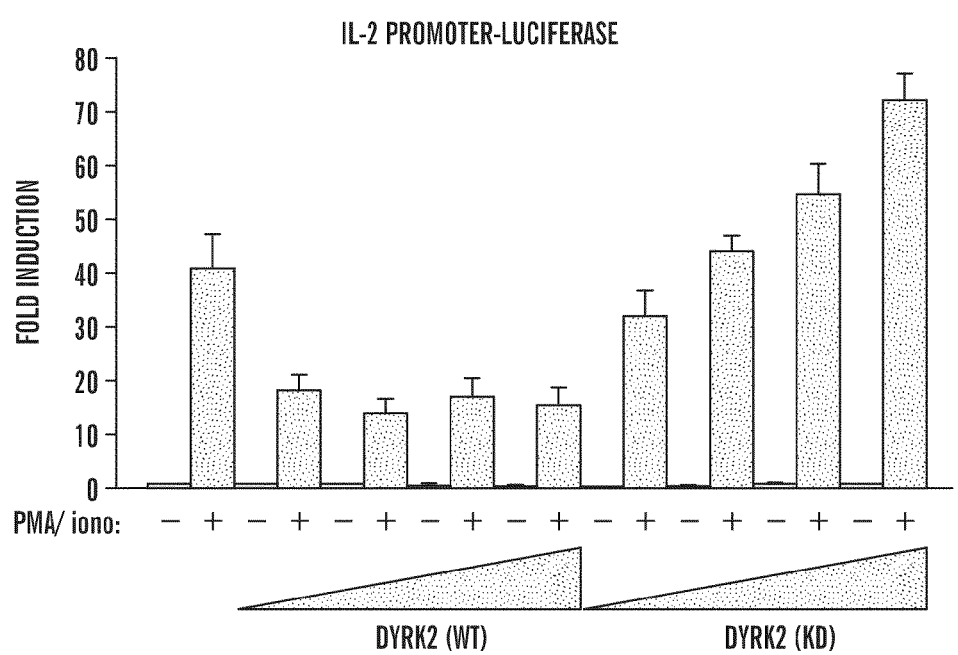
FIGS. 8A-8C show that DYRK2 inhibits NFAT-dependent reporter activity and endogenous IL-2 expression.
Figure 8B:
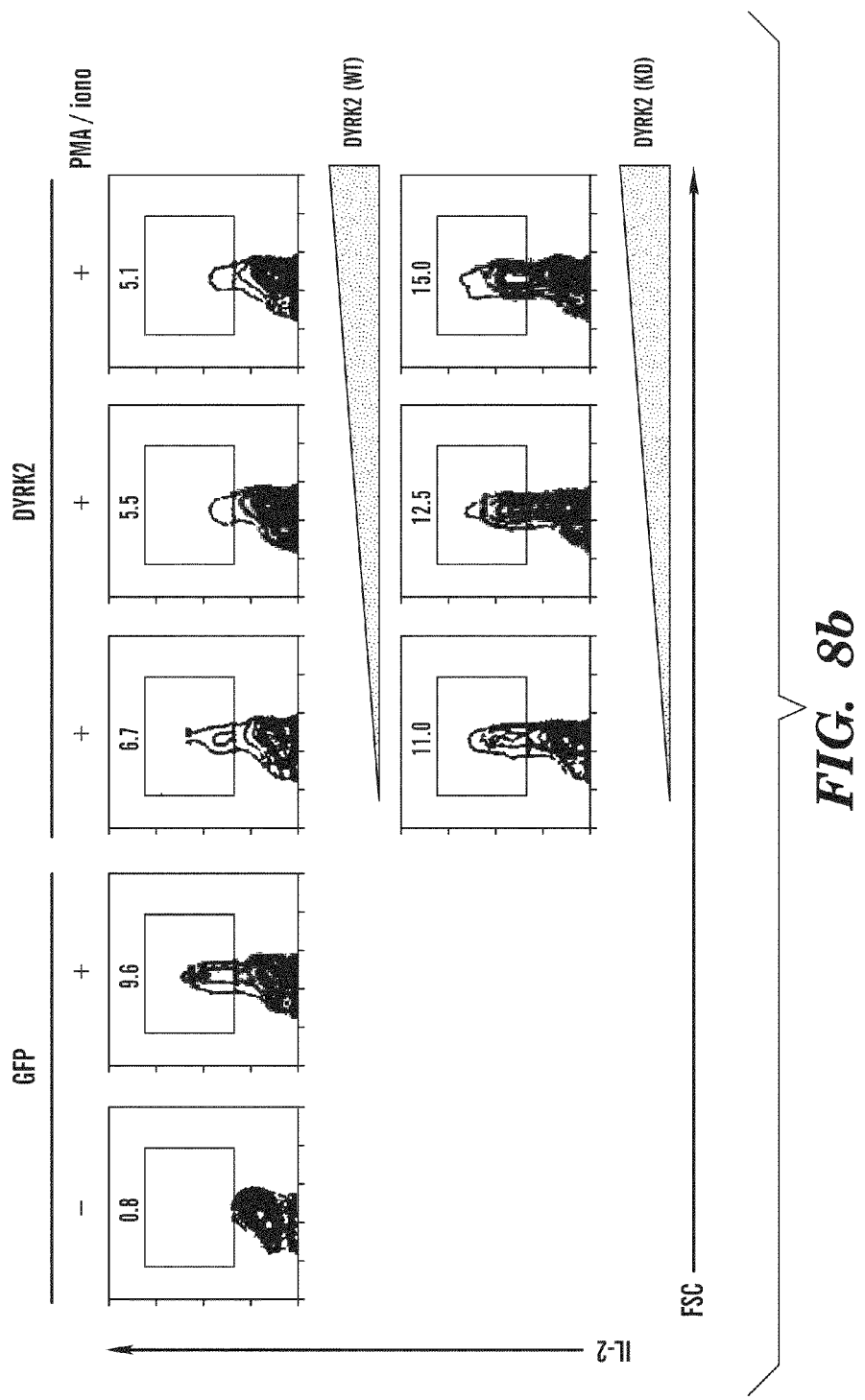
Figure 8C:
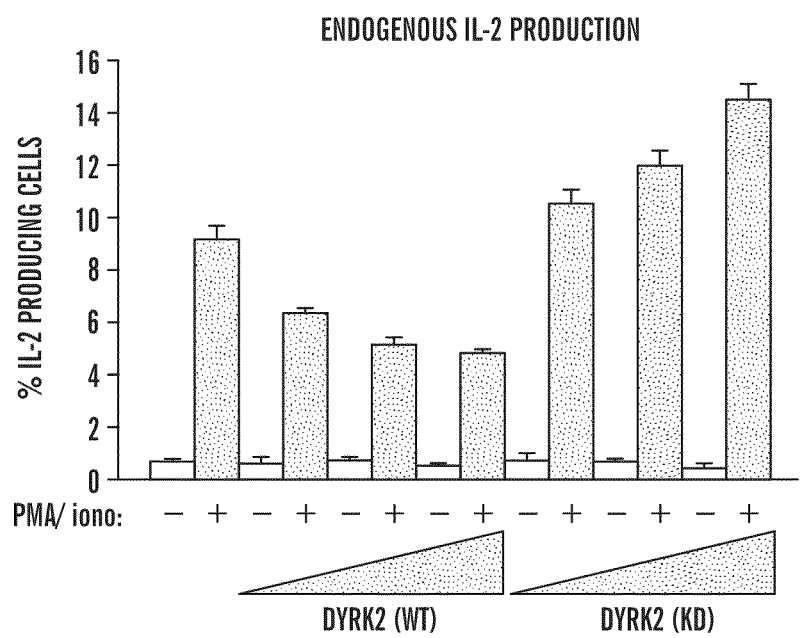

We asked whether DYRK expression regulated the transcriptional activity of NFAT utilizing the kinase-dead mutant of DYRK2 as an inhibitor of DYRK activity in cells[30,31]. Jurkat T cells were co-transfected with an IL-2 promoter-driven luciferase reporter plasmid and increasing amounts of expression plasmids for either wild type (WT) or kinase-dead (KD) DYRK2; one day later, the cells were stimulated for 6 h with PMA and ionomycin and reporter activity was measured. WT DYRK2 strongly diminished NFAT-dependent activity, while the KD mutant behaved as an inhibitor by increasing NFAT-dependent luciferase activity at higher concentrations (FIG. 8A). Similar results were obtained using luciferase reporters containing tandem copies of the ARRE2 NFAT:AP-1 site of the IL-2 promoter[32] as well as the κ3 site of the TNFα promoter[33]. In related experiments expression WT DYRK2 also diminished, the production of endogenous IL-2 by stimulated Jurkat T cells in a dose-dependent manner while KD DYRK2 again had an inhibitory effect, when expressed at high concentrations, by increasing IL-2 production under these conditions (FIGS. 8B, 8C). Furthermore, we detected endogenous DYRK2 co-immunoprecipitating with HA-NFAT1 stably expressed at low endogenous levels in a Jurkat cell line; in this respect DYRK may resemble the SRR-1 kinase CK1, which forms a stable complex with NFAT under resting conditions but dissociates following activation[10]. A DYRK-NFAT interaction supports the hypothesis that DYRK is a physiological NFAT kinase: kinase-substrate interactions of this type are known to be critical in many other signal transduction pathways, although they are often transient and difficult to detect at endogenous levels of expression[34].

Discussion

We have shown that genome-wide RNAi screening in *Drosophila* is a valid and powerful strategy for exploring novel aspects of signal transduction in mammalian cells, provided that key members of the signaling pathway are evolutionarily conserved and represented in the *Drosophila* genome. We have used the method to identify conserved regulators of the purely vertebrate transcription factor, NFAT; to our knowledge, this is the first example of a genome-wide RNAi screen that crosses evolutionary boundaries in this manner. The strategy was successful because *Drosophila* developed an evolutionary niche that was later used by $Ca^{2+}$-regulated NFAT proteins when they emerged in vertebrates. Using this approach we have identified DYRK as a novel physiological regulator of NFAT, and the first SP-3 motif-directed kinase. It is likely that conserved aspects of the regulation of other mammalian processes will also be successfully defined by developing assays in *Drosophila* cells.

Our data suggest that DYRK regulates NFAT phosphorylation by a mechanism in which DYRK phosphorylates the NFAT regulatory domain within the conserved SP-3 motif, and thereby facilitates further phosphorylation of the NFAT regulatory domain by GSK3. A similar sequential mechanism may regulate progressive dephosphorylation of NFAT, whereby dephosphorylation of the SRR-1 motif promotes dephosphorylation of the SP-2 and SP-3 motifs by increasing their accessibility to calcineurin[9]. It is likely that class II DYRKs (DYRK2, 3 and 4) which are localized to the cytoplasm[25], function primarily as "maintenance" kinases that sustain the phosphorylation status of cytoplasmic NFAT in resting cells, whereas class I DYRKs (DYRK1A and 1B), which are localized to the nucleus[25], re-phosphorylate nuclear NFAT and promote its nuclear export. Notably, DYRK1A and the endogenous calcineurin regulator RCN/DSCR1/calcipressin-1 are both localized to the Down Syndrome Critical Region on chromosome 21. Thus overexpression of these negative regulators of NFAT in Down Syndrome could contribute, by inhibiting NFAT activation, to the severe neurological and immune developmental defects associated with chromosome 21 trisomy[35].

REFERENCES

1. Rao, A., Luo, C. & Hogan, P. G. Transcription factors of the NFAT family: regulation and function. Annu Rev Immunol 15, 707-47 (1997).
2. Crabtree, G. R. & Olson, E. N. NFAT signaling: choreographing the social lives of cells. Cell 109 Suppl, S67-79 (2002).
3. Hogan, P. G., Chen, L., Nardone, J. & Rao, A. Transcriptional regulation by calcium, calcineurin, and NFAT. Genes Dev 17, 2205-32 (2003).
4. Salazar, C. & Hofer, T. Allosteric regulation of the transcription factor NFAT1 by multiple phosphorylation sites: a mathematical analysis. J Mol Biol 327, 31-45 (2003).
5. Salazar, C. & Hofer, T. Activation of the transcription factor NFAT1: concerted or modular regulation? FEBS Lett 579, 621-6 (2005).
6. Feske, S., Okamura, H., Hogan, P. G. & Rao, A. Ca2+/calcineurin signalling in cells of the immune system. Biochem Biophys Res Commun 311, 1117-32 (2003).
7. Beals, C. R., Sheridan, C. M., Turck, C. W., Gardner, P. & Crabtree, G. R. Nuclear export of NF-ATc enhanced by glycogen synthase kinase-3. Science 275, 1930-4 (1997).

8. Zhu, J. et al. Intramolecular masking of nuclear import signal on NF-AT4 by casein kinase I and MEKK1. Cell 93, 851-61 (1998).
9. Okamura, H. et al. Concerted dephosphorylation of the transcription factor NFAT1 induces a conformational switch that regulates transcriptional activity. Mol Cell 6, 539-50 (2000).
10. Okamura, H. et al. A conserved docking motif for CK1 binding controls the nuclear localization of NFAT1. Mol Cell Biol 24, 4184-95 (2004).
11. Macian, F., Lopez-Rodriguez, C. & Rao, A. Partners in transcription: NFAT and AP-1. Oncogene 20, 2476-89 (2001).
12. Boutros, M. et al. Genome-wide RNAi analysis of growth and viability in *Drosophila* cells. Science 303, 832-5 (2004).
13. Kiger, A. A. et al. A functional genomic analysis of cell morphology using RNA interference. J Biol 2, 27 (2003).
14. Echard, A., Hickson, G. R., Foley, E. & O'Farrell, P. H. Terminal cytokinesis events uncovered after an RNAi screen. Curr Biol 14, 1685-93 (2004).
15. Yeromin, A. V., Roos, J., Stauderman, K. A. & Cahalan, M. D. A store-operated calcium channel in *Drosophila* S2 cells. J Gen Physiol 123, 167-82 (2004).
16. Myers, E. W. et al. A whole-genome assembly of *Drosophila*. Science 287, 2196-204 (2000).
17. Aramburu, J. et al. Affinity-driven peptide selection of an NFAT inhibitor more selective than cyclosporin A. Science 285, 2129-33 (1999).
18. Roderick, H. L. & Bootman, M. D. Calcium influx: is Homer the missing link? Curr Biol 13, R976-8 (2003).
19. Kim, E. & Sheng, M. PDZ domain proteins of synapses. Nat Rev Neurosci 5, 771-81 (2004).
20. Roos, J. et al. STIM1, an essential and conserved component of store-operated Ca2+ channel function. J Cell Biol 169, 435-45 (2005).
21. Liou, J. et al. STIM is a Ca2+ sensor essential for Ca2+-store-depletion-triggered Ca2+ influx. Curr Biol 15, 1235-41 (2005).
22. Zhang, S. L. et al. STIM1 is a Ca(2+) sensor that activates CRAC channels and migrates from the Ca(2+) store to the plasma membrane. Nature 437, 902-5 (2005).
23. Clipstone, N. A., Fiorentino, D. F. & Crabtree, G. R. Molecular analysis of the interaction of calcineurin with drug-immunophilin complexes. J Biol Chem 269, 26431-7 (1994).
24. Kannan, N. & Neuwald, A. F. Evolutionary constraints associated with functional specificity of the CMGC protein kinases MAPK, CDK, GSK, SRPK, DYRK, and CK2alpha. Protein Sci 13, 2059-77 (2004).
25. Becker, W. & Joost, H. G. Structural and functional characteristics of Dyrk, a novel subfamily of protein kinases with dual specificity. Prog Nucleic Acid Res Mol Biol 62, 1-17 (1999).
26. Lochhead, P. A., Sibbet, G., Morrice, N. & Cleghon, V. Activation-loop autophosphorylation is mediated by a novel transitional intermediate form of DYRKs. Cell 121, 925-36 (2005).
27. Himpel, S. et al. Specificity determinants of substrate recognition by the protein kinase DYRK1A. J Biol Chem 275, 2431-8 (2000).
28. Campbell, L. E. & Proud, C. G. Differing substrate specificities of members of the DYRK family of arginine-directed protein kinases. FEBS Lett 510, 31-6 (2002).
29. Woods, Y. L. et al. The kinase DYRK phosphorylates protein-synthesis initiation factor eIF2Bepsilon at Ser539 and the microtubule-associated protein tau at Thr212: potential role for DYRK as a glycogen synthase kinase 3-priming kinase. Biochem J 355, 609-15 (2001).
30. Kentrup, H. et al. Dyrk, a dual specificity protein kinase with unique structural features whose activity is dependent on tyrosine residues between subdomains VII and VIII. J Biol Chem 271, 3488-95 (1996).
31. Wiechmann, S. et al. Unusual function of the activation loop in the protein kinase DYRK1A. Biochem Biophys Res Commun 302, 403-8 (2003).
32. Macian, F., Garcia-Rodriguez, C. & Rao, A. Gene expression elicited by NFAT in the presence or absence of cooperative recruitment of Fos and Jun. Embo J 19, 4783-95 (2000).
33. Esensten, J. H. et al. NFAT5 binds to the TNF promoter distinctly from NFATp, c, 3 and 4, and activates TNF transcription during hypertonic stress alone. Nucleic Acids Res 33, 3845-54 (2005).
34. Johnson, S. A. & Hunter, T. Kinomics: methods for deciphering the kinome. Nat Methods 2, 17-25 (2005).
35. Bhattacharyya, A. & Svendsen, C. N. Human neural stem cells: a new tool for studying cortical development in Down's syndrome. Genes Brain Behav 2, 179-86 (2003).
36. Brizuela, L., Richardson, A., Marsischky, G. & Labaer, J. The FLEXGene repository: exploiting the fruits of the genome projects by creating a needed resource to face the challenges of the post-genomic era. Arch Med Res 33, 318-24 (2002).
37. Arziman, Z., Horn, T. & Boutros, M. E-RNAi: a web application to design optimized RNAi constructs. Nucleic Acids Res 33, W582-8 (2005).
38. Yu, H. et al. Annotation transfer between genomes: protein-protein interologs and protein-DNA regulogs. Genome Res 14, 1107-18 (2004).
39. Remm, M. & Sonnhammer, E. Classification of transmembrane protein families in the *Caenorhabditis elegans* genome and identification of human orthologs. Genome Res 10, 1679-89 (2000).
40. Notredame, C., Higgins, D. G. & Heringa, J. T-Coffee: A novel method for fast and accurate multiple sequence alignment. J Mol Biol 302, 205-17 (2000).
41. Storm, C. E. & Sonnhammer, E. L. Automated ortholog inference from phylogenetic trees and calculation of orthology reliability. Bioinformatics 18, 92-9 (2002).
42. Ogawa, H., Ishiguro, K., Gaubatz, S., Livingston, D. M. & Nakatani, Y. A complex with chromatin modifiers that occupies E2F- and Myc-responsive genes in G0 cells. Science 296, 1132-6 (2002).
43. Grynkiewicz, G., Poenie, M. & Tsien, R. Y. A new generation of Ca2+ indicators with greatly improved fluorescence properties. J Biol Chem 260, 3440-50 (1985).

EXAMPLE 3

Table I

List of candidates that were positive in the secondary screen, classified into the categories in Table I. The first column indicates whether or not the candidate was retested in the confirmatory screen (NT, not tested); if tested, the summed localization score from 3 separate experiments is shown (see Methods). Other columns list gene names, Flybase numbers, and human orthologues as obtained from Homologene (for the kinase category, the phylogenetic analysis described in Methods was used in addition), and number of predicted off-targets with exact match of 21-nt, 37 candidates with >10 off-targets are not listed.

Table II

Analysis of expression, RNAi phenotype in thapsigargin-treated cells, and amplicon off-targets for calcineurin subunits and related proteins. Expression level of the subunits in S2R+ cells was estimated by RT-PCR analysis, and the effect of their depletion on NFAT nuclear localization in thapsigargin (TG)-treated cells was evaluated (+++, strong inhibition; −, no inhibition). The DRSC amplicons targeting each of the subunits were analyzed for predicted off-targets with exact matches of 21-, 20-, or 19-nt as described in Methods. Description of the off-targets is provided in Table III. Red indicates off-targets belonging to the same family as the primary targets.

Of the three isoforms of calcineurin A, the amplicon for CanA1 and one amplicon each for Pp2b-14D and CanA-14F show no predicted off-targets. CanA1 is poorly expressed and its depletion does not inhibit NFAT nuclear translocation, while Pp2B-14D and CanA-14F are both expressed and depletion of either isoform results in strong inhibition of NFAT nuclear translocation.

Why does depletion of the moderately expressed isoform CanA-14F give similar inhibition as depletion of the more highly expressed isoform Pp2B-14D? Different methods have different sensitivities, and while the eye is able to discern subtle changes in the nuclear localization of NFAT, such visual estimates are not as quantitative as (for instance) estimating extent of dephosphorylation by western blotting.

Of the three isoforms of calcineurin B, two (CanB and CanB2) are strongly related to mammalian calcineurin B while CG32812 is more distantly related, resembling mammalian CHP. RNAi against either CanB or CanB2 gave equivalent inhibition (~70%) of NFAT nuclear localization, even though CanB is barely expressed while CanB2 is expressed at high levels. This is most likely due to the fact that CanB and CanB2 are reciprocal off-targets, with 20 nt overlap in their respective amplicons DRSC 18449 and DRSC07355.

Table IV

Amplicon off-targets for selected candidates that were evaluated in additional experiments. Scores of the candidates in the confirmatory screen, evaluating the effects of their RNAi-mediated depletion on NFAT nuclear accumulation in resting cells, are shown (taken from Table I). For each candidate with positive DRSC amplicons, predicted off-targets with exact matches of 21-, 20-, or 19-nt are listed. Description of the off-targets is provided below. Red indicates off-targets belonging to the same family as the primary targets that were positive in the initial screen.

The amplicon corresponding to the GSK3 homologue sgg (DRSC18832) gave the highest score but also has a high number of off-targets. None of these off-targets corresponds to gskt (DRSC14056), which gave a low score of 1 in the primary screen.

The amplicon corresponding to the highest-scoring CK1 family member gish has no predicted off-targets, indicating that it represents a bonafide regulator of NFAT. Clear cross-inactivation exists for amplicons DRSC16929, DRSC20231 and DRSC19863, corresponding to the CK1 isoforms dco, CK1alpha/CG2028 and CG2577, each of which has a positive localization score of 1. Further work is necessary to determine whether the scores associated with the other isoforms reflect expression levels of the isoforms, off-target effects, or both.

We are fortunate that for the two candidates—DYRK and STIM—that we focused on for this study, there are no predicted off-targets for exact matches of either 21, 20 or 19 nt.

TABLE 1

| Score in secondary screen | Gene | FBGN | Number of potential 21nt off-targets | Human orthologs (NCBI Homologene) | Description of the human orthologs (NCBI Gene) |
|---|---|---|---|---|---|
| PHOSPHATASES | | | | | |
| 5 | Ptip | FBgn0039111 | 0 | PTPMT1 | protein tyrosine phosphatase, mitochondrial 1 |
| 3 | CanA1 | FBgn0010015 | 0 | PPP3CC | protein phosphatase 3 (formerly 2B), catalytic subunit, gamma isoform |
| 3 | flw | FBgn0000711 | 1 | PPP1CB | protein phosphatase 1, catalytic subunit, beta isoform |
| 3 | PpD6 | FBgn0005779 | 1 | | |
| 3 | wob | FBgn0027492 | 0 | PPP2R5E | protein phosphatase 2, regulatory subunit B (B56), epsilon isoform |
| 1 | CanB | FBgn0010014 | 0 | PPP3R1 | protein phosphatase 3 (formerly 2B), regulatory subunit B, 19 kDa, alpha isoform |
| 1 | CanB2 | FBgn0015614 | 0 | PPP3R1 | protein phosphatase 3 (formerly 2B), regulatory subunit B, 19 kDa, alpha isoform |
| 1 | CG32812 | FBgn0025642 | 0 | LOC63928 | hepatocellular carcinoma antigen gene 520/ related to mammalian CHP |
| 0 | Pp2B-14D | FBgn0011826 | 1 | PPP3CB | protein phosphatase 3 (formerly 2B), catalytic subunit, beta isoform |
| PROTEIN KINASES | | | | | |
| 6 | sgg | FBgn0003371 | 3 | GSK3B | glycogen synthase kinase 3 beta |
| 5 | CG7125 | FBgn0038603 | 0 | PRKD | protein kinase D |
| 4 | CG31640 | FBgn0051640 | 0 | DDR | |
| 4 | gish | FBgn0011253 | 0 | CSNK1G | casein kinase 1, gamma |
| 4 | inaC | FBgn0004784 | 0 | PRKCB1 | protein kinase C, beta 1 |
| 3 | CG12147 | FBgn0037325 | 0 | CSNK1 | casein kinase 1 family |
| 3 | CkIIalpha | FBgn0000258 | 0 | CSNK2A1.2 | casein kinase 2, alpha |
| 3 | pll | FBgn0010441 | 0 | IRAK | |
| 2 | CG2905, Nipped-A | FBgn0004661 | 0 | TRRAP | transformation/transcription domain-associated protein |
| 2 | aPKC | FBgn0022131 | 0 | PRKCI | protein kinase C, iota |

TABLE 1-continued

| Score in secondary screen | Gene | FBGN | Number of potential 21nt off-targets | Human orthologs (NCBI Homologene) | Description of the human orthologs (NCBI Gene) |
|---|---|---|---|---|---|
| 2 | CG11489 | FBgn0025702 | 0 | SRPK1 | SFRS protein kinase 1 |
| 2 | CG32687 | FBgn0052687 | 0 | LOC116064 | hypothetical protein LOC116064 |
| 2 | CG6498 | FBgn0036511 | 0 | MAST2 | microtubule associated serine/threonine kinase 2 |
| 2 | CG7097 | FBgn0034421 | 0 | MAP4K3 | mitogen-activated protein kinase kinase kinase kinase 3 |
| 2 | l(1)G0148 | FBgn0028360 | 0 | CDC7 | CDC7 cell division cycle 7 |
| 2 | Pkc53E | FBgn0003091 | 0 | PRKCA | protein kinase C, alpha |
| 2 | Pkcdelta | FBgn0030387 | 0 | PRKCD | protein kinase C, delta |
| 2 | polo | FBgn0003124 | 0 | PLK1 | polo-like kinase 1 |
| 2 | trc | FBgn0003744 | 0 | STK38, STK38L | serine/threonine kinase 38 like |
| 1 | CG40478 | FBgn0069975 | 0 | DYRK | dual-specificity tyrosine-(γ)-phosphorylation regulated kinase |
| 1 | CG2577 | FBgn0030384 | 3 | CSNK1 | casein kinase 1 family |
| 1 | CG4168 | FBgn0028888 | 0 | | |
| 1 | CG5483 | FBgn0038816 | 0 | | |
| 1 | CG7094 | FBgn0032650 | 0 | CSNK1 | casein kinase 1 family |
| 1 | CkIalpha | FBgn0015024 | 3 | CSNK1A1 | casein kinase 1, alpha 1 |
| 1 | Cks | FBgn0010314 | 0 | CKS1B | CDC28 protein kinase regulatory subunit 1B |
| 1 | dco | FBgn0002413 | 0 | CSNK1D, E | casein kinase 1, delta/epsilon |
| 1 | for | FBgn0000721 | 2 | PRKG1 | protein kinase, cGMP-dependent, type I |
| 1 | gskt | FBgn0046332 | 0 | GSK3A | |
| 1 | phl | FBgn0003079 | 2 | BRAF | v-raf murine sarcoma viral oncogene homolog B1 |
| 1 | Pk61C | FBgn0020386 | 0 | PDPK1 | 3-phosphoinositide dependent protein kinase 1 |
| 1 | Pkc98E | FBgn0003093 | 0 | PRKCE | protein kinase C, epsilon |
| 1 | Tie | FBgn0014073 | 4 | | |
| 0 | CG11533 | FBgn0039908 | 0 | | |
| 0 | CG9962 | FBgn0031441 | 0 | CSNK1 | casein kinase 1 family |
| 0 | CG10579 | FBgn0005640 | 0 | ALS2CR7, PFTK1 | PFTAIRE protein kinase 1 |
| 0 | png | FBgn0000826 | 0 | | |
| NT | CG17698 | FBgn0040056 | 0 | CAMKK2 | calcium/calmodulin-dependent protein kinase kinase 2, beta |
| NT | gek | FBgn0023081 | 0 | CDC428PA, B | CDC42 binding protein kinase alpha (DMPK-like) |
| OTHER KINASES/ KINASE-RELATED | | | | | |
| 1 | Pi3K59F | FBgn0015277 | 0 | PIK3C3 | phosphoinositide-3-kinase, class 3 |
| 0 | CG8298 | FBgn0033673 | 0 | | |
| 0 | Pdk | FBgn0017558 | 0 | PDK3 | pyruvate dehydrogenase kinase, isoenzyme 3 |
| NT | CG3809 | FBgn0037995 | 0 | | |
| NT | CG6218 | FBgn0038321 | 0 | NAGK | N-acetylglucosamine kinase |
| NT | CG6364 | FBgn0039179 | 0 | UCK2 | uridine-cytidine kinase 2 |
| NT | dlg | FBgn0001624 | 8 | DLG1 | discs, large homolog 1 |
| MISCELLANEOUS/ CALCIUM-RELATED | | | | | |
| 5 | CG14387 | FBgn0038089 | 0 | | |
| 4 | TpnC4 | FBgn0033027 | 0 | | |
| 4 | TpnC73F | FBgn0010424 | 0 | | |
| 3 | Stim | FBgn0045073 | 0 | STIM1 | stromal interaction molecule 1 |
| 3 | Cam | FBgn0000253 | 0 | CALM2 | calmodulin 2 (phosphorylase kinase, delta) |
| 3 | CG11165 | FBgn0033238 | 2 | | |
| 3 | CG13898 | FBgn0035161 | 0 | | |
| 2 | norPA | FBgn0004625 | 0 | PLCB4 | phospholipase C, beta 4 |
| 2 | TpnC41C | FBgn0013348 | 0 | | |
| 2 | TpnC47D | FBgn0010423 | 0 | | |
| 1 | CG13526 | FBgn0034774 | 0 | | |
| 1 | CG31345 | FBgn0051345 | 0 | CAPSL | calcyphosine-like |
| 1 | CG31650 | FBgn0031673 | 0 | RCN2 | reticulocalbin 2, EF-hand calcium binding domain |
| 1 | CG31958 | FBgn0051958 | 2 | | |
| 1 | CG31960 | FBgn0051960 | 2 | | |
| 1 | TpnC25D | FBgn0031692 | 1 | | |
| MEMBRANE SIGNALLING | | | | | |
| 5 | CG6919 | FBgn0038980 | 0 | HTR4 | 5-hydroxytryptamine (serotonin) receptor 4 |
| 4 | CG30340 | FBgn0050340 | 0 | | |
| 4 | DopR | FBgn0011582 | 4 | DRD1 | dopamine receptor D1 |
| 4 | Gr47a | FBgn0041242 | 0 | | |
| 4 | Or85d | FBgn0037594 | 0 | | |
| 4 | Su(fu) | FBgn0005355 | 0 | SUFU | suppressor of fused homolog (Drosophila) |
| 3 | Ac3 | FBgn0023416 | 0 | ADCY3 | adenylate cyclase 3 |

TABLE 1-continued

| Score in secondary screen | Gene | FBGN | Number of potential 21nt off-targets | Human orthologs (NCBI Homologene) | Description of the human orthologs (NCBI Gene) |
|---|---|---|---|---|---|
| 3 | Gyc-89Db | FBgn0038436 | 0 | | |
| 3 | homer | FBgn0025777 | 0 | HOMER2 | homer homolog 2 |
| 3 | mav | FBgn0039914 | 0 | TGFB3 | transforming growth factor, beta 3 |
| 3 | PGRP-LE | FBgn0030695 | 0 | PGLYRP3 | peptidoglycan recognition protein 3 |
| 2 | cenB1A | FBgn0039056 | 0 | CENTB2 | centaurin, beta 2 |
| 2 | CG10823 | FBgn0038880 | 0 | | |
| 2 | CG11319 | FBgn0031835 | 0 | DPP10 | dipeptidylpeptidase 10 |
| 2 | CG6989 | FBgn0038063 | 0 | | |
| 2 | fz3 | FBgn0027343 | 0 | | |
| 2 | N | FBgn0004647 | 0 | NOTCH1 | Notch homolog 1, translocation-associated |
| 2 | Plc21C | FBgn0004611 | 0 | PLCB1 | phospholipase C, beta 1 (phosphoinositide-specific) |
| 2 | pxb | FBgn0053207 | 1 | | |
| 2 | sog | FBgn0003463 | 0 | CHRD | chordin |
| 2 | spz | FBgn0003495 | 0 | | |
| 1 | 1Bw | FBgn0004364 | 0 | | |
| 1 | CG16752 | FBgn0029768 | 0 | | |
| 1 | CG17262 | FBgn0031499 | 0 | | |
| 1 | Crag | FBgn0025864 | 0 | MYCPBP | c-myc promoter binding protein |
| 1 | Grip | FBgn0040917 | 0 | GRIP1 | glutamate receptor interacting protein 1 |
| 1 | nkd | FBgn0002945 | 0 | | |
| 1 | sl | FBgn0003416 | 0 | PLCG1 | phospholipase C, gamma 1 |
| 0 | bm | FBgn0000221 | 0 | B3GALT2 | UDP-Gal:betaGlcNAc beta 1,3-galactosyltransferase, polypeptide 2 |
| 0 | CG10747 | FBgn0032845 | 0 | PLCXD2 | phosphatidylinositol-specific phospholipase C, X domain containing 2 |
| 0 | CG31350 | FBgn0051350 | 2 | | |
| 0 | fz2 | FBgn0016797 | 0 | FZD8 | frizzled homolog 8 |
| 0 | Rab-RP1 | FBgn0015788 | 0 | RAB32 | RAB32, member RAS oncogene family |
| 0 | skf | FBgn0050021 | 0 | MPP7 | membrane protein, palmitoylated 7 |
| NT | Alg10 | FBgn0052076 | 0 | | |
| NT | CG30361 | FBgn0050361 | 4 | GRM4 | glutamate receptor, metabotropic 4 |
| NT | rho-5 | FBgn0041723 | 0 | | |
| NT | Sema-1a | FBgn0011259 | 0 | SEMA6D | sema domain, transmembrane domain (TM), and cytoplasmic domain, (semaphorin) 6D |
| NT | sif | FBgn0019652 | 0 | | |
| NT | Syx1A | FBgn0013343 | 0 | STX1A | syntaxin 1A |
| NT | tinc | FBgn0038554 | 0 | | |
| CATION CHANNELS AND TRANSPORTERS | | | | | |
| 5 | CG13223 | FBgn0033599 | 0 | SLC24A6 | solute carrier family 24 (sodium/potassium/calcium exchanger), member 6 |
| 5 | CG14741 | FBgn0037989 | 0 | ATP8B2 | ATPase, Class I, type 8B, member 2 |
| 4 | CG10465 | FBgn0033017 | 0 | KCTD10 | potassium channel tetramerisation domain containing 10 |
| 4 | CG6737 | FBgn0032294 | 0 | | |
| 4 | Cng | FBgn0014462 | 0 | CNGA3 | cyclic nucleotide gated channel alpha 3 |
| 4 | GluRIIA | FBgn0004620 | 0 | | |
| 4 | inx6 | FBgn0027107 | 0 | | |
| 4 | Irk3 | FBgn0032706 | 0 | | |
| 3 | Ca-beta | FBgn0015608 | 4 | | |
| 3 | Ca-P60A | FBgn0004551 | 0 | ATP2A1 | ATPase, Ca++ transporting, cardiac muscle, fast twitch 1 |
| 3 | CG11155 | FBgn0039927 | 0 | GRIK3 | glutamate receptor, ionotropic, kainate 3 |
| 3 | CG2165 | FBgn0025704 | 0 | ATP2B3 | ATPase, Ca++ transporting, plasma membrane 3 |
| 3 | CG32792 | FBgn0052792 | 0 | | |
| 3 | CG3367 | FBgn0029871 | 2 | | |
| 3 | CG4450 | FBgn0032113 | 0 | | |
| 3 | CG6812 | FBgn0036843 | 0 | SFXN2 | sideroflexin 2 |
| 3 | KaiRIA | FBgn0028422 | 1 | GRIA4 | glutamate receptor, ionotrophic, AMPA 4 |
| 3 | ppk21 | FBgn0039675 | 0 | | |
| 3 | trp | FBgn0003861 | 0 | | |
| 2 | Ca-alpha1D | FBgn0001991 | 0 | CACNA1D | calcium channel, voltage-dependent, L type, alpha 1D subunit |
| 2 | Catx | FBgn0013995 | 0 | SLC8A3 | solute carrier family 8 (sodium-calcium exchanger), member 3 |
| 2 | CG12376 | FBgn0033323 | 0 | SLC24A6 | solute carrier family 24 (sodium/potassium/calcium exchanger), member 6 |
| 2 | CG12904 | FBgn0033510 | 0 | KCNT2 | potassium channel, subfamily T, member 2 |
| 2 | CG1698 | FBgn0033443 | 1 | | |
| 2 | CG31284 | FBgn0051284 | 0 | | |

TABLE 1-continued

| Score in secondary screen | Gene | FBGN | Number of potential 21nt off-targets | Human orthologs (NCBI Homologene) | Description of the human orthologs (NCBI Gene) |
|---|---|---|---|---|---|
| 2 | CG31729 | FBgn0051729 | 0 | ATP9B | ATPase, Class II, type 9B |
| 2 | CG3822 | FBgn0038837 | 0 | GRIK1 | glutamate receptor, ionotropic, kainate 1 |
| 2 | CG4536 | FBgn0029904 | 5 | | |
| 2 | CG9361 | FBgn0037690 | 0 | KCNK9 | potassium channel, subfamily K, member 9 |
| 2 | elk | FBgn0011589 | 0 | KCNH8 | potassium voltage-gated channel, subfamily H (eag-related), member 8 |
| 2 | GluClalpha | FBgn0024963 | 0 | GLRA3 | glycine receptor, alpha 3 |
| 2 | GluRIII | FBgn0031293 | 0 | | |
| 2 | Irk2 | FBgn0039081 | 0 | KCNJ9 | potassium inwardly-rectifying channel, subfamily J, member 9 |
| 2 | KCNQ | FBgn0033494 | 3 | KCNQ5 | potassium voltage-gated channel, KQT-like subfamily, member 5 |
| 2 | nAcRalpha-34E | FBgn0028875 | 0 | CHRNA7 | cholinergic receptor, nicotinic, alpha polypeptide 7 |
| 2 | nAcRalpha-96Aa | FBgn0000036 | 0 | CHRNA3 | cholinergic receptor, nicotinic, alpha polypeptide 3 |
| 2 | Nmdar1 | FBgn0010399 | 1 | GRIN1 | glutamate receptor, ionotropic, N-methyl D-aspartate 1 |
| 2 | Ork1 | FBgn0017561 | 0 | KCNK4 | potassium channel, subfamily K, member 4 |
| 2 | sei | FBgn0003353 | 0 | KCNH6 | potassium voltage-gated channel, subfamily H (eag-related), member 6 |
| 1 | Ca-alpha1T | FBgn0029846 | 0 | | |
| 1 | cac | FBgn0005563 | 0 | CACNA1A | calcium channel, voltage-dependent, P/Q type, alpha 1A subunit |
| 1 | CG10830 | FBgn0038839 | 0 | KCTD12 | potassium channel tetramerisation domain containing 12 |
| 1 | CG31201 | FBgn0051201 | 1 | GRIA4 | glutamate receptor, ionotrophic, AMPA 4 |
| 1 | CG32770 | FBgn0052770 | 0 | | |
| 1 | CG33298 | FBgn0032120 | 0 | ATP10A | ATPase, Class V, type 10A |
| 1 | CG40146 | FBgn0039941 | 0 | | |
| 1 | CG5621 | FBgn0038840 | 0 | | |
| 1 | CG8743 | FBgn0036904 | 0 | MCOLN3 | mucolipin 3 |
| 1 | CG9935 | FBgn0039916 | 1 | GRIA1 | glutamate receptor, ionotropic, AMPA 1 |
| 1 | eag | FBgn0000535 | 0 | KCNH1 | potassium voltage-gated channel, subfamily H |
| 1 | Glu-RIB | FBgn0028431 | 1 | GRIA2 | glutamate receptor, ionotropic, AMPA 2 |
| 1 | GluRIIB | FBgn0020429 | 0 | | |
| 1 | Ir | FBgn0039061 | 0 | KCNJ5 | potassium inwardly-nectifying channel, subfamily J, member 5 |
| 1 | l(2)01810 | FBgn0010497 | 0 | | |
| 1 | nAcRalpha-96Ab | FBgn0000039 | 1 | CHRNA2 | cholinergic receptor, nicotinic, alpha polypeptide 2 |
| 1 | nAcRbeta-64B | FBgn0000038 | 0 | CHRNA4 | cholinergic receptor, nicotinic, alpha polypeptide 4 |
| 1 | nAcRbeta-96A | FBgn000411B | 0 | CHRNB4 | cholinergic receptor, nicotinic, beta polypeptide |
| 1 | Nmdar2 | FBgn0014432 | 0 | GRIN2B | glutamate receptor, ionotropic, N-methyl D-aspartate 2B |
| 1 | nompC | FBgn0016920 | 0 | | |
| 1 | pain | FBgn0060296 | 0 | | |
| 1 | Pkd2 | FBgn0041195 | 0 | PKD2L1 | polycystic kidney disease 2-like 1 |
| 1 | ShaI | FBgn0005564 | 0 | KCND3 | potassium voltage-gated channel, ShaI-related subfamily, member 3 |
| 1 | Sip1 | FBgn0010620 | 0 | TFIP11 | tuftelin interacting protein 11 |
| 1 | sio | FBgn0003429 | 0 | KCNMA1 | potassium large conductance calcium-activated channel, subfamily M, alpha member 1 |
| 0 | Anktm1/TrpA1 | FBgn0035934 | 0 | TRPA1 | transient receptor potential cation channel, subfamily A, member 1 |
| 0 | CG12455 | FBgn0028859 | 0 | CACNA2D3 | calcium channel, voltage-dependent, alpha 2/delta 3 subunit |
| 0 | CG13762 | FBgn0040333 | 1 | PKD2L1 | polycystic kidney disease 2-like 1 |
| 0 | CG14647 | FBgn0037244 | 0 | KCTD9 | potassium channel tetrameristation domain containing 9 |
| 0 | CG17922 | FBgn0034656 | 0 | CNGB1 | cyclic nucleotide gated channel beta 1 |
| 0 | CG32704 | FBgn0052704 | 0 | | |
| 0 | CG32810 | FBgn0025394 | 0 | KCTD5 | potassium channel tetramerisation domain containing 5 |
| 0 | CG4301 | FBgn0030747 | 0 | ATP11B | ATPase, Class VI, type 11B |
| 0 | CG9472 | FBgn0036874 | 0 | PKD1L3 | polycystic kidney disease 1-like 3 |
| 0 | clumsy | FBgn0026255 | 0 | GRIK2 | glutamate receptor, ionotropic, kainste 2 |
| 0 | cngl | FBgn0029090 | 3 | | |
| 0 | Glu-RI | FBgn0004619 | 0 | GRIA3 | glutamate receptor, ionotrophic, AMPA 3 |
| 0 | Nckx30C | FBgn0028704 | 0 | SLC24A2 | solute carrier family 24 (sodium/potassium/calcium exchanger), member 2 |
| 0 | Rya-r44F | FBgn0011286 | 0 | RYR2 | ryanodine receptor 2 (cardiac) |

TABLE 1-continued

| Score in secondary screen | Gene | FBGN | Number of potential 21nt off-targets | Human orthologs (NCBI Homologene) | Description of the human orthologs (NCBI Gene) |
|---|---|---|---|---|---|
| 0 | Shab | FBgn0003383 | 0 | KCNB1 | potassium voltage-gated channel, Shab-related subfamily, member 1 |
| 0 | SK | FBgn0029761 | 0 | KCNN3 | potassium intermediate/small conductance calcium-activated channel, subfamily N, member 3 |
| 0 | trpl | FBgn0005614 | 0 | | |
| NT | CG2196 | FBgn0039872 | 1 | | |
| NT | nAcRalpha-808 | FBgn0037212 | 0 | | |
| OTHER TRANSPORTERS | | | | | |
| 3 | ATPsyn-CI6 | FBgn0016119 | 0 | | |
| 3 | CG1599 | FBgn0033452 | 0 | SYBL1 | synaptobrevin-like 1 |
| 3 | CG31116 | FBgn0051116 | 0 | CLCN2 | chloride channel 2 |
| 3 | CG31158 | FBgn0051158 | 0 | | |
| 3 | CG31305 | FBgn0051305 | 0 | SLC25A1 | solute carrier family 25 (mitochondrial carrier; citrate transporter), member 1 |
| 3 | CG6901 | FBgn0038414 | 0 | | |
| 3 | Mst84Db | FBgn0004173 | 0 | | |
| 2 | CG3860 | FBgn0034951 | 0 | OSBPL1A | oxysterol binding protein-like 1A |
| 2 | CG3902 | FBgn0036824 | 1 | ACADSB | acyl-Coenzyme A dehydrogenase, short/branched chain |
| 2 | CG5127 | FBgn0039335 | 0 | | |
| 2 | CG7442 | FBgn0037140 | 0 | | |
| 2 | CG7578 | FBgn0028538 | 0 | ARFGEF1 | ADP-ribosylation factor guanine nucleotide-exchange factor 1 |
| 2 | CG9270 | FBgn0032908 | 0 | ABCC2 | ATP-binding cassette, sub-family C (CFTR/MRP), member 2 |
| 1 | CG31731 | FBgn0028539 | 0 | | |
| 1 | CG8389 | FBgn0034063 | 0 | | |
| 1 | rdgB | FBgn0003218 | 0 | PITPNM2 | phosphatidylinositol transfer protein, membrane-associated 2 |
| 1 | w | FBgn0003996 | 0 | | |
| 0 | CG33214 | FBgn0053214 | 0 | GLG1 | golgi apparatus protein 1 |
| 0 | CG7458 | FBgn0037144 | 0 | | |
| NT | Beach1 | FBgn0043362 | 0 | WDFY3 | WD repeat and FYVE domain containing 3 |
| NT | CG12539 | FBgn0030586 | 0 | | |
| NT | CG14482 | FBgn0034245 | 0 | | |
| NT | CG14691 | FBgn0037829 | 0 | SV2A | synaptic vesicle glycoprotein 2A |
| NT | CG17119 | FBgn0039045 | 0 | CTNS | cystinosis, nephropathic |
| NT | CG18324 | FBgn0033905 | 0 | SLC25A34 | solute carrier family 25, member 34 |
| NT | CG3071 | FBgn0023527 | 0 | UTP15 | UTP15, U3 small nucleolar ribonucleoprotein |
| NT | CG32230 | FBgn0052230 | 0 | | |
| NT | CG6142 | FBgn0039415 | 0 | | |
| NT | CG7181 | FBgn0037097 | 0 | | |
| NT | CG7830 | FBgn0032015 | 0 | TUSC3 | tumor suppressor candidate 3 |
| NT | CG9990 | FBgn0039594 | 0 | | |
| NT | Cyp49a1 | FBgn0033524 | 0 | CYP27A1 | cytochrome P450, family 27, subfamily A, polypeptide 1 |
| NT | didum | FBgn0015933 | 0 | MYO5A | myosin VA (heavy polypeptide 12, myoxin) |
| NT | ERp60 | FBgn0033663 | 1 | PDIA3 | protein disulfide isomerase-associated 3 |
| NT | Pbprp2 | FBgn0011280 | 0 | | |
| NT | Syx6 | FBgn0037084 | 3 | STX10 | syntaxin 10 |
| MISCELLANEOUS/ OTHER | | | | | |
| 6 | Prosalpha7 | FBgn0023175 | 0 | PSMA3 | proteasome (prosome, macropain) subunit, alpha type, 3 |
| 5 | CG3812 | FBgn0030421 | 0 | AGPAT1 | 1-acylglycerol-3-phosphate O-acyltransferase 1 (lysophosphatidic acid acyltransferase, alpha) |
| 4 | bif | FBgn0014133 | 3 | | |
| 4 | CG11727 | FBgn0030299 | 0 | | |
| 4 | CG2781 | FBgn0037534 | 0 | ELOVL7 | ELOVL family member 7, elongation of long chain fatty acids |
| 4 | CG4960 | FBgn0039371 | 0 | C19orf32 | chromosome 19 open reading frame 32 |
| 4 | CG7304 | FBgn0036527 | 0 | GALNT11 | UDP-N-acetyl-alpha-D-galactosamine:polypeptide N-acetylgalactosaminyltransferase 11 (GalNAc T11) |
| 4 | CG8258 | FBgn0033342 | 0 | CCT8 | chaperonin containing TCP1, subunit 8 (theta) |
| 4 | CRMP | FBgn0023023 | 0 | DPYS | dihydropyrimidinase |
| 4 | Eip63F-1 | FBgn0004910 | 0 | | |
| 3 | Act57B | FBgn0000044 | 5 | ACTB | actin, beta |
| 3 | CG11299 | FBgn0034897 | 0 | SESN3 | sestrin 3 |

TABLE 1-continued

| Score in secondary screen | Gene | FBGN | Number of potential 21nt off-targets | Human orthologs (NCBI Homologene) | Description of the human orthologs (NCBI Gene) |
|---|---|---|---|---|---|
| 3 | CG6509 | FBgn0032363 | 0 | DLG5 | discs, large homolog 5 |
| 3 | CG9342 | FBgn0032904 | 0 | MTP | microsomal triglyceride transfer protein (large polypeptide, 88 kDa) |
| 3 | CG9467 | FBgn0037758 | 0 | KCTD3 | potassium channel tetrameristation domain containing 3 |
| 3 | eIF-2beta | FBgn0004926 | 0 | EIF2S2 | eukaryotic translation initiation factor 2, subunit 2 beta, 38 kDa |
| 3 | fzo | FBgn0011596 | 0 | MFN1 | milofusin 1 |
| 3 | prox | FBgn0004596 | 0 | PROX1 | proxpero-related homeobox 1 |
| 3 | Su(var)3-9 | FBgn0003600 | 0 | EIF2S3 | eukaryotic translation initiation factor 2, subunit 3 gamma, 52 kDa |
| 2 | 14-3-3epsilon | FBgn0020238 | 0 | YWHAE | tyrosine 3-monoxygenase/tryptophan 5-monooxygenase activation protein, epsilon polypeptid |
| 2 | ac | FBgn0000022 | 3 | ASCL2 | achaele-acute complex-like 2 |
| 2 | Arp66B | FBgn0011744 | 0 | ACTR3 | ARP3 actin-related protein 3 homolog |
| 2 | CG10069 | FBgn0034611 | 0 | SLC37A2 | solute carrier family 37 (glycerol-3-phosphate transporter), member 2 |
| 2 | CG11600 | FBgn0038068 | 1 | | |
| 2 | CG11608 | FBgn0038069 | 0 | LIPL3 | lipase-like, ab-hydrolase domain containing 3 |
| 2 | CG14625 | FBgn0040358 | 4 | | |
| 2 | CG2678 | FBgn0014931 | 0 | | |
| 2 | CG3074 | FBgn0034709 | 0 | TINAGL1 | tubulointerstitial nephritis antigen-like 1 |
| 2 | CG32635 | FBgn0052635 | 1 | | |
| 2 | CG4448 | FBgn0039067 | 0 | | |
| 2 | CG5278 | FBgn0038986 | 3 | | |
| 2 | CG5802 | FBgn0038863 | 0 | SLC35B1 | solute carrier family 35, member B1 |
| 2 | CG7140 | FBgn0037147 | 0 | | |
| 2 | Rad51D | FBgn0030931 | 0 | XRCC2 | X-ray repair complementing defective repair in Chinese hamster cells 2 |
| 1 | cer | FBgn0034443 | 0 | | |
| 1 | CG6330 | FBgn0039464 | 0 | UPP2 | uridine phosphorylase 2 |
| 1 | CG7568 | FBgn0039673 | 0 | WDR69 | WD repeat domain 69 |
| 1 | CG9326 | FBgn0032885 | 0 | MPP6 | membrane protein, pelmitoylated 6 (MAGUK p55 subfamily member 6) |
| 1 | CG9784 | FBgn0030761 | 0 | PIB5PA | phosphatidylinositol (4,5) bisphosphate 5-phosphatase, A |
| 1 | cnc | FBgn0000338 | 0 | | |
| 1 | eIF2B-beta | FBgn0024996 | 0 | EIF2B2 | eukaryotic translation initiation factor 2B, subunit 2 beta, 39 kDa |
| 1 | gammaTub23C | FBgn0004176 | 0 | TUBG1 | tubulin, gamma 1 |
| 1 | Hn | FBgn0001208 | 0 | PAH | phenylalanine hydroxylase |
| 1 | Pgant35A | FBgn0001970 | 0 | GALNT11 | UDP-N-acetyl-alpha-D-galactosamine:polypeptide N-acetylgalactosaminyltransferase 11 (GalNAc T11) |
| 1 | pgant4 | FBgn0051956 | 0 | | |
| 1 | skpA | FBgn0025637 | 1 | LOC401713 | organ of Corti protein 2; RNA polymerase II elongation factor-like protein OCP2; cyclin A/CDK2-associated p19 |
| 0 | CG15408 | FBgn0031523 | 0 | | |
| 0 | CG4500 | FBgn0028519 | 0 | ACSBG1 | acyl-CoA synthetase bubblegum family member 1 |
| 0 | CG7348 | FBgn0036940 | 0 | | |
| 0 | CG9647 | FBgn0035729 | 0 | | |
| 0 | D | FBgn0000411 | 1 | | |
| 0 | nahode | FBgn0034797 | 0 | | |
| 0 | Pde6 | FBgn0038237 | 0 | PDE11A | phosphodiesterase 11A |
| 0 | sdt | FBgn0003349 | 1 | MPP5 | membrane protein, palmitoylated 5 (MAGUK p55 subfamily member 5) |
| 0 | TSG101 | FBgn0036666 | 0 | TSG101 | tumor susceptibility gene 101 |
| NT | Aats-cys | FBgn0027091 | 0 | CARS | cysteinyl-tRNA synthetase |
| NT | Aats-met | FBgn0027083 | 0 | MARS2 | methionine-tRNA synthetase 2 |
| NT | Acp70A | FBgn0003034 | 0 | | |
| NT | Act79B | FBgn0000045 | 5 | ACTG2 | actin, gamma 2, smooth muscle, enteric |
| NT | Ahcy13 | FBgn0014455 | 0 | AHCY | S-adenosylhomocysteine hydrolase |
| NT | amon | FBgn0023179 | 0 | PCSK2 | proprotein convertase subtilisin/kexin type 2 |
| NT | asparagine-synthetase | FBgn0041607 | 0 | | |
| NT | ATbp | FBgn0039946 | 5 | | |
| NT | BEAF-32 | FBgn0015602 | 0 | | |
| NT | beat-Ic | FBgn0028644 | 8 | | |
| NT | beat-Vb | FBgn0038092 | 0 | | |
| NT | Bin1 | FBgn0024491 | 0 | SAP18 | sin3-associated polypeptide, 18 kDa |
| NT | BM-40-SPARC | FBgn0026562 | 0 | SPARCL1 | SPARC-like 1 (mast9, hevin) |
| NT | btsz | FBgn0010940 | 0 | | |

TABLE 1-continued

| Score in secondary screen | Gene | FBGN | Number of potential 21nt off-targets | Human orthologs (NCBI Homologene) | Description of the human orthologs (NCBI Gene) |
|---|---|---|---|---|---|
| NT | bwa | FBgn0045064 | 0 | ASAH3L | N-acylsphingosine amidohydrolase 3-like |
| NT | CG10168 | FBgn0039087 | 0 | | |
| NT | CG11107 | FBgn0033160 | 0 | DHX15 | DEAH (Asp-Glu-Ala-His) box polypeptide 15 |
| NT | CG12162 | FBgn0037329 | 0 | POLDIP2 | polymerase (DNA-directed), delta interacting protein 2 |
| NT | CG13643 | FBgn0040601 | 0 | | |
| NT | CG13779 | FBgn0040954 | 0 | | |
| NT | CG14869 | FBgn0038341 | 0 | | |
| NT | CG15105 | FBgn0034412 | 0 | | |
| NT | CG1571 | FBgn0029993 | 0 | DNAI2 | dynein, axonemal, intermediate polypeptide 2 |
| NT | CG16710 | FBgn0039101 | 0 | | |
| NT | CG16857 | FBgn0028482 | 0 | | |
| NT | CG17294 | FBgn0032032 | 0 | HDHD2 | haloacid dehalogenase-like hydrolase domain containing 2 |
| NT | CG17826 | FBgn0036227 | 0 | FBN2 | fibrillin 2 (congenital contractural arachnodactyly) |
| NT | CG18493 | FBgn0038701 | 0 | | |
| NT | CG2051 | FBgn0037376 | 0 | HAT1 | histone acetyltransferase 1 |
| NT | CG3066 | FBgn0037515 | 0 | | |
| NT | CG31115 | FBgn0051115 | 0 | MTAP | methylthioedenosine phosphorylase |
| NT | CG31159 | FBgn0051159 | 0 | GFM2 | G elongation factor, mitochondrial 2 |
| NT | CG31224 | FBgn0051224 | 0 | | |
| NT | CG31287 | FBgn0051287 | 0 | | |
| NT | CG31453 | FBgn0051453 | 0 | TRIP13 | thyroid hormone receptor interactor 13 |
| NT | CG31716 | FBgn0051716 | 0 | | |
| NT | CG32284 | FBgn0052284 | 0 | | |
| NT | CG3231 | FBgn0027522 | 0 | RBBP6 | retinoblastoma binding protein 6 |
| NT | CG32557 | FBgn0052557 | 0 | | |
| NT | CG32700 | FBgn0052700 | 0 | | |
| NT | CG32727 | FBgn0052727 | 0 | DNAJC15 | DnaJ (Hsp40) homolog, subfamily C, member 15 |
| NT | CG33100 | FBgn0053100 | 0 | EIF4E2 | eukaryotic translation initiation factor 4E member 2 |
| NT | CG3356 | FBgn0034989 | 0 | UBE3C | ubiquitin protein ligase E3C |
| NT | CG3605 | FBgn0031493 | 0 | SF3B2 | splicing factor 3b, subunit 2, 145 kDa |
| NT | CG3554 | FBgn0036004 | 0 | | |
| NT | CG3700 | FBgn0034796 | 1 | TMPRSS9 | transmembrane protease, serine 9 |
| NT | CG3940 | FBgn0037788 | 0 | | |
| NT | CG4017 | FBgn0032143 | 0 | CPB1 | carboxypeptidase B1 |
| NT | CG4030 | FBgn0034585 | 0 | RABEP1 | rabaptin, RAB GTPase binding effector protein 1 |
| NT | CG4090 | FBgn0038492 | 1 | | |
| NT | CG4291 | FBgn0031287 | 0 | WBP4 | WW domain binding protein 4 (formin binding protein 21) |
| NT | CG4302 | FBgn0027073 | 0 | UGT2B10, UGT2B11, UGT2B28 | UDP glucuronosyltransferase 2 family, polypeptide B10, B11, B28 |
| NT | CG4653 | FBgn0030776 | 0 | | |
| NT | CG4747 | FBgn0043456 | 0 | N-PAC | cytokine-like nuclear factor n-pac |
| NT | CG4851 | FBgn0032358 | 0 | PPT2 | palmitoyl-protein thioesterase 2 |
| NT | CG4901 | FBgn0032194 | 0 | DHX33 | DEAH (Asp-Glu-Ala-His) box polypeptide 33 |
| NT | CG5103 | FBgn0036784 | 0 | TKT | transketolase (Wernicke-Korsakoff syndrome) |
| NT | CG5122 | FBgn0032471 | 0 | | |
| NT | CG5191 | FBgn0038803 | 0 | | |
| NT | CG5587 | FBgn0036780 | 0 | LOC283871 | hypothetical protein LOC283871 |
| NT | CG5715 | FBgn0039180 | 0 | | |
| NT | CG6041 | FBgn0029826 | 1 | TMPRSS9 | transmembrane protease, serine 9 |
| NT | CG6656 | FBgn0038912 | 0 | | |
| NT | CG6717 | FBgn0031924 | 0 | SERPIN8S | serpin peptidase inhibitor, clade 8 (ovalbumin), member 5 |
| NT | CG6763 | FBgn0039069 | 1 | | |
| NT | CG5764 | FBgn0037899 | 0 | C15orf15 | chromosome 15 open reading frame 15 |
| NT | CG6841 | FBgn0036828 | 0 | C20orf14 | chromosome 20 open reading frame 14 |
| NT | CG6906 | FBgn0036261 | 0 | | |
| NT | CG6937 | FBgn0038989 | 0 | MKI67IP | MKI67 (FHA domain) interacting nucleoter phosphoprotein |
| NT | CG7017 | FBgn0036951 | 0 | | |
| NT | CG7290 | FBgn0036949 | 0 | | |
| NT | CG7928 | FBgn0039740 | 0 | | |
| NT | CG8117 | FBgn0030683 | 0 | TCEA2 | transcription elongation factor A (SII), 2 |
| NT | CG9220 | FBgn0030662 | 0 | CHSY1 | carbohydrate (chondroitin) synthase 1 |
| NT | CG8383 | FBgn0037697 | 0 | | |
| NT | CG9520 | FBgn0032078 | 0 | C1GALT1 | core 1 synthase, glycoprotein-N-acetylgalactosamine 3-beta-galactosyltransferase, 1 |

TABLE 1-continued

| Score in secondary screen | Gene | FBGN | Number of potential 21nt off-targets | Human orthologs (NCBI Homologene) | Description of the human orthologs (NCBI Gene) |
|---|---|---|---|---|---|
| NT | CG9535 | FBgn0027501 | 0 | UAP1 | UDP-N-acetylglucosamine pyrophosphorylase 1 |
| NT | CG9550 | FBgn0029939 | 2 | | |
| NT | CG9843 | FBgn0037237 | 0 | | |
| NT | CG9947 | FBgn0030752 | 0 | TMEM30A | transmembrane protein 30A |
| NT | comm3 | FBgn0053209 | 0 | | |
| NT | CtBP | FBgn0020496 | 1 | CTBP1 | C-terminal binding protein 1 |
| NT | dbo | FBgn0040230 | 0 | KLHL20 | kelch-like 20 (*Drosophila*) |
| NT | Dhfr | FBgn0004087 | 0 | DHFR | dihydrofolate reductase |
| NT | dmrt11E | FBgn0030477 | 2 | | |
| NT | drm | FBgn0024244 | 0 | | |
| NT | eas1 | FBgn0010110 | 1 | | |
| NT | ec | FBgn0025376 | 1 | | |
| NT | Ef1alpha100E | FBgn0000557 | 1 | EEF1A2 | eukaryotic translation elongation factor 1 alpha 2 |
| NT | faf | FBgn0005632 | 0 | USP9X | ubiquitin specific peptidase 9, X-linked (fat facets-like, *Drosophila* |
| NT | fbp | FBgn0032820 | 0 | FBP1 | fructose-1,6-bisphosphatase 1 |
| NT | fred | FBgn0051774 | 0 | | |
| NT | GsD5 | FBgn0010041 | 5 | | |
| NT | GsE2 | FBgn0063498 | 0 | | |
| NT | Hand | FBgn0032209 | 0 | HAND2 | heart and neural crest derivatives expressed 2 |
| NT | HGTX | FBgn0040318 | 0 | NKX6-1 | NK6 transcription factor related, locus 1 |
| NT | Hsp60B | FBgn0011244 | 0 | | |
| NT | l(2)k05713 | FBgn0022160 | 0 | GPD2 | glycerol-3-phosphate dehydrogenase 2 |
| NT | l(3)IX-14 | FBgn0002478 | 0 | LMLN | leishmanolysin-like (metallopeptidase MB family) |
| NT | lota | FBgn0005830 | 2 | LOC441636 | similar to submaxillary apomucin |
| NT | Map60 | FBgn0010342 | 0 | | |
| NT | Mes-4 | FBgn0039559 | 0 | WHSC | Wolf-Hirschhorn syndrome candidate 1 |
| NT | Mgaf2 | FBgn0039738 | 0 | MGAT2 | mannosyl (alpha-1,5-)-glycoprotein beta-1,2-N-acetylglucosaminyltransferase |
| NT | mol | FBgn0028528 | 0 | NIP | homolog of *Drosophila* Numb-interacting protein |
| NT | mre11 | FBgn0020270 | 0 | MRE11A | MRE11 meiotic recombination 11 homolog A |
| NT | mRpL15 | FBgn0036990 | 1 | MRPL15 | mitochondrial ribosomal protein L15 |
| NT | mRpL2a | FBgn0037833 | 0 | MRPL37 | mitochondrial ribosomal protein L37 |
| NT | nbs | FBgn0026198 | 1 | NBN | nibrin |
| NT | NfI | FBgn0042696 | 0 | NFIA | nuclear factor I/A |
| NT | nos | FBgn0002962 | 2 | NOS1 | nitric oxide synthase 1 |
| NT | Odc1 | FBgn0013307 | 0 | ODC1 | ornithine decarboxylase 1 |
| NT | Peb | FBgn0004181 | 0 | PRB1, PRB2 | proline-rich protein BstNI subfamily 1, proline rich protein BstNI subfamily 2 |
| NT | PH4alphaEFB | FBgn0039776 | 0 | P4HA1 | procollagen-proline, 2-oxoglutarate 4-dioxygenase (proline 4-hydroxylase), alpha polypeptide I |
| NT | Phax | FBgn0033380 | 0 | RNUXA | RNA U, small nuclear RNA export adaptor |
| NT | ple | FBgn0005626 | 0 | TH | tyrosine hydroxylase |
| NT | Rb97D | FBgn0004903 | 2 | LOC144983 | heterogeneous nuclear ribonucleoprotein A1 like |
| NT | Rbp2 | FBgn0010256 | 0 | WBSCR1 | Williams-Beuren syndrome chromosome region 1 |
| NT | RpI1 | FBgn0019938 | 0 | POLR1A | polymerase (RNA) I polypeptide A |
| NT | RpL10Aa | FBgn0038281 | 0 | RPL10A | ribosomal protein L10a |
| NT | RpS10b | FBgn0031035 | 0 | RPS10 | ribosomal protein S10 |
| NT | Rrp1 | FBgn0004584 | 0 | APEX1 | APEX nuclease (multifunctional DNA repair enzyme) 1 |
| NT | salr | FBgn0000287 | 0 | SALL3 | sal-like 3 |
| NT | sda | FBgn0015541 | 1 | ARTS-1 | type 1 tumor necrosis factor receptor shedding aminopeptidase regulator |
| NT | SF1 | FBgn0025571 | 0 | SF1 | splicing factor 1 |
| NT | shn | FBgn0003396 | 0 | | |
| NT | Sirt2 | FBgn0038788 | 0 | SIRT2 | sirtuin (silent mating type information regulation 2 homolog) 2 |
| NT | snRNP69D | FBgn0016940 | 0 | SNRPD1 | small nuclear ribonucleoprotein D1 polypeptide 16 kDa |
| NT | Spn43Ab | FBgn0024293 | 0 | | |
| NT | Spt3 | FBgn0037981 | 1 | | |
| NT | sqd | FBgn0003498 | 0 | | |
| NT | ST6Gal | FBgn0035050 | 0 | ST6GAL2 | ST6 beta-galactosamide alpha-2,6-sialyltranferase 2 |
| NT | stau | FBgn0003520 | 0 | STAU | staufen, RNA binding protein |
| NT | stich1 | FBgn0016941 | 1 | | |
| NT | svr | FBgn0004648 | 0 | CPD | carboxypeptidase D |
| NT | T3dh | FBgn0017482 | 1 | ADHFE1 | alcohol dehydrogenase, iron containing, 1 |
| NT | Tdp1 | FBgn0051953 | 0 | TDP1 | tyrosyl-DNA phosphodiesterase 1 |

TABLE 1-continued

| Score in secondary screen | Gene | FBGN | Number of potential 21nt off-targets | Human orthologs (NCBI Homologene) | Description of the human orthologs (NCBI Gene) |
|---|---|---|---|---|---|
| NT | tth | FBgn0030502 | 5 | | |
| NT | Ugt86Dd | FBgn0040256 | 0 | | |
| NOVEL | | | | | |
| 5 | CG17142 | FBgn0035112 | 0 | | |
| 4 | CG14076 | FBgn0036829 | 0 | | |
| 4 | CG14870 | FBgn0038342 | 0 | EPPB9 | B9 protein |
| 4 | CG31145 | FBgn0051145 | 0 | FAM20C | family with sequence similarity 20, member C |
| 4 | CG31203 | FBgn0051203 | 0 | | |
| 4 | CG31288 | FBgn0051288 | 0 | | |
| 4 | CG4585 | FBgn0025335 | 0 | | |
| 4 | CG7706 | FBgn0038640 | 0 | SLC4A1AP | solute carrier family 4 (anion exchanger), member 1, adaptor protein |
| 4 | Osi10 | FBgn0037417 | 0 | | |
| 3 | CG14084 | FBgn0036855 | 0 | | |
| 3 | CG14556 | FBgn0039413 | 0 | | |
| 3 | CG14744 | FBgn0033324 | 0 | SLC24A6 | solute carrier family 24 (sodium/potassium/calcium exchanger), member 6 |
| 3 | CG14945 | FBgn0032402 | 0 | | |
| 3 | CG17005 | FBgn0032109 | 0 | | |
| 3 | CG1968 | FBgn0033401 | 0 | COG6 | component of oligomeric golgi complex 6 |
| 3 | CG1971 | FBgn0039881 | 0 | | |
| 3 | CG3566 | FBgn0029854 | 0 | CYB5-M | outer mitochondrial membrane cytochrome b5 |
| 3 | CG4786 | FBgn0037012 | 0 | | |
| 3 | CG8740 | FBgn0027585 | 0 | | |
| 3 | CG9264 | FBgn0032911 | 0 | | |
| 3 | CG9525 | FBgn0032080 | 0 | | |
| 2 | CG10946 | FBgn0029974 | 0 | | |
| 2 | CG1113 | FBgn0037304 | 0 | | |
| 2 | CG11381 | FBgn0029568 | 3 | | |
| 2 | CG12688 | FBgn0029707 | 0 | | |
| 2 | CG12958 | FBgn0034018 | 0 | | |
| 2 | CG14314 | FBgn0038581 | 0 | | |
| 2 | CG14354 | FBgn0039376 | 0 | | |
| 2 | CG15897 | FBgn0029857 | 0 | WDR4 | WD repeat domain 4 |
| 2 | CG16786 | FBgn0034974 | 0 | | |
| 2 | CG30389 | FBgn0050389 | 0 | TMEM57 | transmembrane protein 57 |
| 2 | CG32224 | FBgn0036950 | 0 | | |
| 2 | CG3704 | FBgn0040346 | 0 | XAB1 | XPA binding protein 1, GTPase |
| 2 | CG4098 | FBgn0036648 | 0 | NUDT9 | nudix (nucleoside diphosphate linked moiety X)-type motif 9 |
| 2 | CG4643 | FBgn0043010 | 0 | FBXO45 | F-box protein 45 |
| 2 | CG5308 | FBgn0037908 | 3 | | |
| 2 | CG5348 | FBgn0034156 | 0 | SLC24A6 | solute carrier family 24 (sodium/potassium/calcium exchanger), member 6 |
| 2 | CG9205 | FBgn0035181 | 0 | | |
| 2 | CG9752 | FBgn0034614 | 0 | C9orf64 | chromosome 9 open reading frame 64 |
| 2 | nes | FBgn0026630 | 0 | C3F | putative protein similar to nessy |
| 1 | CG10514 | FBgn0039312 | 0 | | |
| 1 | CG13659 | FBgn0039319 | 0 | | |
| 1 | CG14160 | FBgn0036068 | 0 | SLC2A5 | solute carrier family 2 (facilitated glucose/fructose transporter), member 5 |
| 1 | CG14515 | FBgn0039648 | 0 | | |
| 1 | CG14629 | FBgn0040398 | 1 | | |
| 1 | CG14743 | FBgn0033326 | 0 | SLC24A6 | solute carrier family 24 (sodium/potassium/calcium exchanger), member 6 |
| 1 | CG18679 | FBgn0040663 | 0 | | |
| 1 | CG2879 | FBgn0025834 | 0 | LRRC8B | leucine rich repeat containing 8 family, member B |
| 1 | CG2921 | FBgn0034689 | 1 | | |
| 1 | CG3106 | FBgn0030148 | 0 | | |
| 1 | CG31410 | FBgn0051410 | 0 | | |
| 1 | CG32159 | FBgn0052159 | 0 | | |
| 1 | CG32637 | FBgn0052637 | 0 | LGR8 | leucine-rich repeat-containing G protein-coupled receptor 8 |
| 1 | CG3634 | FBgn0037026 | 0 | ST7 | suppression of tumorigenicity 7 |
| 1 | CG8858 | FBgn0033698 | 0 | KIAA0368 | KIAA0368 |
| 1 | mars | FBgn0033845 | 0 | DLG7 | discs, large homolog 7 |
| 1 | Osi16 | FBgn0051561 | 0 | | |
| 1 | sip2 | FBgn0031878 | 0 | | |
| 0 | CG10095 | FBgn0037993 | 2 | | |
| 0 | CG10183 | FBgn0039093 | 2 | | |

TABLE 1-continued

| Score in secondary screen | Gene | FBGN | Number of potential 21nt off-targets | Human orthologs (NCBI Homologene) | Description of the human orthologs (NCBI Gene) |
|---|---|---|---|---|---|
| 0 | CG13188 | FBgn0033668 | 8 | | |
| 0 | CG14162 | FBgn0040823 | 0 | | |
| 0 | CG14471 | FBgn0033049 | 0 | | |
| 0 | CG2185 | FBgn0037358 | 0 | CHP | calcium binding protein P22 |
| 0 | CG2656 | FBgn0037478 | 0 | ATPBD1C | ATP binding domain 1 family, member C |
| 0 | CG31189 | FBgn0051189 | 0 | | |
| 0 | CG32432 | FBgn0052432 | 0 | | |
| 0 | CG3536 | FBgn0050267 | 0 | CNGA1 | cyclic nucleotide gated channel alpha 1 |
| 0 | l(1)G0331 | FBgn0029944 | 8 | | |
| 0 | Osi18 | FBgn0037428 | 0 | | |
| 0 | ppk13 | FBgn0032912 | 0 | | |
| NT | CG10200 | FBgn0033968 | 0 | | |
| NT | CG10424 | FBgn0036848 | 0 | FLJ10769 | hypothetical protein FLJ10769 |
| NT | CG10589 | FBgn0037035 | 0 | | |
| NT | CG11073 | FBgn0034693 | 0 | | |
| NT | CG11113 | FBgn0033165 | 0 | | |
| NT | CG11310 | FBgn0037067 | 0 | | |
| NT | CG11576 | FBgn0039882 | 0 | C20orf54 | chromosome 20 open reading frame 54 |
| NT | CG11634 | FBgn0032968 | 0 | | |
| NT | CG11672 | FBgn0037563 | 0 | | |
| NT | CG11699 | FBgn0030311 | 0 | | |
| NT | CG11750 | FBgn0030294 | 0 | | |
| NT | CG11839 | FBgn0039271 | 0 | CCDC16 | coiled-coil domain containing 16 |
| NT | CG11847 | FBgn0039281 | 0 | SDCCAG1 | serologically defined colon cancer antigen 1 |
| NT | CG11875 | FBgn0039301 | 0 | NUP37 | nucleoporin 37 kDa |
| NT | CG11881 | FBgn0039638 | 0 | | |
| NT | CG11926 | FBgn0031640 | 0 | MON1A | MON1 homolog A |
| NT | CG12508 | FBgn0040995 | 0 | | |
| NT | CG12584 | FBgn0037257 | 0 | | |
| NT | CG12608 | FBgn0030630 | 1 | PAK1IP1 | PAK1 interacting protein 1 |
| NT | CG12672 | FBgn0030886 | 1 | | |
| NT | CG12985 | FBgn0030881 | 0 | RDBP | RD RNA binding protein |
| NT | CG13014 | FBgn0030759 | 1 | | |
| NT | CG13021 | FBgn0029669 | 0 | | |
| NT | CG13075 | FBgn0036563 | 0 | | |
| NT | CG13086 | FBgn0032770 | 0 | | |
| NT | CG13088 | FBgn0032047 | 0 | PGDS | prostaglandin D2 synthase, hematopoietic |
| NT | CG13169 | FBgn0033704 | 0 | | |
| NT | CG13239 | FBgn0037197 | 0 | | |
| NT | CG13364 | FBgn0026879 | 0 | HSPC016 | hypothetical protein HSPC016 |
| NT | CG13538 | FBgn0034820 | 0 | | |
| NT | CG13552 | FBgn0034864 | 0 | | |
| NT | CG13599 | FBgn0039128 | 0 | | |
| NT | CG13615 | FBgn0039199 | 2 | | |
| NT | CG13623 | FBgn0039205 | 0 | | |
| NT | CG13654 | FBgn0039290 | 0 | | |
| NT | CG13785 | FBgn0031901 | 0 | | |
| NT | CG13836 | FBgn0039060 | 0 | | |
| NT | CG1394 | FBgn0030277 | 9 | | |
| NT | CG13984 | FBgn0031796 | 0 | | |
| NT | CG14017 | FBgn0031721 | 0 | MGC35043 | hypothetical protein MGC35043 |
| NT | CG14047 | FBgn0040390 | 0 | | |
| NT | CG14082 | FBgn0036851 | 1 | | |
| NT | CG14131 | FBgn0036205 | 0 | | |
| NT | CG14252 | FBgn0039462 | 0 | | |
| NT | CG14423 | FBgn0029646 | 3 | | |
| NT | CG14448 | FBgn0037191 | 0 | | |
| NT | CG14453 | FBgn0037179 | 2 | | |
| NT | CG14550 | FBgn0039405 | 1 | DSCR5 | Down syndrome critical region gene 5 |
| NT | CG14563 | FBgn0037139 | 0 | | |
| NT | CG14564 | FBgn0037131 | 0 | | |
| NT | CG14565 | FBgn0037129 | 0 | | |
| NT | CG14574 | FBgn0037104 | 0 | | |
| NT | CG14609 | FBgn0037483 | 0 | KIAA1212 | KIAA1212 |
| NT | CG14659 | FBgn0037284 | 0 | | |
| NT | CG14662 | FBgn0037291 | 0 | | |
| NT | CG14843 | FBgn0038230 | 0 | | |
| NT | CG14850 | FBgn0038239 | 0 | | |
| NT | CG14931 | FBgn0032374 | 0 | | |
| NT | CG15059 | FBgn0030905 | 0 | | |
| NT | CG15133 | FBgn0032619 | 0 | | |
| NT | CG15152 | FBgn0032665 | 0 | | |
| NT | CG15278 | FBgn0032554 | 0 | | |
| NT | CG1529 | FBgn0031144 | 1 | ZNF569 | zinc finger protein 569 |
| NT | CG15366 | FBgn0030080 | 0 | | |
| NT | CG15376 | FBgn0029692 | 5 | | |

TABLE 1-continued

| Score in secondary screen | Gene | FBGN | Number of potential 21nt off-targets | Human orthologs (NCBI Homologene) | Description of the human orthologs (NCBI Gene) |
|---|---|---|---|---|---|
| NT | CG15432 | FBgn0031603 | 2 | | |
| NT | CG15471 | FBgn0029726 | 0 | | |
| NT | CG15488 | FBgn0032440 | 0 | | |
| NT | CG15513 | FBgn0039705 | 0 | ATG16L | ATG16 autophagy related 16-like |
| NT | CG15771 | FBgn0029801 | 0 | HDHD4 | haloacid dehalogenase-like hydrolase domain containing 4 |
| NT | CG15784 | FBgn0029766 | 1 | | |
| NT | CG15888 | FBgn0038131 | 0 | | |
| NT | CG1678 | FBgn0031176 | 0 | | |
| NT | CG16865 | FBgn0028919 | 0 | FLJ22965 | hypothetical protein FLJ22965 |
| NT | CG16964 | FBgn0032385 | 0 | | |
| NT | CG17261 | FBgn0031501 | 0 | | |
| NT | CG17267 | FBgn0038821 | 0 | | |
| NT | CG17282 | FBgn0038857 | 0 | | |
| NT | CG17382 | FBgn0039080 | 0 | | |
| NT | CG17786 | FBgn0039187 | 1 | CNOT6 | CCR4-NOT transcription complex, subunit 6 |
| NT | CG17807 | FBgn0034748 | 0 | LOC91801 | hypothetical protein BC015183 |
| NT | CG17952 | FBgn0034657 | 0 | | |
| NT | CG18145 | FBgn0032189 | 0 | | |
| NT | CG18275 | FBgn0029523 | 2 | | |
| NT | CG18368 | FBgn0033864 | 0 | | |
| NT | CG18600 | FBgn0038601 | 0 | | |
| NT | CG1896 | FBgn0039870 | 0 | | |
| NT | CG2016 | FBgn0037289 | 0 | | |
| NT | CG2124 | FBgn0030217 | 0 | FLJ13149 | hypothetical protein FLJ13149 |
| NT | CG2889 | FBgn0030206 | 0 | | |
| NT | CG30010 | FBgn0050010 | 0 | MGC70857 | similar to RIKEN cDNA C030006K11 gene |
| NT | CG30101 | FBgn0050101 | 1 | | |
| NT | CG30109 | FBgn0050109 | 0 | P53CSV | p53-inducible cell-survival factor |
| NT | CG30363 | FBgn0050363 | 0 | | |
| NT | CG30419 | FBgn0050419 | 0 | | |
| NT | CG31093 | FBgn0051093 | 0 | | |
| NT | CG31389 | FBgn0051389 | 0 | | |
| NT | CG31407 | FBgn0051407 | 0 | | |
| NT | CG31825 | FBgn0051825 | 1 | | |
| NT | CG31989 | FBgn0051989 | 0 | | |
| NT | CG31998 | FBgn0051998 | 0 | | |
| NT | CG32021 | FBgn0052021 | 1 | | |
| NT | CG32345 | FBgn0052345 | 3 | | |
| NT | CG32436 | FBgn0052436 | 0 | | |
| NT | CG32639 | FBgn0052639 | 0 | | |
| NT | CG32783 | FBgn0029686 | 0 | | |
| NT | CG33109 | FBgn0053109 | 0 | | |
| NT | CG33267 | FBgn0053267 | 2 | | |
| NT | CG3330 | FBgn0039511 | 0 | | |
| NT | CG33301 | FBgn0053301 | 3 | | |
| NT | CG33340 | FBgn0053340 | 0 | | |
| NT | CG3406 | FBgn0036008 | 0 | PRO1855 | hypothetical protein PRO1855 |
| NT | CG3501 | FBgn0034791 | 0 | C14orf122 | chromosome 14 open reading frame 122 |
| NT | CG3546 | FBgn0029716 | 4 | | |
| NT | CG3596 | FBgn0025645 | 0 | | |
| NT | CG3713 | FBgn0040343 | 0 | | |
| NT | CG3764 | FBgn0036684 | 0 | | |
| NT | CG3800 | FBgn0034802 | 0 | ZNF9 | zinc finger protein 9 (a cellular retroviral nucleic acid binding protein) |
| NT | CG3805 | FBgn0031665 | 0 | | |
| NT | CG3973 | FBgn0029881 | 0 | | |
| NT | CG40402 | FBgn0058402 | 0 | | |
| NT | CG4627 | FBgn0033808 | 0 | C16orf51 | chromosome 16 open reading frame 51 |
| NT | CG4820 | FBgn0037876 | 0 | ZNF136 | zinc finger protein 136 |
| NT | CG5237 | FBgn0038593 | 1 | KIAA1409 | KIAA1409 |
| NT | CG5323 | FBgn0034362 | 0 | | |
| NT | CG5386 | FBgn0038945 | 10 | | |
| NT | CG5467 | FBgn0039433 | 3 | | |
| NT | CG5468 | FBgn0039434 | 0 | | |
| NT | CG5538 | FBgn0038052 | 0 | | |
| NT | CG5955 | FBgn0035997 | 0 | | |
| NT | CG6018 | FBgn0034736 | 0 | | |
| NT | CG6073 | FBgn0039417 | 0 | LOC51236 | brain protein 16 |
| NT | CG6195 | FBgn0038723 | 1 | DRG2 | developmentally regulated GTP binding protein 2 |
| NT | CG6301 | FBgn0034161 | 0 | | |
| NT | CG6480 | FBgn0036964 | 0 | FRG1 | FSHD region gene 1 |
| NT | CG6569 | FBgn0038909 | 0 | MYH2 | myosin, heavy polypeptide 2, skeletal muscle, adult |
| NT | CG6614 | FBgn0032369 | 0 | TTC18 | tetratricopeptide repeat domain 18 |

TABLE 1-continued

| Score in secondary screen | Gene | FBGN | Number of potential 21nt off-targets | Human orthologs (NCBI Homologene) | Description of the human orthologs (NCBI Gene) |
|---|---|---|---|---|---|
| NT | CG6631 | FBgn0039206 | 0 | | |
| NT | CG7053 | FBgn0030960 | 0 | FLJ11773 | hypothetical protein FLJ11773 |
| NT | CG7200 | FBgn0032671 | 1 | JMJD4 | jumonji domain containing 4 |
| NT | CG7242 | FBgn0040494 | 0 | | |
| NT | CG7381 | FBgn0038098 | 0 | | |
| NT | CG7567 | FBgn0039670 | 0 | | |
| NT | CG8031 | FBgn0038110 | 0 | C2orf4 | chromosome 2 open reading frame 4 |
| NT | CG8420 | FBgn0037664 | 0 | | |
| NT | CG8538 | FBgn0038223 | 0 | | |
| NT | CG8852 | FBgn0031548 | 1 | LRRTM4 | leucine rich repeat transmembrane neuronal 4 |
| NT | CG9328 | FBgn0032886 | 0 | | |
| NT | CG9380 | FBgn0035094 | 0 | | |
| NT | CG9773 | FBgn0037609 | 0 | | |
| NT | CR32205 | FBgn0052205 | 1 | | |
| NT | Edg78E | FBgn0000551 | 0 | | |
| NT | l(1)G0196 | FBgn0027279 | 0 | KIAA0433 | KIAA0433 protein |
| NT | l(1)G0222 | FBgn0028343 | 0 | | |
| NT | Mkm1 | FBgn0029152 | 1 | MKRN1 | makorin, ring finger protein, 1 |
| NT | msb1l | FBgn0027949 | 0 | | |
| NT | MTA1-like | FBgn0027951 | 4 | MTA1 | metastasis associated 1 |
| NT | nito | FBgn0027548 | 0 | RBM15 | RNA binding motif protein 15 |
| NT | olf186-M | FBgn0015522 | 0 | | |
| NT | Osi13 | FBgn0037422 | 0 | | |
| NT | Osi17 | FBgn0037427 | 0 | | |
| NT | Osi19 | FBgn0037429 | 0 | | |
| NT | Pcp | FBgn0003046 | 0 | | |
| NT | sano | FBgn0034408 | 0 | | |
| NT | T48 | FBgn0004359 | 0 | | |
| NT | yellow-d2 | FBgn0034856 | 0 | | |

TABLE II

| Gene | Description | CG | Amplicon No. | Expression | Inhibition of NFAT nuclear localization in TG-treated cells | # of potential off-targets of 21nt |
|---|---|---|---|---|---|---|
| CanA1 | Calcineurin A1 | CG1455 | DRSC18600 | +/− | − | 0 |
| Pp2B-14D | Protein phosphatase 2B at 14D | CG9842 | DRSC23315 | ++ | +++ | 0 |
| | | | DRSC20270 | | +++ | 1 |
| CanA-14F | Calcineurin A at 14F | CG9619 | DRSC23296 | + | +++ | 0 |
| | | | DRSC20211 | | +++ | 13 |
| CanB | Calcineurin B | CG4209 | DRSC18449 | +/− | ++ | 0 |
| CanB2 | Calcineurin B2 | CG11217 | DRSC07355 | ++ | ++ | 0 |
| CG32812 | CG32812 | CG32812 | DRSC18478 | + | − | 0 |

| Gene | Identity of potential off-targets of 21nt | # of potential off-targets of 20nt | Identity of potential off-targets of 20nt | # of potential off-targets of 19nt | Identity of potential off-targets of 19nt | Comments |
|---|---|---|---|---|---|---|
| CanA1 | | 0 | | 1 | CG7952 | |
| Pp2B-14D | | 0 | | 0 | | |
| | | | CG12238 | 2 | CG12238, CG32223 | 3 | CG12238, CG32223, CG32025 | |
| CanA-14F | | 0 | | 0 | | |
| | not listed | 56 | not listed | 183 | not listed | CG9642 (Pp2B-14D) has 18 matches with this amplicon. |
| CanB | | 1 | CG11217 (CanB2) | 2 | CG11217 (CanB2), CG15859 | |
| CanB2 | | 1 | CG4209 (CanB) | 2 | CG4209 (CanB), CG5744 | |
| CG32812 | | 0 | | 0 | | |

TABLE III

| Molecule in Suppl Table III | Potential off-target | Description of the potential off-target (NCBI Gene) |
|---|---|---|
| I. DIRECT NFAT KINASES | | |
| Shaggy (sgg. CG2621) | CG13772 (neuroligin) | neurexin binding; ectoderm development and neurogenesis; |
| | CG4771 | NA |
| | CG12199 (kek5) | peroxidase activity, cell adhesion, defense response; reactive oxygen species metabolism; transmission of nerve impulse; |
| | CG1049 (cct1) | choline-phosphate cytidylyltransferase activity; |
| | CG5907 (frq) | calcium sensitive guanylate cyclase activator activity; calmodulin binding; neurotransmitter secretion; synaptic transmission; |
| | CG32538 (nAcRalpha-18C) | nicotinic acetylcholine-activated cation-selective channel activity; muscle contraction; nerve-nerve synaptic |
| | CG9176 (eng1) | intracellular cyclic nucleotide activated cation channel activity; potassium channel activity; sensory perception; signal transduction; |
| | CG3427 (epec) | cAMP-dependent protein kinase regulator activity; small GTPase mediated signal transduction; |
| | CG33513 (nmdar2) | N-methyl-D-aspartate selective glutamate receptor activity; cation transport; nerve-nerve synaptic transmission; |
| | CG13290 | NA |
| | CG12708 | NA |
| | CG4136 | nucleobase, nucleoside, nucleotide and nucleic acid metabolism; regulation of transcription from RNA polymerase II promoter; ligand-dependent nuclear receptor activity; |
| Gasket (gsk. CG11338, CG31003) | CG12212 (peb) | transcription factor activity; leading edge cell fate determination; ectoderm development; photoreceptor cell morphogenesis; maintenance of tracheal epithelial integrity; negative regulation of JNK cascade; |
| CG12147 | CG6205 (por) | acyltransferase activity; cell adhesion; regulation of Wnt receptor signaling pathway; |
| | CG14895 (pak3) | receptor signaling protein serine/threonine kinase activity; MAPKKK cascade; actin filament organization; cell proliferation; cytoskeleton organization and biogenesis; |
| | CG18214 (trio) | Rho guanyl-nucleotide exchange factor activity; actin cytoskeleton organization and biogenesis; axon guidance; central and peripheral nervous system development; transmission of nerve impulse. |
| Disc overgrown (den. CG2048) | CG2028 | receptor signaling protein serine/threonine kinase activity; Wnt receptor signaling pathway; negative regulation of smoothened signaling pathway; regulation of proteolysis and peptidolysis; |
| CK1 alpha (CG2028) | CG2048 (ckIalpha) | receptor signaling protein serine/threonine kinase activity; Wnt receptor signaling pathway; negative regulation of smoothened signaling pathway; regulation of proteolysis and peptidolysis; |
| | CG2577 | receptor signaling protein serine/threonine kinase activity; casein kinase I activity; |
| | CG9102 (bab2) | transcription factor activity; chromatin assembly or disassembly; eye-antennal disc metamorphosis; sex determination; female gonad development; leg morphogenesis; transmission of nerve impulse. |
| | CG7838 (bab1) | receptor signaling protein serine/threonine kinase activity; chromosome segregation; mitotic spindle checkpoint regulation of exit from mitosis. |
| | CG7892 (nmo) | receptor signaling protein serine/threonine kinase activity; anti-apoptosis; cell proliferation; establishment of planar polarity; eye morphogenesis; wing morphogenesis; negative regulation of Wnt receptor signaling pathway; negative regulation of frizzled signaling pathway; |
| | CG16973 (msn) | JUN kinase kinase kinase kinase activity; small GTPase regulator activity; oogenesis; photoreceptor cell morphogenesis; regulation of cell shape; |
| CG2577 | CG2048 | receptor signaling protein serine/threonine kinase activity; casein kinase I activity; cell communication; circadias rhythm; imaginal disc growth; regulation of ecdysteroid secretion; regulation of protein-nucleus import; |
| | CG2028 | receptor signaling protein serine/threonine kinase activity; Wnt receptor signaling pathway; negative regulation of smoothened signaling pathway; regulation of proteolysis and peptidolysis; |
| | CG7838 (bab1) | receptor signaling protein serine/threonine kinase activity; chromosome segregation; mitotic spindle checkpoint; regulation of exit from mitosis |
| | CG7236 | receptor signaling protein serine/threonine kinase activity; cytokinesis; regulation of progression through cell cycle; |
| | CG3228 (kurz) | ATP-dependent helicase activity; nuclear mRNA splicing, via spliceosome; proteolysis and peptidolysis. |
| CG7094 | CG9135 | guanyl-nucleotide exchange factor activity; proteolysis and peptidolysis. |
| CG9962 | CG5621 | glutamate-gated ion channel activity; kainate selective glutamate receptor activity; potassium channel activity; nerve-nerve synaptic transmission. |
| II. OTHER KINASES | | |
| CG31640 | CG33531 (ddr) | transmembrane receptor protein tyrosine kinase activity; cell-cell adhesion; ectoderm development; mesoderm development; nervous system development; |
| | CG2699 (Pi3K21B) | phosphoinositide 3-kinase regulator activity; insulin receptor signaling pathway; positive regulation of cell size; positive regulation of growth; regulation of cell proliferation; regulation of cell size; |
| Pelle (pil. CG5974) | CG5263 | mRNA 3′-UTR binding; translation repressor activity; |
| l(l)G0148 (CG32742) | CG9463 | alpha-mannosidase activity; hydrolase activity, hydrolyzing N-glycosyl compounds. |

TABLE III-continued

|  | Potential off-target | Description of the potential off-target (NCBI Gene) |
|---|---|---|
| Pole hole (phl. CG2845) | CG8522 (HLH106) | fatty acid biosynthesis; positive regulation of transcription; transcription from RNA polymerase II promoter; |
|  | CG11073 | NA |
|  | CG3634 | NA |
|  | CG15105 | transcription regulator activity; ubiquitin-protein ligase activity; |
|  | CG3198 | nuclear mRNA splicing, via spliceosome |
|  | CG17299 | receptor signaling protein serine/threonine kinase activity; defense response; fatty acid metabolism; regulation of phosphate metabolism; response to stress |
|  | CG8465 | NA |
| Foraging (for. CG10033) | CG7826 (mnb) | receptor signaling protein serine/threonine kinase activity; nervous system development; ectoderm development; olfactory learning; cell proliferation; circadian rhythm; induction of apoptosis; learning and/or memory; |
|  | CG32629 | NA |
|  | CG13472 | NA |
|  | CG18389 (Elp93F) | transcription factor activity; autophagy; ecdysone-mediated induction of salivary gland cell death; induction of apoptosis by hormones; larval midgut histolysis; |
|  | CG9310 (hnf4) | steroid hormone receptor activity; regulation of transcription from RNA polymerase II promoter; endoderm development; mesoderm development; |
|  | CG16902 (Hr4) | steroid hormone receptor activity; metamorphosis; regulation of transcription from RNA polymerase II promotor |
|  | CG4013 (smr) | corepressor activity; regulation of transcription from RNA polymerase II promoter. |
|  | CG8949 | NA |
|  | CG14447 (grip) | glutamate receptor binding; determination of muscle attachment site; |
|  | CG5683 (Aef1) | RNA polymerase II transcription factor activity; cell proliferation; |
|  | CG32180 (elp74EF) | specific RNA polymerase II transcription factor activity; autophagy; cell death; salivary gland cell death mesoderm development; oogenesis; |
|  | CG32423 | mRNA processing; |
|  | CG3696 (kis) | ATP-dependent helicase activity; blastoderm segmentation; chromatin assembly or disassembly; |
|  | CG3695 (MED23) | RNA polymerase II transcription mediator activity; mediator complex; |
|  | CG14023 | NA |
|  | CG13109 (tal) | transcription coactivator activity; signal transducer activity; border follicle cell migration; |
|  | CG9381 (mura) | learning and/or memory; olfactory learning; |
|  | CG5466 | NA |
|  | CG12254 (MED25) | RNA polymerase II transcription mediator activity; |
|  | CG9354 (RpL34b) | nucleic acid binding; structural constituent of ribosome; |
|  | CG6575 (glec) | carbohydrate binding; cell adhesion; heterophilic cell adhesion; nervous system development. |
|  | CG14366 | NA |
|  | CG1161 | NA |
|  | CG10732 | NA |
|  | CG7368 | NA |
|  | CG12432 | NA |
|  | CG17888 (Pdp1) | transcription factor activity; circadian rhythm; mesoderm development; |
| PI3K59F (CG5373) | CG3856 (Oamb) | octopamine receptor activity; octopamine/tyramine signaling pathway; ovulation; |
|  | CG14619 | cysteine-type endopeptidase activity; ubiquitin thiolesterase activity; ubiquitin-specific protease activity |
|  | CG10989 | NA |
| III. OTHER |  |  |
| CG6919 | CG18208 | G-protein coupled receptor protein signaling pathway; transmission of nerve impulse. |
| CG31288 | CG15415 | NA |
|  | CG32381 (une-13-4A) | neurotransmitter secretion; synaptic vesicle priming. |
| Molecule in Suppl Table II |  |  |
| CanA1 (CG1455) | CG7952 (giant) | negative regulation of transcription from RNA polymerase II promoter; posterior head segmentation; terminal region determination; zygotic determination of anterior/posterior axis; ring gland development; salivary gland development; torso signaling pathway. |
| Pp2B-14D (CG98-42) | CG12238 (l(1)G0084) | chromatin binding; transcription regulator activity; gene silencing; oogenesis. |
|  | CG32223 | NA |
|  | CG32025 | NA |
| CanA-14F (CG9819) | not listed |  |
| CanB (CG4209) | CG11217 (CanB2) | calcium-dependent protein serine/threonine phosphatase activity; cell homeostasis; neurotransmitter secretion; vesicle-mediated transport. |
|  | CG15859 | NA |

TABLE III-continued

| | Potential off-target | Description of the potential off-target (NCBI Gene) |
|---|---|---|
| CG11217 (CanB2) | CG4209 (CanB) | calcium-dependent protein serine/threonine phosphatase activity; cell homeostasis; neurotransmitter secretion; vesicle-mediated transport. |
| | CG5744 | calcium-mediated signaling; sensory perception; signal transduction; visual perception. |

TABLE IV

| | Score in primary screen | Gene | Description of the human homologus | CG | FBgn | Amplicon No. | # of potential off-targets of 21nt | Identity of potential off-targets of 21nt | # of potential off-targets of 20nt | Identity of potential off-targets of 20nt | # of potential off-targets of 19nt | Identity of potential off-targets of 19nt |
|---|---|---|---|---|---|---|---|---|---|---|---|---|
| I. DIRECT NFAT KINASES | | | | | | | | | | | | |
| GSK3 | 6 | shaggy (sgg) | GSK3B | CG2621 | FBgn0003371 | DRSC18832 | 4 | CG5907, CG13772, CG12199, CG1049 | 7 | CG5907, CG13772, CG12199, CG1049, CG32538, CG9178, CG3427 | 12 | CG4771, CG5907, CG13772, CG12199, CG1049, CG32538, CG9178, CG3427, CG32513, CG13290, CG12708, CG4136 |
| | 1 | gsskel (gskt) | GSK3A | CG11338, CG31003 | FBgn0046332 | DRSC14058 | 0 | | 0 | | 1 | CG12212 |
| CK1 | 4 | gagamesh (gish) | CSNK1G | CG8963 | FBgn0011253 | DRSC16154 | 0 | | 0 | | 0 | |
| | 3 | CG12147 | CSNK1 | CG12147 | FBgn0037325 | DRSC12192 | 0 | | 2 | CG6205, CG14895 | 3 | CG6205, CG14895, CG18214 |
| | 1 | discs overgrown (dco) | CSNK1E | CG2048 | FBgn0002413 | DRSC16929 | 0 | | 1 | CG2028 | 1 | CG2028 |
| | 1 | CK1alpha | CSNK1A1 | CG2028 | FBgn0015024 | DRSC20231 | 3 | CG2048, CG2577, CG7836 | 4 | CG2048, CG2577, CG7836, CG18973 | 6 | CG2048, CG2577, CG7836, CG18973, CG7892, CG9102 |
| | 1 | CG2577 | CSNK1 | CG2577 | FBgn0030364 | DRSC19663 | 3 | CG2028, CG2048, CG7838 | 4 | CG2028, CG2048, CG7838, CG7236 | 5 | CG2028, CG2048, CG7838, CG7236, CG3228 |
| | 1 | CG7094 | CSNK1 | CG7094 | FBgn0032650 | DRSC03005 | 0 | | 1 | CG9135 | 1 | CG9135 |
| | 0 | CG9962 | CSNK1 | CG9962 | FBgn0031441 | DRSC00739 | 0 | | 0 | | 1 | CG5621 |
| DYRK | 1 | CG40478 | DYRKZ | CG40476 | FBgn0009975 | DRSC21055 | 0 | | 0 | | 0 | |
| I. OTHER KINASES | | | | | | | | | | | | |
| DDR | 4 | CG31640 | DDR | CG31640 | FBgn0051640 | DRSC2504 | 0 | | 2 | CG33531, CG2699 | 2 | CG33531, CG2699 |
| IRAK | 3 | pI (pola) | IRAK | CG5974 | FBgn0010441 | DRSC17026 | 0 | | 1 | CG5263 | 1 | CG5263 |
| CK2 | 4 | CK1alpha | CSNK2A | CG17520 | FBgn0000256 | DRSC11945 | 0 | | 0 | | 0 | |
| CDC7 | 2 | l(l)G0148 | CDC7 | CG32742 | FBgn0026360 | DRSC18429 | 0 | | 1 | CG9483 | 1 | CG9483 |
| TRRAP | 2 | Nipped-A | TRRAP | CG2905, CG33554 | FBgn0004661, FBgn0053554, FBgn0039969 | DRSC4882 | 0 | | 0 | | 0 | |
| RAF | 1 | phl (pola hols) | RAF | CG2845 | FBgn0003079 | DRSC18821 | 2 | CG11073, CG8522 | 4 | CG11073, CG8522, CG3634, CG15105 | 7 | CG3196, CG11073, CG8522, CG3834, CG15105, CG17299, CG8485 |
| PRKG1 | 1 | for (for aging) | PRKG1 | CG10033 | FBgn0000721 | DRSC00195 | 2 | CG32629, CG18389 | 4 | CG32629, CG18389, CG7825, CG9310 | 27 | |
| PI3K | 1 | PI3K59F | PIK3C3 | CG5373 | FBgn0015277 | DRSC04840 | 0 | | 2 | CG14619, CG10969 | 3 | CG14619, CG3856, CG10969 |
| I. OTHER | | | | | | | | | | | | |
| HTR | 5 | CG6919 | HTR4 | CG5919 | FBgn0038980 | DRSC16134 | 0 | | 0 | | 1 | CG16205 |
| FAM20 | 4 | CG31145 | FAM20C | CG31145 | FBgn0051145 | DRSC14671 | 0 | | 0 | | 0 | |
| | 4 | CG31288 | | CG31288 | FBgn0051288 | DRSC14667 | 0 | | 1 | CG15415 | 2 | CG15415, CG32381 |
| B9 | 4 | CG14870 | EPPB9 | CG14870 | FBgn0038342 | DRSC14993 | 0 | | 0 | | 0 | |
| | 4 | CG4585 | | CG4585 | FBgn0025335 | DRSC4475 | 0 | | 0 | | 0 | |
| PGLYRP | 3 | CG8995 | PGLYRP3 | CG8995 | FBgn0030695 | DRSC20137 | 0 | | 0 | | 0 | |

TABLE IV-continued

| Gene | Score in primary screen | Description of the human homologus | CG | FBgn | Amplicon No. | # of potential off-targets of 21nt | Identity of potential off-targets of 21nt | # of potential off-targets of 20nt | Identity of potential off-targets of 20nt | # of potential off-targets of 19nt | Identity of potential off-targets of 19nt |
|---|---|---|---|---|---|---|---|---|---|---|---|
| STM Stm | 3 | STM1 | CG9129 | FBgn0045073 | DRSC20158 | 0 | | 0 | | 0 | |
| Cathepsin 8 CG3074 | 2 | CTS8 | CG3074 | FBgn0034709 | DRSC4334 | 0 | | 0 | | 0 | |

What is claimed:

1. A recombinant cell comprising heterologous nucleic acid having at least 90% homology to SEQ ID NO:1 or SEQ ID NO:2, encoding at least one mammalian Nuclear Factor of Activated T cells (NFAT) regulator protein, wherein the NFAT regulator protein is an orai polypeptide or a homologue or a derivative thereof; and the recombinant cell is an isolated cell.

2. The recombinant cell of claim 1, wherein the cell is a mammalian, human, rodent, insect or *Xenopus* cell.

3. The recombinant cell of claim 2, wherein the heterologous nucleic acid is a human gene sequence.

4. The recombinant cell of claim 1, further comprising heterologous nucleic acid encoding a second mammalian NFAT regulator protein, wherein the second NFAT regulator protein is a stromal interaction molecule (STIM) protein.

5. The recombinant cell of claim 4, wherein the cell is a mammalian, human, rodent, insect or *Xenopus* cell.

6. The recombinant cell of claim 5, wherein the heterologous nucleic acid encoding the first and second NFAT regulator proteins are human gene sequences.

7. The recombinant cell of claim 4, wherein the heterologous nucleic acid encoding the second NFAT regulator proteins is expressed in the cell to produce heterologous STIM polypeptides.

8. The recombinant cell of claim 1, wherein the heterologous nucleic acid encodes an ORAI1 polypeptide or a homologue or derivative thereof.

9. The recombinant cell of claim 8, further comprising heterologous nucleic acid encoding an ORAI2 polypeptide or a homologue or derivative thereof, or an ORAI3 polypeptide or a homologue or derivative thereof, or a combination thereof.

10. The recombinant cell of claim 1, wherein the heterologous nucleic acid has at least 90% homology to SEQ ID NO: 1.

11. The recombinant cell of claim 1, wherein the heterologous nucleic acid has at least 90% homology to SEQ ID NO: 2.

12. An isolated recombinant cell that expresses a heterologous mammalian orai polypeptide selected from ORAI1, ORAI2, ORAI3 or a homologue or derivative thereof, from a heterologous nucleic acid having at least 90% homology to SEQ ID NO:1, SEQ ID NO:2, or SEQ ID NO: 3.

13. The isolated recombinant cell of claim 12, wherein the isolated cell is a mammalian, human, rodent, insect or *Xenopus* cell.

14. The isolated recombinant cell of claim 12 or 13, wherein the heterologous orai polypeptide is expressed from a heterologous human orai gene.

15. An isolated recombinant cell comprising a heterologous mammalian ORAI gene that has at least 90% homology to SEQ ID NO:1, SEQ ID NO:2, or SEQ ID NO:3, wherein the heterologous gene encodes an orai polypeptide or a homologue or derivative thereof; and a heterologous stromal interaction molecule (STIM) gene.

16. The recombinant cell of claim 15, wherein the cell is an isolated, mammalian, human, rodent, insect, or *Xenopus* cell.

17. The recombinant cell of claim 16, wherein the ORAI gene and the STIM gene are human nucleic acid sequences.

18. The recombinant cell of claim 16, wherein the ORAI gene and the STIM gene are expressed in the cell to produce heterologous ORAI and heterologous stromal interaction molecule (STIM) polypeptides.

19. A method for screening for a test agent that modulates the activity of an ORAI polypeptide, the method comprising: a) providing a cell, wherein the cell expresses a recombinant mammalian ORAI polypeptide or homologue or derivative thereof, encoded by an NFAT regulator gene, wherein the NFAT regulator gene has at least 90% homology to SEQ ID: No:1, SEQ ID No:2, or SEQ ID No:3, to form a calcium release-activated Ca2+ (CRAC) channel; b) contacting the cell with a test agent; and c) measuring the store-operated calcium entry of the calcium release-activated Ca2+(CRAC) channel, wherein a change in the store-operated calcium entry of the calcium release-activated Ca2+ (CRAC) channel as compared to the store-operated calcium entry of the calcium release-activated Ca2+ (CRAC) channel in the absence of the test agent indicates that the test agent is capable of modulating the activity of the calcium release-activated Ca2+ (CRAC) channel.

20. The method of claim 19, wherein the ORAI polypeptide is an ORAI1 polypeptide.

21. The method of claim 19, wherein the ORAI polypeptide is an ORAI2 polypeptide.

22. The method of claim 19, wherein the ORAI polypeptide is an ORAI3 polypeptide.

23. A recombinant cell in vitro comprising heterologous nucleic acid encoding at least one mammalian NFAT regulator protein, wherein the NFAT regulator protein is an orai polypeptide or a homologue or derivative thereof, wherein the heterologous nucleic acid encoding the at least one NFAT regulator protein has at least 90% homology to SEQ ID NO:1, SEQ ID NO:2, or SEQ ID NO:3.

24. The recombinant cell of claim 23, wherein the heterologous nucleic acid has at least 90% homology to SEQ ID NO: 1.

25. The recombinant cell of claim 23, wherein the heterologous nucleic acid has at least 90% homology to SEQ ID NO: 2.

26. The recombinant cell of claim 23, wherein the heterologous nucleic acid has at least 90% homology to SEQ ID NO: 3.

27. A recombinant cell in vitro comprising heterologous nucleic acid encoding at least one Nuclear Factor of Activated T cells (NFAT) regulator protein, wherein the heterologous nucleic acid is a mammalian NFAT regulator gene, wherein the NFAT regulator gene is ORAI1, ORAI2, or ORAI3, wherein ORAI 1 comprises SEQ ID NO: 1 or a sequence 95% homologous thereto, ORAI 2 comprises SEQ ID NO:2 or a sequence 95% homologous thereto, ORAI 3 comprises SEQ ID NO:3 or a sequence 95% homologous thereto, further comprising a heterologous mammalian NFAT regulator gene, wherein the NFAT regulator gene is stromal interaction molecule (STIM) gene.

* * * * *